(12) United States Patent
Jaffrey et al.

(10) Patent No.: US 12,391,948 B2
(45) Date of Patent: Aug. 19, 2025

(54) RNA-REGULATED FUSION PROTEINS AND METHODS OF THEIR USE

(71) Applicant: CORNELL UNIVERSITY, Ithaca, NY (US)

(72) Inventors: Samie R. Jaffrey, New York, NY (US); Jiahui Wu, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 849 days.

(21) Appl. No.: 17/637,940

(22) PCT Filed: Aug. 31, 2020

(86) PCT No.: PCT/US2020/048781
§ 371 (c)(1),
(2) Date: Feb. 24, 2022

(87) PCT Pub. No.: WO2021/042050
PCT Pub. Date: Mar. 4, 2021

(65) Prior Publication Data
US 2022/0290161 A1  Sep. 15, 2022

Related U.S. Application Data

(60) Provisional application No. 62/894,651, filed on Aug. 30, 2019.

(51) Int. Cl.
| | |
|---|---|
| *C12N 15/62* | (2006.01) |
| *A61K 31/7105* | (2006.01) |
| *C07K 19/00* | (2006.01) |
| *C12N 5/071* | (2010.01) |
| *C12N 9/02* | (2006.01) |
| *C12N 15/115* | (2010.01) |
| *C12N 15/52* | (2006.01) |
| *C12N 15/85* | (2006.01) |
| *C12Q 1/6816* | (2018.01) |

(52) U.S. Cl.
CPC ........... *C12N 15/62* (2013.01); *C12N 5/0602* (2013.01); *C12N 15/115* (2013.01); *C12N 15/52* (2013.01); *C12N 15/85* (2013.01); *C12Q 1/6816* (2013.01); *C12Y 111/01011* (2013.01); *C12Y 113/12013* (2013.01); *C12Y 201/01043* (2013.01); *C12Y 603/0401* (2013.01); *C07K 2319/60* (2013.01); *C07K 2319/61* (2013.01); *C07K 2319/85* (2013.01); *C12N 2310/16* (2013.01); *C12N 2800/107* (2013.01)

(58) Field of Classification Search
None
See application file for complete search history.

(56) References Cited

U.S. PATENT DOCUMENTS

| | | | |
|---|---|---|---|
| 9,388,418 B2 | 7/2016 | Rossi et al. | |
| 2008/0300187 A1* | 12/2008 | Sauvageau | C07K 14/47 435/375 |
| 2012/0213737 A1 | 8/2012 | Zhu et al. | |
| 2014/0255361 A1 | 9/2014 | Wandless et al. | |
| 2019/0185934 A1 | 6/2019 | Jaffrey et al. | |

OTHER PUBLICATIONS

International Search Report and Written Opinion for corresponding International Application No. PCT/US2020/048781 (mailed Feb. 8, 2021).
Wu et al., "Live Imaging of mRNA using RNA-Stabilized Fluorogenic Proteins," Nat. Method. 16(9):862-865 (2019).
Song et al., "Imaging RNA Polymerase III Transcription Using a Photostable RNA-Fluorophore Complex," Nat. Chem. Biol. 13(11):1187-1194 (2017).
Extended European Search Report for European Application No. 20950485.1 (mailed Mar. 4, 2025).
Tok et al., "A Comparative Binding Study of Modified Bovine Immunodeficiency Virus TAR RNA Against its TAT Peptide," Bioorg. Med. Chem. Lett. 14(24):6101-6105 (2004).
Bonger et al., "Small-Molecule Displacement of a Cryptic Degron Causes Conditional Protein Degradation," Nat. Chem. Biol. 7(8):531-537 (2011).
Battiste et al., "α Helix-RNA Major Groove Recognition in an HIV-1 Rev Peptide-RRE RNA Complex," Science 273:1547-1551 (1996).
Legault et al., "NMR Structure of the Bacteriophage λ N Peptide/boxB RNA Complex: Recognition of a GNRA Fold by an Arginine-Rich Motif," Cell 93(2):289-299 (1998).
Yamamoto et al., "A Novel RNA Motif that Binds Efficiently and Specifically to the Tate Protein of HIV and Inhibits the Trans-Activation by Tate of Transcription in vitro and in vivo," Genes to Cells 5:371-388 (2000).
Rakhit et al., "Evaluation of FKBP and DHFR based Destabilizing Domains in *Saccharomyces cerevisiae*," Bioorg. Med. Chem. Lett. 21(17):4965-4968 (2011) [Author manuscript].
Iwamoto et al., "A General Chemical Method to Regulate Protein Stability in the Mammalian Central Nervous System," Chem. Biol. 17(9):981-988 (2010) [Author Manuscript].
Athanassiou et al., "Structural Mimicry of Retroviral Tat Proteins by Constrained β-Hairpin Peptidomimetics: Ligands with High Affinity and Selectivity for Viral TAR RNA Regulatory Elements," J. Am. Chem. Soc. 126(22):6906-6913 (2004).

(Continued)

*Primary Examiner* — Manjunath N Rao
*Assistant Examiner* — Jae W Lee
(74) *Attorney, Agent, or Firm* — Troutman Pepper Locke LLP (Rochester)

(57) ABSTRACT

The present disclosure is directed to RNA-regulated fusion proteins comprising a protein of interest and an RNA-regulated destabilization domain. Also disclosed are RNA aptamers that bind specifically to a RNA-regulated destabilization domain. Nucleic acid molecules encoding the RNA-regulated fusion proteins and RNA aptamers and methods of use thereof are also disclosed.

10 Claims, 49 Drawing Sheets

Specification includes a Sequence Listing.

(56) References Cited

OTHER PUBLICATIONS

Chen et al., "A Peptide Interaction in the Major Groove of RNA Resembles Protein Interactions in the Minor Groove of DNA," Proc. Natl. Acad. Sci. USA 92:5077-5081 (1995).
Chen and Frankel, "An RNA-Binding Peptide from Bovine Immunodeficiency Virus Tat Protein Recognizes an Unusual RNA Structure," Biochemistry 33:2708-2715 (1994).
Koren et al., "The Eukaryotic Proteome is Shaped by E3 Ubiquitin Ligases Targeting C-Terminal Degrons," Cell 173:1622-1635 (2018).
Smith et al., "Altering the Context of an RNA Bulge Switches the Binding Specificities of Two Viral Tat Proteins," Biochemistry 37:10808-10814 (1998).

* cited by examiner

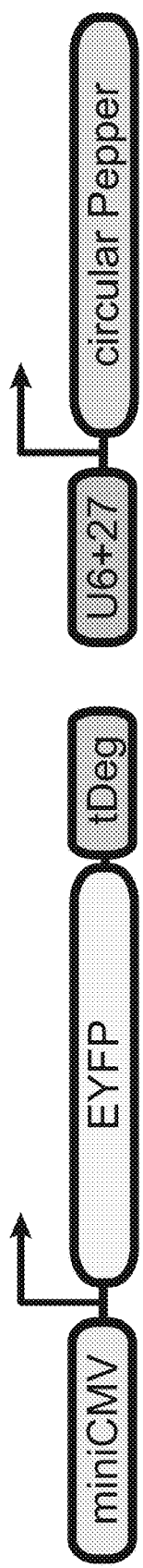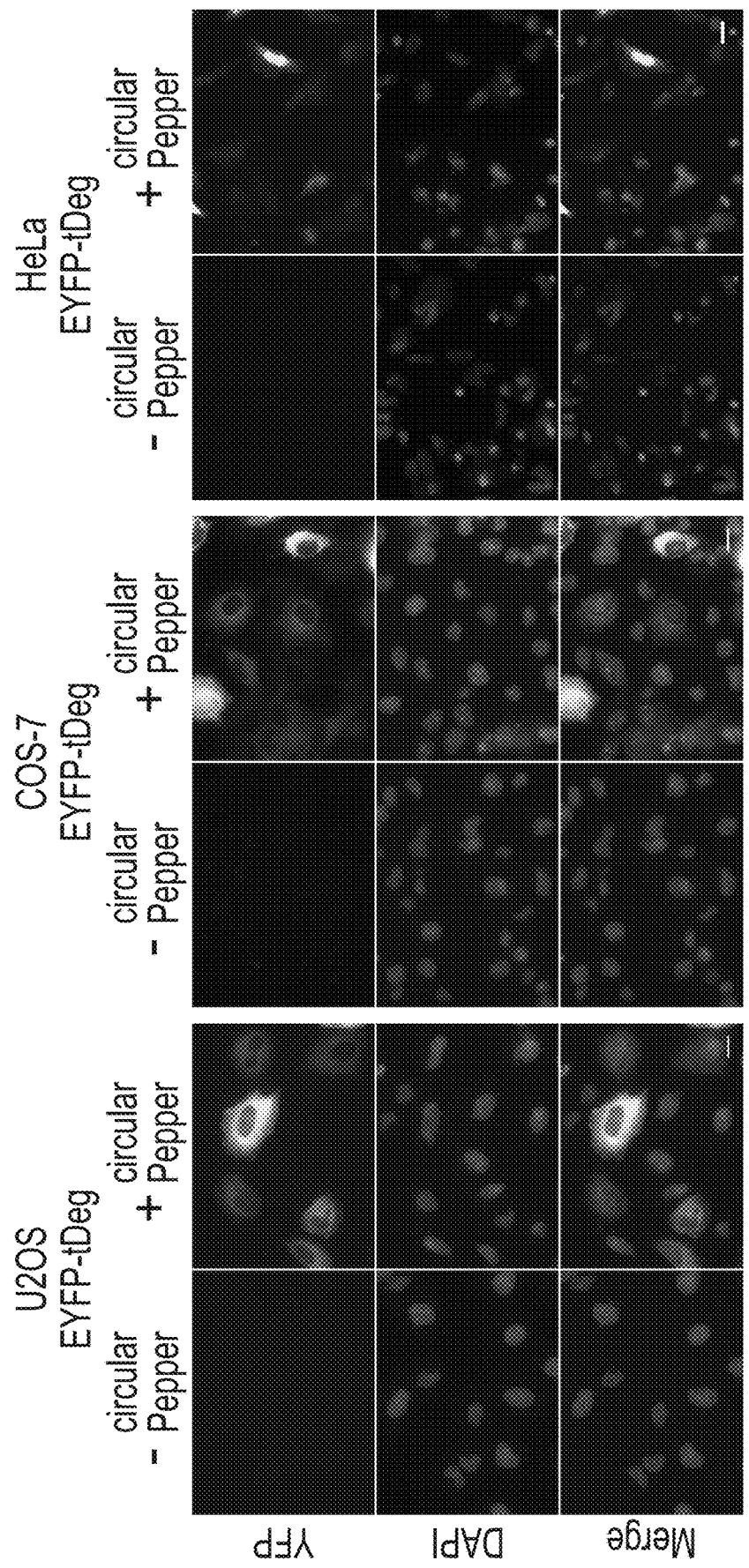
FIG. 5A
FIG. 5B   FIG. 5C   FIG. 5D

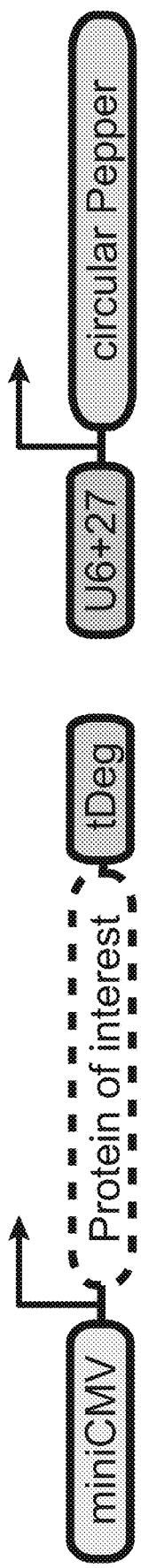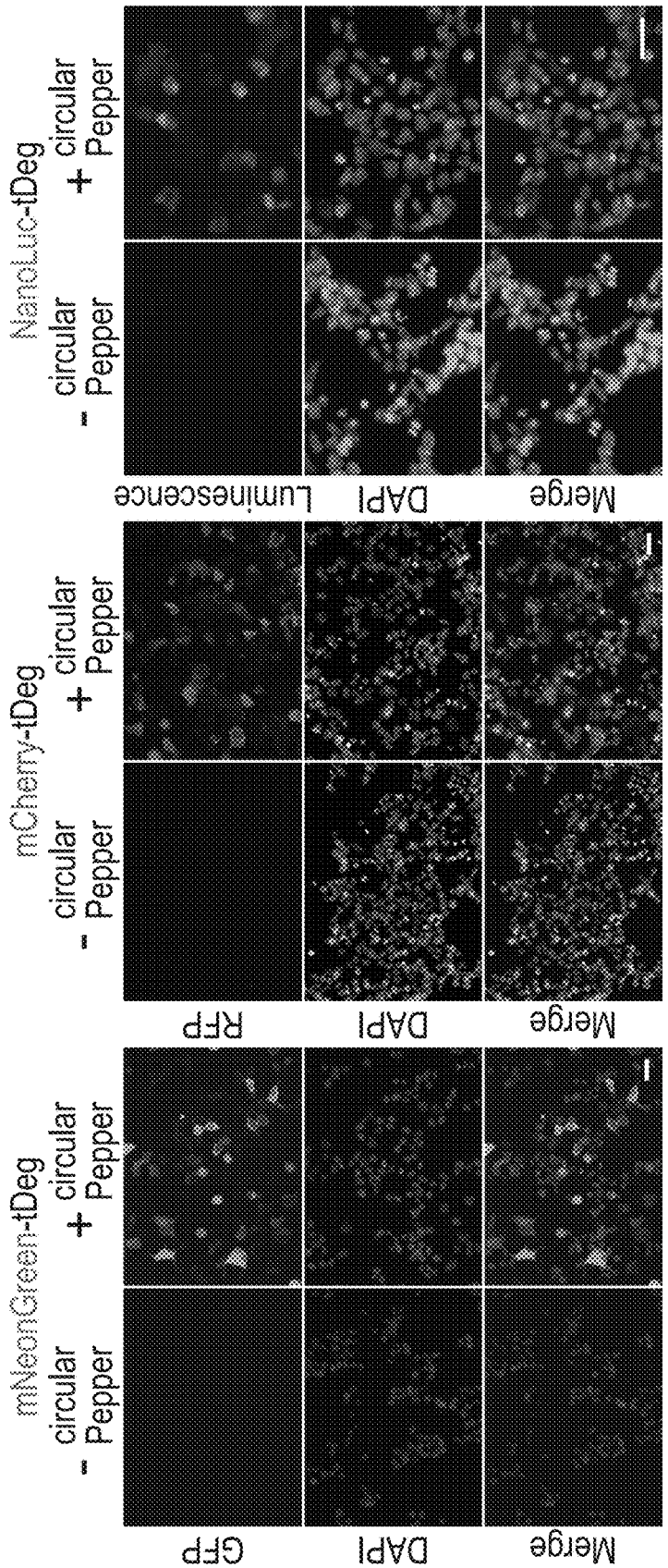
FIG. 6A
FIG. 6B
FIG. 6C
FIG. 6D

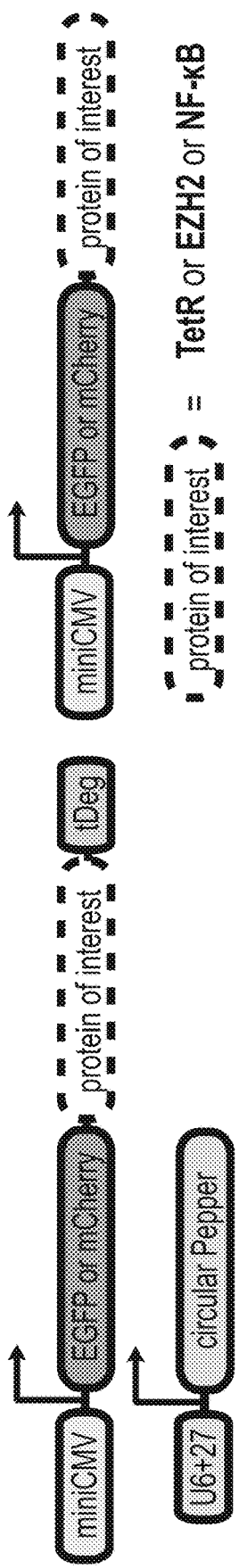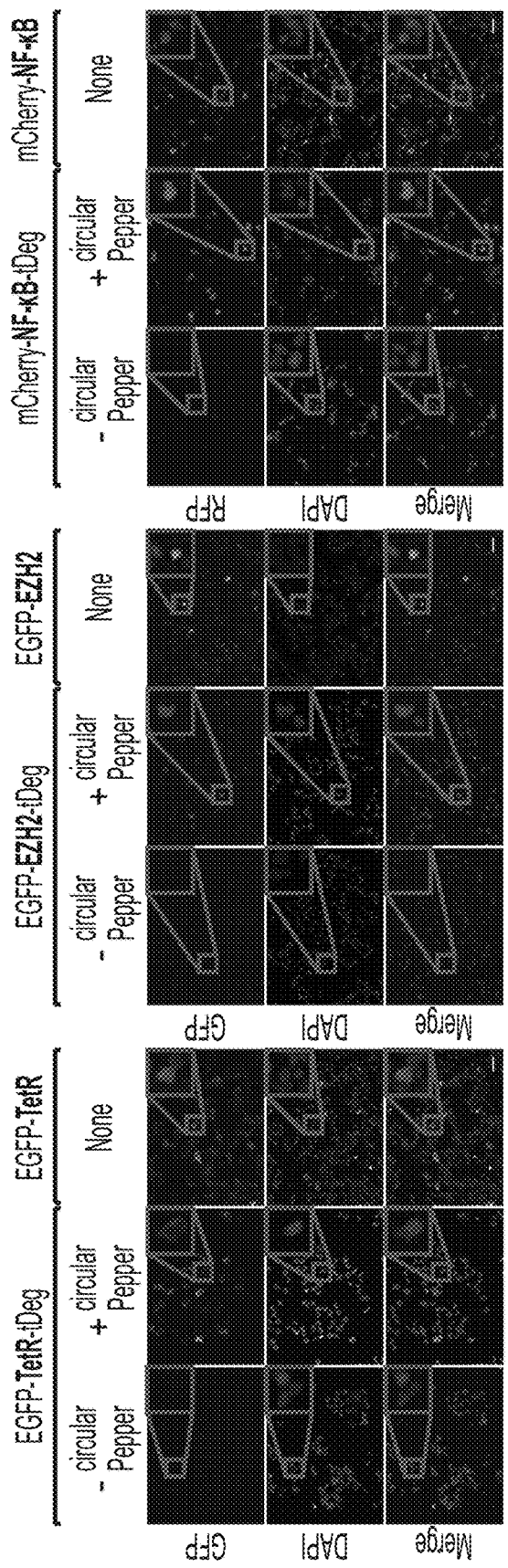
FIG. 7A
FIG. 7B
FIG. 7C
FIG. 7D

FIG. 9A

(Pepper)₁₀ tag (586 bp):

⚆⚆⚆⚆⚆⚆⚆⚆⚆⚆ = Pepper variants (highlighted in blue or orange)

▬ = Different linkers (highlighted in black boxes)

(Pepper)₁₀ tag sequence:

GGCTGTCTGCAGGTTATCCTGGGAGTCCAGGCCAAACTATTACGAAAAACATCCGACG Linker1 CGCGGACAACCAAACTTACAACGGCAAA Linker2

AAACCTTCACAAAAACAGACAAACG Linker2 GCGGACAACCAAACTTACAACGGCAAA Linker3 GACCTGCTAGATAGTTAGG TCATTACTGGAGCCGGTATCAAGACGGAAGGGCAAGATATTGACACG Linker4 GACCTGCTAGATAGTTAGG Linker5

TTCTTAGGCATT AAAGATTGACTGCAATTCCGATTAGACGTACAG Linker6 GATCATAAGCAATACGTACACTGTCCAATCC Linker5 GGACAACCAATTGACATACATCACACCACAACTC Linker8

CGGACAACCAATTGACATACATCACACCACAACTC Linker9

(F30-1xPepper)₁₀ tag (1466 bp):

Y = F30 variants (underlined with navy, magenta, or green)

⌇ = Pepper variants (highlighted in blue or orange)

▬ = Different linkers (highlighted in black boxes)

(F30-1xPepper)₁₀ tag sequence:

TTGCCATGTGTATGTGGGATGCGTTGCCACGTTCCCACATACTCTGATGATCGCTAGCAAACGTTGTCAGTTCATTTAGTCCAGGTAC
                F30-1xPepper                                          F30 variant1

CGGATCATTCATGGCAAGTCCAGGCAATCTATTAGGAAAATCATCCGACGTGGCGGATGGTTGCCACGTTCCCGCATAGTCGTGAT
                                Linker1                                F30 variant2

CATCCGCTAGCAAAGCTGGCGGAAAATCTCACAAATCACGTCAAACCGAGGTACCGGATGAGATTCATGCGAGCTGGCGGAAAATCTCACAAATCACGTCAAAC
                                               Linker2

GTGCCGTGTGTAGGATGGTTGCCACGTTCCTACACACTCTGAGATCGCTAGCAAATGCCATGTGTATGTGGGATGCGTTGCCACGTTCCCGCATAGTCGTGAT
                F30 variant3                                         F30 variant1

CGGATCCGTACGGCGGATCCGGATATCAATCTATTACAATTCAGGCAATCTGCCATGTGTATGTGGGATGCGTTGCCACGTTCCCACATAGTCGTGAT
              Linker3                                        F30 variant1

GATCCGCTAGCAAATATCAAGATCGAACGGCCAAGATATTGTCACCGAGGTACCGGATCATTCATGGCAAGTATCAAGATCGAACGGCCAAGATATTGTCAC
                                                Linker4

*FIG. 9B*

FIG. 12C
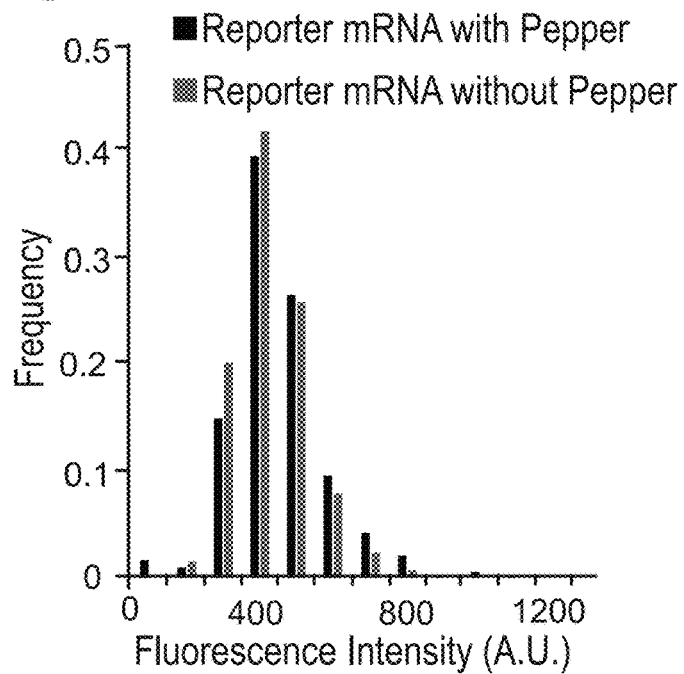
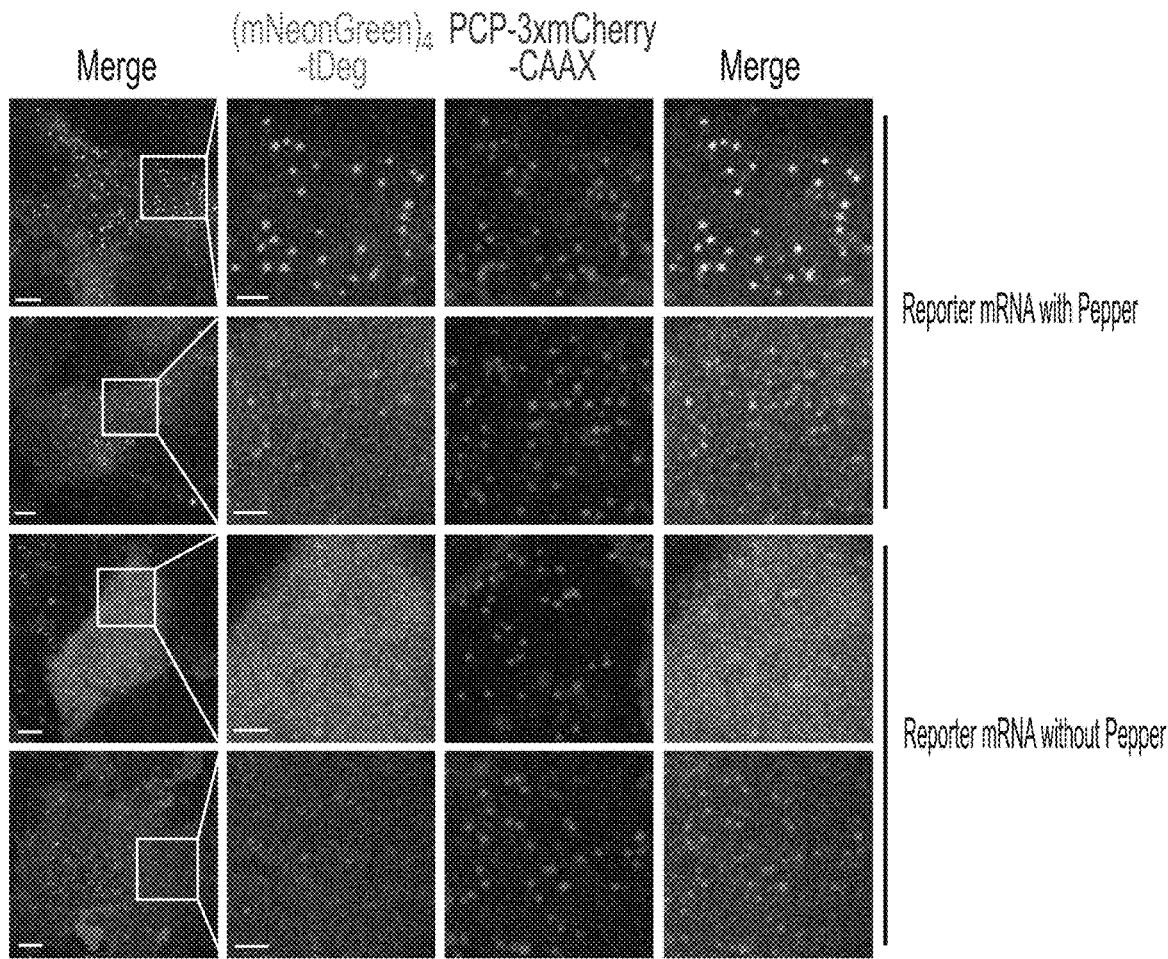
FIG. 12D

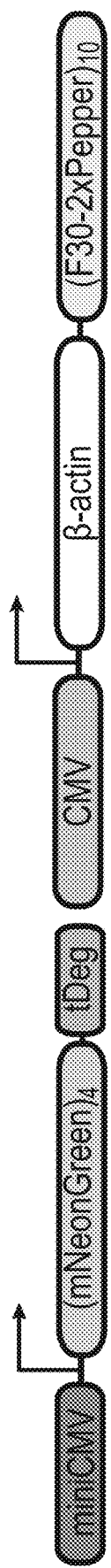
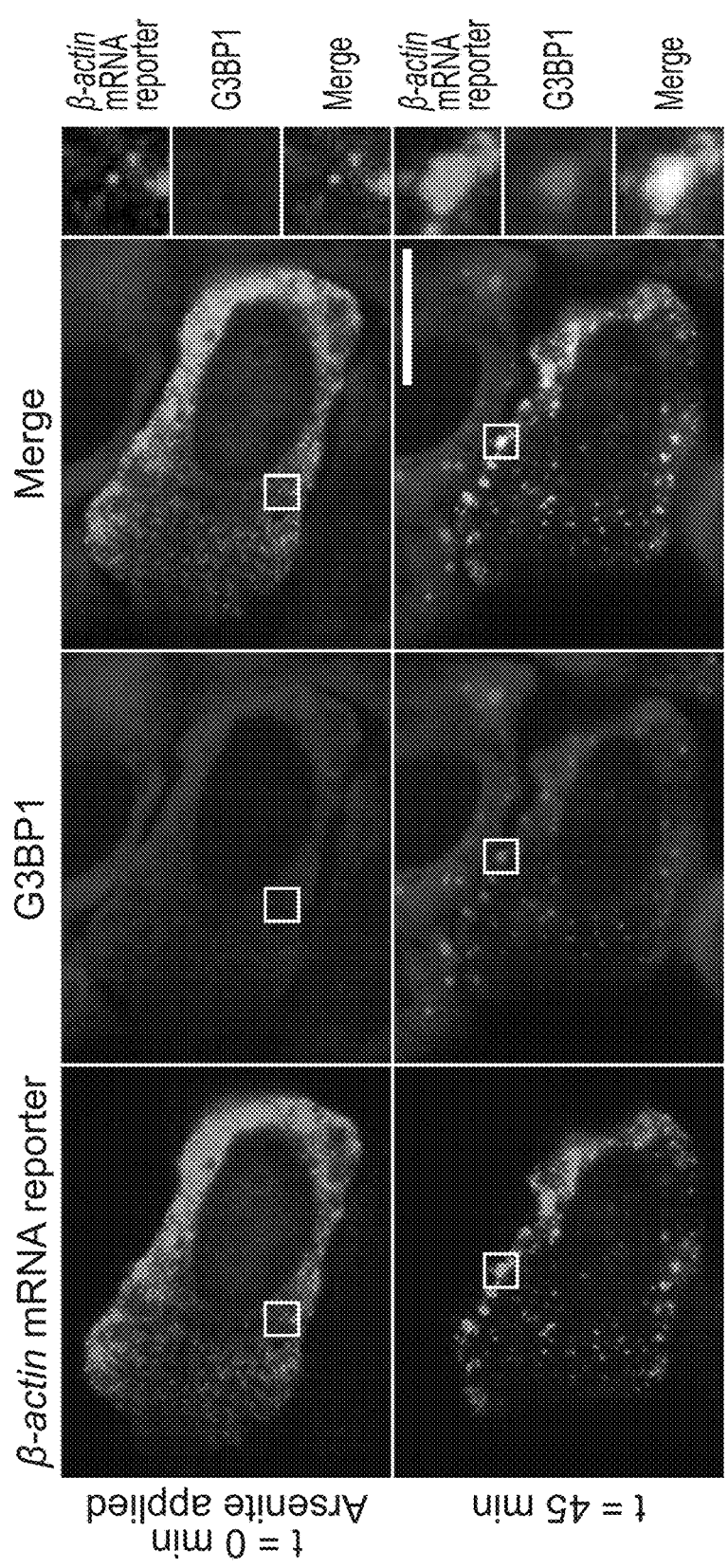
FIG. 15A
FIG. 15B

RNA-REGULATED FUSION PROTEINS AND METHODS OF THEIR USE

This application is a national stage application under 35 U.S.C. § 371 of International Application No. PCT/US2020/048781, filed Aug. 31, 2020, which claims priority benefit of U.S. Provisional Patent Application Ser. No. 62/894,651 filed Aug. 30, 2019, which is hereby incorporated by reference in its entirety.

This invention was made with government support under Grant Number MH109087 awarded by the National Institutes of Health. The government has certain rights in the invention.

FIELD OF THE DISCLOSURE

This present disclosure relates to RNA-regulated fusion proteins and methods of their use.

BACKGROUND

Fluorogenic RNA aptamers are RNA aptamers that bind otherwise nonfluorescent molecules and switch them to a fluorescent form. These fluorogenic dyes can be applied to cells, enabling RNAs tagged with these fluorogenic aptamers to be imaged using fluorescence microscopy (Paige et al., "RNA Mimics of Green Fluorescent Protein," *Science* 333: 642-646 (2011) and Braselmann et al., "A Multicolor Riboswitch-Based Platform for Imaging of RNA in Live Mammalian Cells," *Nat. Chem. Biol.* 14:964-971 (2018)). However, few fluorogenic aptamers have been developed since there are not many fluorogenic dyes that meet the criteria required for use in live cells. For example, most dyes show nonspecific fluorescence activation by cellular lipids or DNA ( Löber, G., "The Fluorescence of Dye—Nucleic Acid Complexes," *Journal of Luminescence* 22:221-265 (1981) and Fam et al., "Recent Advances in Fluorescent Probes for Lipid Droplets," *Materials (Basel)* 11 (2018)). This nonspecific binding leads to background fluorescence that obscures the fluorescence of the RNA-dye complexes. Another problem is that the fluorogenic dyes are not genetically encoded and therefore need to be added exogenously for RNA imaging. A genetically encoded conditionally fluorescent dye would provide a simple alternative to the use of fluorogenic RNA aptamers.

The present disclosure is directed to overcoming deficiencies in the art.

SUMMARY

A first aspect of the disclosure relates to a nucleic acid molecule encoding an RNA-regulated fusion protein. The nucleic acid molecule includes: a first nucleic acid sequence encoding a protein of interest and a second nucleic acid sequence encoding an RNA-regulated destabilization domain, where the second nucleic acid sequence is operably coupled to the first nucleic acid sequence.

Another aspect of the disclosure relates to a nucleic acid molecule encoding a lentiviral transactivator of transcription (Tar) RNA aptamer sequence.

A further aspect of the disclosure relates to an RNA-regulated fusion protein comprising a protein of interest and an RNA-regulated destabilization domain.

Yet another aspect of the disclosure relates to a molecular complex comprising: an RNA-regulated fusion protein comprising (i) a protein of interest and (ii) an RNA-regulated destabilization domain; and an RNA aptamer bound specifically to the RNA-regulated destabilization domain.

Another aspect of the invention relates to a method of imaging RNA in a cell. This method involves providing a first vector encoding an RNA-regulated fusion protein, where the RNA-regulated fusion protein comprises a fluorescent protein, a bioluminescent protein, or an enzyme fused to an RNA-regulated destabilization domain; providing a second vector encoding an RNA molecule comprising (i) an RNA sequence of interest and (ii) an RNA aptamer sequence, where the RNA-regulated destabilization domain specifically binds to the RNA aptamer sequence; transfecting a host cell with the first vector and the second vector; and imaging said transfected cells.

Yet another aspect of the invention relates to a method of imaging RNA in a cell. This method involves providing a vector encoding an RNA-regulated fusion protein, where the RNA-regulated fusion protein comprises a fluorescent protein, a bioluminescent protein, or an enzyme fused to an RNA-regulated destabilization domain; transfecting a host cell with the first vector; contacting said transfected cell with an RNA molecule comprising (i) an RNA sequence of interest and (ii) an RNA aptamer sequence, where the RNA-regulated destabilization domain specifically binds to the RNA aptamer sequence; and imaging said contacted cells.

A further aspect of the invention relates to a method of selectively modifying an RNA-binding protein. This method involves providing a first expression vector encoding an RNA-regulated fusion protein, where the RNA-regulated fusion protein comprises an enzyme fused to an RNA-regulated destabilization domain; providing a second expression vector encoding (i) an RNA sequence of interest and (ii) an RNA aptamer sequence, where the RNA-regulated destabilization domain specifically binds to the RNA aptamer sequence; transfecting a host cell with the first and second expression vectors; and allowing the enzyme to be expressed, where the expressed enzyme selectively modifies a protein that binds to the RNA sequence of interest.

Another aspect of the invention relates to a method of regulating expression of an RNA-stabilized protein of interest. This method involves providing a first vector encoding an RNA-regulated fusion protein, where the RNA-regulated fusion protein comprises a protein of interest fused to an RNA-regulated destabilization domain; providing a second vector encoding an RNA aptamer sequence, where the RNA-regulated destabilization domain specifically binds to the RNA aptamer sequence; providing a host cell comprising a functional ubiquitination system; transfecting the host cell with the first and second expression vectors; and expressing the first and second expression vectors within the host cell, where said expressing the first and second expression vectors regulates proteomic stability of the RNA-regulated fusion protein; and where, in the absence of any expressed RNA aptamer sequence in the host cell, the RNA-regulated destabilization domain promotes degradation of the RNA-regulated fusion protein by the ubiquitination system; and where the RNA-regulated fusion protein is stabilized by the expressed RNA aptamer sequence.

Another aspect of the invention relates to a method of regulating expression of an RNA-stabilized protein of interest. This method involves providing a first vector encoding an RNA-regulated fusion protein, where the RNA-regulated fusion protein comprises a protein of interest fused to an RNA-regulated destabilization domain; providing a second vector encoding an RNA aptamer sequence, where the RNA-regulated destabilization domain specifically binds to the RNA aptamer sequence; providing a mammalian cell lysate or solution comprising (i) a ubiquitin ligase, (ii) proteosomal degradation machinery, (iii) transcriptional machinery, and (iv) translational machinery; contacting the mammalian cell lysate or solution with the first and second expression vectors; and expressing the first and second expression vectors, where said expressing the first and second expression vectors regulates proteomic stability of the RNA-regulated fusion protein; and where, in the absence of any expressed RNA aptamer sequence in the cell lysate or solution, the RNA-regulated destabilization domain promotes degradation of the RNA-regulated fusion protein by the proteosomal degradation system; and where the RNA-regulated fusion protein is stabilized by the expressed RNA aptamer sequence.

Another aspect of the present application relates to a treatment method. This method involves contacting a cell with an RNA aptamer, where upon said contacting, the aptamer interacts with an RNA-regulated destabilization domain fused to a protein of interest in the cell to stabilize the protein of interest in the cell.

Another aspect of the present invention relates to a treatment method. This method involves contacting a cell with a vector according to the present application under conditions effective to express an RNA molecule as described herein to treat the cell.

The examples described herein below demonstrate the use of RNA-regulated fluorescent fusion proteins whose fluorescence is stabilized by RNA aptamers. In some embodiments, the RNA-regulated fluorescent fusion proteins are highly unstable until they bind RNA aptamers inserted in mRNAs, resulting in fluorescent RNA-protein complexes that enable live imaging of mRNA in living cells. In some embodiments, the technology described herein is an imaging system that bypasses the limitations of using fluorogenic RNA aptamers and conditionally fluorescent small molecule dyes for imaging. In some embodiments, this is achieved by engineering a peptide degron sequence whose activity can be regulated by an RNA aptamer. When fused to a fluorescent protein, this peptide degron sequence can send the fluorescent protein to degradation. However, this degradation function of the peptide degron is impeded when bound to a specific RNA aptamer sequence. In some embodiments, a peptide degron sequence causes rapid degradation of the unbound fluorescent proteins when expressed in mammalian cells. This is different from previous methods. In some embodiments, methods described herein utilize an RNA aptamer sequence that can effectively abrogate the degradation function of the peptide degron once they are bound. This is also different from previous methods. Methods described herein enable fluorescent proteins and other proteins to carry out their native function only when they are bound to a specific RNA sequence. In the case of enhanced yellow fluorescent protein (EYFP), a 38 fold fluorescent enhancement was observed when bound to the engineered RNA aptamer described herein.

BRIEF DESCRIPTION OF THE DRAWINGS

FIG. 1A is a schematic drawing of a Pepper RNA-regulated protein destabilization domain, tDeg. tDeg is a bifunctional peptide that includes the Tat peptide, which is capable of binding to the Pepper RNA aptamer, and the previously described C-terminal Arg-Arg-Arg-Gly degron (Bonger et al., "Small-Molecule Displacement of a Cryptic Degron Causes Conditional Protein Degradation," *Nat. Chem. Biol.* 7:531-7 (2011), which is hereby incorporated by reference in its entirety). When fused to a protein of interest, tDeg causes protein degradation. However, the protein destabilization function of tDeg is impeded when it binds to the Pepper RNA aptamer. Amino acids Arg-Gly, highlighted in a black box, are appended to the C-terminus of Tat to make the full Arg-Arg-Arg-Gly degron. FIG. 1B demonstrates that Pepper RNA stabilizes EYFP fused to tDeg in cells. To test whether tDeg functions as an RNA-regulated destabilization domain, EYFP-tDeg was coexpressed with different circular RNAs, and the yellow fluorescence in HEK293T cells was imaged. Without circular wild-type TAR RNA or its variants, cells coexpressing EYFP-tDeg and the circular control RNA only showed minimal fluorescence above background fluorescence. Cells exhibit yellow fluorescence only when circular wild-type TAR RNA, TAR Variant-1, or TAR Vairnat-2 (named Pepper) was coexpressed. Notably, higher yellow fluorescence signals were observed in the cytosol compared to the nucleus when EYFP-tDeg was coexpressed with the circular wild-type TAR RNA or its variants. This is consistent with the cytosolic expression of small circular RNAs using the Tornado expression system (Litke & Jaffrey, "Highly Efficient Expression of Circular RNA Aptamers in Cells Using Autocatalytic Transcripts," *Nat. Biotechnol.* 37:667-675 (2019), which is hereby incorporated by reference in its entirety). All cells were stained with Hoechst dye. Scale bar, 40 μm. FIG. 1C shows the summary data of normalized fluorescence of untransfected HEK293T cells, or HEK293T cells expressing EYFP or EYFP-tDeg with different RNAs as in (FIG. 1B). Total cellular yellow fluorescence of individual cells is plotted (n=4 independent cell cultures). Values are means±s.d. **$P_{circular\ wild-type\ TAR}=7.9\times10^{-113}$; $P_{circular\ TAR\ Variant-1}=2.1\times10^{-117}$; **$P_{circular\ TAR\ Variant-2}=1.7\times10^{-115}$ by one-way ANOVA.

In FIG. 1B, it was shown that tDeg confers protein instability to EYFP. However, the lack of yellow fluorescence of EYFP-tDeg in FIG. 1B could be due to protein misfolding or aggregation. In FIG. 3A, whether the lack of yellow fluorescence of EYFP-tDeg is due to proteasomal degradation was examined. In these experiments, HEK293T cells were transiently transfected with a plasmid expressing EYFP-tDeg. These cells were then treated with vehicle (DMSO) or a proteasome inhibitor (10 µM MG132) for 7 hours, respectively. When treated with vehicle (DMSO), minimal yellow fluorescence was detected. This result is consistent with the result from FIG. 1B. However, when proteasome activity was inhibited by treatment of 10 µM MG132 for 7 hours, the yellow fluorescence of EYFP-tDeg was restored. Thus, this confirmed that the tDeg tag markedly reduces the stability of EYFP by inducing its proteasomal degradation. All cells were stained with Hoechst dye. Scale bar, 40 µm. In FIG. 3B, normalized total cellular yellow fluorescence of individual cells is plotted (n=3 independent cell cultures). Values are means±s.d. ****P=$5.6 \times 10^{-36}$ by unpaired two-tailed Student's t-test.

In FIGS. 1B and 1C, it was shown that circular wild-type TAR, Variant-1, and Variant-2 showed 24-fold, 36-fold, and 38-fold fluorescence increases, respectively. However, the improved efficiency in stabilizing EYFP-tDeg protein could be due to uneven expression levels of the EYFP-tDeg mRNA, or the uneven expression levels of the circular TAR RNA variants. Here, the relative expression of EYFP-tDeg mRNA (FIG. 4A) and the relative expression of circular TAR RNA variants (FIG. 4B) was compared. In these experiments, HEK293T cells were transiently transfected with a plasmid expressing EYFP-tDeg and the corresponding circular TAR RNA variant as shown in FIGS. 1B and 1C. Total RNA was extracted by TRIzol® extraction. EYFP-tDeg mRNA expression level was quantified using RT-qPCR. Each circular TAR RNA variant's expression level was quantified by running the extracted total RNA on a TBE-Urea gel followed by SYBR™ Gold nucleic acid gel staining. These results show that there is no significant expression difference in the EYFP-tDeg mRNA or the circular TAR RNA variants. Thus, this confirms that the engineered circular TAR RNA variants indeed show higher efficiency in stabilizing tDeg-tagged EYFP. Data were collected from two independent cell cultures. Values are means±s.d.

FIGS. 5A-5G demonstrate that tDeg can be regulated by the Pepper RNA aptamer in diverse mammalian cell types. In FIGS. 1A-1C, it was shown that EYFP-tDeg can be regulated by the Pepper RNA aptamer in HEK293T cells. Here, whether tDeg can be regulated by the Pepper RNA aptamer in various mammalian cell types was examined (FIG. 5A). In these experiments, U2OS cells (FIG. 5B, FIG. 5E), COS-7 cells (FIG. 5C, FIG. 5F), or HeLa cells (FIG. 5D, FIG. 5G) were transiently expressed EYFP-tDeg with and without the circular Pepper RNA aptamer, respectively. In each case, cells showed low or undetectable levels of yellow fluorescence without the circular Pepper RNA aptamer. The yellow fluorescence of EYFP-tDeg was only restored when the circular Pepper RNA aptamer was coexpressed. Thus, tDeg can be regulated by the Pepper RNA aptamer in diverse mammalian cell types. All cells were stained with Hoechst dye. Scale bar, 20 µm. Normalized total cellular fluorescence (FIGS. 5E, 5F, and 5G) of individual cells is plotted (n=3 independent cell cultures). Values are means±s.d. **$P_{U2OS}$=$5.7 \times 10^{-59}$; $P_{COS-7}$=$1.6 \times 10^{-46}$; **$P_{HeLa}$=$2.0 \times 10^{-139}$ by unpaired two-tailed Student's t-test.

FIGS. 6A-6G demonstrate that tDeg confers Pepper RNA-dependent regulation to diverse proteins. To test whether Pepper RNA stabilizes different proteins fused to tDeg, HEK293T cells expressing mNeonGreen (FIG. 6B, FIG. 6E), mCherry (FIG. 6C, FIG. 6F), and the luciferase NanoLuc (FIG. 6D, FIG. 6G) fused to a C-terminal tDeg tag with and without circular Pepper RNA (FIG. 6A) were imaged, respectively. In each case, there was a considerable increase of fluorescence (FIG. 6E, FIG. 6F) or bioluminescence (FIG. 6G) of the tDeg-tagged protein only when circular Pepper RNA was coexpressed in cells. For detecting bioluminescence, cells were incubated in media with furimazine (from Promega Nano-Glo® Luciferase Assay System, diluted 100×) and imaged using a 460±25 nm emission filter cube. All cells were stained with Hoechst dye. Scale bar, 40 µm. Normalized total cellular fluorescence (FIG. 6E and FIG. 6F) or bioluminescence (FIG. 6G) of individual cells is plotted (n=3 independent cell cultures). Values are means±s.d. **$P_{mNeonGreen-tDeg}$=$1.1 \times 10^{-123}$; $P_{mCherry-tDeg}$=$3.0 \times 10^{-131}$; **$P_{NanoLuc-tDeg}$=$1.7 \times 10^{-120}$ by unpaired two-tailed Student's t-test.

FIGS. 7A-7G demonstrate that tDeg confers Pepper RNA-dependent regulation to diverse proteins. In FIGS. 6A-6G, it was shown that tDeg confers Pepper RNA-dependent regulation of different fluorescent proteins and the luciferase, NanoLuc (Hall et al., "Engineered Luciferase Reporter from a Deep Sea Shrimp Utilizing a Novel Imidazopyrazinone Substrate," *ACS Chem. Biol.* 7:1848-57 (2012), which is hereby incorporated in its entirety). Whether tDeg confers Pepper-dependent regulation to proteins with different functions and localizations in cells was tested here (FIG. 7A). In these experiments, HEK293T cells transiently expressed EGFP-TetR-tDeg (FIG. 7B, FIG. 7E), EGFP-EZH2-tDeg (FIG. 7C, FIG. 7F), or mCherry-NF-κB-tDeg (FIG. 7D, FIG. 7G), with and without the circular Pepper RNA aptamer, respectively. In each case, proteins were nearly undetectable unless coexpressed with the circular Pepper RNA. Furthermore, protein localization of these proteins without tDeg and the circular Pepper RNA was compared to their stabilized counterparts by tDeg and circular Pepper RNA. It was observed that EGFP-TetR-tDeg with circular Pepper RNA showed more green fluorescent signals in the cytosol compared to EGFP-TetR. Significant change of protein localization in the case of EGFP-EZH2-tDeg or mCherry-NF-κB-tDeg with the circular Pepper RNA was not observed. It was concluded that tDeg is a versatile tag for RNA-dependent protein stabilization. All cells were stained with Hoechst dye. Scale bar, 40 µm. Normalized total cellular fluorescence (FIGS. 7E, 7F, and 7G) of individual cells is plotted (n=3 independent cell cultures). Values are means±s.d. **$P_{EGFP-TetR4Deg}$=$2.9 \times 10^{-136}$; $P_{EGFP-EZH2-tDeg}$$1.1 \times 10^{-120}$; **$P_{mCherry-NF-\kappa B-tDeg}$=$3.5 \times 10^{-119}$ by unpaired two-tailed Student's t-test.

FIGS. 9A-9D show the design of Pepper tags for imaging mRNA. Design and sequences of four Pepper tags used in FIG. 8B: (Pepper)$_{10}$ (FIG. 9A; SEQ ID NO: 119), (F30-1× Pepper)$_{10}$ (FIG. 9B; SEQ ID NO: 120), (Pepper)$_{20}$ (FIG. 9C; SEQ ID NO: 121), and (F30-1×Pepper)$_{10}$ (FIG. 9D; SEQ ID NO: 122).

In FIG. 8B, it was observed that (F30-2×Pepper)$_{10}$ is the optimal tag for imaging mRNAs in live cells. To further optimize the system of using Pepper RNA-regulated fluorogenic protein to image mRNAs, it was determined whether increasing the number of fluorescent mNeonGreen could increase the fluorescence signal to background noise ratio of the mobile green fluorescent puncta. In these experiments, an mCherry mRNA reporter tagged with (F30-2×Pepper)$_{10}$ and tandem fluorescent mNeonGreen with 2, 3, or 4 copies were transiently expressed, respectively, in cells. Here, an increase of fluorescence intensity of the green fluorescent puncta as the number of tandem mNeonGreen increased from 2, 3, to 4 copies, respectively (FIG. 10B) and (FIG. 10C) was observed. mRNAs tagged with (F30-1×Pepper)$_{10}$ using the (mNeonGreen)$_4$-tDeg fluorescent fusion protein were also re-tested. It was shown that puncta were detectable, but not as pronounced as when the (F30-2×Pepper)$_{10}$ tag was used. Thus, it was concluded that (mNeonGreen)$_4$-tDeg provides a high signal to noise ratio for imaging mRNAs. Scale bar, 20 µm. FIG. 10C is a graph showing the fluorescence intensity of green fluorescent puncta of individual cells is plotted (n=3 independent cell cultures). Values are means±s.d. **$P_{(Pepper)20:(F30-2\times Pepper)10}$=4.6×10$^{19}$; $P_{(mNeonGreen)2\text{-}tDeg:(mNeonGreen)3\text{-}tDeg}$=7.7×10$^{-9}$; $P_{(mNeonGreen)2\text{-}tDeg:(mNeonGreen)4\text{-}tDeg}$=2.5×10$^{-29}$; $P_{(mNeonGreen)3\text{-}tDeg:(mNeonGreen)4\text{-}tDeg}$=2.0×10$^{-9}$; **$P_{(F30-2\times Pepper)10:(F30-1\times Pepper)10}$=5.6×10$^{-17}$ by one-way ANOVA.

FIG. 11A is a schematic representation of the DNA plasmid constructs used for imaging mRNAs in the nucleus and cytosol. To image nascent transcription of mRNA, cells coexpressing an mCherry mRNA reporter containing a 3'UTR green Pepper mRNA tag, (F30-2×Pepper)$_{10}$, and a green fluorescent fusion protein, (mNeonGreen)$_4$-tDeg were imaged (FIG. 11B). Cytosolic green fluorescent puncta reflecting mCherry mRNA transcripts and nuclear green fluorescent puncta, potentially reflecting mCherry mRNA transcripts were observed. Less green fluorescent puncta in the nucleus were observed as compared to the cytosol. This potentially reflects that most of the nuclear mCherry mRNA transcripts were exported out of the nucleus. Scale bar, 20 µm. FIG. 11C is a graph providing summary data of cytosolic and nuclear mRNA fluorescence intensity in FIG. 11B (n=201 fluorescent puncta). Values are means±s.d. This experiment was performed three times with similar results.

FIGS. 12A-12D demonstrate that Pepper tag and fluorescent fusion protein enable visualization of individual mRNAs. To examine whether the puncta observed when imaging Pepper-tagged mRNAs might be stable degradation intermediates, northern blot was performed on total RNA extracted from cells expressing (F30-2×Pepper)$_{10}$-tagged mCherry RNA transcripts with and without coexpressing the fluorescent fusion protein, (mNeonGreen)$_4$-tDeg. In these experiments, only full-length mRNA transcript was detected (FIG. 12A). Therefore, it was concluded that the fluorescent puncta in cells largely reflects the full-length transcript, and that degraded or liberated Pepper aptamers do not accumulate in cells. To assess whether the mobile green fluorescent puncta seen in cells expressing Pepper-tagged mRNAs represent single mRNAs, a previously described mRNA imaging method in which the resulting puncta were validated to represent single mRNA was used (Yan et al., "Dynamics of Translation of Single mRNA Molecules In Vivo," Cell 165:976-89 (2016), which is hereby incorporated by reference in its entirety). This system uses 24 PP7 RNA hairpins in the 3'UTR of a reporter mRNA, and a 3×mCherry-CAAX protein fused to PCP (PP7 coat protein), the PP7-binding protein. The PCP-3×mCherry-CAAX fusion protein is anchored to the membrane via the CAAX sequence, which reduces puncta motility and facilitates quantitative fluorescence measurements. A PP7-containing reporter mRNA was imaged with and without the (F30-2×Pepper)$_{10}$ tag (FIG. 12B). The (mNeonGreen)$_4$-tDeg fluorescent fusion protein was used to image the Pepper-tagged mRNAs. If the Pepper tag or the green fluorescent fusion protein caused mRNA to aggregate, the Pepper-tagged reporter mRNA puncta would have been expected to have higher red fluorescence (from PCP-3×mCherry-CAAX) compared to the reporter mRNA puncta without the Pepper tag. The results of these experiments showed that the red fluorescence intensity distribution of the reporter mRNA is not significantly different with and without the Pepper tag (FIG. 12C) (Black bars, 19 cells, 485 mRNAs; Shaded bars, 13 cells, 384 mRNAs). This suggests that the Pepper tag and the green fluorescent fusion protein do not cause mRNA aggregation. Furthermore, colocalization between the green and magenta fluorescent puncta was observed only when the reporter mRNA contained the Pepper tag (FIG. 12D). These results suggest that the green fluorescent puncta observed using the Pepper tag and green fluorescent fusion protein are indeed individual mRNAs. Scale bar, 5 µm (left panel in FIG. 12D), 1 µm (right panel in FIG. 12D). In FIG. 12D, the experiment of reporter mRNA with Pepper was performed three times with similar results, the experiment of reporter mRNA without Pepper was performed twice with similar results.

FIG. 13E shows western blotting results using an anti-ubiquitin antibody of untransfected cells and cells expressing (mNeonGreen)$_4$-tDeg. Significant difference in the ubiquitinated proteins were not observed. As a control, untransfected cells treated with a proteasome inhibitor (10 μM MG132) for 5 hours showed a significant increase of the ubiquitinated proteins (FIG. 13E). Thus, these results suggest that expression of fluorescent RNA-regulated fusion proteins does not overload proteasome activity in cells. Data shown here is a representative image from 2 independent cell cultures.

FIGS. 15A-15C demonstrate the imaging of green Pepper-tagged β-actin mRNA in live cells. FIG. 15A shows DNA plasmid constructs used for imaging β-actin mRNA in live cells. To image β-actin mRNA localization in response to arsenite stress, a β-actin mRNA reporter containing a 3'UTR green Pepper mRNA tag, (F30-2×Pepper)$_{10}$ was constructed (FIG. 15B). Cells coexpressing this β-actin mRNA reporter and a green fluorescent RNA-regulated fusion protein, (mNeonGreen)$_4$-tDeg were imaged before and 45 minutes after arsenite (500 μM) treatment to induce stress granules. Individual mRNA transcripts were observed to rapidly accumulated to form stress granules as evidenced by coexpression of tetramethylrhodamine-labeled HaloTag-G3BP1 to label stress granules. Scale bar, 20 μm. FIG. 15C shows the fluorescence ratio of foci/cytosol in untreated cells vs. arsenite treated cells is plotted (n=3 independent cell cultures). Values are means±s.d. ****P=2.5×10$^{-31}$ by unpaired two-tailed Student's t-test.

In FIGS. 15A-15C, cytosolic green fluorescent puncta were shown to accumulate in stress granules to form foci upon application of 500 μM arsenite. However, the formation of green fluorescent foci in stress granules could be due to aggregation of the fluorescent RNA-regulated fusion protein, (mNeonGreen)$_4$-tDeg, regardless of the present of the β-actin mRNA. To test whether this is the case, (mNeonGreen)$_4$-tDeg was coexpressed with circular Pepper RNA in U2OS cells (FIG. 16A). Before arsenite treatment, cytosolic green fluorescent was observed without any puncta, which is consistent with the results in FIGS. 5A-5G. Upon application of 500 μM arsenite, green fluorescent foci formation was not observed (FIG. 15B). These results confirmed that the formation of green fluorescent foci in FIGS. 15A-15C were indeed due to the β-actin mRNA. This experiment was performed twice with similar results. Scale bar, 20 μm.

FIG. 18C is a schematic showing that a selectively activated biotin ligase (TurboID-tDeg) specifically biotinylates an RNA-binding protein (CELF1) that bind to the RNA sequence of interest (EDEN15). FIG. 18D shows that TurboID-tDeg enables selective biotinylation of CELF1, while minimizing nonspecific biotinylation of proteins that do not bind to the RNA of interest (EDEN15).

DETAILED DESCRIPTION

Figure 1A:
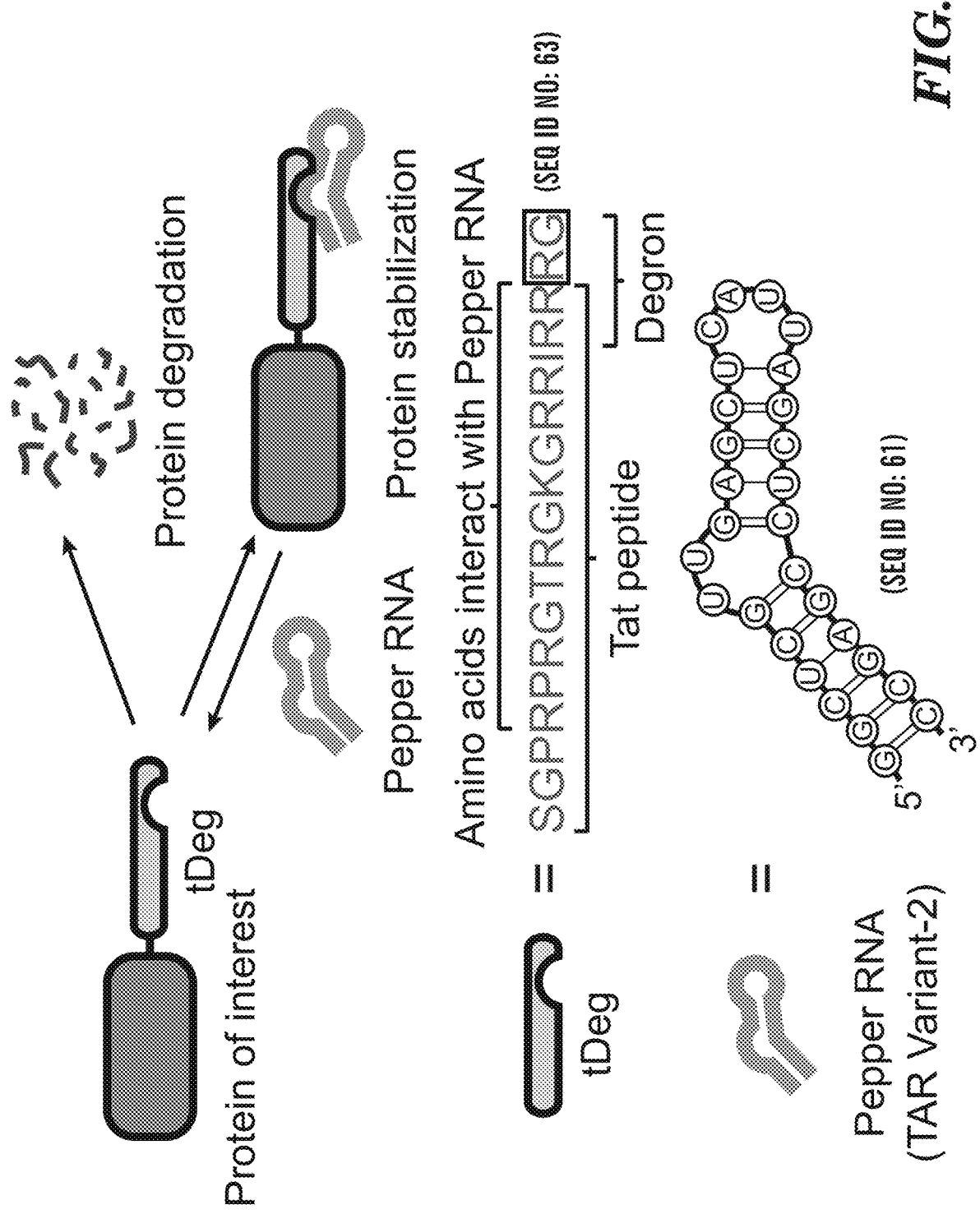
FIGS. 1A-1C show the design and optimization of an RNA-regulated protein destabilization domain.

A first aspect of the disclosure relates to a nucleic acid molecule encoding an RNA-regulated fusion protein. The nucleic acid molecule includes: a first nucleic acid sequence encoding a protein of interest and a second nucleic acid sequence encoding an RNA-regulated destabilization domain, where the second nucleic acid sequence is operably coupled to the first nucleic acid sequence.

The terms protein and polypeptide are generally used interchangeably and refer to a single polypeptide chain. It will be appreciated that such polypeptide chains may bind to other polypeptides or proteins, or other molecules such as cofactors. The terms protein and polypeptide also refer to variants, mutants, biologically active fragments, modifications, analogs and/or derivatives of the polypeptides described herein. The term fusion protein refers to a protein that is comprised of two or more amino acid sequences, from two or more proteins or polypeptide sequences that are not found linked in nature and that are physically linked by a peptide bond.

A protein of interest refers to a protein/polypeptide that is desired and/or being assessed. In other words, a protein of interest may be any protein. In some embodiments, the protein of interest is a protein that is the subject of research. In some embodiments, the protein of interest is known to be involved in a disease state, and is specifically targeted in treatment of the disease state.

In some embodiments, the protein of interest is a fluorescent protein, a bioluminescent protein, an enzyme, or a transcriptional regulator.

In some embodiments, the protein of interest is a florescent protein. As used herein, the term "fluorescent protein" refers to a protein or polypeptide which fluoresces, or emits light, when excited with appropriate electromagnetic radiation.

Suitable fluorescent proteins include, without limitation, Green Fluorescent Protein, Enhanced Green Fluorescent Protein (EGFP), Enhanced Yellow Fluorescent Protein (EYFP), Venus, mVenus, Citrine, mCitrine, Cerulean, mCerulean, Orange Fluorescent Protein (OFP), mNeonGreen, moxNeonGreen, mCherry, mTagBFP, Venus, mVenus, mTurquoise, mScarlet, mWasabi, mOrange, and dTomato. Suitable fluorescent protein amino acid sequences are shown in Table 1 below.

TABLE 1

Exemplary Fluorescent Protein Amino Acid Sequences

| Fluorescent Protein | Amino Acid Sequence | SEQ ID NO: |
|---|---|---|
| Green Fluorescent Protein (GFP) | MSKGEELFTGVVPILVELDGDVNGHKFSVSGEGEGDATYGKLTLKFI CTIGKLPVPWPTLVITFSYGVQCFSRYPDHMKQHDFFKSAMPEGYVQ ERTIFFKDDGNYKTRAEVKFEGDTLVNRIELKGIDFKEDGNILGHKL EYNYNSHNVYIMADKQKNGIKVNFKIRHNIEDGSVQLADHYQQNTPI GDGPVLLPDNHYLSTQSALSKDPNEKRDHMVLLEFVTAAGITHGMDE LYK | 1 |
| Enhanced Green Fluorescent Protein (EGFP) | MVSKGEELFTGVVPILVELDGDVNGHKFSVSGEGEGDATYGKLTLKF ICTIGKLPVPWPTLVTILTYGVQCFSRYPDHMKQHDFFKSAMPEGYV QERTIFFKDDGNYKTRAEVKFEGDTLVNRIELKGIDFKEDGNILGHK LEYNYNSHNVYIMADKQKNGIKVNFKIRHNIEDGSVQLADHYQQNTP IGDGPVLLPDNHYLSTQSALSKDPNEKRDHMVLLEFVTAAGITLGMD ELYK | 2 |
| Enhanced Yellow Fluorescent Protein (EYFP) | MVSKGEELFTGVVPILVELDGDVNGHKFSVSGEGEGDATYGKLTLKF ICTIGKLPVPWPTLVTTFGYGLQCFARYPDHMKQHDFFKSAMPEGYV QERTIFFKDDGNYKTRAEVKFEGDTLVNRIELKGIDFKEDGNILGHK LEYNYNSHNVYIMADKQKNGIKVNFKIRHNIEDGSVQLADHYQQNTP IGDGPVLLPDNHYLSYQSALSKDPNEKRDHMVLLEFVTAAGITLGMD ELYK | 3 |
| Venus | MVSKGEELFTGVVPILVELDGDVNGHKFSVSGEGEGDATYGKLTLKL ICTIGKLPVPWPTLVTTLGYGLQCFARYPDHMKQHDFFKSAMPEGYV QERTIFFKDDGNYKTRAEVKFEGDTLVNRIELKGIDFKEDGNILGHK LEYNYNSHNVYITADKQKNGIKANFKIRHNIEDGSVQLADHYQQNTP IGDGPVLLPDNHYLSYQSALSKDPNEKRDHMVLLEFVTAAGITLGMD ELYK | 4 |

TABLE 1-continued

Exemplary Fluorescent Protein Amino Acid Sequences

| Fluorescent Protein | Amino Acid Sequence | SEQ ID NO: |
|---|---|---|
| mVenus | MVSKGEELFTGVVPILVELDGDVNGHKFSVSGEGEGDATYGKLTLKL ICTIGKLPVPWPTLVTTLGYGLQCFARYPDHMKQHDFFKSAMPEGYV QERTIFFKDDGNYKTRAEVKFEGDTLVNRIELKGIDFKEDGNILGHK LEYNYNSHNVYITADKQKNGIKANFKIRHNIEDGGVQLADHYQQNTP IGDGPVLLPDNHYLSYQSKLSKDPNEKRDHMVLLEFVTAAGITLGMD ELYK | 5 |
| Citrine | MVSKGEELFTGVVPILVELDGDVNGHKFSVSGEGEGDATYGKLTLKF ICTIGKLPVPWPTLVTTFGYGLMCFARYPDHMKQHDFFKSAMPEGYV QERTIFFKDDGNYKTRAEVKFEGDTLVNRIELKGIDFKEDGNILGHK LEYNYNSHNVYIMADKQKNGIKVNFKIRHNIEDGSVQLADHYQQNTP IGDGPVLLPDNHYLSYQSALSKDPNEKRDHMVLLEFVTAAGITLGMD ELYK | 6 |
| mCitrine | MVSKGEELFTGVVPILVELDGDVNGHKFSVSGEGEGDATYGKLTLKF ICTIGKLPVPWPTLVITFGYGLMCFARYPDHMKQHDFFKSAMPEGYV QERTIFFKDDGNYKTRAEVKFEGDTLVNRIELKGIDFKEDGNILGHK LEYNYNSHNVYIMADKQKNGIKVNFKIRHNIEDGSVQLADHYQQNTP IGDGPVLLPDNHYLSYQSKLSKDPNEKRDHMVLLEFVTAAGITLGMD ELYK | 7 |
| Cerulean | MVSKGEELFTGVVPILVELDGDVNGHKFSVSGEGEGDATYGKLTLKF ICTIGKLPVPWPTLVTILTWGVQCFARYPDHMKQHDFFKSAMPEGYV QERTIFFKDDGNYKTRAEVKFEGDTLVNRIELKGIDFKEDGNILGHK LEYNAISDNVYITADKQKNGIKANFKIRHNIEDGSVQLADHYQQNTP IGDGPVLLPDNHYLSTQSALSKDPNEKRDHMVLLEFVTAAGITLGMD ELYK | 8 |
| mCerulean | MVSKGEELFTGVVPILVELDGDVNGHKFSVSGEGEGDATYGKLTLKF ICTIGKLPVPWPTLVTILTWGVQCFARYPDHMKQHDFFKSAMPEGYV QERTIFFKDDGNYKTRAEVKFEGDTLVNRIELKGIDFKEDGNILGHK LEYNAISDNVYITADKQKNGIKANFKIRHNIEDGSVQLADHYQQNTP IGDGPVLLPDNHYLSTQSKLSKDPNEKRDHMVLLEFVTAAGITLGMD ELYK | 9 |
| Orange Fluorescent Protein (OFP) | MNLSKNVSVSVYMKGNVNNHEFEYDGEGGGDPYTGKYSMKMTLRGQN CLPFSYDIITTAFQYGFRVFTKYPEGIVDYFKDSLPDAFQWNRRIVF EDGGVLNMSSDITYKDNVLHGDVWAVGVNFPPNGPVMKNEIVMEEPT EETFTPKNGVLVGFCPKAYLLKDGSYYYGNMTTFYRSKKSGQAPPGY HFVKHRLVKINVGHGFKTVEQTEYATAHVSDLPK | 10 |
| mNeon Green | MVSKGEEDNMASLPATHELHIFGSINGVDFDMVGQGTGNPNDGYEEL NLKSTKGDLQFSPWILVPHIGYGFHQYLPYPDGMSPFQAAMVDGSGY QVHRTMQFEDGASLTVNYRYTYEGSHIKGEAQVKGTGFPADGPVMTN SLTAADWCRSKKTYPNDKTIISTFKWSYTTGNGKRYRSTARTTYTFA KPMAANYLKNQPMYVFRKTELKHSKTELNFKEWQKAFTDVMGMDELY K | 11 |
| moxNeon Green | MVSKGEEDNMASLPATHELHIFGSINGVDFDMVGQGTGNPNDGYEEL NLKSTKGDLQFSPWILVPHIGYGFHQYLPYPDGMSPFQAAMVDGSGY QVHRTMQFEDGASLTVNYRYTYEGSHIKGEAQVKGTGFPADGPVMTN SLTAADWSRSKKTYPNDKTIISTFKWSYTTGNGKRYRSTARTTYTFA KPMAANYLKNQPMYVFRKTELKHSKTELNFKEWQKAFTDVMGMDELY K | 12 |
| mCherry | MVSKGEEDNMAIIKEFMRFKVHMEGSVNGHEFEIEGEGEGRPYEGTQ TAKLKVTKGGPLPFAWDILSPQFMYGSKAYVKHPADIPDYLKLSFPE GFKWERVMNFEDGGVVTVTQDSSLQDGEFIYKVKLRGTNFPSDGPVM QKKTMGWEASSERMYPEDGALKGEIKQRLKLKDGGHYDAEVKTTYKA KKPVQLPGAYNVNIKLDITSHNEDYTIVEQYERAEGRHSTGGMDELY K (GenBank Accession No. QEM23462.1, which is hereby incorporated by reference in its entirety) | 13 |
| mTagBFP | MVSKGEELIKENMHMKLYMEGTVDNHHFKCTSEGEGKPYEGTQTMRI KVVEGGPLPFAFDILATSFLYGSKTFINHTQGIPDFFKQSFPEGFTW ERVTTYEDGGVLTATQDTSLQDGCLIYNVKIRGVNFTSNGPVMQKKT LGWEAFTETLYPADGGLEGRNDMALKLVGGSHLIANAKTTYRSKKPA KNLKMPGVYYVDYRLERIKEANNETYVEQHEVAVARYCDLPSKLGHK LN | 14 |
| Venus | MVSKGEELFTGVVPILVELDGDVNGHKFSVSGEGEGDATYGKLTLKL ICTIGKLPVPWPTLVTTLGYGLQCFARYPDHMKQHDFFKSAMPEGYV QERTIFFKDDGNYKTRAEVKFEGDTLVNRIELKGIDFKEDGNILGHK LEYNYNSHNVYITADKQKNGIKANFKIRHNIEDGGVQLADHYQQNTP | 15 |

TABLE 1-continued

Exemplary Fluorescent Protein Amino Acid Sequences

| Fluorescent Protein | Amino Acid Sequence | SEQ ID NO: |
|---|---|---|
| | IGDGPVLLPDNHYLSYQSALSKDPNEKRDHMVLLEFVTAAGITLGMD ELYK | |
| mVenus | MVSKGEELFTGVVPILVELDGDVNGHKFSVSGEGEGDATYGKLTLKL ICTIGKLPVPWPTLVTTLGYGLQCFARYPDHMKQHDFFKSAMPEGYV QERTIFFKDDGNYKTRAEVKFEGDTLVNRIELKGIDFKEDGNILGHK LEYNYNSHNVYITADKQKNGIKANFKIRHNIEDGGVQLADHYQQNTP IGDGPVLLPDNHYLSYQSKLSKDPNEKRDHMVLLEFVTAAGITLGMD ELYK | 16 |
| mTurquoise | MVSKGEELFTGVVPILVELDGDVNGHKFsysGEGEGDATyGKLTLKF ICTIGKLPVPWPTLVTILSWGVQCFARYPDHMKQHDFFKSAMPEGYV QERTIFFKDDGNYKTRAEVKFEGDTLVNRIELKGIDFKEDGNILGHK LEYNYISDNVYITADKQKNGIKANFKIRHNIEDGGVQLADHYQQNTP IGDGPVLLPDNHYLSTQSKLSKDPNEKRDHMVLLEFVTAAGITLGMD ELYK | 17 |
| mScarlet | MVSKGEAVIKEFMRFKVHMEGSMNGHEFEIEGEGEGRPYEGTQTAKL KVIKGGPLPFSWDILSPQFMYGSRAFTKHPADIPDYYKQSFPEGFKW ERVMNFEDGAVIVTQDTSLEDGTLIYKVKLRGINFPPDGPVMQKKT MGWEASTERLYPEDGVLKGDIKMALRLKDGGRYLADFKITYKAKKPV QMPGAYNVDRKLDITSHNEDYTVVEQYERSEGRHSTGGMDELYK | 18 |
| mWasabi | MVSKGEETTMGVIKPDMKIKLKMEGNVNGHAFVIEGEGEGKPYDGTN TINLEVKEGAPLPFSYDILTTAFSYGNRAFTKYPDDIPNYFKQSFPE GYSWERTMTFEDKGIVKVKSDISMEEDSFIYEIHLKGENFPPNGPVM QKETTGWDASTERMYVRDGVLKGDVKMKLLLEGGGHHRVDFKTIYRA KKAVKLPDYHFVDHRIEILNHDKDYNKVIVYETAVARNSTDGMDELY K | 19 |
| mOrange | MVSKGEENNMAIIKEFMRFKVRMEGSVNGHEFEIEGEGEGRPYEGFQ TAKLKVTKGGPLPFAWDILSPQFTYGSKAYVKHPADIPDYFKLSFPE GFKWERVMNFEDGGVVIVTQDSSLQDGEFIYKVKLRGINFPSDGPVM QKKTMGWEASSERMYPEDGALKGEIKMRLKLKDGGHYTSEVKITYKA KKPVQLPGAYIVGIKLDITSHNEDYTIVEQYERAEGRHSTGGMDELY K | 20 |
| dTomato | MVSKGEEVIKEFMRFKVRMEGSMNGHEFEIEGEGEGRPYEGTQTAKL KVTKGGPLPFAWDILSPQFMYGSKAYVKHPADIPDYKKLSFPEGFKW ERVMNFEDGGLVTVTQDSSLQDGTLIYKVKMRGINFPPDGPVMQKKT MGWEASTERLYPRDGVLKGEIHQALKLKDGGHYLVEFKTIYMAKKPV QLPGYYYVDTKLDITSHNEDYTIVEQYERSEGRHHLFLYGMDELYK | 21 |

In other embodiments, the protein of interest is a bioluminescent protein. As used herein, the term "bioluminescent protein" refers to any protein capable of acting on a suitable substrate and producing luminescence. As used herein, the term "substrate" refers to any molecule capable of producing or absorbing luminescence with a bioluminescent protein.

Suitable bioluminescent proteins include, without limitation, luciferase, β-galactosidase, β-lactamase, peroxidase, alkaline phosphatase, β-glucuronidase, and β-glucosidase. Exemplary bioluminescent amino acid sequences are shown in Table 2 below.

TABLE 2

Exemplary Bioluminescent Protein Amino Acid Sequences

| Bioluminescent Protein | Amino Acid Sequence | SEQ ID NO: |
|---|---|---|
| Nanoluc luciferase (Nluc) | MVFTLEDFVGDWRQTAGYNLDQVLEQGGVSSLFQNLGVSVTP IQRIVLSGENGLKIDIHVIIPYEGLSGDQMGQIEKIFKVVYP VDDHHFKVILHYGTLVIDGVTPNMIDYFGRPYEGIAVFDGKK ITVTGTLWNGNKIIDERLINPDGSLLFRVTINGVTGWRLCER ILA (GenBank Accession No. AFI79290.1, which is hereby incorporated by reference in its entirety) | 22 |
| Firefly luciferase | MEDAKNIKKGPAPFYPLEDGTAGEQLHKAMKRYALVPGTIAF TDAHIEVNITYAEYFEMSVRLAEAMKRYGLNTNHRIVVCSEN SLQFFMPVLGALFIGVAVAPANDIYNERELLNSMNISQPTVV FVSKKGLQKILNVQKKLPIIQKIIIMDSKTDYQGFQSMYTFV TSHLPPGFNEYDFVPESFDRDKTIALIMNSSGSTGLPKGVAL PHRTACVRFSHARDPIFGNQIIPDTAILSVVPFHHGFGMFTT | 23 |

TABLE 2-continued

Exemplary Bioluminescent Protein Amino Acid Sequences

| Bioluminescent Protein | Amino Acid Sequence | SEQ ID NO: |
|---|---|---|
| | LGYLICGFRVVLMYRFEEELFLRSLQDYKIQSALLVPTLFSF<br>FAKSTLIDKYDLSNLHEIASGGAPLSKEVGEAVAKRFHLPGI<br>RQGYGLTETTSAILITPEGDDKPGAVGKVVPFFEAKVVDLDT<br>GKTLGVNQRGELCVRGPMIMSGYVNNPEATNALIDKDGWLHS<br>GDIAYWDEDEHFFIVDRLKSLIKYKGYQVAPAELESILLQHP<br>NIFDAGVAGLPDDDAGELPAAVVVLEHGKTMTEKEIVDYVAS<br>QVTTAKKLRGGVVFVDEVPKGLTGKLDARKIREILIKAKKGG<br>KSKL<br>(GenBank Accession No. CAB91857.1, which is hereby incorporated by reference in its entirety) | |
| Renilla luciferase (Rluc) | MASKVYDPEQRKRMITGPQWWARCKQMNVLDSFINYYDSEKH<br>AENAVIFLHGNAASSYLWRHVVPHIEPVARCIIPDLIGMGKS<br>GKSGNGSYRLLDHYKYLTAWFELLNLPKKIIFVGHDWGACLA<br>FHYSYEHQDKIKAIVHAESVVDVIESWDEWPDIEEDIALIKS<br>EEGEKMVLENNFFVETMLPSKIMRKLEPEEFAAYLEPFKEKG<br>EVRRPTLSWPREIPLVKGGKPDVVQIVRNYNAYLRASDDLPK<br>MFIESDPGFFSNAIVEGAKKFPNTEFVKVKGLHFSQEDAPDE<br>MGKYIKSFVERVLKNEQ<br>(GenBank Accession No. ABA41680.1, which is hereby incorporated by reference in its entirety) | 24 |
| Gaussia luciferase | MGVKVLFALICIAVAEAKPTENNEDFNIVAVASNFATTDLDA<br>DRGKLPGKKLPLEVLKEMEANARKAGCTRGCLICLSHIKCTP<br>KMKKFIPGRCHTYEGDKESAQGGIGEAIVDIPEIPGFKDLEP<br>MEQFIAQVDLCVDCTTGCLKGLANVQCSDLLKKWLPQRCATF<br>ASKIQGQVDKIKGAGGD<br>(GenBank Accession No. BAR71165.1, which is hereby incorporated by reference in its entirety) | 25 |
| β-galactosidase | VVLQRRDWENPGVTQLNRLAAHPPFASWRNSEEARTDRPSQQ<br>LRSLNGEWRFAWFPAPEAVPESWLECDLPEADTVVVPSNWQM<br>HGYDAPIYTNVTYPITVNPPFVPTENPTGCYSLTFNVDESWL<br>QEGQTRIIFDGVNSAFHLWCNGRWVGYGQDSRLPSEFDLSAF<br>LRAGENRLAVMVLRWSDGSYLEDQDMWRMSGIFRDVSLLHKP<br>TTQISDFHVATRFNDDFSRAVLEAEVQMCGELRDYLRVTVSL<br>WQGETQVASGTAPFGGEIIDERGGYADRVTLRLNVENPKLWS<br>AEIPNLYRAVVELHTADGTLIEAEACDVGFREVRIENGLLLL<br>NGKPLLIRGVNRHEHHPLHGQVMDEQTMVQDILLMKQNNFNA<br>VRCSHYPNHPLWYTLCDRYGLYVVDEANIETHGMVPMNRLTD<br>DPRWLPAMSERVTRMVQRDRNHPSVIIWSLGNESGHGANHDA<br>LYRWIKSVDPSRPVQYEGGGADTTATDIICPMYARVDEDQPF<br>PAVPKWSIKKWLSLPGETRPLILCEYAHAMGNSLGGFAKYWQ<br>AFRQYPRLQGGFVWDWVDQSLIKYDENGNPWSAYGGDFGDTP<br>NDRQFCMNGLVFADRTPHPALIEAKHQQQFFQFRLSGQTIEV<br>TSEYLFRHSDNELLHWMVALDGKPLASGEVPLDVAPQGKQLI<br>ELPELPQPESAGQLWLTVRVVQPNATAWSEAGHISAWQQWRL<br>AENLSVTLPAASHAIPHLTTSEMDFCIELGNKRWQFNRQSGF<br>LSQMWIGDKKQLLTPLRDQFTRAPLDNDIGVSEATRIDPNAW<br>VERWKAAGHYQAEAALLQCTADTLADAVLITTAHAWQHQGKT<br>LFISRKTYRIDGSGQMAITVDVEVASDTPHPARIGLNCQLAQ<br>VAERVNWLGLGPQENYPDRLTAACFDRWDLPLSDMYTPYVFP<br>SENGLRCGTRELNYGPHQWRGDFQFNISRYSQQQLMETSHRH<br>LLHAEEGTWLNIDGFHMGIGGDDSWSPSVSAEFQLSAGRYHY<br>QLVWCQK<br>(GenBank Accession No. CAB90353.1, which is hereby incorporated by reference in its entirety) | 26 |
| β-lactamase (HaloTag) | MSIQHFRVALIPFFAAFCLPVFAHPETLVKVKDAEDQLGARV<br>GYIELDLNSGKILESFRPEERFPMMSTFKVLLCGAVLSRIDA<br>GQEQLGRRIHYSQNDLVEYSPVTEKHLTDGMTVRELCSAAIT<br>MSDNTAANLLLTTIGGPKELTAFLHNMGDHVTRLDRWEPELN<br>EAIPNDERDTTMPVAMATTLRKLLTGELLTLASRQQLIDWME<br>ADKVAGPLLRSALPAGWFIADKSGAGERGSRGIIAALGPDGK<br>PSRIVVIYTTGSQATMDERNRQIAEIGASLIKHW<br>(GenBank Accession No. AEQ28652.1, which is hereby incorporated by reference in its entirety) | 27 |
| Ascorbate peroxidase 1, cytosolic (*Glycine max*) | MGKSYPTVSADYQKAVEKAKKKLRGFIAEKRCAPLMLRLAWH<br>SAGTFDKGTKTGGPFGTIKHPAELAHSANNGLDIAVRLLEPL<br>KAEFPILSYADFYQLAGVVAVEVTGGPEVPFHPGREDKPEPP<br>PEGRLPDATKGSDHLRDVFGKAMGLTDQDIVALSGGHTIGAA<br>HKERSGFEGPWTSNPLIFDNSYFTELLSGEKEGLLQLPSDKA<br>LLSDPVFRPLVDKYAADEDAFFADYAEAHQKLSELGFADA | 28 |

TABLE 2-continued

Exemplary Bioluminescent Protein Amino Acid Sequences

| Bioluminescent Protein | Amino Acid Sequence | SEQ ID NO: |
|---|---|---|
| | (GenBank Accession No. NP_001237785.1, which is hereby incorporated by reference in its entirety) | |
| Ascorbate peroxidase 1 (*Arabidopsis thaliana*) | MTKNYPTVSEDYKKAVEKCRRKLRGLIAEKNCAPIMVRLAWH SAGTFDCQSRTGGPFGTMRFDAEQAHGANSGIHIALRLLDPI REQFPTISFADFHQLAGVVAVEVTGGPDIPFHPGREDKPQPP PEGRLPDATKGCDHLRDVFAKQMGLSDKDIVALSGAHTLGRC HKDRSGFEGAWTSNPLIFDNSYFKELLSGEKEGLLQLVSDKA LLDDPVFRPLVEKYAADEDAFFADYAEAHMKLSELGFADA (GenBank Accession No. NP_172267.1, which is hereby incorporated by reference in its entirety) | 29 |
| Ascorbate peroxidase 2 (*Arabidopsis thaliana*) | MVKKSYPEVKEEYKKAVQRCKRKLRGLIAEKHCAPIVLRLAW HSAGTFDVKTKTGGPFGTIRHPQELAHDANNGLDIAVRLLDP IKELFPILSYADFYQLAGVVAVEITGGPEIPFHPGRLDKVEP PPEGRLPQATKGVDHLRDVFGRMGLNDKDIVALSGGHTLGRC HKERSGFEGAWTPNPLIFDNSYFKEILSGEKEGLLQLPTDKA LLDDPLFLPFVEKYAADEDAFFEDYTEAHLKLSELGFADKE (GenBank Accession No. AEE74792.1, which is hereby incorporated by reference in its entirety) | 30 |
| Ascorbate peroxidase (*Pisum sativum*) | MGKSYPTVSPDYQKAIEKAKRKLRGLIAEKKCAPLILRLAWH SAGTFDSKTKTGGPFGTIKHQAELAHGANNGLDIAVRLLEPI KEQFPIVSYADFYQLAGVVAVEITGGPEVPFHPGREDKPEPP PEGRLPDATKGSDHLRDVFGKAMGLSDQDIVALSGGHTIGAA HKERSGFEGPWTSNPLIFDNSYFTELLTGEKDGLLQLPSDKA LLTDSVFRPLVEKYAADEDVFFADYAEAHLKLSELGFAEA (GenBank Accession No. AAA33645.1, which is hereby incorporated by reference in its entirety) | 31 |
| APEX2 (soybean ascorbate peroxidase) | MGKSYPTVSADYQDAVEKAKKKLRGFIAEKRCAPLMLRLAFH SAGTFDKGTKTGGPFGTIKHPAELAHSANNGLDIAVRLLEPL KAEFPILSYADFYQLAGVVAVEVTGGPKVPFHPGREDKPEPP PEGRLPDPTKGSDHLRDVFGKAMGLTDQDIVALSGGHTIGAA HKERSGFEGPWTSNPLIFDNSYFTELLSGEKEGLLQLPSDKA LLSDPVFRPLVDKYAADEDAFFADYAEAHQKLSELGFADA (see, e.g., Ganapathy et al., "Compartment-Specific Labeling of Bacterial Periplasmic Proteins by Peroxidase-Mediated Biotinylation," ACS Infect. Dis. 4(6): 918-925 (2018) and Lam et al., "Directed Evolution of APEX2 for Electron Microscopy and Proximity Labeling," Nature Methods 12:51-54 (2014), which are hereby incorporated by reference in their entirety) | 32 |
| Horseradish peroxidase (*Armoracia rusticana*) | MQLTPTFYDNSCPNVSNIVRDTIVNELRSDPRIAASILRLHF HDCFVNGCDASILLDNTTNANSARGFPVIDRMKAAVESACPR TVSCADLLTIAAQQSVTLAGGPSWRVPLGRRDSLQAFLDLAN ANLPAPFFTLPQLKDSFRNVGLNRSSDLVALSGGHTFGKNQC RFIMDRLYNFSNTGLPDPILNITYLQTLRGLCPLNGNLSALV DFDLRTPTIFDNKYYVNLEEQKGLIQSDQELFSSPNATDTIP LVRSFANSTQTFFNAFVEAMDRMGNITPLTGTQGQIRLNCRV VNSNS (GenBank Accession No. CAA00083.1, which is hereby incorporated by reference in its entirety) | 33 |
| Alkaline phosphatase | MKQSTIALALLPLLFTPVTKARTPEMPLQGTAVDGGGGSMHA SLEVLENRAAQGDITAPGGARRLTGDQTAALRDSLSDKPAKN IILLIGDGMGDSEITAARNYAEGAGGFFKGIDALPLTGQYTH YALNKKTGKPDYVTDSAASATAWSTGVKTYNGALGVDIHEKD HPTILEMAKAAGLATGNVSTAELQDATPAALVAHVTSRKCYG PSATSEKCPGNALEKGGKGSITEQLLNARADVTLGGGAKTFA ETATAGEWQGKTLREQAQARGYQLVSDAASLNSVTEANQQKP LLGLFADGNMPVRWLGPKATYHGNIDKPAVTCTPNPQRNDSV PTLAQMTDKAIELLSKNEKGFFLQVEGASIDKQDHAANPCGQ IGETVDLDEAVQRALEFAKKEGNTLVIVTADHAHASQIVAPD TKAPGLTQALNTKDGAVMVMSYGNSEEDSQEHTGSQLRIAAY GPHAANVVGLTDQTDLFYTMKAALGLK (GenBank Accession No. AAK73766.1, which is hereby incorporated by reference in its entirety) | 34 |
| Alkaline phosphatase (*Escherichia coli*) | MKQSTIALALLPLLFTPVTKARTPEMPVLENRAAQGDITAPG GARRLTGDQTAALRDSLSDKPAKNIILLIGDGMGDSEITAAR NYAEGAGGFFKGIDALPLTGQYTHYALNKKTGKPDYVTDSAA SATAWSTGVKTYNGALGVDIHEKDHPTILEMAKAAGLATGNV STAELQDATPAALVAHVTSRKCYGPSATSEKCPGNALEKGGK | 35 |

TABLE 2-continued

Exemplary Bioluminescent Protein Amino Acid Sequences

| Bioluminescent Protein | Amino Acid Sequence | SEQ ID NO: |
|---|---|---|
| | GSITEQLLNARADVTLGGGAKTFAETATAGEWQGKTLREQAQ<br>ARGYQLVSDAASLNSVTEANQQKPLLGLFADGNMPVRWLGPK<br>ATYHGNIDKPAVTCTPNPQRNDSVPTLAQMTDKAIELLSKNE<br>KGFFLQVEGASIDKQDHAANPCGQIGETVDLDEAVQRALEFA<br>KKEGNTLVIVTADHAHASQVVAPDTKAPGLTQALNTKDGAVM<br>VMSYGNSEEDSQEHTGSQLRIAAYGPHAANVVGLTDQTDLFY<br>TMKAALGLK<br>(GenBank Accession No. WP_001364609.1, which is hereby incorporated by reference in its entirety) | |
| β-glucuronidase (*Escherichia coli*) | MLRPVETPTREIKKLDGLWAFSLDRENCGIDQRWWESALQES<br>RAIAVPGSFNDQFADADIRNYAGNVWYQREVFIPKGWAGQRI<br>VLRFDAVTHYGKVWVNNQEVMEHQGGYTPFEADVTPYVIAGK<br>SVRITVCVNNELNWQTIPPGMVITDENGKKKQSYFHDFFNYA<br>GIHRSVMLYTTPNTWVDDITVVTHVAQDCNHASVDWQVVANG<br>DVSVELRDADQQVVATGQGTSGTLQVVNPHLWQPGEGYLYEL<br>CVTAKSQTECDIYPLRVGIRSVAVKGQQFLINHKPFYFTGFG<br>RHEDADLRGKGFDNVLMVHDHALMDWIGANSYRTSHYPYAEE<br>MLDWADEHGIVVIDETAAVGFNLSLGIGFEAGNKPKELYSEE<br>AVNGETQQAHLQAIKELIARDKNHPSVVMWSIANEPDTRPQV<br>HGNISPLAEATRKLDPTRPITCVNVMFCDAHTDTISDLFDVL<br>CLNRYYGWYVQSGDLETAEKVLEKELLAWQEKLHQPIIITEY<br>GVDTLAGLHSMYTDMWSEEYQCAWLDMYHRVFDRVSAVVGEQ<br>VWNFADFATSQGILRVGGNKKGIFTRDRKPKSAAFLLQKRWT<br>GMNFGEKPQQGGKQ<br>(GenBank Accession No. AAC53703.1, which is hereby incorporated by reference in its entirety) | 36 |
| β-glucosidase (*Francisella tularensis*) | MSTNSNIRQKLGQLIMMDFRYWGEDSNNQRIPFTKINDIVNK<br>IFKDYNLGGFILFRENIQNNEQVISLLRDLQANTNTPIFFAT<br>DQEGGRVNRLQQGTSGCGNMALAATDNPHNAYTMAKIIGDEL<br>YSLGININFAPAVDVNSNKNNPIIGVRSYSDNPDIVIDYAKN<br>AINGYHDAKIIDCIKHFPGHGDTATDSHLGNVNLDKTLKELQ<br>TTELLPFSKLARDCSMIMTAHISVPALDDTQYQSVSTSENIY<br>VPATLSYKIITKLLKQQMKFDGLVVSDAMDMHAIAKHFGTIE<br>ASKLAILAGIDILLMPVRVWSENDLYKLEELFCELEKGYNQN<br>SNFANAVDNVYTNITDFKAKHKLDESLIFKLSQDEQLKYANQ<br>IVNSNKHQQIALDIAKQSTTVVKNSGIIPCDLNKLKNILIVD<br>SDNQRLADFHSELQKIVLDNNSNVIINCENINNHNIKTIIEN<br>ADLILLISANLREYNQTYSYITSIKPEQTINIAALTPYDINY<br>IDNIINYVCIYGATSMDQTNYTKTSLKINIQTTLENIFGNKE<br>IKGVLPVSL<br>(GenBank Accession No. AAC53703.1, which is hereby incorporated by reference in its entirety) | 37 |

The protein of interest may be an enzyme. In some embodiments, the enzyme is selected from the group consisting of a ligase and a methyltransferase.

As described herein, the term "ligase" refers to an enzyme that catalyzes the joining of two large molecules by forming a new chemical bond, usually with accompanying hydrolysis of a small pendant chemical group on one of the larger molecules or the enzyme catalyzing the linking together of two compounds. Suitable ligases include, without limitation, DNA ligases, RNA ligases, amino acid—tRNA ligases (e.g., tyrosine—tRNA ligase, tryptophan—tRNA ligase, threonine—tRNA ligase, leucine—tRNA ligase, isoleucine—tRNA ligase, lysine—tRNA ligase, alanine—tRNA ligase, valine—tRNA ligase, methionine—tRNA ligase, serine—tRNA ligase, aspartate—tRNA ligase, D-alanine—tRNA ligase, glycine—tRNA ligase, proline—tRNA ligase, cysteine—tRNA ligase, glutamate—tRNA ligase, glutamine—tRNA ligase, arginine—tRNA ligase, phenylalanine—tRNA ligase, histidine—tRNA ligase, asparagine—tRNA ligase, aspartate—tRNA ligase, glutamate—tRNA ligase), acetate—CoA ligase, succinate—CoA ligase, biotin—CoA ligase (i.e., biotin ligase), carboxylic acid—CoA ligase, acetate—CoA ligase, and aspartate—ammonia ligase (see, e.g., McDonald, Andrew, "The Enzyme List Class 6—Ligases," *ExplorEnz Database* (2019), which is hereby incorporated by reference in its entirety).

In some embodiments, the ligase is a biotin ligase. As described herein, biotin ligases catalyze the formation of biotin-5′-AMP anhydride, which diffuses out of the active site to biotinylate proximal endogenous proteins on nucleophilic residues such as lysine. In some embodiments, the biotin ligase is selected from TurboID, miniTurbo, and *E. coli* BirA (see, e.g., Branon et al., "Efficient Proximity Labeling in Living Cells and Organisms with TurboID," *Nat. Biotechnol.* 36(9):880-887 (2018), which is hereby incorporated by reference in its entirety).

The methyltransferase may be a histone methyltransferase, an N-terminal methyltransferase, a DNA/RNA methyltransferase, a natural product methyltransferase, a non-SAM dependent methyltransferase, or a radical SAM methyltransferase. As described herein, histone methyl transferases catalyze the transfer of one, two, or three methyl groups to lysine and arginine residues of histone proteins. In some embodiments, the histone methyltransferase is a histone-lysine N-methyltransferase selected from the group consisting of enhancer of zeste homolog 1 (EZH1), enhancer of zeste homolog 2 (EZH2), disruptor of telomeric silencing 1-like (DOT1-like), ASH1L, euchromatic histone-lysine N-methyltransferase 1 (EHMT1), euchromatic histone-lysine N-methyltransferase 2 (EHMT2), histone-lysine N-methyltransferase 2A, histone-lysine N-methyltransferase 2D (KMT2D), lysine N-methyltransferase 2C (KMT2C), myeloid/lymphoid or mixed-lineage leukemia 4 (MLL4), lysine methyltransferase 2E, and nuclear receptor binding SET domain protein 1 (NSD1). In other embodiments, the histone methyltransferase is a histone-arginine N-methyltransferases selected from the group consisting of protein arginine N-methyltransferase 1, protein arginine N-methyltransferase 3, protein arginine N-methyltransferase 4, protein arginine N-methyltransferase 5, and protein arginine N-methyltransferase 7.

Non-limiting examples of suitable enzymes are identified in Table 3 below.

TABLE 3

Exemplary Enzyme Amino Acid Sequences

| Enzyme | Amino Acid Sequence | SEQ ID NO: |
|---|---|---|
| E. coli BirA (Biotin-CoA ligase) | MKDNTVPLKLIALLANGEFHSGEQLGETLGMSRAAINKHIQTLR DWGVDVFTVPGKGYSLPEPIQLLNAKQILGQLDGGSVAVLPVID STNQYLLDRIGELKSGDACIAEYQQAGRGRRGRKWFSPFGANLY LSMFWRLEQGPAAAIGLSLVIGIVMAEVLRKLGADKVRVKWPND LYLQDRKLAGILVELTGKTGDAAQIVIGAGINMAMRRVEESVVN QGWITLQEAGINLDRNTLAAMLIRELRAALELFEQEGLAPYLSR WEKLDNFINRPVKLIIGDKEIFGISRGIDKQGALLLEQDGIIKP WMGGEISLRSAEK (GenBank Accession No. NP_418404.1, which is hereby incorporated by reference in its entirety) | 38 |
| miniTurbo biotin ligase | MIPLLNAKQILGQLDGGSVAVLPVVDSTNQYLLDRIGELKSGDA CIAEYQQAGRGSRGRKWFSPFGANLYLSMFWRLKRGPAAIGLGP VIGIVMAEALRKLGADKVRVKWPNDLYLQDRKLAGILVELAGIT GDAAQIVIGAGINVAMRRVEESVVNQGWITLQEAGINLDRNTLA AMLIRELRAALELFEQEGLAPYLSRWEKLDNFINRPVKLIIGDK EIFGISRGIDKQGALLLEQDGVIKPWMGGEISLRSAEK (see, e.g., Branon et al., "Efficient Proximity Labeling in Living Cells and Organisms with TurboID," Nat. Biotechnol. 36(9):880-887 (2018), which is hereby incorporated by reference in its entirety) | 39 |
| Turbo ID biotin ligase | MKDNTVPLKLIALLANGEFHSGEQLGETLGMSRAAINKHIQTLR DWGVDVFTVPGKGYSLPEPIPLLNAKQILGQLDGGSVAVLPVVD STNQYLLDRIGELKSGDACIAEYQQAGRGSRGRKWFSPFGANLY LSMFWRLKRGPAAIGLGPVIGIVMAEALRKLGADKVRVKWPNDL YLQDRKLAGILVELAGITGDAAQIVIGAGINVAMRRVEESVVNQ GWITLQEAGINLDRNTLAATLIRELRAALELFEQEGLAPYLPRW EKLDNFINRPVKLIIGDKEIFGISRGIDKQGALLLEQDGVIKPW MGGEISLRSAEK (see, e.g., Branon et al., "Efficient Proximity Labeling in Living Cells and Organisms with TurboID," Nat. Biotechnol. 36(9):880-887 (2018), which is hereby incorporated by reference in its entirety) | 40 |
| Biotin ligase (Mammalian expression vector pCBio) | MDYKDDDDKSPRSMKDNTVPLKLIALLANGEFHSGEQLGETLGM SRAAINKHIQTLRDWGVDVFTVPGKGYSLPEPIQLLNAKQILGQ LDGGSVAVLPVIDSTNQYLLDRIGELKSGDACIAEYQQAGRGRR GRKWFSPFGANLYLSMFWRLEQGPAAAIGLSLVIGIVMAEVLRK LGADKVRVKWPNDLYLQDRKLAGILVELTGKTGDAAQIVIGAGI NMAMRRVEESVVNQGWITLQEAGINLDRNTLAAMLIRELRAALE LFEQEGLAPYLSRWEKLDNFINRPVKLIIGDKEIFGISRGIDKQ GALLLEQDGIIKPWMGGEISLRSAEK (GenBank Accession No. ABF74577.1, which is hereby incorporated by reference in its entirety) | 41 |
| Enhancer of Zeste Homolog 2 (Homo sapiens) methyltransferase | MGQTGKKSEKGPVCWRKRVKSEYMRLRQLKRFRRADEVKSMFSS NRQKILERTEILNQEWKQRRIQPVHILTSVSSLRGTRECSVISD LDFPTQVIPLKTLNAVASVPIMYSWSPLQQNFMVEDETVLHNIP YMGDEVLDQDGTFIEELIKNYDGKVHGDRECGFINDEIFVELVN ALGQYNDDDDDDGDDPEEREEKQKDLEDHRDDKESRPPRKFPS DKIFEAISSMFPDKGTAEELKEKYKELTEQQLPGALPPECTPNI DGPNAKSVQREQSLHSFHTLFCRRCFKYDCFLHPFHATPNTYKR KNTETALDNKPCGPQCYQHLEGAKEFAAALTAERIKTPPKRPGG RRRGRLPNNSSRPSTPTINVLESKDTDSDREAGTETGGENNDKE EEEKKDETSSSSEANSRCQTPIKMKPNIEPPENVEWSGAEASMF RVLIGTYYDNFCAIARLIGTKTCRQVYEFRVKESSIIAPAPAED VDTPPRKKKRKHRLWAAHCRKIQLKKDGSSNHVYNYQPCDHPRQ PCDSSCPCVIAQNFCEKFCQCSSECQNRFPGCRCKAQCNTKQCP CYLAVRECDPDLCLICGAADHWDSKNVSCKNCSIQRGSKKHLLL APSDVAGWGIFIKDPVQKNEFISEYCGEIISQDEADRRGKVYDK YMCSFLFNLNNDFVVDATRKGNKIRFANHSVNPNCYAKVMMVNG DHRIGIFAKRAIQTGEELFFDYRYSQADALKYVGIEREMEIP (GenBank Accession No. AAC51520.1, which is hereby incorporated by reference in its entirety) | 42 |

Additional suitable proteins of interest include, but are not limited to, a G-protein coupled receptor (GPCR), a nuclear receptor, a voltage gated ion channel, a ligand gated channel, a receptor tyrosine kinase, a growth factor, a phosphatase, a protein kinase, a viral regulator, a bacterial cell division protein, a scaffold protein, a DNA repair protein, a cytoskeletal protein, a ribosome, a histone deacetylase, an apoptosis regulator, a chaperone protein, a kinase, a phosphorylase, a phosphatase, deacetylase, a cytoskeletal protein (e.g., myosin, actin, dynein, kinesin, and tubulin).

As described herein, a G-protein coupled receptor (GPCR) refers to a membrane protein which binds to a signaling molecule. Upon binding, a conformational change occurs, which allows binding of the GPCR to, and activation of, a G-protein. The activated G-protein then interacts with an effector molecule, which is typically involved in a second messenger pathway. Suitable G-protein coupled receptors may be selected from the group consisting of a luteinizing hormone receptor, a follicle stimulating hormone receptor, a thyroid stimulating hormone receptor, a calcitonin receptor, a glucagon receptor, a glucagon-like peptide 1 receptor (GLP-1), a metabotropic glutamate receptor, a parathyroid hormone receptor, a vasoactive intestinal peptide receptor, a secretin receptor, a growth hormone releasing factor (GRF) receptor, protease-activated receptors (PARs), cholecystokinin receptors, somatostatin receptors, melanocortin receptors, nucleotide receptors (e.g., ADP receptors), adenosine receptors, thromboxane receptors, platelet activating factor receptor, adrenergic receptors, 5-hydroxytryptamine (5-HT) receptors, a chemokine receptor (e.g., CXCR4, CCR5), chemokine receptors, neuropeptide receptors, opioid receptors, erythropoietin receptor, von Willebrand receptor, parathyroid hormone (PTH) receptor, vasoactive intestinal peptide (VIP) receptor, and collagen receptors. Exemplary protease-activated receptors include, without limitation, PAR1, PAR2, PAR3, or PAR4 receptors.

In some embodiments, the protein of interest is a transcription factor. Transcription factors include proteins that are involved in gene regulation in prokaryotic and/or eukaryotic organisms. In one embodiment, transcription factors have a positive effect on gene expression and, thus, may be referred to as an activator or a transcriptional activation factor. In another embodiment, a transcription factor negatively regulates gene expression and, thus, may be referred to as a repressor or a transcription repression factor. Suitable transcription factors include, without limitation, c-Myc, c-Fos, c-Jun, CREB, GATA-2, GAL4, GAL4Np16, c-Myb, MyoD, and NFκB, and tetR. Exemplary transcription factors are identified in Table 4 below.

TABLE 4

Exemplary Transcription Factor Amino Acid Sequences

| Transcription Factor | Amino Acid Sequence | SEQ ID NO: |
|---|---|---|
| c-Myc (Homo sapiens) | MPLNVSFTNRNYDLDYDSVQPYFYCDEEENFYQQQQQSELQPPAP SEDIWKKFELLPTPPLSPSRRSGLCSPSYVAVTPFSLRGDNDGGG GSFSTADQLEMVTELLGGDMVNQSFICDPDDETFIKNIIIQDCMW SGFSAAAKLVSEKLASYQAARKDSGSPNPARGHSVCSTSSLYLQD LSAAASECIDPSVVFPYPLNDSSSPKSCASQDSSAFSPSSDSLLS STESSPQGSPEPLVLHEETPPTTSSDSEEEQEDEEEIDVVSVEKR QAPGKRSESGSPSAGGHSKPPHSPLVLKRCHVSTHQHNYAAPPST RKDYPAAKRVKLDSVRVLRQISNNRKCTSPRSSDTEENVKRRTHN VLERQRRNELKRSFFALRDQIPELENNEKAPKVVILKKATAYILS VQAEEQKLISEEDLLRKRREQLKHKLEQLRNSCA (GenBank Accession No. AAA36340.1, which is hereby incorporated by reference in its entirety) | 43 |
| c-Fos (Homo sapiens) | MMFSGFNADYEASSSRCSSASPAGDSLSYYHSPADSFSSMGSPVN AQDFCTDLAVSSANFIPTVTAISTSPDLQWLVQPALVSSVAPSQT RAPHPFGVPAPSAGAYSRAGVVKTMTGGRAQSIGRRGKVEQLSPE EEEKRRIRRERNKMAAAKCRNRRRELTDTLQAETDQLEDEKSALQ TEIANLLKEKEKLEFILAAHRPACKIPDDLGFPEEMSVASLDLTG GLPEVATPESEEAFTLPLLNDPEPKPSVEPVKSISSMELKTEPFD DFLFPASSRPSGSETARSVPDMDLSGSFYAADWEPLHSGSLGMGP MATELEPLCIPVVICTPSCTAYTSSFVFTYPEADSFPSCAAAHRK GSSSNEPSSDSLSSPTLLAL (GenBank Accession No. AAA52471.1, which is hereby incorporated by reference in its entirety) | 44 |
| c-Jun (Homo sapiens) | MTAKMETTFYDDALNASFLPSESGPYGYSNPKILKQSMTLNLADP VGSLKPHLRAKNSDLLTSPDVGLLKLASPELERLIIQSSNGHITT TPTPTQFLCPKNVTDEQEGFAEGFVRALAELHSQNTLPSVTSAAQ PVNGAGMVAPAVASVAGGSGSGGFSASLHSEPPVYANLSNFNPGA LSSGGGAPSYGAAGLAFPAQPQQQQQPPHHLPQQMPVQHPRLQAL KEEPQTVPEMPGETPPLSPIDMESQERIKAERKRMRNRIAASKCR KRKLERIARLEEKVKTLKAQNSELASTANMLREQVAQLKQKVMNH VNSGCQLMLTQQLQTF (GenBank Accession No. NP_002219.1, which is hereby incorporated by reference in its entirety) | 45 |
| CREB (Homo sapiens) | MIMESGAENQQSGDAAVTEAENQQMTVQAQPQIATLAQVSMPAAH ATSSAPTVTLVQLPNGQTVQVHGVIQAAQPSVIQSPQVQTVQIST IAESEDSQESVDSVTDSQKRREILSRRPSYRKILNDLSSDAPGVP RIEEEKSEEETSAPAITIVTVPTPIYQTSSGQYIAITQGGAIQLA NNGTDGVQGLQTLTMTNAAATQPGTTILQYAQTTDGQQILVPSNQ VVVQAASGDVQTYQIRTAPTSTIAPGVVMASSPALPTQPAEEEAR KREVRLMKNREAARECRRKKKEYVKCLENRVAVLENQNKTLIEEL | 46 |

TABLE 4-continued

Exemplary Transcription Factor Amino Acid Sequences

| Transcription Factor | Amino Acid Sequence | SEQ ID NO: |
|---|---|---|
| | KALKDLYCHKSD<br>(GenBank Accession No. AAA35715.1, which is hereby incorporated by reference in its entirety) | |
| GATA-2<br>(Homo sapiens) | MEVAPEQPGWMAHPAVLNAQHPDSHHPGLAHNYMEPAHVLPPDEV<br>DVFFNHLDSQGNPYYANPAQRGVSYSPAHARLTGGQMCRPHLLHS<br>PGLPWLDGGKAALSAAHHKTWTVSPFSKTPLHPSAAGGPGGHSLC<br>TQGLGVGGGSSGSSVASLTPTAAHSGSHLFGFPPPRHPKELSPDPS<br>TTGAASPASSSAGGSSARGEDKDGVKYQASLTESMKMESGRPLRP<br>GLATMGTQPATHHPIPTYPSYVPAAAHDYSSGLFHPGSFLGGPAS<br>SFTPKQRSKTRSCSEGRECVNCGATATPLWRRDGTGHYLCNACGF<br>YHKMKGQNRPLIKPKRRLSAARRAGTCCANCQTTITTLWRRNANG<br>DPVCNACGLYYKLHNVNRPLTMKKEGIQTRNRKMSNKSKKSKKGA<br>ECFEELSKCMQEKSSPFSAAALAGHMAPMGHLPPFSHSGHILPTP<br>TPIHPSSSLSFGHPHPSSMVTAMG<br>(GenBank Accession No. AAA35869.1, which is hereby incorporated by reference in its entirety) | 47 |
| GAL4<br>(Saccharomyce revisiae) | MKLLSSIEQACDICRLKKLKCSKEKPKCAKCLKNNWECRYSPKTK<br>RSPLTRAHLTEVESRLERLEQLFLLIFPREDLDMILKMDSLQDIK<br>ALLTGLFVQDNVNKDAVTDRLASVETDMPLTLRQHRISATSSSEE<br>SSNKGQRQLTVSIDSAAHHDNSTIPLDFMPRDALHGFDWSEEDDM<br>SDGLPFLKTDPNNNGFFGDGSLLCILRSIGFKPENYTNSNVNRLP<br>TMITDRYTLASRSTTSRLLQSYLNNFHPYCPIVHSPTLMMLYNNQ<br>IEIASKDQWQILFNCILAIGAWCIEGESTDIDVFYYQNAKSHLTS<br>KVFESGSIILVTALHLLSRYTQWRQKTNTSYNFHSFSIRMAISLG<br>LNRDLPSSFSDSSILEQRRRIWWSVYSWEIQLSLLYGRSIQLSQN<br>TISFPSSVDDVQRTTTGPTIYHGIIETARLLQVFTKIYELDKTVT<br>AEKSPICAKKCLMICNEIEEVSRQAPKFLQMDISTTALTNLLKEH<br>PWLSFTRFELKWKQLSLIIYVLRDFFTNFTQKKSQLEQDQNDHQS<br>YEVKRCSIMLSDAAQRTVMSVSSYMDNHNVTPYFAWNCSYYLFNA<br>VLVPIKTLLSNSKSNAENNETAQLLQQINTVLMLLKKLATFKIQT<br>CEKYIQVLEEVCAPFLLSQCAIPLPHISYNNSNGSAIKNIVGSAT<br>IAQYPTLPEENVNNISVKYVSPGSVGPSPVPLKSGASFSDLVKLL<br>SNRPPSRNSPVTIPRSTPSHRSVTPFLGQQQQLQSLVPLTPSALF<br>GGANFNQSGNIADSSLSFTFTNSSNGPNLITTQTNSQALSQPIAS<br>SNVHDNFMNNEITASKIDDGNNSKPLSPGWTDQTAYNAFGITTGM<br>FNTTTMDDVYNYLFDDEDTPPNPKKE<br>(GenBank Accession No. AAA34626.1, which is hereby incorporated by reference in its entirety) | 48 |
| GAL4Np16<br>(Saccharomyce revisiae) | MKLLSSIEQACDICRLKKLKCSKEKPKCAKCLKNNWECRYSPKTK<br>RSPLTRAHLTEVESRLERLEQLFLLIFPREDLDMILKMDSLQDIK<br>ALLTGLFVQDNVNKDAVTDRLASVETDMPLTLRQHRISATSSSEE<br>SSNKGQRQLTVSIEFSRGRTRNNYGSTIEGLLDLPDDDDAPAEAG<br>LVAPRMSFLSAGQRPRRLSTTAPITDVSLVDELRLDGEEVDMTPA<br>DALDDFDLEMLGDVESPSPGMTHDPVSYGALDVDDFEFEQMFTDA<br>LGIDDFGG<br>(GenBank Accession No. AAN86074.1, which is hereby incorporated by reference in its entirety) | 49 |
| c-Myb<br>(Homo sapiens) | MARRPRHSIYSSDEDDEDFEMCDHDYDGLLPKSGKRHLGKTRWTR<br>EE<br>(GenBank Accession No. AAA72118.1, which is hereby incorporated by reference in its entirety) | 50 |
| MyoD<br>(Mus musculus) | MELLSPPLRDIDLTGPDGSLCSFETADDFYDDPCFDSPDLRFFED<br>LDPRLVHVGALLKPEEHAHFSTAVHPGPGAREDEHVRAPSGHHQA<br>GRCLLWACKACKRKTTNADRRKAATMRERRRLSKVNEAFETLKRC<br>ISSNPNQRLPKVEILRNAIRYIEGLQALLRDQDAAPPGAAAFYAP<br>GPLPPGRGSEHYSGDSASSPRSNCSDGMMDYSGPPSGPRRQNGY<br>DTAYYSEAVRESRPGKSAAVSSLDCLSSIVERISIDSPAAPALLL<br>ADAPPESPPGPPEGASLSDTEQGTQTPSPDAAPQCPAGSNPNAIY<br>QVL<br>(GenBank Accession No. AAA39798.1, which is hereby incorporated by reference in its entirety) | 51 |
| NF-κB<br>(Homo sapiens) | MDELFPLIFPAEQPKQRGMRFRYKCEGRSAGSIPGERSTDTTKTH<br>PTIKINGYTGPGTVRISLVTKDPPHRPHPHELVGKDCRDGFYEAE<br>LCPDRCIHSFQNLGIQCVKKRDLEQAISQRIQTNNNPFQVPIEEQ<br>RGDYDLNAVRLCFQVTVRDPSGRPLRLPPVLSHPIFDNRAPNTAE<br>LKICRVNRNSGSCLGGDEIFLLCDKVQKEDIEVYFTGPGWEARGS<br>FSQADVHRQVAIVFRTPPYADPSLQAPVRVSMQLRRPSDRELSEP<br>MEFQYLPDTDDRHRIEEKRKRTYETFKSIMKKSPFSGPTDPRPPP<br>RRIAVPSRSSASVPKPAPQPYPFTSSLSTINYDEFPTMVFPSGQI | 52 |

TABLE 4-continued

Exemplary Transcription Factor Amino Acid Sequences

| Transcription Factor | Amino Acid Sequence | SEQ ID NO: |
|---|---|---|
| | SQASALAPAPPQVLPQAPAPAPAPAMVSALAQAPAPVPVLAPGPP<br>QAVAPPAPKPTQAGEGTLSEALLQLQFDDEDLGALLGNSTDPAVF<br>TDLASVDNSEFQQLLNQGIPVAPHTTEPMLMEYPEAITRLVTAQR<br>PPDPAPAPLGAPGLPNGLLSGDEDFSSIADMDFSALLSQISS<br>(GenBank Accession No. 2006293A, which is hereby incorporated by reference in its entirety) | |
| TetR (*Proteobacteria*) | MFISDKVSSMTKLQPNTVIRAALDLLNEVGVDGLTTRKLAERLGV<br>QQPALYWHFRNKRALLDALAEAMLAENHTHSVPRADDDWRSFLIG<br>NARSFRQALLAYRDGARIHAGTRPGAPQMETADAQLRFLCEAGFS<br>AGDAVNALMTISYFTVGAVLEEQAGDSDAGERGGTVEQAPLSPLL<br>RAAIDAFDEAGPDAAFEQGLAVIVDGLAKRRLVVRNVEGPRKGDD<br>(GenBank Accession No. WP_000470728.1, which is hereby incorporated by reference in its entirety) | 53 |

Additional exemplary transcription factors are identified in Table 5 below.

TABLE 5

Additional Exemplary Transcription Factors

| Transcription Factor Family | Transcriptions Factors |
|---|---|
| Basic Helix-Loop-Helix (bHLH) Family | AHR, ARNT/HIF-1 beta, ASCL1/Mash1, ASCL2/Mash2, CLOCK, DEC2, HAND1, HAND2, HES-1, HES-4, HIF-1 alpha/HIF1A, HIF-2, alpha/EPAS1, c-Maf, Max, MESP1, MITF, MLX, Mxi1, c-Myc, MYCL1/L-Myc, MYF-5, MyoD, Myogenin, NeuroD1, NeuroD2, Neurogenin-1, Neurogenin-2, Neurogenin-3, Olig1, Olig2, Olig3, SCL/Tal1, SREBP2, TCF-12/HTF4, TFEB, Twist-1 Twist-2, UTF1 |
| Basic Leucine Zipper (bZIP) Family | ATF1, ATF2, ATF4, BACH1, BATF, BATF3, c-Fos, CEBP alpha, CEBP epsilon, CREB, FosB/G0S3, FRA-1, GADD153, HSF1, HSF2, HSF4, c-Jun, JunB, JunD, c-Maf, MafB, MafF, MafG, MafK, Max, MITF, MLX, Mxi1, MYB, c-Myc, MYCL1/L-Myc, NFIL3/E4BP4, Nrf1, Nrf2, NRL, OASIS/CREB3L1, SREBP2, TSC22, XBP1 |
| ETS (E-twenty six) Family | ELF3, Ets-1, ETV1, ETV2/ER71, ETV5, ETV6, FLI1, PU.1/Spi-1, Spi-B |
| Forkhead Domain Family | FoxC1, FoxC2, FoxD3, FoxF1, FoxF2, FoxH1, FoxJ1, FoxJ3, FoxK1, FOXL2, FoxM1, FoxN1, FoxO1/FKHR, FoxO3, FoxP1, FoxP2, FoxP3, FoxP4, HNF-3 alpha/FoxA1, HNF-3 beta/FoxA2 |
| GATA Family | GATA-1, GATA-2, GATA-3, GATA-4, GATA-5, GATA-6, TRPS1 |
| Hypoxia Inducible Factors (HIFs) Family | HIF-1, HIF-2, HIF-3, ARNT/HIF-1 beta |
| High Mobility Group (HMG) Family | HMGA1B, HMGA2, HMGB1/HMG-1, HMGB3, HMGN1, LEF1, SOX1, SOX2, SOX3, SOX5, SOX6, SOX7, SOX9, SOX10, SOX11, • SOX15, SOX17, SOX18, SOX21, TCF7/TCF1, TCF7L1/TCF3 |
| Homeodomain (Hox) Family | ADNP, ARX, ATBF1/ZFHX3, CDX2, CDX4, CRX, DLX5, DUX4, DUX4/DUX4c, DUX4c, EMX2, GBX2, Goosecoid, HHEX, HNF-6/ONECUT1, HOXA1, HOXB1, HOXB7, HOXB13, HOXD10, Islet-1, Islet-2, LHX5, LIM1, MSX1, MSX2, Nanog, NKX2.2, NKX2.5, NKX3.1, NKX6.1, Oct-1, Oct-3/4, Oct-4A, Oct-4B, ONECUT2/OC-2, Otx2, PDX-1/IPF1, PHOX2B, PITX2, POU3F2, Prox1, SATB1, TCF-2/HNF-1 beta, TCF-3/E2A, TGIF1, TTF-1/NKX2-1, VSTM2L, ZEB1 |
| Immunoglobulin-Like Domain Family | CSL, NFκB, p50 (NFκB1), p52 (NFκB2), p53, p63/TP73L, NFκBp65/RelA, RelB, c-Rel, STAT (STAT1, STAT2, STAT3, STAT4, STAT5a/b, STAT5a, STAT5b, STAT6) |
| Interferon-Regulatory Factor (IRF) Family | IRF1, IRF2, IRF3, IRF4, IRF5, IRF6, IRF8 |
| Kruppel-like Family | KLF2, KLF4, KLF5, KLF6, KLF10, KLF12, KLF17 |
| Paired Box (Pax) Family | Pax2, Pax3, Pax4, Pax5/BSAP, Pax6, Pax7 |
| Mothers against decapentaplegic homolog (Smad) Family | FOXL2, Smad1, Smad2, Smad2/3, Smad3, Smad4, Smad5, Smad7, Smad8, Smad9 |
| Additional Transcription | AP-2 beta, AP-2 gamma, AP-2 epsilon, Autoimmune Regulator/AIRE, BLIMP1/PRDM1, C1D, DACH2, DC-SCRIPT/ZNF366, DIDO1, E2F- |

TABLE 5-continued

Additional Exemplary Transcription Factors

| Transcription Factor Family | Transcriptions Factors |
|---|---|
| Factors | 1, E2F-2, E2F-4, EGR1, GLI-1, GLI-2, GLI-3, HNF-4 alpha/NR2A1, HNF-4 gamma/NR2A2, LMO2, LMO4, LPP, MEF2C, PREB, RFX6, Teneurin-1, Teneurin-2, Teneurin-4, TFCP2L1, ZSCAN21 |

RNA-regulated destabilization domains are amino acid sequences that, when functionally coupled to a protein of interest, modulate the stability of the protein of interest in a RNA-dependent manner. In some embodiments, when the RNA-regulated destabilization domain is fused to a protein of interest, the RNA-regulated destabilization domain mediates protein degradation. In accordance with such embodiments, the protein destabilization function of the RNA-regulated destabilization domain is impeded when it binds to a specific RNA molecule (e.g., an aptamer).

In some embodiments, the RNA-regulated destabilization domain comprises a bifunctional peptide comprising an RNA-binding domain and a degron peptide. The RNA-binding domain may be any peptide to which an RNA molecule can bind, where such binding sterically inhibits the interaction of the degron peptide with a proteosomal pathway component (e.g., an E3 ubiquitin ligase). Thus, in some embodiments, the RNA-binding domain is MDARTRR-RERRAEKQAQWKAAN (lambdaN; SEQ ID NO: 123), which is derived from the lambda bacteriophage antiterminator protein N. In accordance with such embodiments, the RNA-binding domain is specific for BoxB (SEQ ID NO: 124): GGGCCCUGAAGAAGGGCCC (see, e.g., "NMR Structure of the Bacteriophage Lambda N Peptide/boxB RNA Complex: Recognition of a GNRA Fold by an Arginine-Rich Motif," Cell 93(2):289-299 (1998), which is hereby incorporated by reference in its entirety).

In other embodiments, the RNA-binding domain is DTRQARRNRRRRWRERQRAAAAR (HIV-1 Rev; SEQ ID NO: 125), which is derived from HIV-1 Rev peptide. In accordance with such embodiments, the RNA-binding domain is specific for RRE RNA (SEQ ID NO: 126): GGUCUGGGCGCAGCGCAAGCUGCGGACAGGCC (see, e.g., Battiste et al., "Alpha Helix—RNA Major Groove Recognition in an HIV-1 Rev Peptide—RRE RNA Complex," Science 273:1547-1551 (1996), which is hereby incorporated by reference in its entirety).

The RNA-regulated destabilization domain may comprise a bifunctional peptide comprising a lentiviral transactivator of transcription (Tat) peptide and a degron peptide.

In some embodiments, the lentiviral Tat peptide is a bovine immunodeficiency virus Tat peptide. In other embodiments, the lentiviral Tat peptide is a human immunodeficiency virus Tat peptide.

According to some embodiments, the Tat peptide has the sequence of RKKRRQRRR (SEQ ID NO: 129). See, e.g., Yamamoto et al., "A Novel RNA Motif that Binds Efficiently and Specifically to the Ttat Protein of HIV and Inhibits the Trans-Activation by Tat of Transcription In Vitro and In Vivo," Genes Cells 5:371-388 (2000), which is hereby incorporated by reference in its entirety.

According to some embodiments, the Tat peptide has the consensus sequence of SEQ ID NO: 54 as follows: XXXXXXXXXXXXXXXX, where X at position 1 can be S or A; X at position 2 can be G or A; X at position 3 can be P or A; X at position 4 can be R or K; X at position 5 can be P, A, I, Y, K, or R; X at position 6 can be R, K, V, or Y; X at position 7 can be G, A, or R; X at position 8 can be T or A; X at position 9 can be R or K; X at position 10 can be G or A; X at position 11 can be K or A; X at position 12 can be G or A; X at position 13 can be R or K; X at position 14 can be I or A; X at position 15 can be R, K, Y, or G; and X at position 16 can be R, K, V, T, or Y. See, e.g., Athanassiou et al., "Structural Mimicry of Retroviral Tat Proteins by Constrained β-Hairpin Peptidomimetics: Ligands with High Affinity and Selectivity for Viral TAR RNA Regulatory Elements," J. Am. Chem. Soc. 126:6906-6913 (2004); Chen & Frankel, "A Peptide Interaction in the Major Groove of RNA Resembles Protein Interactions in the Minor Groove of DNA," Proc. Natl. Acad. Sci. USA 92:5077-5081 (1995); and Koren et al., "The Eukaryotic Proteome is Shaped by E3 Ubiquitin Ligases Targeting C-Terminal Degrons," Cell 173:1622-1635 (2018), which are hereby incorporated by reference in their entirety). For example, the Tat peptide may have the amino acid sequence of SEQ ID NO: 55 as follows: SGPRPRGTRGKGRIRR.

In some embodiments, the lentiviral Tat peptide comprises an RNA binding site. The RNA binding site may correspond to amino acid residues 4-17 of SEQ ID NO: 54 or amino acid residues 4-17 of SEQ ID NO: 55.

In some embodiments, the RNA binding site is specific for an RNA aptamer. An aptamers is a nucleic acid molecule that binds with high affinity and specificity to a target. Nucleic acid aptamers may be single-stranded, partially single-stranded, partially double-stranded, or double-stranded nucleotide sequences. Aptamers include, without limitation, defined sequence segments and sequences comprising nucleotides (e.g., ribonucleotides, nucleotide analogs, modified nucleotides, and nucleotides comprising backbone modifications, branchpoints, and non-nucleotide residues, groups, or bridges). Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

As described herein, the RNA binding site is specific for an RNA aptamer having the consensus sequence of SEQ ID NO: 56 as follows: NNNNN-SHSYWSBMNNNNDSBHBSNNNNN, where N can be A, C, G, or U; S can be C or G; H can be A, C, or U; Y can be C or U; W can be A or U; B can be C, G, or U; M can be A or C; and D can be A, G, or U. Thus, in some embodiments, the RNA aptamer has the sequence of wild-type TAR RNA (SEQ ID NO: 57) as follows: GGCUCGUGUAGCUCAUUAGCUCCGAGCC.

According to some embodiments, the RNA binding site is specific for an RNA aptamer having the consensus sequence of SEQ ID NO: 58 as follows: NNNNN- SHCYSWSBMNNNNDSBHBSNNNNN, where N can be A, C, G, or U; S can be C or G; H can be A, C, or U; Y can be C or U; W can be A or U; B can be C, G, or U; M can be A or C; and D can be A, G, or U. Thus, in some embodiments, the RNA aptamer has the sequence of TAR Variant-1 (SEQ ID NO: 59) as follows: GGCUCGU-CUGAGCUCAUUAGCUCCGAGCC.

In other embodiments, the RNA binding site is specific for an RNA aptamer having the consensus sequence of SEQ ID NO: 60 as follows: NNNNNSI-TYSWSBMNNNNDSBHBSNNNNN, where N can be A, C, G, or U; S can be C or G; H can be A, C, or U; Y can be C or U; W can be A or U; B can be C, G, or U; M can be A or C; and D can be A, G, or U. Thus, in some embodiments, the RNA aptamer has the sequence of TAR Variant-2 (Pepper; SEQ ID NO: 61) as follows: GGCUCGUUGAG-CUCAUUAGCUCCGAGCC.

In further embodiments, the RNA binding site is specific for an RNA aptamer having the sequence of HIV TAR (SEQ ID NO: 128) as follows: ACGAAGC-UUGAUCCCGUUUGCCGGUCGAUCGCUUCGA.

As used herein, the term "degron" or "degradation signal" or "degron peptide" refers to an amino acid element within a protein that is sufficient for recognition and degradation by a proteolytic system. In some embodiments, the degron is a ubiquitin-pathway degron. In accordance with such embodiments, the degron comprises a region specific for E3 binding (see, e.g., Ravid & Hochstrasser, "Diversity of Degradation Signals in the Ubiquitin-Proteasome System," *Nat. Rev. Mol. Cell Biol.* 9:679-689 (2008), which is hereby incorporated by reference in its entirety).

The degron peptide may be selected from a monopeptide, a dipeptide, a tripeptide, a tetrapeptide, a pentapeptide, a hexapeptide, a heptapeptide, or an octapeptide. Exemplary degron peptides are well known in the art and are listed in Table 6 below.

TABLE 6

Exemplary Degron Peptides

| Degron Peptide | Amino Acid Sequences |
| --- | --- |
| Monopeptide | P, E |
| Dipeptide | RG, GG, EE, AP, RP, NP, DP, CP, EP, QP, GP, HP, IP, LP, KP, MP, FP, PP, SP, TP, WP, YP, VP, SA, SR, SN, SD, SC, SE, SQ, SG, SH, SI, SL, SK, SM, SF, SP, SS, ST, SW, SY, SV, AN, RN, NN, DN, CN, EN, QN, GN, HN, IN, LN, KN, MN, FN, PN, SN, TN, WN, YN, VN, AD, RD, ND, DD, CD, ED, QD, GD, HD, ID, LD, KD, MD, FD, PD, SD, TD, WD, YD, VD, CA, CR, CN, CD, CC, CE, CQ, CG, CH, CI, CL, CK, CM, CF, CP, CS, CT, CW, CY, CV, AE, RE, NE, DE, CE, EE, QE, GE, HE, IE, LE, KE, ME, FE, PE, SE, TE, WE, YE, VE |

In some embodiments, the degron peptide is SEQ ID NO: 130 as follows: RRRG. In accordance with such embodiments, the destabilization domain has the sequence of HIV Tat-RRRG (SEQ ID NO: 127) as follows: RKKRRQRRRG.

In other embodiments, the degron peptide is selected from the group consisting of FKBP12, dihydrofolate reductase, and derivates thereof. See, e.g., Rakhit et al., "Evaluation of FKBP and DHFR Based Destabilizing Domains in *Saccharomyces Cerevisiae,*" *Bioorg. Med. Chem. Lett.* 21:4965-4968 (2011) and Iwamoto et al., "A General Chemical Method to Regulate Protein Stability in the Mammalian Central Nervous System," *Chem. Biol.* 17:981-988 (2010), which are hereby incorporated by reference in their entirety). In some embodiments, the FKBP12 is a human FKBP12. In some embodiments, the dihydrofolate reductase is an *E. coli* dehydrate reductase (ecDHFR). As described herein, aptamers that selectively bind to FKBP12, DHFR, or derivatives thereof may be used to confer stability to a protein of interest comprising FKBP12, ecDHFR, or a derivative thereof as a fusion partner.

In some embodiments, the destabilization domain has the consensus sequence of SEQ ID NO: 62 as follows: XXXXXXXXXXXXXXXXXx, where X at position 1 can be S or A; X at position 2 can be G or A; X at position 3 can be P or A; X at position 4 can be R or K; X at position 5 can be P, A, I, Y, K, or R; X at position 6 can be R, K, V, or Y; X at position 7 can be G, A, or R; X at position 8 can be T or A; X at position 9 can be R or K; X at position 10 can be G or A; X at position 11 can be K or A; X at position 12 can be G or A; X at position 13 can be R or K; X at position 14 can be I or A; X at position 15 can be R, K, Y, or G; X at position 16 can be R, K, V, T, or Y; X at position 17 can be any amino acid but preferably R, G, E, S, or C; and x at position 18 is optional and can be any amino acid, but preferably G, E, O, N, D, or E.

In some embodiments the destabilization domain has the sequence of tDeg (SEQ ID NO: 63) as follows: SGPR-PRGTRGKGRRIRRRG.

The nucleic acid molecule described herein may further comprise a third nucleic acid sequence encoding a second protein of interest, wherein the third nucleic acid sequence is located between the first nucleic acid sequence and second nucleic acid sequence. Suitable proteins of interest are described in more detail above and include, without limitation, a fluorescent protein, a bioluminescent protein, an enzyme, or a transcriptional regulator.

Another aspect of the invention relates to a nucleic acid molecule encoding a lentiviral transactivator of transcription (Tar) RNA aptamer sequence.

In some embodiments, the lentiviral transactivator of transcription (Tar) RNA aptamer sequence is a bovine immunodeficiency virus (BIV) Tar sequence. In other embodiments, the lentiviral transactivator of transcription (Tar) RNA sequence is a human immunodeficiency virus (HIV) Tar sequence.

According to some embodiments, the nucleic acid molecule encoding the lentiviral Tar RNA sequence is a DNA molecule according to the consensus sequence of SEQ ID NO: 64 as follows: NNNNN-SHSYWSBMNNNNDSBHBSNNNNN, where N can be A, C, G, or T; S can be C or G; H can be A, C, or T; Y can be C or T; W can be A or T; B can be C, G, or T; M can be A or C; and D can be A, G, or T. For example, the nucleic acid molecule encoding the lentiviral Tar RNA sequence may be a DNA molecule encoding wild-type TAR RNA as follows: GGCTCGTGTAGCTCATTAGCTCCGAGCC (SEQ ID NO: 65).

According to some embodiments, the nucleic acid molecule encoding the lentiviral TAR RNA sequence is a DNA molecule according to the consensus sequence of SEQ ID NO: 66 as follows: NNNNN-SHCYSWSBMNNNNDSBHBSNNNNN, where N can be A, C, G, or T; S can be C or G; H can be A, C, or T; Y can be C or T; W can be A or T; B can be C, G, or T; M can be A or C; and D can be A, G, or T. For example, the nucleic acid molecule encoding the lentiviral Tar RNA sequence may be a DNA molecule encoding TAR Variant-1 as follows: GGCTCGTCTGAGCTCATTAGCTCCGAGCC (SEQ ID NO: 67).

According to some embodiments, the nucleic acid molecule encoding the lentiviral TAR RNA sequence is a DNA molecule according to the consensus sequence of SEQ ID NO: 68 as follows: NNNNNSI-TYSWSBMNNNNDSBHBSNNNNN, where N can be A, C, G, or T; S can be C or G; H can be A, C, or T; Y can be C or T; W can be A or T; B can be C, G, or T; M can be A or C; and D can be A, G, or T. For example, the nucleic acid molecule encoding the lentiviral Tar RNA sequence may be a DNA molecule encoding TAR Variant-2 (Pepper) as follows: GGCTCGTTGAGCTCATTAGCTCCGAGCC (SEQ ID NO: 69).

Suitable additional lentiviral transactivator of transcription (Tar) RNA aptamer sequences of the present application are shown in Table 7 below.

TABLE 7

TAR RNA Sequences

| TAR RNA | Sequence | SEQ ID NO: |
|---|---|---|
| (Pepper)$_{10}$tag | GGCUCGUCUGAGCUCAUUAGCUCCGAGCCGUCCAGCGCAAACUAU UACGAAAAACAUCCGACGGGCUCGUUGAGCUCAUUAGCUCCGAGC CCGCUGCGGAAAACCUCACAAAAACACGACAAACGGGCUCGUUGA GCUCAUUAGCUCCGAGCCCGCCGACAACCCACAAACUUACAACCA GGCAAACGGCUCGUCUGAGCUCAUUAGCUCCGAGCCGUAUCAAGA CCGAACGGCGCAAGAUAUUGACACGGGCUCGUUGAGCUCAUUAGC UCCGAGCCCGACCUCGCUAGAUAUGUUAGGUUCUUAGGCAUUGGC UCGUUGAGCUCAUUAGCUCCGAGCCAAAGAUCGACUGCAAUUCCG AUUAGACGUACACGGCUCGUCUGAGCUCAUUAGCUCCGAGCCGAU CCAACCUACUUCCUCCAUAACUAACCUCCGGCUCGUUGAGCUCAU UAGCUCCGAGCCGAUCAUAACGCAAUACCGUACACUGUCCAAUCC GGCUCGUUGAGCUCAUUAGCUCCGAGCCGGACAACCAAUCGACAU ACAUCACACCACAACUCGGCUCGUCUGAGCUCAUUAGCUCCGAGC C | 70 |
| (F30-1xPepper)$_{10}$tag | UUGCCAUGUGUAUGUGGGAUGCGUUGCCACGUUUCCCACAUACUC UGAUGAUCCGCUAGCAAAGGCUCGUCUGAGCUCAUUAGCUCCGAG CCCGAGGUACCGGAUCAUUCAUGGCAAGUCCAGCGCAAUCUAUUA CGAAAAUCAUCCGACGUCGCGAUGUCUAUGCGGGAUGCGUUGCCA CGUUUCCCGCAUAGUCUGAUCAUCCGCUAGCAAAGGCUCGUUGAG CUCAUUAGCUCCGAGCCCGAGGUACCGGAUGAUUCAUCGCGACGC UGCGGAAAAUCUCACAAAAUCACGUCAAACGUCGCCGUGUGUGUG UAGGAUGCGUUGCCACGUUUCCUACACACUCUGACGAUCCGCUAG CAAAGGCUCGUUGAGCUCAUUAGCUCCGAGCCCGAGGUACCGGAU CGUUCACGGCGACGCCGAUAAUCCACAUACUUACAAUCAGGCAAU CUUGCCAUGUGUAUGUGGGAUGCGUUGCCACGUUUCCCACAUACU CUGAUGAUCCGCUAGCAAAGGCUCGUUGAGCUCAUUAGCUCCGAG CCCGAGGUACCGGAUCAUUCAUGGCAAGUAUCAAGAUCGAACGGC GCAAGAUAUUGUCACGUCGCGAUGUCUAUGCGGGAUGCGUUGCCA CGUUUCCCGCAUAGUCUGAUCAUCCGCUAGCAAAGGCUCGUCUGA GCUCAUUAGCUCCGAGCCCGAGGUACCGGAUGAUUCAUCGCGACG UCCUCGCUAGAUAUGUUAGGUUCUUAGGCAUUUCGCCGUGUGUGU GUAGGAUGCGUUGCCACGUUUCCUACACACUCUGACGAUCCGCUA GCAAAGGCUCGUUGAGCUCAUUAGCUCCGAGCCCGAGGUACCGGA UCGUUCACGGCGAAAAGAUCGUCUGCAAUUCCGAUUAGACGUACA CUUGCCAUGUGUAUGUGGGAUGCGUUGCCACGUUUCCCACAUACU CUGAUGAUCCGCUAGCAAAGGCUCGUUGAGCUCAUUAGCUCCGAG CCCGAGGUACCGGAUCAUUCAUGGCAAGAUCCAAGCUACUUCCUC CAUACCUAUCCUCCUCGCGAUGUCUAUGCGGGAUGCGUUGCCACG UUUCCCGCAUAGUCUGAUCAUCCGCUAGCAAAGGCUCGUUGAGCU CAUUAGCUCCGAGCCCGAGGUACCGGAUGAUUCAUCGCGAGAUCA UAACGCAAUACCGUACACUGUCCAAUCCUCGCCGUGUGUGUGUAG GAUGCGUUGCCACGUUUCCUACACACUCUGACGAUCCGCUAGCAA AGGCUCGUCUGAGCUCAUUAGCUCCGAGCCCGAGGUACCGGAUCG UUCACGGCGAGGAUAAUCAAUCCACAUACAUCACACCACAAUUCU UGCCAUGUGUAUGUGGGAUGCGUUGCCACGUUUCCCACAUACUCU GAUGAUCCGCUAGCAAAGGCUCGUCUGAGCUCAUUAGCUCCGAGC CGAGGUACCGGAUCAUUCAUGGCAA | 71 |
| (Pepper)$_{20}$-tag | GGCUCGUCUGAGCUCAUUAGCUCCGAGCCGUCCAGCGCAAACUAU UACGAAAAACAUCCGACGGGCUCGUUGAGCUCAUUAGCUCCGAGC CCGCUGCGGAAAACCUCACAAAAACACGACAAACGGGCUCGUUGA GCUCAUUAGCUCCGAGCCCGCCGACAACCCACAAACUUACAACCA GGCAAACGGCUCGUCUGAGCUCAUUAGCUCCGAGCCGUAUCAAGA CCGAACGGCGCAAGAUAUUGACACGGGCUCGUUGAGCUCAUUAGC UCCGAGCCCGACCUCGCUAGAUAUGUUAGGUUCUUAGGCAUUGGC UCGUUGAGCUCAUUAGCUCCGAGCCAAAGAUCGACUGCAAUUCCG | 72 |

TABLE 7-continued

TAR RNA Sequences

| TAR RNA | Sequence | SEQ ID NO: |
|---|---|---|
| | AUUAGACGUACACGGCUCGUCUGAGCUCAUUAGCUCCGAGCCGAU<br>CCAACCUACUUCCUCCAUAACUAACCUCCGGCUCGUUGAGCUCAU<br>UAGCUCCGAGCCGAUCAUAACGCAAUACCGUACACUGUCCAAUCC<br>GGCUCGUUGAGCUCAUUAGCUCCGAGCCGGACAACCAAUCGACAU<br>ACAUCACACCACAACUCGGCUCGUCUGAGCUCAUUAGCUCCGAGC<br>CGAAUUGGUCGUUCUUCUUGGCGGCCGCUCGACUAAGGUGACAAC<br>UGGACAAACCCUCGGCUCGUUGAGCUCAUUAGCUCCGAGCCGACU<br>CUCACCAACAAGACAAAAACUACUCUUCUAGGCUCGUUGAGCUCA<br>UUAGCUCCGAGCCUAAACACUCAAGCAUACAUUGUGCCUAUUUCU<br>UGGCUCGUCUGAGCUCAUUAGCUCCGAGCCAUGCUCUCACGAAUU<br>UCAAAACACGGACAAGGGGCUCGUUGAGCUCAUUAGCUCCGAGCC<br>CGUUCCACGUCCAAUACGAUUACUUACCUUUCGGGCUCGUUGAGC<br>UCAUUAGCUCCGAGCCCGCAGCUACAUCACUUCCACUCAGGACAU<br>UCAAGGGCUCGUCUGAGCUCAUUAGCUCCGAGCCCUCCACAAGUC<br>UCAACCACAGAAACUACCAAAUGGGCUCGUUGAGCUCAUUAGCUC<br>CGAGCCCACUCCUACCUCAAACCUCUUCCCACAAAACUGGGGCUC<br>GUUGAGCUCAUUAGCUCCGAGCCCCCAUUCCAACAUACCAAAUCA<br>AAAACAAUUACUGGCUCGUCUGAGCUCAUUAGCUCCGAGCCAGCC<br>CACAUCUCUCACUACUAUCAAAAACCAAACGGCUCGUUGAGCUCA<br>UUAGCUCCGAGCC | |
| (F30-<br>2xPepper)₁₀tag | UUGCCAUGUGUAUGUGGGAAGCGUAGAAAGGCUCGUUGAGCUCAU<br>UAGCUCCGAGCCCGACUACGUUUCCCACAUACUCUGAUGAUCCGC<br>UAGCAAAGGCUCGUCUGAGCUCAUUAGCUCCGAGCCCGAGGUACC<br>GGAUCAUUCAUGGCAAGUCCAGCGCAAUCUAUUACGAAAAUCAUC<br>CGACGUCGCGAUGUCUAUGCGGGAAGCGUAGAAAGGCUCGUCUGA<br>GCUCAUUAGCUCCGAGCCCGACUACGUUUCCCGCAUAGUCUGAUC<br>AUCCGCUAGCAAAGGCUCGUUGAGCUCAUUAGCUCCGAGCCCGAG<br>GUACCGGAUGAUUCAUCGCGACGCUGCGGAAAAUCUCACAAAAUC<br>ACGUCAAACGUCGCCGUGUGUGUAGGAAGCGUAGAAAGGCUCG<br>UCUGAGCUCAUUAGCUCCGAGCCCGACUACGUUUCCUACACACUC<br>UGACGAUCCGCUAGCAAAGGCUCGUUGAGCUCAUUAGCUCCGAGC<br>CCGAGGUACCGGAUCGUUCACGGCGACGCCGAUAAUCCACAUACU<br>UACAAUCAGGCAAUCUUGCCAUGUGUAUGUGGGAAGCGUAGAAAG<br>GCUCGUUGAGCUCAUUAGCUCCGAGCCCGACUACGUUUCCCACAU<br>ACUCUGAUGAUCCGCUAGCAAAGGCUCGUUGAGCUCAUUAGCUCC<br>GAGCCCGAGGUACCGGAUCAUUCAUGGCAAGUAUCAAGAUCGAAC<br>GGCGCAAGAUAUUGUCACGUCGCGAUGUCUAUGCGGGAAGCGUAG<br>AAAGGCUCGUUGAGCUCAUUAGCUCCGAGCCCGACUACGUUUCCC<br>GCAUAGUCUGAUCAUCCGCUAGCAAAGGCUCGUCUGAGCUCAUUA<br>GCUCCGAGCCCGAGGUACCGGAUGAUUCAUCGCGACGUCCUCGCU<br>AGAUAUGUUAGGUUCUUAGGCAUUUCGCCGUGUGUGUGUAGGAAG<br>CGUAGAAAGGCUCGUUGAGCUCAUUAGCUCCGAGCCCGACUACGU<br>UUCCUACACACUCUGACGAUCCGCUAGCAAAGGCUCGUCUGAGCU<br>CAUUAGCUCCGAGCCCGAGGUACCGGAUCGUUCACGGCGAAAAGA<br>UCGUCUGCAAUUCCGAUUAGACGUACACUUGCCAUGUGUAUGUGG<br>GAAGCGUAGAAAGGCUCGUCUGAGCUCAUUAGCUCCGAGCCCGAC<br>UACGUUUCCCACAUACUCUGAUGAUCCGCUAGCAAAGGCUCGUUG<br>AGCUCAUUAGCUCCGAGCCCGAGGUACCGGAUCAUUCAUGGCAAG<br>AUCCAAGCUACUUCCUCCAUACCUAUCCUCCUCGCGAUGUCUAUG<br>CGGGAAGCGUAGAAAGGCUCGUCUGAGCUCAUUAGCUCCGAGCCC<br>GACUACGUUUCCCGCAUAGUCUGAUCAUCCGCUAGCAAAGGCUCG<br>UUGAGCUCAUUAGCUCCGAGCCCGAGGUACCGGAUGAUUCAUCGC<br>GAGAUCAUAACGCAAUACCGUACACUGUCCAAUCCUCGCCGUGUG<br>UGUGUAGGAAGCGUAGAAAGGCUCGUCUGAGCUCAUUAGCUCCGA<br>GCCCGACUACGUUUCCUACACACUCUGACGAUCCGCUAGCAAAGG<br>CUCGUUGAGCUCAUUAGCUCCGAGCCCGAGGUACCGGAUCGUUCA<br>CGGCGAGGAUAAUCAAUCCACAUACAUCACACCACAAUUCUUGCC<br>AUGUGUAUGUGGGAAGCGUAGAAAGGCUCGUCUGAGCUCAUUAGC<br>UCCGAGCCCGACUACGUUUCCCACAUACUCUGAUGAUCCGCUAGC<br>AAAGGCUCGUCUGAGCUCAUUAGCUCCGAGCCCGAGGUACCGGAU<br>CAUUCAUGGCAA | 73 |

In some embodiments, the nucleic acid molecule further encodes at least one additional RNA aptamer. Thus, in some embodiments, the nucleic acid molecule may encode a lentiviral transactivator of transcription (Tar) RNA aptamer operably coupled to at least one additional RNA aptamer. The at least one additional aptamer may be a S-adenosyl-methionine (SAM)-binding aptamer. For example, the nucleic acid molecule may encodes a SAM-binding aptamer operably linked to the lentiviral transactivator of transcription (Tar) RNA aptamer. As described herein, binding of SAM to its aptamer promotes folding of other linked aptamers, such as Pepper. In this way, the expressed RNA is a "sensor" which couples SAM levels to Pepper folding.

Also contemplated are nucleic acid molecules encoding a protein-binding RNA sequence. Thus, in some embodiments, the nucleic acid molecule encodes a non-lentiviral transactivator of transcription (Tar) RNA sequence. In accordance with such embodiments, the protein-binding RNA sequence is BoxB or RRE.

Some embodiments of the present application relate to a vector comprising a nucleic acid molecule described herein (i.e., a nucleic acid molecule encoding an RNA-regulated fusion protein and/or a lentiviral transactivator of transcription (Tar) RNA sequence). As used herein, the term vector means any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5' to 3') orientation and correct reading frame. The vector contains the necessary elements for the transcription and/or translation of the inserted protein and/or RNA coding sequences of the present application.

In one embodiment, the vector is a plasmid. Numerous vectors suitable for use in the compositions of the present application are known to those of skill in the art, and many are commercially available. The following vectors are provided by way of example; for eukaryotic cells: pcDNA3.1 (+), Tornado (Litke & Jaffrey, "Highly Efficient Expression of Circular RNA Aptamers in Cells Using Autocatalytic Transcripts," Nat. Biotechnol. 37(6):667-675(2019), which is hereby incorporated by reference in its entirety), pXT1, pSG5 (Stratagene), pSVK3, pBPV, pMSG, and pSVLSV40 (Pharmacia). However, any other vector may be used so long as it is compatible with the cell.

In another embodiment, the vector is a viral vector. Suitable viral expression vectors include, but are not limited to, viral vectors based on vaccinia virus; poliovirus; adenovirus (see, e.g., PCT Patent Application Publication Nos. WO 94/12649 to Gregory et al., WO 93/03769 to Crystal et al., WO 93/19191 to Haddada et al., WO 94/28938 to Wilson et al., WO 95/11984 to Gregory, and WO 95/00655 to Graham, which are hereby incorporated by reference in their entirety); adeno-associated virus (see, e.g., Flannery et al., "Efficient Photoreceptor-Targeted Gene Expression In Vivo by Recombinant Adeno-Associated Virus," PNAS 94:6916-6921 (1997); Bennett et al., "Real-Time, Noninvasive In Vivo Assessment of Adeno-Associated Virus-Mediated Retinal Transduction," Invest. Opthalmol. Vis. Sci. 38:2857-2863 (1997); Jomary et al., "Nonviral Ocular Gene Transfer," Gene Ther. 4:683-690 (1997); Rolling et al., "Evaluation of Adeno-Associated Virus-Mediated Gene Transfer into the Rat Retina by Clinical Fluorescence Photography," Hum. Gene. Ther. 10:641-648 (1999); Ali et al., "Gene Transfer Into the Mouse Retina Mediated by an Adeno-Associated Viral Vector," Hum. Mol. Genet. 5:591-594 (1996); Samulski et al., "Helper-Free Stocks of Recombinant Adeno-Associated Viruses: Normal Integration Does not Require Viral Gene Expression," J. Vir. 63:3822-3828 (1989); Mendelson et al., "Expression and Rescue of a Nonselected Marker from an Integrated AAV Vector," Virol. 166:154-165 (1988); and Flotte et al., "Stable In Vivo Expression of the Cystic Fibrosis Transmembrane Conductance Regulator With an Adeno-Associated Virus Vector," PNAS 90:10613-10617 (1993), which are hereby incorporated by reference in their entirety); SV40; herpes simplex virus; human immunodeficiency virus (see, e.g., Miyoshi et al., "Stable and Efficient Gene Transfer into the Retina Using an HIV-Based Lentiviral Vector," PNAS 94:10319-10323 (1997), which is hereby incorporated by reference in its entirety); a retroviral vector, e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus and the like.

As described herein supra, the nucleic acid molecules encoding a protein of interest described herein may be inserted into a vector in the sense (i.e., 5' to 3') direction, such that the nucleic acid sequence encoding an RNA-regulated fusion protein is properly oriented for the expression of the encoded protein under the control of a promoter of choice. In some embodiments, the nucleic acid molecules encoding a RNA aptamer are inserted into the vector in the sense direction, such that the nucleic acid molecule encoding the RNA aptamer is properly oriented for the expression of a desired RNA aptamer. Single or multiple nucleic acid molecules may be ligated into an appropriate vector in this way, under the control of a suitable promoter, to prepare a nucleic acid construct. A promoter is a DNA sequence which contains the binding site for RNA polymerase and initiates transcription of a downstream nucleic acid sequence. In one embodiment, the vector comprises a promoter. Thus, in some embodiments, the vector comprises a nucleic acid molecule encoding a lentiviral transactivator of transcription (Tar) aptamer (e.g., Pepper) operably coupled to a promoter. In other embodiments, the vector comprises a nucleic acid molecule encoding a lentiviral transactivator of transcription (Tar) aptamer (e.g., Pepper) and at least one additional aptamer sequence (e.g., a S-adenosylmethionine (SAM)-binding aptamer) operably coupled to a promoter.

The promoter may be a constitutively active promoter (i.e., a promoter that is constitutively in an active or "on" state), an inducible promoter (i.e., a promoter whose state, active or inactive state, is controlled by an external stimulus, e.g., the presence of a particular temperature, compound, or protein), a spatially restricted promoter (i.e., transcriptional control element, enhancer, etc.) (e.g., tissue specific promoter, cell type specific promoter, etc.), or a temporally restricted promoter (i.e., the promoter is in the "on" state or "off" state during specific stages of a biological process).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., RNA Polymerase I, RNA Polymerase II, RNA Polymerase III). The promoter may be a viral promoter. Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., "U6 Promoter-Driven siRNAs with Four Uridine 3' Overhangs Efficiently Suppress Targeted Gene Expression in Mammalian Cells," Nat. Biotechnol. 20:497-500 (2002), which is hereby incorporated by reference in its entirety), an enhanced U6 promoter (e.g., Xia et al., "An Enhanced U6 Promoter for Synthesis of Short Hairpin RNA," Nucleic Acids Res. 31(17):e100 (2003), which is hereby incorporated by reference in its entirety), a human H1 promoter ("H1"), and the like. In some embodiments the promoter is a phage promoter, e.g., a T7 promoter that has been engineered to be expressed in a mammalian cell.

Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter, steroid-regulated promoter, metal-regulated promoter, estrogen receptor-regulated promoter, etc. Inducible promoters can therefore be regulated by molecules including, but not limited to, doxycycline, RNA polymerase, e.g., T7 RNA polymerase, an estrogen receptor, an estrogen receptor fusion, etc.

In some embodiments, the promoter is a eukaryotic RNA polymerase promoter or a derivative thereof. Exemplary RNA polymerase II promoters include, without limitation, cytomegalovirus ("CMV"), phosphoglycerate kinase-1 ("PGK-1"), and elongation factor 1α ("EF1α") promoters. In yet another embodiment, the promoter is a eukaryotic RNA polymerase III promoter selected from the group consisting of U6, H1, 56, 7SK, and derivatives thereof.

The RNA Polymerase promoter may be mammalian. Suitable mammalian promoters include, without limitation, human, murine, bovine, canine, feline, ovine, porcine, ursine, and simian promoters. In one embodiment, the RNA polymerase promoter sequence is a human promoter.

According to one embodiment, the vector is a plasmid and has the sequence of pCMV-mCherry-(F30-2×Pepper)$_{10}$ (SEQ ID NO: 74; GenBank Accession No. MN052904.1, which is hereby incorporated by reference) as follows:

```
   1 GACGGATCGG GAGATCTCCC GATCCCCTAT GGTGCACTCT CAGTACAATC
  51 TGCTCTGATG CCGCATAGTT AAGCCAGTAT CTGCTCCCTG CTTGTGTGTT
 101 GGAGGTCGCT GAGTAGTGCG CGAGCAAAAT TAAGCTACA ACAAGGCAAG
 151 GCTTGACCGA CAATTGCATG AAGAATCTGC TTAGGGTTAG GCGTTTTGCG
 201 CTGCTTCGCG ATGTACGGGC CAGATATACG CGTTGACATT GATTATTGAC
 251 TAGTTATTAA TAGTAATCAA TTACGGGGTC ATTAGTTCAT AGCCCATATA
 301 TGGAGTTCCG CGTTACATAA CTTACGGTAA ATGGCCCGCC TGGCTGACCG
 351 CCCAACGACC CCCGCCCATT GACGTCAATA ATGACGTATG TTCCCATAGT
 401 AACGCCAATA GGGACTTTCC ATTGACGTCA ATGGGTGGAG TATTTACGGT
 451 AAACTGCCCA CTTGGCAGTA CATCAAGTGT ATCATATGCC AAGTACGCCC
 501 CCTATTGACG TCAATGACGG TAAATGGCCC GCCTGGCATT ATGCCCAGTA
 551 CATGACCTTA TGGGACTTTC CTACTTGGCA GTACATCTAC GTATTAGTCA
 601 TCGCTATTAC CATGGTGATG CGGTTTTGGC AGTACATCAA TGGGCGTGGA
 651 TAGCGGTTTG ACTCACGGGG ATTTCCAAGT CTCCACCCCA TTGACGTCAA
 701 TGGGAGTTTG TTTTGGCACC AAAATCAACG GGACTTTCCA AAATGTCGTA
 751 ACAACTCCGC CCCATTGAC GCAAATGGG GGTAGGCGTG TACGGTGGGA
 801 GGTCTATATA AGCAGAGCTC TCTGGCTAAC TAGAGAACCC ACTGCTTACT
 851 GGCTTATCGA AATTAATACG ACTCACTATA GGGAGACCCA AGCTGGCTAG
 901 CGTTTAAACT TAAGCTTGCC ACCATGGTGA GCAAGGGCGA GGAGGATAAC
 951 ATGGCCATCA TCAAGGAGTT CATGCGCTTC AAGGTGCACA TGGAGGGCTC
1001 CGTGAACGGC CACGAGTTCG AGATCGAGGG CGAGGGCGAG GGCCGCCCCT
1051 ACGAGGGCAC CCAGACCGCC AAGCTGAAGG TGACCAAGGG TGGCCCCCTG
1101 CCCTTCGCCT GGGACATCCT GTCCCCTCAG TTCATGTACG GCTCCAAGGC
1151 CTACGTGAAG CACCCCGCCG ACATCCCCGA CTACTTGAAG CTGTCCTTCC
1201 CCGAGGGCTT CAAGTGGGAG CGCGTGATGA ACTTCGAGGA CGGCGGCGTG
1251 GTGACCGTGA CCCAGGACTC CTCCCTGCAG GACGGCGAGT TCATCTACAA
1301 GGTGAAGCTG CGCGGCACCA ACTTCCCCTC CGACGGCCCC GTAATGCAGA
1351 AGAAGACCAT GGGCTGGGAG GCCTCCTCCG AGCGGATGTA CCCCGAGGAC
1401 GGCGCCCTGA AGGGCGAGAT CAAGCAGAGG CTGAAGCTGA AGGACGGCGG
1451 CCACTACGAC GCTGAGGTCA AGACCACCTA CAAGGCCAAG AAGCCCGTGC
1501 AGCTGCCCGG CGCCTACAAC GTCAACATCA AGTTGGACAT CACCTCCCAC
1551 AACGAGGACT ACACCATCGT GGAACAGTAC GAACGCGCCG AGGGCCGCCA
```

-continued

```
1601  CTCCACCGGC GGCATGGACG AGCTGTACAA GTAACTCGAG ATCCGTTACG
1651  GCCGGAATCA ATCGCTAATC ACTCAACTTG CCATGTGTAT GTGGGAAGCG
1701  TAGAAAGGCT CGTTGAGCTC ATTAGCTCCG AGCCCGACTA CGTTTCCCAC
1751  ATACTCTGAT GATCCGCTAG CAAAGGCTCG TCTGAGCTCA TTAGCTCCGA
1801  GCCCGAGGTA CCGGATCATT CATGGCAAGT CCAGCGCAAT CTATTACGAA
1851  AATCATCCGA CGTCGCGATG TCTATGCGGG AAGCGTAGAA AGGCTCGTCT
1901  GAGCTCATTA GCTCCGAGCC CGACTACGTT TCCCGCATAG TCTGATCATC
1951  CGCTAGCAAA GGCTCGTTGA GCTCATTAGC TCCGAGCCCG AGGTACCGGA
2001  TGATTCATCG CGACGCTGCG GAAAATCTCA CAAAATCACG TCAAACGTCG
2051  CCGTGTGTGT GTAGGAAGCG TAGAAAGGCT CGTCTGAGCT CATTAGCTCC
2101  GAGCCCGACT ACGTTTCCTA CACACTCTGA CGATCCGCTA GCAAAGGCTC
2151  GTTGAGCTCA TTAGCTCCGA GCCCGAGGTA CCGGATCGTT CACGGCGACG
2201  CCGATAATCC ACATACTTAC AATCAGGCAA TCTTGCCATG TGTATGTGGG
2251  AAGCGTAGAA AGGCTCGTTG AGCTCATTAG CTCCGAGCCC GACTACGTTT
2301  CCCACATACT CTGATGATCC GCTAGCAAAG GCTCGTTGAG CTCATTAGCT
2351  CCGAGCCCGA GGTACCGGAT CATTCATGGC AAGTATCAAG ATCGAACGGC
2401  GCAAGATATT GTCACGTCGC GATGTCTATG CGGGAAGCGT AGAAAGGCTC
2451  GTTGAGCTCA TTAGCTCCGA GCCCGACTAC GTTTCCCGCA TAGTCTGATC
2501  ATCCGCTAGC AAAGGCTCGT CTGAGCTCAT TAGCTCCGAG CCCGAGGTAC
2551  CGGATGATTC ATCGCGACGT CCTCGCTAGA TATGTTAGGT TCTTAGGCAT
2601  TTCGCCGTGT GTGTGTAGGA AGCGTAGAAA GGCTCGTTGA GCTCATTAGC
2651  TCCGAGCCCG ACTACGTTTC CTACACACTC TGACGATCCG CTAGCAAAGG
2701  CTCGTCTGAG CTCATTAGCT CCGAGCCCGA GGTACCGGAT CGTTCACGGC
2751  GAAAAGATCG TCTGCAATTC CGATTAGACG TACACTTGCC ATGTGTATGT
2801  GGGAAGCGTA GAAAGGCTCG TCTGAGCTCA TTAGCTCCGA GCCCGACTAC
2851  GTTTCCCACA TACTCTGATG ATCCGCTAGC AAAGGCTCGT TGAGCTCATT
2901  AGCTCCGAGC CCGAGGTACC GGATCATTCA TGGCAAGATC CAAGCTACTT
2951  CCTCCATACC TATCCTCCTC GCGATGTCTA TGCGGGAAGC GTAGAAAGGC
3001  TCGTCTGAGC TCATTAGCTC CGAGCCCGAC TACGTTTCCC GCATAGTCTG
3051  ATCATCCGCT AGCAAAGGCT CGTTGAGCTC ATTAGCTCCG AGCCCGAGGT
3101  ACCGGATGAT TCATCGCGAG ATCATAACGC AATACCGTAC ACTGTCCAAT
3151  CCTCGCCGTG TGTGTGTAGG AAGCGTAGAA AGGCTCGTCT GAGCTCATTA
3201  GCTCCGAGCC CGACTACGTT TCCTACACAC TCTGACGATC CGCTAGCAAA
3251  GGCTCGTTGA GCTCATTAGC TCCGAGCCCG AGGTACCGGA TCGTTCACGG
3301  CGAGGATAAT CAATCCACAT ACATCACACC ACAATTCTTG CCATGTGTAT
3351  GTGGGAAGCG TAGAAAGGCT CGTCTGAGCT CATTAGCTCC GAGCCCGACT
3401  ACGTTTCCCA CATACTCTGA TGATCCGCTA GCAAAGGCTC GTCTGAGCTC
3451  ATTAGCTCCG AGCCCGAGGT ACCGGATCAT TCATGGCAAG AATTGGTCGT
3501  TCTTCTTGGC GGCCGCTCGA CTAAATCACC GGTAATCTTC TTGTCCATCT
3551  AGACCTTATA AAGATCTTTG TACAAGGGCC CGTTTAAACC CGCTGATCAG
```

```
3601 CCTCGACTGT GCCTTCTAGT TGCCAGCCAT CTGTTGTTTG CCCCTCCCCC
3651 GTGCCTTCCT TGACCCTGGA AAGGTGCCAC TCCCACTGTC CTTTCCTAAT
3701 AAAATGAGGA AATTGCATCG CATTGTCTGA GTAGGTGTCA TTCTATTCTG
3751 GGGGGTGGGG GTGGGGGCAG GACAGCAAGG GGGAGGATTG GGAAGACAAT
3801 AGCAGGCATG CTGGGATGC GGTGGGCTCT ATGGCTTCTG AGGCGGAAAG
3851 AACCAGCTGG GGCTCTAGGG GGTATCCCCA CGCGCCCTGT AGCGGCGCAT
3901 TAAGCGCGGC GGGTGTGGTG GTTACGCGCA GCGTGACCGC TACACTTGCC
3951 AGCGCCCTAG CGCCCGCTCC TTTCGCTTTC TTCCCTTCCT TTCTCGCCAC
4001 GTTCGCCGGC TTTCCCCGTC AAGCTCTAAA TCGGGGCTC CCTTTAGGGT
4051 TCCGATTTAG TGCTTTACGG CACCTCGACC CCAAAAAACT TGATTAGGGT
4101 GATGGTTCAC GTAGTGGGCC ATCGCCCTGA TAGACGGTTT TTCGCCCTTT
4151 GACGTTGGAG TCCACGTTCT TTAATAGTGG ACTCTTGTTC CAAACTGGAA
4201 CAACACTCAA CCCTATCTCG GTCTATTCTT TTGATTTATA AGGGATTTTG
4251 CCGATTTCGG CCTATTGGTT AAAAAATGAG CTGATTTAAC AAAAATTTAA
4301 CGCGAATTAA TTCTGTGGAA TGTGTGTCAG TTAGGGTGTG GAAAGTCCCC
4351 AGGCTCCCCA GCAGGCAGAA GTATGCAAAG CATGCATCTC AATTAGTCAG
4401 CAACCAGGTG TGGAAAGTCC CCAGGCTCCC CAGCAGGCAG AAGTATGCAA
4451 AGCATGCATC TCAATTAGTC AGCAACCATA GTCCCGCCCC TAACTCCGCC
4501 CATCCCGCCC CTAACTCCGC CCAGTTCCGC CCATTCTCCG CCCCATGGCT
4551 GACTAATTTT TTTTATTTAT GCAGAGGCCG AGGCCGCCTC TGCCTCTGAG
4601 CTATTCCAGA AGTAGTGAGG AGGCTTTTTT GGAGGCCTAG CTTTTGCAA
4651 AAAGCTCCCG GGAGCTTGTA TATCCATTTT CGGATCTGAT CAAGAGACAG
4701 GATGAGGATC GTTTCGCATG ATTGAACAAG ATGGATTGCA CGCAGGTTCT
4751 CCGGCCGCTT GGGTGGAGAG GCTATTCGGC TATGACTGGG CACAACAGAC
4801 AATCGGCTGC TCTGATGCCG CCGTGTTCCG GCTGTCAGCG CAGGGGCGCC
4851 CGGTTCTTTT TGTCAAGACC GACCTGTCCG GTGCCCTGAA TGAACTGCAG
4901 GACGAGGCAG CGCGGCTATC GTGGCTGGCC ACGACGGGCG TTCCTTGCGC
4951 AGCTGTGCTC GACGTTGTCA CTGAAGCGGG AAGGGACTGG CTGCTATTGG
5001 GCGAAGTGCC GGGGCAGGAT CTCCTGTCAT CTCACCTTGC TCCTGCCGAG
5051 AAAGTATCCA TCATGGCTGA TGCAATGCGG CGGCTGCATA CGCTTGATCC
5101 GGCTACCTGC CCATTCGACC ACCAAGCGAA ACATCGCATC GAGCGAGCAC
5151 GTACTCGGAT GGAAGCCGGT CTTGTCGATC AGGATGATCT GGACGAAGAG
5201 CATCAGGGGC TCGCGCCAGC CGAACTGTTC GCCAGGCTCA AGGCGCGCAT
5251 GCCCGACGGC GAGGATCTCG TCGTGACCCA TGGCGATGCC TGCTTGCCGA
5301 ATATCATGGT GGAAAATGGC CGCTTTTCTG GATTCATCGA CTGTGGCCGG
5351 CTGGGTGTGG CGGACCGCTA TCAGGACATA GCGTTGGCTA CCCGTGATAT
5401 TGCTGAAGAG CTTGGCGGCG AATGGGCTGA CCGCTTCCTC GTGCTTTACG
5451 GTATCGCCGC TCCCGATTCG CAGCGCATCG CCTTCTATCG CCTTCTTGAC
5501 GAGTTCTTCT GAGCGGGACT CTGGGGTTCG AAATGACCGA CCAAGCGACG
5551 CCCAACCTGC CATCACGAGA TTTCGATTCC ACCGCCGCCT TCTATGAAAG
5601 GTTGGGCTTC GGAATCGTTT TCCGGGACGC CGGCTGGATG ATCCTCCAGC
```

```
5651  GCGGGGATCT CATGCTGGAG TTCTTCGCCC ACCCCAACTT GTTTATTGCA
5701  GCTTATAATG GTTACAAATA AAGCAATAGC ATCACAAATT TCACAAATAA
5751  AGCATTTTTT TCACTGCATT CTAGTTGTGG TTTGTCCAAA CTCATCAATG
5801  TATCTTATCA TGTCTGTATA CCGTCGACCT CTAGCTAGAG CTTGGCGTAA
5851  TCATGGTCAT AGCTGTTTCC TGTGTGAAAT TGTTATCCGC TCACAATTCC
5901  ACACAACATA CGAGCCGGAA GCATAAAGTG TAAAGCCTGG GGTGCCTAAT
5951  GAGTGAGCTA ACTCACATTA ATTGCGTTGC GCTCACTGCC CGCTTTCCAG
6001  TCGGGAAACC TGTCGTGCCA GCTGCATTAA TGAATCGGCC AACGCGCGGG
6051  GAGAGGCGGT TTGCGTATTG GGCGCTCTTC CGCTTCCTCG CTCACTGACT
6101  CGCTGCGCTC GGTCGTTCGG CTGCGGCGAG CGGTATCAGC TCACTCAAAG
6151  GCGGTAATAC GGTTATCCAC AGAATCAGGG GATAACGCAG GAAAGAACAT
6201  GTGAGCAAAA GGCCAGCAAA AGGCCAGGAA CCGTAAAAAG GCCGCGTTGC
6251  TGGCGTTTTT CCATAGGCTC CGCCCCCCTG ACGAGCATCA CAAAAATCGA
6301  CGCTCAAGTC AGAGGTGGCG AAACCCGACA GGACTATAAA GATACCAGGC
6351  GTTTCCCCCT GGAAGCTCCC TCGTGCGCTC TCCTGTTCCG ACCCTGCCGC
6401  TTACCGGATA CCTGTCCGCC TTTCTCCCTT CGGGAAGCGT GGCGCTTTCT
6451  CATAGCTCAC GCTGTAGGTA TCTCAGTTCG GTGTAGGTCG TTCGCTCCAA
6501  GCTGGGCTGT GTGCACGAAC CCCCCGTTCA GCCCGACCGC TGCGCCTTAT
6551  CCGGTAACTA TCGTCTTGAG TCCAACCCGG TAAGACACGA CTTATCGCCA
6601  CTGGCAGCAG CCACTGGTAA CAGGATTAGC AGAGCGAGGT ATGTAGGCGG
6651  TGCTACAGAG TTCTTGAAGT GGTGGCCTAA CTACGGCTAC ACTAGAAGAA
6701  CAGTATTTGG TATCTGCGCT CTGCTGAAGC CAGTTACCTT CGGAAAAAGA
6751  GTTGGTAGCT CTTGATCCGG CAAACAAACC ACCGCTGGTA GCGGTTTTTT
6801  TGTTTGCAAG CAGCAGATTA CGCGCAGAAA AAAAGGATCT CAAGAAGATC
6851  CTTTGATCTT TTCTACGGGG TCTGACGCTC AGTGGAACGA AAACTCACGT
6901  TAAGGGATTT TGGTCATGAG ATTATCAAAA AGGATCTTCA CCTAGATCCT
6951  TTTAAATTAA AAATGAAGTT TTAAATCAAT CTAAAGTATA TATGAGTAAA
7001  CTTGGTCTGA CAGTTACCAA TGCTTAATCA GTGAGGCACC TATCTCAGCG
7051  ATCTGTCTAT TTCGTTCATC CATAGTTGCC TGACTCCCCG TCGTGTAGAT
7101  AACTACGATA CGGGAGGGCT TACCATCTGG CCCCAGTGCT GCAATGATAC
7151  CGCGAGACCC ACGCTCACCG GCTCCAGATT TATCAGCAAT AAACCAGCCA
7201  GCCGGAAGGG CCGAGCGCAG AAGTGGTCCT GCAACTTTAT CCGCCTCCAT
7251  CCAGTCTATT AATTGTTGCC GGGAAGCTAG AGTAAGTAGT TCGCCAGTTA
7301  ATAGTTTGCG CAACGTTGTT GCCATTGCTA CAGGCATCGT GGTGTCACGC
7351  TCGTCGTTTG GTATGGCTTC ATTCAGCTCC GGTTCCCAAC GATCAAGGCG
7401  AGTTACATGA TCCCCCATGT TGTGCAAAAA AGCGGTTAGC TCCTTCGGTC
7451  CTCCGATCGT TGTCAGAAGT AAGTTGGCCG CAGTGTTATC ACTCATGGTT
7501  ATGGCAGCAC TGCATAATTC TCTTACTGTC ATGCCATCCG TAAGATGCTT
7551  TTCTGTGACT GGTGAGTACT CAACCAAGTC ATTCTGAGAA TAGTGTATGC
7601  GGCGACCGAG TTGCTCTTGC CCGGCGTCAA TACGGGATAA TACCGCGCCA
```

-continued

```
7651  CATAGCAGAA CTTTAAAAGT GCTCATCATT GGAAAACGTT CTTCGGGGCG

7701  AAAACTCTCA AGGATCTTAC CGCTGTTGAG ATCCAGTTCG ATGTAACCCA

7751  CTCGTGCACC CAACTGATCT TCAGCATCTT TTACTTTCAC CAGCGTTTCT

7801  GGGTGAGCAA AAACAGGAAG GCAAAATGCC GCAAAAAAGG GAATAAGGGC

7851  GACACGGAAA TGTTGAATAC TCATACTCTT CCTTTTTCAA TATTATTGAA

7901  GCATTTATCA GGGTTATTGT CTCATGAGCG GATACATATT TGAATGTATT

7951  TAGAAAAATA AACAAATAGG GGTTCCGCGC ACATTTCCCC GAAAAGTGCC

8001  ACCTGACGTC
```

According to one embodiment, the vector is a plasmid and has the sequence of pminiCMV-(mNeonGreen)$_4$-tDeg (SEQ ID NO: 75; GenBank Accession No. MN052905.1, which is hereby incorporated by reference) as follows:

```
   1  GACGGATCGG GAGATCTCCC GATCCCCTAT GGTGCACTCT CAGTACAATC

51  TGCTCTGATG CCGCATAGTT AAGCCAGTAT CTGCTCCCTG CTTGTGTGTT

101  GGAGGTCGCT GAGTAGTGCG CGAGCAAAAT TTAAGCTACA ACAAGGCAAG

151  GCTTGACCGA CAATTGCATG AAGAATCTGC TTAGGGTTAG GCGTTTTGCG

201  CTGCTTCGCG ATGTACGGGC CAGATATACG CGTTGGTAGG CGTGTACGGT

251  GGGAGGCCTA TATAAGCAGA GCTAAGCTTG CCACCATGGT GAGCAAGGGC

301  GAGGAGGATA ACATGGCCTC TCTCCCAGCA CACATGAGT TACACATCTT

351  TGGCTCCATC AACGGTGTGG ACTTTGACAT GGTGGGTCAG GGCACCGGCA

401  ATCCAAATGA TGGTTATGAG GAGTTAAACC TGAAGTCCAC CAAGGGTGAC

451  CTCCAGTTCT CCCCCTGGAT TCTGGTCCCT CATATCGGGT ATGGCTTCCA

501  TCAGTACCTG CCCTACCCTG ACGGGATGTC GCCTTTCCAG GCCGCCATGG

551  TAGATGGCTC CGGATACCAA GTCCATCGCA CAATGCAGTT TGAAGATGGT

601  GCCTCCCTTA CTGTTAACTA CCGCTACACC TACGAGGGAA GCCACATCAA

651  AGGAGAGGCC CAGGTGAAGG GGACTGGTTT CCCTGCTGAC GGTCCTGTGA

701  TGACCAACTC GCTGACCGCT GCGGACTGGT GCAGGTCGAA GAAGACTTAC

751  CCCAACGACA AAACCATCAT CAGTACCTTT AAGTGGAGTT ACACCACTGG

801  AAATGGCAAG CGCTACCGGA GCACTGCGCG GACCACCTAC ACCTTTGCCA

851  AGCCAATGGC GGCTAACTAT CTGAAGAACC AGCCGATGTA CGTGTTCCGT

901  AAGACGGAGC TCAAGCACTC CAAGACCGAG CTCAACTTCA AGGAGTGGCA

951  AAAGGCCTTT ACCGATGTGA TGGGCATGGA CGAGCTGTAC AAGGGTGGAC

1001  ATATGGGCAC AGGGTCCACA GGCGGTACCG GCGGAGTTTC CAAAGGAGAA

1051  GAAGACAATA TGGCATCACT CCCCGCAACC CACGAGTTGC ATATTTTCGG

1101  TTCAATTAAT GGAGTAGATT TCGATATGGT TGGCCAGGGA ACAGGAAACC

1151  CAAACGACGG ATATGAAGAG CTTAATCTCA AAAGTACCAA AGGCGATCTG

1201  CAATTTTCTC CGTGGATACT CGTGCCACAC ATTGGATACG GATTTCACCA

1251  ATATCTCCCG TATCCGGATG GAATGTCCCC CTTTCAAGCA GCAATGGTGG

1301  ACGGGAGTGG TTATCAGGTA CACAGAACCA TGCAGTTCGA GGACGGGGCT

1351  TCTCTGACCG TAAATTATAG GTATACTTAT GAAGGCTCAC ATATTAAGGG

1401  CGAAGCACAG GTTAAAGGAA CCGGGTTTCC TGCGGATGGC CCCGTCATGA

1451  CTAATTCTCT GACAGCCGCA GATTGGTGTC GCTCCAAAAA GACATACCCG
```

-continued

```
1501  AATGATAAGA CTATAATCTC AACATTCAAA TGGTCCTATA CGACAGGCAA
1551  CGGGAAACGA TATAGATCCA CGGCTCGAAC AACTTACACA TTCGCTAAAC
1601  CTATGGCCGC CAATTACCTC AAAAATCAGC CCATGTATGT GTTTAGGAAA
1651  ACCGAATTGA AGCATTCTAA AACGGAACTT AATTTTAAGG AATGGCAGAA
1701  GGCTTTCACA GACGTAATGG GGATGGATGA ACTCTATAAA TCAGGTCTCG
1751  AGTCCTCAGG GGGAACGGGT GGGTCCGGAG GAGTTAGTAA AGGTGAAGAG
1801  GACAATATGG CAAGTTTGCC TGCGACTCAC GAGCTTCATA TCTTTGGGTC
1851  TATAAATGGC GTTGACTTCG ATATGGTTGG CCAAGGTACT GGCAACCCCA
1901  ATGACGGTTA CGAGGAGTTG AATCTCAAGT CCACAAAAGG TGATCTTCAG
1951  TTCAGCCCTT GGATTCTCGT ACCTCATATT GGATATGGCT TTCACCAGTA
2001  CCTTCCATAC CCAGACGGTA TGTCACCCTT TCAAGCTGCG ATGGTGGATG
2051  GTTCCGGCTA TCAGGTCCAC CGAACGATGC AATTCGAGGA CGGGGCCAGC
2101  CTCACCGTTA ATTATAGGTA CACCTATGAG GGAAGTCACA TAAAGGGAGA
2151  AGCCCAAGTG AAAGGAACAG GATTCCCAGC TGATGGTCCA GTAATGACGA
2201  ACTCCTTGAC AGCGGCTGAC TGGTGTAGAA GCAAAAGAC GTATCCTAAT
2251  GACAAGACCA TCATTAGCAC TTTCAAATGG AGTTATACCA CAGGAAACGG
2301  CAAACGGTAC AGAAGCACTG CTAGAACTAC CTACACTTTC GCAAAGCCGA
2351  TGGCTGCAAA CTATTTGAAG AATCAGCCCA TGTACGTGTT TCGAAAAACG
2401  GAACTTAAGC ACAGTAAGAC TGAACTTAAT TTCAAGGAGT GGCAGAAGGC
2451  GTTCACGGAT GTCATGGGTA TGGATGAACT GTATAAGGGA GGGTCTGGCA
2501  CTGGGGGCAC TGCCAGCAGC GGATCCGGTG GCGGTGTGAG CAAGGGCGAG
2551  GAGGATAACA TGGCCTCTCT CCCAGCGACA CATGAGTTAC ACATCTTTGG
2601  CTCCATCAAC GGTGTGGACT TTGACATGGT GGGTCAGGGC ACCGGCAATC
2651  CAAATGATGG TTATGAGGAG TTAAACCTGA AGTCCACCAA GGGTGACCTC
2701  CAGTTCTCCC CCTGGATTCT GGTCCCTCAT ATCGGGTATG GCTTCCATCA
2751  GTACCTGCCC TACCCTGACG GGATGTCGCC TTTCCAGGCC GCCATGGTAG
2801  ATGGCTCCGG ATACCAAGTC ATCGCACAA TGCAGTTTGA AGATGGTGCC
2851  TCCCTTACTG TTAACTACCG CTACACCTAC GAGGGAAGCC ACATCAAAGG
2901  AGAGGCCCAG GTGAAGGGGA CTGGTTTCCC TGCTGACGGT CCTGTGATGA
2951  CCAACTCGCT GACCGCTGCG GACTGGTGCA GGTCGAAGAA GACTTACCCC
3001  AACGACAAAA CCATCATCAG TACCTTTAAG TGGAGTTACA CCACTGGAAA
3051  TGGCAAGCGC TACCGGAGCA CTGCGCGGAC CACCTACACC TTTGCCAAGC
3101  CAATGGCGGC TAACTATCTG AAGAACCAGC CGATGTACGT GTTCCGTAAG
3151  ACGGAGCTCA AGCACTCCAA GACCGAGCTC AACTTCAAGG AGTGGCAAAA
3201  GGCCTTTACC GATGTGATGG GCATGGACGA GCTGTACAAG GCGGAAGAT
3251  CCGGTGGTGG TTCTGGTCCT CGTCCCCGTG GTACTCGTGG TAAAGGTCGC
3301  CGTATTCGTC GCCGCGGTTA ATCTAGAGGG CCCGTTTAAA CCCGCTGATC
3351  AGCCTCGACT GTGCCTTCTA GTTGCCAGCC ATCTGTTGTT TGCCCCTCCC
3401  CCGTGCCTTC CTTGACCCTG GAAAGGTGCC ACTCCCACTG TCCTTTCCTA
3451  ATAAAATGAG GAAATTGCAT CGCATTGTCT GAGTAGGTGT CATTCTATTC
```

```
                            -continued
3501   TGGGGGGTGG GGGTGGGGGC AGGACAGCAA GGGGGAGGAT TGGGAAGACA

3551   ATAGCAGGCA TGCTGGGGAT GCGGTGGGCT CTATGGCTTC TGAGGCGGAA

3601   AGAACCAGCT GGGGCTCTAG GGGGTATCCC CACGCGCCCT GTAGCGGCGC

3651   ATTAAGCGCG GCGGGTGTGG TGGTTACGCG CAGCGTGACC GCTACACTTG

3701   CCAGCGCCCT AGCGCCCGCT CCTTTCGCTT TCTTCCCTTC CTTTCTCGCC

3751   ACGTTCGCCG GCTTTCCCCG TCAAGCTCTA AATCGGGGGC TCCCTTTAGG

3801   GTTCCGATTT AGTGCTTTAC GGCACCTCGA CCCCAAAAAA CTTGATTAGG

3851   GTGATGGTTC ACGTAGTGGG CCATCGCCCT GATAGACGGT TTTTCGCCCT

3901   TTGACGTTGG AGTCCACGTT CTTTAATAGT GGACTCTTGT TCCAAACTGG

3951   AACAACACTC AACCCTATCT CGGTCTATTC TTTTGATTTA TAAGGGATTT

4001   TGCCGATTTC GGCCTATTGG TTAAAAAATG AGCTGATTTA ACAAAAATTT

4051   AACGCGAATT AATTCTGTGG AATGTGTGTC AGTTAGGGTG TGGAAAGTCC

4101   CCAGGCTCCC CAGCAGGCAG AAGTATGCAA AGCATGCATC TCAATTAGTC

4151   AGCAACCAGG TGTGGAAAGT CCCCAGGCTC CCCAGCAGGC AGAAGTATGC

4201   AAAGCATGCA TCTCAATTAG TCAGCAACCA TAGTCCCGCC CCTAACTCCG

4251   CCCATCCCGC CCCTAACTCC GCCCAGTTCC GCCCATTCTC CGCCCCATGG

4301   CTGACTAATT TTTTTATTT ATGCAGAGGC CGAGGCCGCC TCTGCCTCTG

4351   AGCTATTCCA GAAGTAGTGA GGAGGCTTTT TTGGAGGCCT AGGCTTTTGC

4401   AAAAAGCTCC CGGGAGCTTG TATATCCATT TTCGGATCTG ATCAAGAGAC

4451   AGGATGAGGA TCGTTTCGCA TGATTGAACA AGATGGATTG CACGCAGGTT

4501   CTCCGGCCGC TTGGGTGGAG AGGCTATTCG GCTATGACTG GGCACAACAG

4551   ACAATCGGCT GCTCTGATGC CGCCGTGTTC CGGCTGTCAG CGCAGGGGCG

4601   CCCGGTTCTT TTTGTCAAGA CCGACCTGTC CGGTGCCCTG AATGAACTGC

4651   AGGACGAGGC AGCGCGGCTA TCGTGGCTGG CCACGACGGG CGTTCCTTGC

4701   GCAGCTGTGC TCGACGTTGT CACTGAAGCG GGAAGGGACT GGCTGCTATT

4751   GGGCGAAGTG CCGGGGCAGG ATCTCCTGTC ATCTCACCTT GCTCCTGCCG

4801   AGAAAGTATC CATCATGGCT GATGCAATGC GGCGGCTGCA TACGCTTGAT

4851   CCGGCTACCT GCCCATTCGA CCACCAAGCG AAACATCGCA TCGAGCGAGC

4901   ACGTACTCGG ATGGAAGCCG GTCTTGTCGA TCAGGATGAT CTGGACGAAG

4951   AGCATCAGGG GCTCGCGCCA GCCGAACTGT TCGCCAGGCT CAAGGCGCGC

5001   ATGCCCGACG GCGAGGATCT CGTCGTGACC CATGGCGATG CCTGCTTGCC

5051   GAATATCATG GTGGAAAATG GCCGCTTTTC TGGATTCATC GACTGTGGCC

5101   GGCTGGGTGT GGCGGACCGC TATCAGGACA TAGCGTTGGC TACCCGTGAT

5151   ATTGCTGAAG AGCTTGGCGG CGAATGGGCT GACCGCTTCC TCGTGCTTTA

5201   CGGTATCGCC GCTCCCGATT CGCAGCGCAT CGCCTTCTAT CGCCTTCTTG

5251   ACGAGTTCTT CTGAGCGGGA CTCTGGGGTT CGAAATGACC GACCAAGCGA

5301   CGCCCAACCT GCCATCACGA GATTTCGATT CCACCGCCGC CTTCTATGAA

5351   AGGTTGGGCT TCGGAATCGT TTTCCGGGAC GCCGGCTGGA TGATCCTCCA

5401   GCGCGGGGAT CTCATGCTGG AGTTCTTCGC CCACCCCAAC TTGTTTATTG

5451   CAGCTTATAA TGGTTACAAA TAAAGCAATA GCATCACAAA TTTCACAAAT

5501   AAAGCATTTT TTTCACTGCA TTCTAGTTGT GGTTTGTCCA AACTCATCAA
```

-continued

```
5551  TGTATCTTAT CATGTCTGTA TACCGTCGAC CTCTAGCTAG AGCTTGGCGT
5601  AATCATGGTC ATAGCTGTTT CCTGTGTGAA ATTGTTATCC GCTCACAATT
5651  CCACACAACA TACGAGCCGG AAGCATAAAG TGTAAAGCCT GGGGTGCCTA
5701  ATGAGTGAGC TAACTCACAT TAATTGCGTT GCGCTCACTG CCCGCTTTCC
5751  AGTCGGGAAA CCTGTCGTGC CAGCTGCATT AATGAATCGG CCAACGCGCG
5801  GGGAGAGGCG GTTTGCGTAT TGGGCGCTCT TCCGCTTCCT CGCTCACTGA
5851  CTCGCTGCGC TCGGTCGTTC GGCTGCGGCG AGCGGTATCA GCTCACTCAA
5901  AGGCGGTAAT ACGGTTATCC ACAGAATCAG GGGATAACGC AGGAAAGAAC
5951  ATGTGAGCAA AAGGCCAGCA AAAGGCCAGG AACCGTAAAA AGGCCGCGTT
6001  GCTGGCGTTT TTCCATAGGC TCCGCCCCCC TGACGAGCAT CACAAAAATC
6051  GACGCTCAAG TCAGAGGTGG CGAAACCCGA CAGGACTATA AAGATACCAG
6101  GCGTTTCCCC CTGGAAGCTC CCTCGTGCGC TCTCCTGTTC CGACCCTGCC
6151  GCTTACCGGA TACCTGTCCG CCTTTCTCCC TTCGGGAAGC GTGGCGCTTT
6201  CTCATAGCTC ACGCTGTAGG TATCTCAGTT CGGTGTAGGT CGTTCGCTCC
6251  AAGCTGGGCT GTGTGCACGA ACCCCCCGTT CAGCCCGACC GCTGCGCCTT
6301  ATCCGGTAAC TATCGTCTTG AGTCCAACCC GGTAAGACAC GACTTATCGC
6351  CACTGGCAGC AGCCACTGGT AACAGGATTA GCAGAGCGAG GTATGTAGGC
6401  GGTGCTACAG AGTTCTTGAA GTGGTGGCCT AACTACGGCT ACACTAGAAG
6451  AACAGTATTT GGTATCTGCG CTCTGCTGAA GCCAGTTACC TTCGGAAAAA
6501  GAGTTGGTAG CTCTTGATCC GGCAAACAAA CCACCGCTGG TAGCGGTTTT
6551  TTTGTTTGCA AGCAGCAGAT TACGCGCAGA AAAAAAGGAT CTCAAGAAGA
6601  TCCTTTGATC TTTTCTACGG GGTCTGACGC TCAGTGGAAC GAAAACTCAC
6651  GTTAAGGGAT TTTGGTCATG AGATTATCAA AAAGGATCTT CACCTAGATC
6701  CTTTTAAATT AAAAATGAAG TTTTAAATCA ATCTAAAGTA TATATGAGTA
6751  AACTTGGTCT GACAGTTACC AATGCTTAAT CAGTGAGGCA CCTATCTCAG
6801  CGATCTGTCT ATTTCGTTCA TCCATAGTTG CCTGACTCCC CGTCGTGTAG
6851  ATAACTACGA TACGGGAGGG CTTACCATCT GGCCCCAGTG CTGCAATGAT
6901  ACCGCGAGAC CCACGCTCAC CGGCTCCAGA TTTATCAGCA ATAAACCAGC
6951  CAGCCGGAAG GGCCGAGCGC AGAAGTGGTC CTGCAACTTT ATCCGCCTCC
7001  ATCCAGTCTA TTAATTGTTG CCGGGAAGCT AGAGTAAGTA GTTCGCCAGT
7051  TAATAGTTTG CGCAACGTTG TTGCCATTGC TACAGGCATC GTGGTGTCAC
7101  GCTCGTCGTT TGGTATGGCT TCATTCAGCT CCGGTTCCCA ACGATCAAGG
7151  CGAGTTACAT GATCCCCCAT GTTGTGCAAA AAAGCGGTTA GCTCCTTCGG
7201  TCCTCCGATC GTTGTCAGAA GTAAGTTGGC CGCAGTGTTA TCACTCATGG
7251  TTATGGCAGC ACTGCATAAT TCTCTTACTG TCATGCCATC CGTAAGATGC
7301  TTTTCTGTGA CTGGTGAGTA CTCAACCAAG TCATTCTGAG AATAGTGTAT
7351  GCGGCGACCG AGTTGCTCTT GCCCGGCGTC AATACGGGAT AATACCGCGC
7401  CACATAGCAG AACTTTAAAA GTGCTCATCA TTGGAAAACG TTCTTCGGGG
7451  CGAAAACTCT CAAGGATCTT ACCGCTGTTG AGATCCAGTT CGATGTAACC
7501  CACTCGTGCA CCCAACTGAT CTTCAGCATC TTTTACTTTC ACCAGCGTTT
```

```
-continued
7551  CTGGGTGAGC AAAAACAGGA AGGCAAAATG CCGCAAAAAA GGGAATAAGG

7601  GCGACACGGA AATGTTGAAT ACTCATACTC TTCCTTTTTC AATATTATTG

7651  AAGCATTTAT CAGGGTTATT GTCTCATGAG CGGATACATA TTTGAATGTA

7701  TTTAGAAAAA TAAACAAATA GGGGTTCCGC GCACATTTCC CCGAAAAGTG

7751  CCACCTGACG TC
```

According to one embodiment, the vector is a plasmid and has the sequence of pCMV-CytERM-mCherry-(F30-2×Pepper)$_{10}$ (SEQ ID NO: 76; GenBank Accession No. MN052906.1, which is hereby incorporated by reference) as follows:

```
   1  GACGGATCGG GAGATCTCCC GATCCCCTAT GGTGCACTCT CAGTACAATC

51  TGCTCTGATG CCGCATAGTT AAGCCAGTAT CTGCTCCCTG CTTGTGTGTT

101  GGAGGTCGCT GAGTAGTGCG CGAGCAAAAT TAAGCTACA ACAAGGCAAG

151  GCTTGACCGA CAATTGCATG AAGAATCTGC TTAGGGTTAG GCGTTTTGCG

201  CTGCTTCGCG ATGTACGGGC CAGATATACG CGTTGACATT GATTATTGAC

251  TAGTTATTAA TAGTAATCAA TTACGGGGTC ATTAGTTCAT AGCCCATATA

301  TGGAGTTCCG CGTTACATAA CTTACGGTAA ATGGCCCGCC TGGCTGACCG

351  CCCAACGACC CCCGCCCATT GACGTCAATA ATGACGTATG TTCCCATAGT

401  AACGCCAATA GGGACTTTCC ATTGACGTCA ATGGGTGGAG TATTTACGGT

451  AAACTGCCCA CTTGGCAGTA CATCAAGTGT ATCATATGCC AAGTACGCCC

501  CCTATTGACG TCAATGACGG TAAATGGCCC GCCTGGCATT ATGCCCAGTA

551  CATGACCTTA TGGGACTTTC CTACTTGGCA GTACATCTAC GTATTAGTCA

601  TCGCTATTAC CATGGTGATG CGGTTTTGGC AGTACATCAA TGGGCGTGGA

651  TAGCGGTTTG ACTCACGGGG ATTTCCAAGT CTCCACCCCA TTGACGTCAA

701  TGGGAGTTTG TTTTGGCACC AAAATCAACG GGACTTTCCA AAATGTCGTA

751  ACAACTCCGC CCCATTGAC GCAAATGGGC GGTAGGCGTG TACGGTGGGA

801  GGTCTATATA AGCAGAGCTC TCTGGCTAAC TAGAGAACCC ACTGCTTACT

851  GGCTTATCGA AATTAATACG ACTCACTATA GGGAGACCCA AGCTGGCTAG

901  CGTTTAAACT TGCCACCATG GACCCTGTGG TGGTGCTGGG GCTCTGTCTC

951  TCCTGTTTGC TTCTCCTTTC ACTCTGGAAA CAGAGCTATG GGGAGGGAA

1001  ACTGGGCGGA AGCGGAGGGA CGGGGGGTTC AGGAACTTCA GGGGGTGTGA

1051  GCAAGGGCGA GGAGGATAAC ATGGCCATCA TCAAGGAGTT CATGCGCTTC

1101  AAGGTGCACA TGGAGGGCTC CGTGAACGGC CACGAGTTCG AGATCGAGGG

1151  CGAGGGCGAG GGCCGCCCCT ACGAGGGCAC CCAGACCGCC AAGCTGAAGG

1201  TGACCAAGGG TGGCCCCCTG CCCTTCGCCT GGGACATCCT GTCCCCTCAG

1251  TTCATGTACG GCTCCAAGGC CTACGTGAAG CACCCCGCCG ACATCCCCGA

1301  CTACTTGAAG CTGTCCTTCC CCGAGGGCTT CAAGTGGGAG CGCGTGATGA

1351  ACTTCGAGGA CGGCGGCGTG GTGACCGTGA CCCAGGACTC CTCCCTGCAG

1401  GACGGCGAGT TCATCTACAA GGTGAAGCTG CGCGGCACCA ACTTCCCCTC

1451  CGACGGCCCC GTAATGCAGA AGAAGACCAT GGGCTGGGAG GCCTCCTCCG

1501  AGCGGATGTA CCCCGAGGAC GGCGCCCTGA AGGGCGAGAT CAAGCAGAGG
```

```
-continued
1551  CTGAAGCTGA AGGACGGCGG CCACTACGAC GCTGAGGTCA AGACCACCTA

1601  CAAGGCCAAG AAGCCCGTGC AGCTGCCCGG CGCCTACAAC GTCAACATCA

1651  AGTTGGACAT CACCTCCCAC AACGAGGACT ACACCATCGT GGAACAGTAC

1701  GAACGCGCCG AGGGCCGCCA CTCCACCGGC GGCATGGACG AGCTGTACAA

1751  GTAACTCGAG ATCCGTTACG GCCGGAATCA ATCGCTAATC ACTCAACTTG

1801  CCATGTGTAT GTGGGAAGCG TAGAAAGGCT CGTTGAGCTC ATTAGCTCCG

1851  AGCCCGACTA CGTTTCCCAC ATACTCTGAT GATCCGCTAG CAAAGGCTCG

1901  TCTGAGCTCA TTAGCTCCGA GCCCGAGGTA CCGGATCATT CATGGCAAGT

1951  CCAGCGCAAT CTATTACGAA AATCATCCGA CGTCGCGATG TCTATGCGGG

2001  AAGCGTAGAA AGGCTCGTCT GAGCTCATTA GCTCCGAGCC CGACTACGTT

2051  TCCCGCATAG TCTGATCATC CGCTAGCAAA GGCTCGTTGA GCTCATTAGC

2101  TCCGAGCCCG AGGTACCGGA TGATTCATCG CGACGCTGCG GAAAATCTCA

2151  CAAAATCACG TCAAACGTCG CCGTGTGTGT GTAGGAAGCG TAGAAAGGCT

2201  CGTCTGAGCT CATTAGCTCC GAGCCCGACT ACGTTTCCTA CACACTCTGA

2251  CGATCCGCTA GCAAAGGCTC GTTGAGCTCA TTAGCTCCGA GCCCGAGGTA

2301  CCGGATCGTT CACGGCGACG CCGATAATCC ACATACTTAC AATCAGGCAA

2351  TCTTGCCATG TGTATGTGGG AAGCGTAGAA AGGCTCGTTG AGCTCATTAG

2401  CTCCGAGCCC GACTACGTTT CCCACATACT CTGATGATCC GCTAGCAAAG

2451  GCTCGTTGAG CTCATTAGCT CCGAGCCCGA GGTACCGGAT CATTCATGGC

2501  AAGTATCAAG ATCGAACGGC GCAAGATATT GTCACGTCGC GATGTCTATG

2551  CGGGAAGCGT AGAAAGGCTC GTTGAGCTCA TTAGCTCCGA GCCCGACTAC

2601  GTTTCCCGCA TAGTCTGATC ATCCGCTAGC AAAGGCTCGT CTGAGCTCAT

2651  TAGCTCCGAG CCCGAGGTAC CGGATGATTC ATCGCGACGT CCTCGCTAGA

2701  TATGTTAGGT TCTTAGGCAT TTCGCCGTGT GTGTGTAGGA AGCGTAGAAA

2751  GGCTCGTTGA GCTCATTAGC TCCGAGCCCG ACTACGTTTC CTACACACTC

2801  TGACGATCCG CTAGCAAAGG CTCGTCTGAG CTCATTAGCT CCGAGCCCGA

2851  GGTACCGGAT CGTTCACGGC GAAAAGATCG TCTGCAATTC CGATTAGACG

2901  TACACTTGCC ATGTGTATGT GGGAAGCGTA GAAAGGCTCG TCTGAGCTCA

2951  TTAGCTCCGA GCCCGACTAC GTTTCCCACA TACTCTGATG ATCCGCTAGC

3001  AAAGGCTCGT TGAGCTCATT AGCTCCGAGC CGAGGTACC GGATCATTCA

3051  TGGCAAGATC CAAGCTACTT CCTCCATACC TATCCTCCTC GCGATGTCTA

3101  TGCGGGAAGC GTAGAAAGGC TCGTCTGAGC TCATTAGCTC CGAGCCCGAC

3151  TACGTTTCCC GCATAGTCTG ATCATCCGCT AGCAAAGGCT CGTTGAGCTC

3201  ATTAGCTCCG AGCCCGAGGT ACCGGATGAT TCATCGCGAG ATCATAACGC

3251  AATACCGTAC ACTGTCCAAT CCTCGCCGTG TGTGTGTAGG AAGCGTAGAA

3301  AGGCTCGTCT GAGCTCATTA GCTCCGAGCC CGACTACGTT TCCTACACAC

3351  TCTGACGATC CGCTAGCAAA GGCTCGTTGA GCTCATTAGC TCCGAGCCCG

3401  AGGTACCGGA TCGTTCACGG CGAGGATAAT CAATCCACAT ACATCACACC

3451  ACAATTCTTG CCATGTGTAT GTGGGAAGCG TAGAAAGGCT CGTCTGAGCT

3501  CATTAGCTCC GAGCCCGACT ACGTTTCCCA CATACTCTGA TGATCCGCTA

3551  GCAAAGGCTC GTCTGAGCTC ATTAGCTCCG AGCCCGAGGT ACCGGATCAT
```

```
3601  TCATGGCAAG AATTGGTCGT TCTTCTTGGC GGCCGCTCGA CTAAATCACC

3651  GGTAATCTTC TTGTCCATCT AGACCTTATA AAGATCTTTG TACAAGGGCC

3701  CGTTTAAACC CGCTGATCAG CCTCGACTGT GCCTTCTAGT TGCCAGCCAT

3751  CTGTTGTTTG CCCCTCCCCC GTGCCTTCCT TGACCCTGGA AAGGTGCCAC

3801  TCCCACTGTC CTTTCCTAAT AAAATGAGGA AATTGCATCG CATTGTCTGA

3851  GTAGGTGTCA TTCTATTCTG GGGGTGGGG GTGGGGGCAG GACAGCAAGG

3901  GGGAGGATTG GGAAGACAAT AGCAGGCATG CTGGGGATGC GGTGGGCTCT

3951  ATGGCTTCTG AGGCGGAAAG AACCAGCTGG GGCTCTAGGG GGTATCCCCA

4001  CGCGCCCTGT AGCGGCGCAT TAAGCGCGGC GGGTGTGGTG GTTACGCGCA

4051  GCGTGACCGC TACACTTGCC AGCGCCCTAG CGCCCGCTCC TTTCGCTTTC

4101  TTCCCTTCCT TTCTCGCCAC GTTCGCCGGC TTTCCCCGTC AAGCTCTAAA

4151  TCGGGGCTC CCTTTAGGGT TCCGATTTAG TGCTTTACGG CACCTCGACC

4201  CCAAAAAACT TGATTAGGGT GATGGTTCAC GTAGTGGGCC ATCGCCCTGA

4251  TAGACGGTTT TTCGCCCTTT GACGTTGGAG TCCACGTTCT TTAATAGTGG

4301  ACTCTTGTTC CAAACTGGAA CAACACTCAA CCCTATCTCG GTCTATTCTT

4351  TTGATTTATA AGGGATTTTG CCGATTTCGG CCTATTGGTT AAAAAATGAG

4401  CTGATTTAAC AAAAATTTAA CGCGAATTAA TTCTGTGGAA TGTGTGTCAG

4451  TTAGGGTGTG GAAAGTCCCC AGGCTCCCCA GCAGGCAGAA GTATGCAAAG

4501  CATGCATCTC AATTAGTCAG CAACCAGGTG TGGAAAGTCC CCAGGCTCCC

4551  CAGCAGGCAG AAGTATGCAA AGCATGCATC TCAATTAGTC AGCAACCATA

4601  GTCCCGCCCC TAACTCCGCC CATCCCGCCC CTAACTCCGC CCAGTTCCGC

4651  CCATTCTCCG CCCCATGGCT GACTAATTTT TTTTATTTAT GCAGAGGCCG

4701  AGGCCGCCTC TGCCTCTGAG CTATTCCAGA AGTAGTGAGG AGGCTTTTTT

4751  GGAGGCCTAG GCTTTTGCAA AAAGCTCCCG GGAGCTTGTA TATCCATTTT

4801  CGGATCTGAT CAAGAGACAG GATGAGGATC GTTTCGCATG ATTGAACAAG

4851  ATGGATTGCA CGCAGGTTCT CCGGCCGCTT GGGTGGAGAG CTATTCGGC

4901  TATGACTGGG CACAACAGAC AATCGGCTGC TCTGATGCCG CCGTGTTCCG

4951  GCTGTCAGCG CAGGGGCGCC CGGTTCTTTT TGTCAAGACC GACCTGTCCG

5001  GTGCCCTGAA TGAACTGCAG GACGAGGCAG CGCGGCTATC GTGGCTGGCC

5051  ACGACGGGCG TTCCTTGCGC AGCTGTGCTC GACGTTGTCA CTGAAGCGGG

5101  AAGGGACTGG CTGCTATTGG GCGAAGTGCC GGGGCAGGAT CTCCTGTCAT

5151  CTCACCTTGC TCCTGCCGAG AAAGTATCCA TCATGGCTGA TGCAATGCGG

5201  CGGCTGCATA CGCTTGATCC GGCTACCTGC CCATTCGACC ACCAAGCGAA

5251  ACATCGCATC GAGCGAGCAC GTACTCGGAT GGAAGCCGGT CTTGTCGATC

5301  AGGATGATCT GGACGAAGAG CATCAGGGGC TCGCGCCAGC CGAACTGTTC

5351  GCCAGGCTCA AGGCGCGCAT GCCCGACGGC GAGGATCTCG TCGTGACCCA

5401  TGGCGATGCC TGCTTGCCGA ATATCATGGT GGAAAATGGC CGCTTTTCTG

5451  GATTCATCGA CTGTGGCCGG CTGGGTGTGG CGGACCGCTA TCAGGACATA

5501  GCGTTGGCTA CCCGTGATAT TGCTGAAGAG CTTGGCGGCG AATGGGCTGA

5551  CCGCTTCCTC GTGCTTTACG GTATCGCCGC TCCCGATTCG CAGCGCATCG
```

```
-continued
5601  CCTTCTATCG CCTTCTTGAC GAGTTCTTCT GAGCGGGACT CTGGGGTTCG

5651  AAATGACCGA CCAAGCGACG CCCAACCTGC CATCACGAGA TTTCGATTCC

5701  ACCGCCGCCT TCTATGAAAG GTTGGGCTTC GGAATCGTTT TCCGGGACGC

5751  CGGCTGGATG ATCCTCCAGC GCGGGGATCT CATGCTGGAG TTCTTCGCCC

5801  ACCCCAACTT GTTTATTGCA GCTTATAATG GTTACAAATA AAGCAATAGC

5851  ATCACAAATT TCACAAATAA AGCATTTTTT TCACTGCATT CTAGTTGTGG

5901  TTTGTCCAAA CTCATCAATG TATCTTATCA TGTCTGTATA CCGTCGACCT

5951  CTAGCTAGAG CTTGGCGTAA TCATGGTCAT AGCTGTTTCC TGTGTGAAAT

6001  TGTTATCCGC TCACAATTCC ACACAACATA CGAGCCGGAA GCATAAAGTG

6051  TAAAGCCTGG GGTGCCTAAT GAGTGAGCTA ACTCACATTA ATTGCGTTGC

6101  GCTCACTGCC CGCTTTCCAG TCGGGAAACC TGTCGTGCCA GCTGCATTAA

6151  TGAATCGGCC AACGCGCGGG GAGAGGCGGT TTGCGTATTG GGCGCTCTTC

6201  CGCTTCCTCG CTCACTGACT CGCTGCGCTC GGTCGTTCGG CTGCGGCGAG

6251  CGGTATCAGC TCACTCAAAG GCGGTAATAC GGTTATCCAC AGAATCAGGG

6301  GATAACGCAG GAAAGAACAT GTGAGCAAAA GGCCAGCAAA AGGCCAGGAA

6351  CCGTAAAAAG GCCGCGTTGC TGGCGTTTTT CCATAGGCTC CGCCCCCCTG

6401  ACGAGCATCA CAAAAATCGA CGCTCAAGTC AGAGGTGGCG AAACCCGACA

6451  GGACTATAAA GATACCAGGC GTTTCCCCCT GGAAGCTCCC TCGTGCGCTC

6501  TCCTGTTCCG ACCCTGCCGC TTACCGGATA CCTGTCCGCC TTTCTCCCTT

6551  CGGGAAGCGT GGCGCTTTCT CATAGCTCAC GCTGTAGGTA TCTCAGTTCG

6601  GTGTAGGTCG TTCGCTCCAA GCTGGGCTGT GTGCACGAAC CCCCCGTTCA

6651  GCCCGACCGC TGCGCCTTAT CCGGTAACTA TCGTCTTGAG TCCAACCCGG

6701  TAAGACACGA CTTATCGCCA CTGGCAGCAG CCACTGGTAA CAGGATTAGC

6751  AGAGCGAGGT ATGTAGGCGG TGCTACAGAG TTCTTGAAGT GGTGGCCTAA

6801  CTACGGCTAC ACTAGAAGAA CAGTATTTGG TATCTGCGCT CTGCTGAAGC

6851  CAGTTACCTT CGGAAAAAGA GTTGGTAGCT CTTGATCCGG CAAACAAACC

6901  ACCGCTGGTA GCGGTTTTTT TGTTTGCAAG CAGCAGATTA CGCGCAGAAA

6951  AAAAGGATCT CAAGAAGATC CTTTGATCTT TTCTACGGGG TCTGACGCTC

7001  AGTGGAACGA AAACTCACGT TAAGGGATTT TGGTCATGAG ATTATCAAAA

7051  AGGATCTTCA CCTAGATCCT TTTAAATTAA AAATGAAGTT TTAAATCAAT

7101  CTAAAGTATA TATGAGTAAA CTTGGTCTGA CAGTTACCAA TGCTTAATCA

7151  GTGAGGCACC TATCTCAGCG ATCTGTCTAT TTCGTTCATC CATAGTTGCC

7201  TGACTCCCCG TCGTGTAGAT AACTACGATA CGGGAGGGCT TACCATCTGG

7251  CCCCAGTGCT GCAATGATAC CGCGAGACCC ACGCTCACCG GCTCCAGATT

7301  TATCAGCAAT AAACCAGCCA GCCGGAAGGG CCGAGCGCAG AAGTGGTCCT

7351  GCAACTTTAT CCGCCTCCAT CCAGTCTATT AATTGTTGCC GGGAAGCTAG

7401  AGTAAGTAGT TCGCCAGTTA ATAGTTTGCG CAACGTTGTT GCCATTGCTA

7451  CAGGCATCGT GGTGTCACGC TCGTCGTTTG GTATGGCTTC ATTCAGCTCC

7501  GGTTCCCAAC GATCAAGGCG AGTTACATGA TCCCCCATGT TGTGCAAAAA

7551  AGCGGTTAGC TCCTTCGGTC CTCCGATCGT TGTCAGAAGT AAGTTGGCCG

7601  CAGTGTTATC ACTCATGGTT ATGGCAGCAC TGCATAATTC TCTTACTGTC
```

```
7651  ATGCCATCCG TAAGATGCTT TTCTGTGACT GGTGAGTACT CAACCAAGTC
7701  ATTCTGAGAA TAGTGTATGC GGCGACCGAG TTGCTCTTGC CCGGCGTCAA
7751  TACGGGATAA TACCGCGCCA CATAGCAGAA CTTTAAAAGT GCTCATCATT
7801  GGAAAACGTT CTTCGGGGCG AAAACTCTCA AGGATCTTAC CGCTGTTGAG
7851  ATCCAGTTCG ATGTAACCCA CTCGTGCACC CAACTGATCT TCAGCATCTT
7901  TTACTTTCAC CAGCGTTTCT GGGTGAGCAA AAACAGGAAG GCAAAATGCC
7951  GCAAAAAAGG GAATAAGGGC GACACGGAAA TGTTGAATAC TCATACTCTT
8001  CCTTTTTCAA TATTATTGAA GCATTTATCA GGGTTATTGT CTCATGAGCG
8051  GATACATATT TGAATGTATT TAGAAAAATA AACAAATAGG GGTTCCGCGC
8101  ACATTTCCCC GAAAAGTGCC ACCTGACGTC
```

According to one embodiment, the vector is a plasmid and has the sequence of pUbC-(mNeonGreen)₄-tDeg (SEQ ID NO: 77; GenBank Accession No. MN052907.1, which is hereby incorporated by reference) as follows:

```
   1  GACGGATCGG GAGATCTCCC GATCCCCTAT GGTGCACTCT CAGTACAATC
  51  TGCTCTGATG CCGCATAGTT AAGCCAGTAT CTGCTCCCTG CTTGTGTGTT
 101  GGAGGTCGCT GAGTAGTGCG CGAGCAAAAT TTAAGCTACA ACAAGGCAAG
 151  GCTTGACCGA CAATTGCATG AAGAATCTGC TTAGGGTTAG GCGTTTTGCG
 201  CTGCTTCGCG ATGTACGGGC CAGATATACG CGTTGGCCTC CGCGCCGGGT
 251  TTTGGCGCCT CCCGCGGGCG CCCCCCTCCT CACGGCGAGC GCTGCCACGT
 301  CAGACGAAGG GCGCAGCGAG CGTCCTGATC CTTCCGCCCG GACGCTCAGG
 351  ACAGCGGCCC GCTGCTCATA AGACTCGGCC TTAGAACCCC AGTATCAGCA
 401  GAAGGACATT TTAGGACGGG ACTTGGGTGA CTCTAGGGCA CTGGTTTTCT
 451  TTCCAGAGAG CGGAACAGGC GAGGAAAAGT AGTCCCTTCT CGGCGATTCT
 501  GCGGAGGGAT CTCCGTGGGG CGGTGAACGC CGATGATTAT ATAAGGACGC
 551  GCCGGGTGTG GCACAGCTAG TTCCGTCGCA GCCGGGATTT GGGTCGCGGT
 601  TCTTGTTTGT GGATCGCTGT GATCGTCACT TGGAAGCTTG CCACCATGGT
 651  GAGCAAGGGC GAGGAGGATA ACATGGCCTC TCTCCCAGCG ACACATGAGT
 701  TACACATCTT TGGCTCCATC AACGGTGTGG ACTTTGACAT GGTGGGTCAG
 751  GGCACCGGCA ATCCAAATGA TGGTTATGAG GAGTTAAACC TGAAGTCCAC
 801  CAAGGGTGAC CTCCAGTTCT CCCCCTGGAT TCTGGTCCCT CATATCGGGT
 851  ATGGCTTCCA TCAGTACCTG CCCTACCCTG ACGGGATGTC GCCTTTCCAG
 901  GCCGCCATGG TAGATGGCTC CGGATACCAA GTCATCGCA CAATGCAGTT
 951  TGAAGATGGT GCCTCCCTTA CTGTTAACTA CCGCTACACC TACGAGGGAA
1001  GCCACATCAA AGGAGAGGCC CAGGTGAAGG GGACTGGTTT CCCTGCTGAC
1051  GGTCCTGTGA TGACCAACTC GCTGACCGCT GCGGACTGGT GCAGGTCGAA
1101  GAAGACTTAC CCCAACGACA AAACCATCAT CAGTACCTTT AAGTGGAGTT
1151  ACACCACTGG AAATGGCAAG CGCTACCGGA GCACTGCGCG GACCACCTAC
1201  ACCTTTGCCA AGCCAATGGC GGCTAACTAT CTGAAGAACC AGCCGATGTA
1251  CGTGTTCCGT AAGACGGAGC TCAAGCACTC CAAGACCGAG CTCAACTTCA
1301  AGGAGTGGCA AAAGGCCTTT ACCGATGTGA TGGGCATGGA CGAGCTGTAC
```

```
1351 AAGGGTGGAC ATATGGGCAC AGGGTCCACA GGCGGTACCG GCGGAGTTTC

1401 CAAAGGAGAA AAGACAATA TGGCATCACT CCCCGCAACC CACGAGTTGC

1451 ATATTTTCGG TTCAATTAAT GGAGTAGATT TCGATATGGT TGGCCAGGGA

1501 ACAGGAAACC CAAACGACGG ATATGAAGAG CTTAATCTCA AAAGTACCAA

1551 AGGCGATCTG CAATTTTCTC CGTGGATACT CGTGCCACAC ATTGGATACG

1601 GATTTCACCA ATATCTCCCG TATCCGGATG AATGTCCCC CTTTCAAGCA

1651 GCAATGGTGG ACGGGAGTGG TTATCAGGTA CACAGAACCA TGCAGTTCGA

1701 GGACGGGGCT TCTCTGACCG TAAATTATAG GTATACTTAT GAAGGCTCAC

1751 ATATTAAGGG CGAAGCACAG GTTAAAGGAA CCGGGTTTCC TGCGGATGGC

1801 CCCGTCATGA CTAATTCTCT GACAGCCGCA GATTGGTGTC GCTCCAAAAA

1851 GACATACCCG AATGATAAGA CTATAATCTC AACATTCAAA TGGTCCTATA

1901 CGACAGGCAA CGGGAAACGA TATAGATCCA CGGCTCGAAC AACTTACACA

1951 TTCGCTAAAC CTATGGCCGC CAATTACCTC AAAAATCAGC CCATGTATGT

2001 GTTTAGGAAA ACCGAATTGA AGCATTCTAA AACGGAACTT AATTTTAAGG

2051 AATGGCAGAA GGCTTTCACA GACGTAATGG GGATGGATGA ACTCTATAAA

2101 TCAGGTCTCG AGTCCTCAGG GGGAACGGGT GGGTCCGGAG GAGTTAGTAA

2151 AGGTGAAGAG GACAATATGG CAAGTTTGCC TGCGACTCAC GAGCTTCATA

2201 TCTTTGGGTC TATAAATGGC GTTGACTTCG ATATGGTTGG CCAAGGTACT

2251 GGCAACCCCA TGACGGTTA CGAGGAGTTG AATCTCAAGT CCACAAAAGG

2301 TGATCTTCAG TTCAGCCCTT GGATTCTCGT ACCTCATATT GGATATGGCT

2351 TTCACCAGTA CCTTCCATAC CCAGACGGTA TGTCACCCTT TCAAGCTGCG

2401 ATGGTGGATG GTTCCGGCTA TCAGGTCCAC CGAACGATGC AATTCGAGGA

2451 CGGGGCCAGC CTCACCGTTA ATTATAGGTA CACCTATGAG GGAAGTCACA

2501 TAAAGGGAGA AGCCCAAGTG AAAGGAACAG GATTCCCAGC TGATGGTCCA

2551 GTAATGACGA ACTCCTTGAC AGCGGCTGAC TGGTGTAGAA GCAAAAAGAC

2601 GTATCCTAAT GACAAGACCA TCATTAGCAC TTTCAAATGG AGTTATACCA

2651 CAGGAAACGG CAAACGGTAC AGAAGCACTG CTAGAACTAC CTACACTTTC

2701 GCAAAGCCGA TGGCTGCAAA CTATTTGAAG AATCAGCCCA TGTACGTGTT

2751 TCGAAAAACG GAACTTAAGC ACAGTAAGAC TGAACTTAAT TTCAAGGAGT

2801 GGCAGAAGGC GTTCACGGAT GTCATGGGTA TGGATGAACT GTATAAGGGA

2851 GGGTCTGGCA CTGGGGGCAC TGCCAGCAGC GGATCCGGTG GCGGTGTGAG

2901 CAAGGGCGAG GAGGATAACA TGGCCTCTCT CCCAGCGACA CATGAGTTAC

2951 ACATCTTTGG CTCCATCAAC GGTGTGGACT TTGACATGGT GGGTCAGGGC

3001 ACCGGCAATC AAATGATGG TTATGAGGAG TTAAACCTGA AGTCCACCAA

3051 GGGTGACCTC CAGTTCTCCC CCTGGATTCT GGTCCCTCAT ATCGGGTATG

3101 GCTTCCATCA GTACCTGCCC TACCCTGACG GGATGTCGCC TTTCCAGGCC

3151 GCCATGGTAG ATGGCTCCGG ATACCAAGTC ATCGCACAA TGCAGTTTGA

3201 AGATGGTGCC TCCCTTACTG TTAACTACCG CTACACCTAC GAGGGAAGCC

3251 ACATCAAAGG AGAGGCCCAG GTGAAGGGGA CTGGTTTCCC TGCTGACGGT

3301 CCTGTGATGA CCAACTCGCT GACCGCTGCG GACTGGTGCA GGTCGAAGAA

3351 GACTTACCCC AACGACAAAA CCATCATCAG TACCTTTAAG TGGAGTTACA
```

```
3401 CCACTGGAAA TGGCAAGCGC TACCGGAGCA CTGCGCGGAC CACCTACACC
3451 TTTGCCAAGC CAATGGCGGC TAACTATCTG AAGAACCAGC CGATGTACGT
3501 GTTCCGTAAG ACGGAGCTCA AGCACTCCAA GACCGAGCTC AACTTCAAGG
3551 AGTGGCAAAA GGCCTTTACC GATGTGATGG GCATGGACGA GCTGTACAAG
3601 GGCGGAAGAT CCGGTGGTGG TTCTGGTCCT CGTCCCCGTG GTACTCGTGG
3651 TAAAGGTCGC CGTATTCGTC GCCGCGGTTA ATCTAGAGGG CCCGTTTAAA
3701 CCCGCTGATC AGCCTCGACT GTGCCTTCTA GTTGCCAGCC ATCTGTTGTT
3751 TGCCCCTCCC CCGTGCCTTC CTTGACCCTG GAAGGTGCC ACTCCCACTG
3801 TCCTTTCCTA ATAAAATGAG GAAATTGCAT CGCATTGTCT GAGTAGGTGT
3851 CATTCTATTC TGGGGGGTGG GGTGGGGC AGGACAGCAA GGGGGAGGAT
3901 TGGGAAGACA ATAGCAGGCA TGCTGGGGAT GCGGTGGGCT CTATGGCTTC
3951 TGAGGCGGAA AGAACCAGCT GGGGCTCTAG GGGGTATCCC CACGCGCCCT
4001 GTAGCGGCGC ATTAAGCGCG GCGGGTGTGG TGGTTACGCG CAGCGTGACC
4051 GCTACACTTG CCAGCGCCCT AGCGCCCGCT CCTTTCGCTT TCTTCCCTTC
4101 CTTTCTCGCC ACGTTCGCCG GCTTTCCCCG TCAAGCTCTA AATCGGGGGC
4151 TCCCTTTAGG GTTCCGATTT AGTGCTTTAC GGCACCTCGA CCCCAAAAAA
4201 CTTGATTAGG GTGATGGTTC ACGTAGTGGG CCATCGCCCT GATAGACGGT
4251 TTTTCGCCCT TTGACGTTGG AGTCCACGTT CTTTAATAGT GGACTCTTGT
4301 TCCAAACTGG AACAACACTC AACCCTATCT CGGTCTATTC TTTTGATTTA
4351 TAAGGGATTT TGCCGATTTC GGCCTATTGG TTAAAAAATG AGCTGATTTA
4401 ACAAAAATTT AACGCGAATT AATTCTGTGG AATGTGTGTC AGTTAGGGTG
4451 TGGAAAGTCC CCAGGCTCCC CAGCAGGCAG AAGTATGCAA AGCATGCATC
4501 TCAATTAGTC AGCAACCAGG TGTGGAAAGT CCCCAGGCTC CCCAGCAGGC
4551 AGAAGTATGC AAAGCATGCA TCTCAATTAG TCAGCAACCA TAGTCCCGCC
4601 CCTAACTCCG CCCATCCCGC CCTAACTCC GCCCAGTTCC GCCCATTCTC
4651 CGCCCCATGG CTGACTAATT TTTTTTATTT ATGCAGAGGC CGAGGCCGCC
4701 TCTGCCTCTG AGCTATTCCA GAAGTAGTGA GGAGGCTTTT TTGGAGGCCT
4751 AGGCTTTTGC AAAAAGCTCC CGGGAGCTTG TATATCCATT TTCGGATCTG
4801 ATCAAGAGAC AGGATGAGGA TCGTTTCGCA TGATTGAACA AGATGGATTG
4851 CACGCAGGTT CTCCGGCCGC TTGGGTGGAG AGGCTATTCG GCTATGACTG
4901 GGCACAACAG ACAATCGGCT GCTCTGATGC CGCCGTGTTC CGGCTGTCAG
4951 CGCAGGGGCG CCCGGTTCTT TTTGTCAAGA CCGACCTGTC CGGTGCCCTG
5001 AATGAACTGC AGGACGAGGC AGCGCGGCTA TCGTGGCTGG CCACGACGGG
5051 CGTTCCTTGC GCAGCTGTGC TCGACGTTGT CACTGAAGCG GGAAGGGACT
5101 GGCTGCTATT GGGCGAAGTG CCGGGGCAGG ATCTCCTGTC ATCTCACCTT
5151 GCTCCTGCCG AGAAAGTATC CATCATGGCT GATGCAATGC GGCGGCTGCA
5201 TACGCTTGAT CCGGCTACCT GCCCATTCGA CCACCAAGCG AAACATCGCA
5251 TCGAGCGAGC ACGTACTCGG ATGGAAGCCG GTCTTGTCGA TCAGGATGAT
5301 CTGGACGAAG AGCATCAGGG GCTCGCGCCA GCCGAACTGT TCGCCAGGCT
5351 CAAGGCGCGC ATGCCCGACG GCGAGGATCT CGTCGTGACC CATGGCGATG
```

-continued

```
5401 CCTGCTTGCC GAATATCATG GTGGAAAATG GCCGCTTTTC TGGATTCATC
5451 GACTGTGGCC GGCTGGGTGT GGCGGACCGC TATCAGGACA TAGCGTTGGC
5501 TACCCGTGAT ATTGCTGAAG AGCTTGGCGG CGAATGGGCT GACCGCTTCC
5551 TCGTGCTTTA CGGTATCGCC GCTCCCGATT CGCAGCGCAT CGCCTTCTAT
5601 CGCCTTCTTG ACGAGTTCTT CTGAGCGGGA CTCTGGGGTT CGAAATGACC
5651 GACCAAGCGA CGCCCAACCT GCCATCACGA GATTTCGATT CCACCGCCGC
5701 CTTCTATGAA AGGTTGGGCT TCGGAATCGT TTTCCGGGAC GCCGGCTGGA
5751 TGATCCTCCA GCGCGGGGAT CTCATGCTGG AGTTCTTCGC CCACCCCAAC
5801 TTGTTTATTG CAGCTTATAA TGGTTACAAA TAAAGCAATA GCATCACAAA
5851 TTTCACAAAT AAAGCATTTT TTCACTGCA TTCTAGTTGT GGTTTGTCCA
5901 AACTCATCAA TGTATCTTAT CATGTCTGTA TACCGTCGAC CTCTAGCTAG
5951 AGCTTGGCGT AATCATGGTC ATAGCTGTTT CCTGTGTGAA ATTGTTATCC
6001 GCTCACAATT CCACACAACA TACGAGCCGG AAGCATAAAG TGTAAAGCCT
6051 GGGGTGCCTA ATGAGTGAGC TAACTCACAT TAATTGCGTT GCGCTCACTG
6101 CCCGCTTTCC AGTCGGGAAA CCTGTCGTGC CAGCTGCATT AATGAATCGG
6151 CCAACGCGCG GGAGAGGCG GTTTGCGTAT TGGGCGCTCT TCCGCTTCCT
6201 CGCTCACTGA CTCGCTGCGC TCGGTCGTTC GGCTGCGGCG AGCGGTATCA
6251 GCTCACTCAA AGGCGGTAAT ACGGTTATCC ACAGAATCAG GGGATAACGC
6301 AGGAAAGAAC ATGTGAGCAA AAGGCCAGCA AAAGGCCAGG AACCGTAAAA
6351 AGGCCGCGTT GCTGGCGTTT TTCCATAGGC TCCGCCCCCC TGACGAGCAT
6401 CACAAAAATC GACGCTCAAG TCAGAGGTGG CGAAACCCGA CAGGACTATA
6451 AAGATACCAG GCGTTTCCCC CTGGAAGCTC CCTCGTGCGC TCTCCTGTTC
6501 CGACCCTGCC GCTTACCGGA TACCTGTCCG CCTTTCTCCC TTCGGGAAGC
6551 GTGGCGCTTT CTCATAGCTC ACGCTGTAGG TATCTCAGTT CGGTGTAGGT
6601 CGTTCGCTCC AAGCTGGGCT GTGTGCACGA ACCCCCCGTT CAGCCCGACC
6651 GCTGCGCCTT ATCCGGTAAC TATCGTCTTG AGTCCAACCC GGTAAGACAC
6701 GACTTATCGC CACTGGCAGC AGCCACTGGT AACAGGATTA GCAGAGCGAG
6751 GTATGTAGGC GGTGCTACAG AGTTCTTGAA GTGGTGGCCT AACTACGGCT
6801 ACACTAGAAG AACAGTATTT GGTATCTGCG CTCTGCTGAA GCCAGTTACC
6851 TTCGGAAAAA GAGTTGGTAG CTCTTGATCC GGCAAACAAA CCACCGCTGG
6901 TAGCGGTTTT TTTGTTTGCA AGCAGCAGAT TACGCGCAGA AAAAAGGAT
6951 CTCAAGAAGA TCCTTTGATC TTTTCTACGG GGTCTGACGC TCAGTGGAAC
7001 GAAAACTCAC GTTAAGGGAT TTTGGTCATG AGATTATCAA AAAGGATCTT
7051 CACCTAGATC CTTTTAAATT AAAAATGAAG TTTTAAATCA ATCTAAAGTA
7101 TATATGAGTA AACTTGGTCT GACAGTTACC AATGCTTAAT CAGTGAGGCA
7151 CCTATCTCAG CGATCTGTCT ATTTCGTTCA TCCATAGTTG CCTGACTCCC
7201 CGTCGTGTAG ATAACTACGA TACGGGAGGG CTTACCATCT GGCCCCAGTG
7251 CTGCAATGAT ACCGCGAGAC CCACGCTCAC CGGCTCCAGA TTTATCAGCA
7301 ATAAACCAGC CAGCCGGAAG GGCCGAGCGC AGAAGTGGTC CTGCAACTTT
7351 ATCCGCCTCC ATCCAGTCTA TTAATTGTTG CCGGGAAGCT AGAGTAAGTA
7401 GTTCGCCAGT TAATAGTTTG CGCAACGTTG TTGCCATTGC TACAGGCATC
```

```
7451 GTGGTGTCAC GCTCGTCGTT TGGTATGGCT TCATTCAGCT CCGGTTCCCA

7501 ACGATCAAGG CGAGTTACAT GATCCCCCAT GTTGTGCAAA AAAGCGGTTA

7551 GCTCCTTCGG TCCTCCGATC GTTGTCAGAA GTAAGTTGGC CGCAGTGTTA

7601 TCACTCATGG TTATGGCAGC ACTGCATAAT TCTCTTACTG TCATGCCATC

7651 CGTAAGATGC TTTTCTGTGA CTGGTGAGTA CTCAACCAAG TCATTCTGAG

7701 AATAGTGTAT GCGGCGACCG AGTTGCTCTT GCCCGGCGTC AATACGGGAT

7751 AATACCGCGC CACATAGCAG AACTTTAAAA GTGCTCATCA TTGGAAAACG

7801 TTCTTCGGGG CGAAAACTCT CAAGGATCTT ACCGCTGTTG AGATCCAGTT

7851 CGATGTAACC CACTCGTGCA CCCAACTGAT CTTCAGCATC TTTTACTTTC

7901 ACCAGCGTTT CTGGGTGAGC AAAAACAGGA AGGCAAAATG CCGCAAAAAA

7951 GGGAATAAGG GCGACACGGA AATGTTGAAT ACTCATACTC TTCCTTTTTC

8001 AATATTATTG AAGCATTTAT CAGGGTTATT GTCTCATGAG CGGATACATA

8051 TTTGAATGTA TTTAGAAAAA TAAACAAATA GGGGTTCCGC GCACATTTCC

8101 CCGAAAAGTG CCACCTGACG TC
```

According to one embodiment, the vector is a plasmid and has the sequence of pAV-U6+27-Tornado-F30-Pepper(TAR Variant-2) (SEQ ID NO: 78; GenBank Accession No. MN052908.1, which is hereby incorporated by reference in its entirety) as follows:

```
   1 GCCGGATCCA AGGTCGGGCA GGAAGAGGGC CTATTTCCCA TGATTCCTTC

51 ATATTTGCAT ATACGATACA AGGCTGTTAG AGAGATAATT AGAATTAATT

101 TGACTGTAAA CACAAAGATA TTAGTACAAA ATACGTGACG TAGAAAGTAA

151 TAATTTCTTG GGTAGTTTGC AGTTTTAAAA TTATGTTTTA AAATGGACTA

201 TCATATGCTT ACCGTAACTT GAAAGTATTT CGATTTCTTG GCTTTATATA

251 TCTTGTGGAA AGGACGAAAC ACCGTGCTCG CTTCGGCAGC ACATATACTA

301 GTCGACGGGC CGCACTCGCC GGTCCCAAGC CCGGATAAAA TGGGAGGGGG

351 CGGGAAACCG CCTAACCATG CCGAGTGCGG CCGCTTGCCA TGTGTATGTG

401 GGACGCGTTG CCACGTTTCC CACATACTCT GATGATCCGC TAGCAAAGGC

451 TCGTTGAGCT CATTAGCTCC GAGCCCGAGG TACCGGATCA TTCATGGCAA

501 GCGGCCGCGG TCGGCGTGGA CTGTAGAACA CTGCCAATGC CGGTCCCAAG

551 CCCGGATAAA AGTGGAGGGT ACAGTCCACG CTCTAGAGCG GACTTCGGTC

601 CGCTTTTTAC TAGGACCTGC AGGCATGCAA GCTTGACGTC GGTTACCGAT

651 ATCCATATGG CGACCGCATC GATCTCGAGC CGAGGACTAG TAACTTGTTT

701 ATTGCAGCTT ATAATGGTTA CAAATAAAGC AATAGCATCA CAAATTTCAC

751 AAATAAAGCA TTTTTTTCAC TGCATTCTAG TTGTGGTTTG TCCAAACTCA

801 TCAATGTATC TTATCATGTC TTACGTAGAT AAGTAGCATG GCGGGTTAAT

851 CATTAACTAC AAGGAACCCC TAGTGATGGA GTTGGCCACT CCCTCTCTGC

901 GCGCTCGCTC GCTCACTGAG GCCGGGCGAC CAAAGGTCGC CCGACGCCCG

951 GGCTTTGCCC GGGCGGCCTC AGTGAGCGAG CGAGCGCGCA GAGAGGGAGT

1001 GGCCAAAGAT CTCTGGCGTA ATAGCGAAGA GGCCCGCACC GATCGCCCTT

1051 CCCAACAGTT GCGCAGCCTG AATGGCTAAT GGGAAATTGT AAACGTTAAT
```

```
1101 ATTTTGTTAA TATTTTGTTA AAATTCGCGT TAAATTTTTG TTAAATCAGC

1151 TCATTTTTTA ACCAATAGGC CGAAATCGGC AAAATCCCTT ATAAATCAAA

1201 AGAATAGACC GAGATAGGGT TGAGTGTTGT TCCAGTTTGG AACAAGAGTC

1251 CACTATTAAA GAACGTGGAC TCCAACGTCA AAGGGCGAAA AACCGTCTAT

1301 CAGGGCGATG GCCCACTACG TGAACCATCA CCCTAATCAA GTTTTTTGGG

1351 GTCGAGGTGC CGTAAAGCAC TAAATCGGAA CCCTAAAGGG ATGCCCCGAT

1401 TTAGAGCTTG ACGGGGAAAG CCGGCGAACG TGGCGAGAAA GGAAGGGAAG

1451 AAAGCGAAAG GAGCGGGCGC TAGGGCGCTG GCAAGTGTAG CGGTCACGCT

1501 GCGCGTAACC ACCACACCCG CCGCGCTTAA TGCGCCGCTA CAGGGCGCGT

1551 CAGGTGGCAC TTTTCGGGGA AATGTGCGCG GAACCCCTAT TTGTTTATTT

1601 TTCTAAATAC ATTCAAATAT GTATCCGCTC ATGAGACAAT AACCCTGATA

1651 AATGCTTCAA TAATATTGAA AAAGGAAGAG TATGAGTATT CAACATTTCC

1701 GTGTCGCCCT TATTCCCTTT TTTGCGGCAT TTTGCCTTCC TGTTTTTGCT

1751 CACCCAGAAA CGCTGGTGAA AGTAAAAGAT GCTGAAGATC AGTTGGGTGC

1801 ACGAGTGGGT TACATCGAAC TGGATCTCAA CAGCGGTAAG ATCCTTGAGA

1851 GTTTTCGCCC CGAAGAACGT TTTCCAATGA TGAGCACTTT TAAAGTTCTG

1901 CTATGTGGCG CGGTATTATC CCGTATTGAC GCCGGGCAAG AGCAACTCGG

1951 TCGCCGCATA CACTATTCTC AGAATGACTT GGTTGAGTAC TCACCAGTCA

2001 CAGAAAAGCA TCTTACGGAT GGCATGACAG TAAGAGAATT ATGCAGTGCT

2051 GCCATAACCA TGAGTGATAA CACTGCGGCC AACTTACTTC TGACAACGAT

2101 CGGAGGACCG AAGGAGCTAA CCGCTTTTTT GCACAACATG GGGGATCATG

2151 TAACTCGCCT TGATCGTTGG GAACCGGAGC TGAATGAAGC CATACCAAAC

2201 GACGAGCGTG ACACCACGAT GCCTGTAGCA ATGGCAACAA CGTTGCGCAA

2251 ACTATTAACT GGCGAACTAC TTACTCTAGC TTCCCGGCAA CAATTAATAG

2301 ACTGGATGGA GGCGGATAAA GTTGCAGGAC CACTTCTGCG CTCGGCCCTT

2351 CCGGCTGGCT GGTTTATTGC TGATAAATCT GGAGCCGGTG AGCGTGGGTC

2401 TCGCGGTATC ATTGCAGCAC TGGGGCCAGA TGGTAAGCCC TCCCGTATCG

2451 TAGTTATCTA CACGACGGGG AGTCAGGCAA CTATGGATGA ACGAAATAGA

2501 CAGATCGCTG AGATAGGTGC CTCACTGATT AAGCATTGGT AACTGTCAGA

2551 CCAAGTTTAC TCATATATAC TTTAGATTGA TTTAAAACTT CATTTTTAAT

2601 TTAAAAGGAT CTAGGTGAAG ATCCTTTTTG ATAATCTCAT GACCAAAATC

2651 CCTTAACGTG AGTTTTCGTT CCACTGAGCG TCAGACCCCG TAGAAAAGAT

2701 CAAAGGATCT TCTTGAGATC CTTTTTTTCT GCGCGTAATC TGCTGCTTGC

2751 AAACAAAAAA ACCACCGCTA CCAGCGGTGG TTTGTTTGCC GGATCAAGAG

2801 CTACCAACTC TTTTTCCGAA GGTAACTGGC TTCAGCAGAG CGCAGATACC

2851 AAATACTGTC CTTCTAGTGT AGCCGTAGTT AGGCCACCAC TTCAAGAACT

2901 CTGTAGCACC GCCTACATAC CTCGCTCTGC TAATCCTGTT ACCAGTGGCT

2951 GCTGCCAGTG GCGATAAGTC GTGTCTTACC GGGTTGGACT CAAGACGATA

3001 GTTACCGGAT AAGGCGCAGC GGTCGGGCTG AACGGGGGGT TCGTGCACAC

3051 CAGCCAGCTT GGAGCGAACG ACCTACACCG AACTGAGATA CCTACAGCGT
```

```
3101 GAGCATTGAG AAAGCGCCAC GCTTCCCGAA GGGAGAAAGG CGGACAGGTA

3151 TCCGGTAAGC GGCAGGGTCG GAACAGGAGA GCGCACGAGG GAGCTTCCAG

3201 GGGGAAACGC CTGGTATCTT TATAGTCCTG TCGGGTTTCG CCACCTCTGA

3251 CTTGAGCGTC GATTTTTGTG ATGCTCGTCA GGGGGGCGGA GCCTATGGAA

3301 AAACGCCAGC AACGCGGCCT TTTTACGGTT CCTGGCCTTT TGCTGGCCTT

3351 TTGCTCACAT GTTCTTTCCT GCGTTATCCC CTGATTCTGT GGATAACCGT

3401 ATTACCGCCT TTGAGTGAGC TGATACCGCT CGCCGCAGCC GAACGACCGA

3451 GCGCAGCGAG TCAGTGAGCG AGGAAGCGGA AGAGCGCCCA ATACGCAAAC

3501 CGCCTCTCCC CGCGCGTTGG CCGATTCATT AATGCAGAGA TCTTTGGCCA

3551 CTCCCTCTCT GCGCGCTCGC TCGCTCACTG AGGCCGGGCG ACCAAAGGTC

3601 GCCCGACGCC CGGGCTTTGC CCGGGCGGCC TCAGTGAGCG AGCGAGCGCG

3651 CAGAGAGGGA GTGGCCAACT CCATCACTAG GGGTTCCTGG AGGGGTGGAG

3701 TCGTGACGTG AATTACGTCA TAGGGTTAGG GAGGTCCTGG ATCGATCCAG

3751 ACATGATAAG ATACATTGAT GAGTTTGGAC AAACCACAAC TAGAATGCAG

3801 TGAAAAAAAT GCTTTATTTG TGAAATTTGT GATGCTATTG CTTTATTTGT

3851 AACCATTATA AGCTGCAATA AACAAGTTAA CAACAACAAT TGCATTCATT

3901 TTATGTTTCA GGTTCAGGGG GAGGTGTGGG AGGTTTTTTA AAGCAAGTAA

3951 AACCTCTACA AATGTGGTAT GGCTGATTAT GATCTCTAGT CAAGGCACTA

4001 TACATCAAAT ATTCCTTATT AACCCCTTTA CAAATTAAAA AGCTAAAGGT

4051 ACACAATTTT TGAGCATAGT TATTAATAGC AGACACTCTA TGCCTGTGTG

4101 GAGTAAGAAA AACAGTATG TTATGATTAT AACTGTTATG CCTACTTATA

4151 AAGGTTACAG AATATTTTTC CATAATTTTC TTGTATAGCA GTGCAGCTTT

4201 TTCCTTTGTG GTGTAAATAG CAAAGCAAGC AAGAGTTCTA TTACTAAACA

4251 CAGCATGACT CAAAAAACTT AGCAATTCTG AAGGAAAGTC CTTGGGGTCT

4301 TCTACCTTTC TCTTCTTTTT TGGAGGAGTA GAATGTTGAG AGTCAGCAGT

4351 AGCCTCATCA TCACTAGATG GCATTTCTTC TGAGCAAAAC AGGTTTTCCT

4401 CATTAAAGGC ATTCCACCAC TGCTCCCATT CATCAGTTCC ATAGGTTGGA

4451 ATCTAAAATA CACAAACAAT TAGAATCAGT AGTTTAACAC ATTATACACT

4501 TAAAATTTT ATATTTACCT TAGAGCTTTA AATCTCTGTA GGTAGTTTGT

4551 CCAATTATGT CACACCACAG AAGTAAGGTT CCTTCACAAA GATCCGGGAC

4601 CAAAGCGGCC ATCGTGCCTC CCCACTCCTG CAGTTCGGGG GCATGGATGC

4651 GCGGATAGCC GCTGCTGGTT TCCTGGATGC CGACGGATTT GCACTGCCGG

4701 TAGAACTCCG CGAGGTCGTC CAGCCTCAGG CAGCAGCTGA ACCAACTCGC

4751 GAGGGGATCG AGCCCGGGGT GGGCGAAGAA CTCCAGCATG AGATCCCCGC

4801 GCTGGAGGAT CATCCAGCCG GCGTCCCGGA AAACGATTCC GAAGCCCAAC

4851 CTTTCATAGA AGGCGGCGGT GGAATCGAAA TCTCGTGATG GCAGGTTGGG

4901 CGTCGCTTGG TCGGTCATTT CGAACCCCAG AGTCCCGCTC AGAAGAACTC

4951 GTCAAGAAGG CGATAGAAGG CGATGCGCTG CGAATCGGGA GCGGCGATAC

5001 CGTAAAGCAC GAGGAAGCGG TCAGCCCATT CGCCGCCAAG CTCTTCAGCA

5051 ATATCACGGG TAGCCAACGC TATGTCCTGA TAGCGGTCCG CCACACCCAG

5101 CCGGCCACAG TCGATGAATC CAGAAAAGCG GCCATTTTCC ACCATGATAT
```

```
5151 TCGGCAAGCA GGCATCGCCA TGGGTCACGA CGAGATCCTC GCCGTCGGGC

5201 ATGCGCGCCT TGAGCCTGGC GAACAGTTCG GCTGGCGCGA GCCCCTGATG

5251 CTCTTGTCCA GATCATCCTG ATCGACAAGA CCGGCTTCCA TCCGAGTACG

5301 TGCTCGCTCG ATGCGATGTT CGCTTGGTGG TCGAATGGGC AGGTAGCCGG

5351 ATCAAGCGTA TGCAGCCGCC GCATTGCATC AGCCATGATG GATACTTTCT

5401 CGGCAGGAGC AAGGTGAGAT GACAGGAGAT CCTGCCCCGG CACTTCGCCC

5451 AATAGCAGCC AGTCCCTTCC CGCTTCAGTG ACAACGTCGA GCACAGCTGC

5501 GCAAGGAACG CCCGTCGTGG CCAGCCACGA TAGCCGCGCT GCCTCGTCCT

5551 GCAGTTCATT CAGGGCACCG GACAGGTCGG TCTTGACAAA AAGAACCGGG

5601 CGCCCCTGCG CTGACAGCCG GAACACGGCG GCATCAGAGC AGCCGATTGT

5651 CTGTTGTGCC CAGTCATAGC CGAATAGCCT CTCCACCCAA GCGGCCGGAG

5701 AACCTGCGTG CAATCCATCT TGTTCAATCA TGCGAAACGA TCCTCATCCT

5751 GTCTCTTGAT CAGATCTTGA TCCCCTGCGC CATCAGATCC TTGGCGGCAA

5801 GAAAGCCATC CAGTTTACTT TGCAGGGCTT CCCAACCTTA CCAGAGGGCG

5851 CCCCAGCTGG CAATTCCGGT TCGCTTGCTG TCCATAAAAC CGCCCAGTCT

5901 AGCTATCGGC ATGTAAGCCC ACTGCAAGCT ACCTGCTTTC TCTTTGCGCT

5951 TGCGTTTTCC CTTGTCCAGA TAGCCCAGTA GCTGACATTC ATCCGGGTC

6001 AGCACCGTTT CTGCGGACTG GCTTTCTACG TGTTCCGCTT CCTTTAGCAG

6051 CCCTTGCGCC CTGAGTGCTT GCGGCAGCGT GAAGCTTTTT GCAAAAGCCT

6101 AGGCCTCCAA AAAAGCCTCC TCACTACTTC TGGAATAGCT CAGAGGCCGA

6151 GGCGGCCTCG GCCTCTGCAT AAATAAAAAA AATTAGTCAG CCATGGGGCG

6201 GAGAATGGGC GGAACTGGGC GGAGTTAGGG GCGGGATGGG CGGAGTTAGG

6251 GGCGGGACTA TGGTTGCTGA CTAATTGAGA TGCATGCTTT GCATACTTCT

6301 GCCTGCTGGG GAGCCTGGGG ACTTTCCACA CCTGGTTGCT GACTAATTGA

6351 GATGCATGCT TTGCATACTT CTGCCTGCTG GGGAGCCTGG GGACTTTCCA

6401 CACCCTAACT GACACACATT CCACA
```

According to one embodiment, the vector is a plasmid and has the sequence of pAV-U6+27-Tornado-F30-TAR Variant-1 (SEQ ID NO: 79; GenBank Accession No. MN052909.1, which is hereby incorporated by reference in its entirety) as follows:

```
   1 GCCGGATCCA AGGTCGGGCA GGAAGAGGGC CTATTTCCCA TGATTCCTTC

51 ATATTTGCAT ATACGATACA AGGCTGTTAG AGAGATAATT AGAATTAATT

101 TGACTGTAAA CACAAAGATA TTAGTACAAA ATACGTGACG TAGAAAGTAA

151 TAATTTCTTG GGTAGTTTGC AGTTTTAAAA TTATGTTTTA AAATGGACTA

201 TCATATGCTT ACCGTAACTT GAAAGTATTT CGATTTCTTG GCTTTATATA

251 TCTTGTGGAA AGGACGAAAC ACCGTGCTCG CTTCGGCAGC ACATATACTA

301 GTCGACGGGC CGCACTCGCC GGTCCCAAGC CCGGATAAAA TGGGAGGGGG

351 CGGGAAACCG CCTAACCATG CCGAGTGCGG CCGCTTGCCA TGTGTATGTG

401 GGACGCGTTG CCACGTTTCC CACATACTCT GATGATCCGC TAGCAAAGGC

451 TCGTCTGAGC TCATTAGCTC CGAGCCCGAG GTACCGGATC ATTCATGGCA
```

```
 501 AGCGGCCGCG GTCGGCGTGG ACTGTAGAAC ACTGCCAATG CCGGTCCCAA
 551 GCCCGGATAA AAGTGGAGGG TACAGTCCAC GCTCTAGAGC GGACTTCGGT
 601 CCGCTTTTTA CTAGGACCTG CAGGCATGCA AGCTTGACGT CGGTTACCGA
 651 TATCCATATG GCGACCGCAT CGATCTCGAG CCGAGGACTA GTAACTTGTT
 701 TATTGCAGCT TATAATGGTT ACAAATAAAG CAATAGCATC ACAAATTTCA
 751 CAAATAAAGC ATTTTTTTCA CTGCATTCTA GTTGTGGTTT GTCCAAACTC
 801 ATCAATGTAT CTTATCATGT CTTACGTAGA TAAGTAGCAT GGCGGGTTAA
 851 TCATTAACTA CAAGGAACCC CTAGTGATGG AGTTGGCCAC TCCCTCTCTG
 901 CGCGCTCGCT CGCTCACTGA GGCCGGGCGA CCAAAGGTCG CCCGACGCCC
 951 GGGCTTTGCC CGGGCGGCCT CAGTGAGCGA GCGAGCGCGC AGAGAGGGAG
1001 TGGCCAAAGA TCTCTGGCGT AATAGCGAAG AGGCCCGCAC CGATCGCCCT
1051 TCCCAACAGT TGCGCAGCCT GAATGGCTAA TGGGAAATTG TAAACGTTAA
1101 TATTTTGTTA ATATTTTGTT AAAATTCGCG TTAAATTTTT GTTAAATCAG
1151 CTCATTTTTT AACCAATAGG CCGAAATCGG CAAAATCCCT TATAAATCAA
1201 AAGAATAGAC CGAGATAGGG TTGAGTGTTG TTCCAGTTTG GAACAAGAGT
1251 CCACTATTAA AGAACGTGGA CTCCAACGTC AAAGGGCGAA AAACCGTCTA
1301 TCAGGGCGAT GGCCCACTAC GTGAACCATC ACCCTAATCA AGTTTTTTGG
1351 GGTCGAGGTG CCGTAAAGCA CTAAATCGGA ACCCTAAAGG GATGCCCCGA
1401 TTTAGAGCTT GACGGGGAAA GCCGGCGAAC GTGGCGAGAA AGGAAGGGAA
1451 GAAAGCGAAA GGAGCGGGCG CTAGGGCGCT GGCAAGTGTA GCGGTCACGC
1501 TGCGCGTAAC CACCACACCC GCCGCGCTTA ATGCGCCGCT ACAGGGCGCG
1551 TCAGGTGGCA CTTTTCGGGG AAATGTGCGC GGAACCCCTA TTTGTTTATT
1601 TTTCTAAATA CATTCAAATA TGTATCCGCT CATGAGACAA TAACCCTGAT
1651 AAATGCTTCA ATAATATTGA AAAGGAAGA GTATGAGTAT TCAACATTTC
1701 CGTGTCGCCC TTATTCCCTT TTTTGCGGCA TTTTGCCTTC CTGTTTTTGC
1751 TCACCCAGAA ACGCTGGTGA AAGTAAAAGA TGCTGAAGAT CAGTTGGGTG
1801 CACGAGTGGG TTACATCGAA CTGGATCTCA ACAGCGGTAA GATCCTTGAG
1851 AGTTTTCGCC CCGAAGAACG TTTTCCAATG ATGAGCACTT TTAAAGTTCT
1901 GCTATGTGGC GCGGTATTAT CCCGTATTGA CGCCGGGCAA GAGCAACTCG
1951 GTCGCCGCAT ACACTATTCT CAGAATGACT TGGTTGAGTA CTCACCAGTC
2001 ACAGAAAAGC ATCTTACGGA TGGCATGACA GTAAGAGAAT TATGCAGTGC
2051 TGCCATAACC ATGAGTGATA ACACTGCGGC CAACTTACTT CTGACAACGA
2101 TCGGAGGACC GAAGGAGCTA ACCGCTTTTT TGCACAACAT GGGGGATCAT
2151 GTAACTCGCC TTGATCGTTG GGAACCGGAG CTGAATGAAG CCATACCAAA
2201 CGACGAGCGT GACACCACGA TGCCTGTAGC AATGGCAACA ACGTTGCGCA
2251 AACTATTAAC TGGCGAACTA CTTACTCTAG CTTCCCGGCA ACAATTAATA
2301 GACTGGATGG AGGCGGATAA AGTTGCAGGA CCACTTCTGC GCTCGGCCCT
2351 TCCGGCTGGC TGGTTTATTG CTGATAAATC TGGAGCCGGT GAGCGTGGGT
2401 CTCGCGGTAT CATTGCAGCA CTGGGGCCAG ATGGTAAGCC CTCCCGTATC
2451 GTAGTTATCT ACACGACGGG GAGTCAGGCA ACTATGGATG AACGAAATAG
```

```
2501 ACAGATCGCT GAGATAGGTG CCTCACTGAT TAAGCATTGG TAACTGTCAG

2551 ACCAAGTTTA CTCATATATA CTTTAGATTG ATTTAAAACT TCATTTTTAA

2601 TTTAAAAGGA TCTAGGTGAA GATCCTTTTT GATAATCTCA TGACCAAAAT

2651 CCCTTAACGT GAGTTTTCGT TCCACTGAGC GTCAGACCCC GTAGAAAAGA

2701 TCAAAGGATC TTCTTGAGAT CCTTTTTTTC TGCGCGTAAT CTGCTGCTTG

2751 CAAACAAAAA AACCACCGCT ACCAGCGGTG GTTTGTTTGC CGGATCAAGA

2801 GCTACCAACT CTTTTTCCGA AGGTAACTGG CTTCAGCAGA GCGCAGATAC

2851 CAAATACTGT CCTTCTAGTG TAGCCGTAGT TAGGCCACCA CTTCAAGAAC

2901 TCTGTAGCAC CGCCTACATA CCTCGCTCTG CTAATCCTGT TACCAGTGGC

2951 TGCTGCCAGT GGCGATAAGT CGTGTCTTAC CGGGTTGGAC TCAAGACGAT

3001 AGTTACCGGA TAAGGCGCAG CGGTCGGGCT GAACGGGGGG TTCGTGCAAC

3051 ACAGCCAGCT TGGAGCGAAC GACCTACACC GAACTGAGAT ACCTACAGCG

3101 TGAGCATTGA GAAAGCGCCA CGCTTCCCGA AGGGAGAAAG GCGGACAGGT

3151 ATCCGGTAAG CGGCAGGGTC GGAACAGGAG AGCGCACGAG GGAGCTTCCA

3201 GGGGGAAACG CCTGGTATCT TTATAGTCCT GTCGGGTTTC GCCACCTCTG

3251 ACTTGAGCGT CGATTTTTGT GATGCTCGTC AGGGGGGCGG AGCCTATGGA

3301 AAAACGCCAG CAACGCGGCC TTTTTACGGT TCCTGGCCTT TTGCTGGCCT

3351 TTTGCTCACA TGTTCTTTCC TGCGTTATCC CCTGATTCTG TGGATAACCG

3401 TATTACCGCC TTTGAGTGAG CTGATACCGC TCGCCGCAGC CGAACGACCG

3451 AGCGCAGCGA GTCAGTGAGC GAGGAAGCGG AAGAGCGCCC AATACGCAAA

3501 CCGCCTCTCC CCGCGCGTTG GCCGATTCAT TAATGCAGAG ATCTTTGGCC

3551 ACTCCCTCTC TGCGCGCTCG CTCGCTCACT GAGGCCGGGC GACCAAAGGT

3601 CGCCCGACGC CCGGGCTTTG CCCGGGCGGC CTCAGTGAGC GAGCGAGCGC

3651 GCAGAGAGGG AGTGGCCAAC TCCATCACTA GGGGTTCCTG GAGGGGTGGA

3701 GTCGTGACGT GAATTACGTC ATAGGGTTAG GGAGGTCCTG GATCGATCCA

3751 GACATGATAA GATACATTGA TGAGTTTGGA CAAACCACAA CTAGAATGCA

3801 GTGAAAAAAA TGCTTTATTT GTGAAATTTG TGATGCTATT GCTTTATTTG

3851 TAACCATTAT AAGCTGCAAT AAACAAGTTA ACAACAACAA TTGCATTCAT

3901 TTTATGTTTC AGGTTCAGGG GGAGGTGTGG GAGGTTTTTT AAAGCAAGTA

3951 AAACCTCTAC AAATGTGGTA TGGCTGATTA TGATCTCTAG TCAAGGCACT

4001 ATACATCAAA TATTCCTTAT TAACCCCTTT ACAAATTAAA AAGCTAAAGG

4051 TACACAATTT TTGAGCATAG TTATTAATAG CAGACACTCT ATGCCTGTGT

4101 GGAGTAAGAA AAAACAGTAT GTTATGATTA TAACTGTTAT GCCTACTTAT

4151 AAAGGTTACA GAATATTTTT CCATAATTTT CTTGTATAGC AGTGCAGCTT

4201 TTTCCTTTGT GGTGTAAATA GCAAAGCAAG CAAGAGTTCT ATTACTAAAC

4251 ACAGCATGAC TCAAAAAACT TAGCAATTCT GAAGGAAAGT CCTTGGGGTC

4301 TTCTACCTTT CTCTTCTTTT TTGGAGGAGT AGAATGTTGA GAGTCAGCAG

4351 TAGCCTCATC ATCACTAGAT GGCATTTCTT CTGAGCAAAA CAGGTTTTCC

4401 TCATTAAAGG CATTCCACCA CTGCTCCCAT TCATCAGTTC CATAGGTTGG

4451 AATCTAAAAT ACACAAACAA TTAGAATCAG TAGTTTAACA CATTATACAC

4501 TTAAAAATTT TATATTTACC TTAGAGCTTT AAATCTCTGT AGGTAGTTTG
```

```
4551 TCCAATTATG TCACACCACA GAAGTAAGGT TCCTTCACAA AGATCCGGGA

4601 CCAAAGCGGC CATCGTGCCT CCCCACTCCT GCAGTTCGGG GGCATGGATG

4651 CGCGGATAGC CGCTGCTGGT TTCCTGGATG CCGACGGATT TGCACTGCCG

4701 GTAGAACTCC GCGAGGTCGT CCAGCCTCAG GCAGCAGCTG AACCAACTCG

4751 CGAGGGGATC GAGCCCGGGG TGGGCGAAGA ACTCCAGCAT GAGATCCCCG

4801 CGCTGGAGGA TCATCCAGCC GGCGTCCCGG AAAACGATTC CGAAGCCCAA

4851 CCTTTCATAG AAGGCGGCGG TGGAATCGAA ATCTCGTGAT GGCAGGTTGG

4901 GCGTCGCTTG GTCGGTCATT TCGAACCCCA GAGTCCCGCT CAGAAGAACT

4951 CGTCAAGAAG GCGATAGAAG GCGATGCGCT GCGAATCGGG AGCGGCGATA

5001 CCGTAAAGCA CGAGGAAGCG GTCAGCCCAT TCGCCGCCAA GCTCTTCAGC

5051 AATATCACGG GTAGCCAACG CTATGTCCTG ATAGCGGTCC GCCACACCCA

5101 GCCGGCCACA GTCGATGAAT CCAGAAAAGC GGCCATTTTC CACCATGATA

5151 TTCGGCAAGC AGGCATCGCC ATGGGTCACG ACGAGATCCT CGCCGTCGGG

5201 CATGCGCGCC TTGAGCCTGG CGAACAGTTC GGCTGGCGCG AGCCCCTGAT

5251 GCTCTTGTCC AGATCATCCT GATCGACAAG ACCGGCTTCC ATCCGAGTAC

5301 GTGCTCGCTC GATGCGATGT TCGCTTGGTG GTCGAATGGG CAGGTAGCCG

5351 GATCAAGCGT ATGCAGCCGC CGCATTGCAT CAGCCATGAT GGATACTTTC

5401 TCGGCAGGAG CAAGGTGAGA TGACAGGAGA TCCTGCCCCG GCACTTCGCC

5451 CAATAGCAGC CAGTCCCTTC CCGCTTCAGT GACAACGTCG AGCACAGCTG

5501 CGCAAGGAAC GCCCGTCGTG GCCAGCCACG ATAGCCGCGC TGCCTCGTCC

5551 TGCAGTTCAT TCAGGGCACC GGACAGGTCG GTCTTGACAA AAAGAACCGG

5601 GCGCCCCTGC GCTGACAGCC GGAACACGGC GGCATCAGAG CAGCCGATTG

5651 TCTGTTGTGC CCAGTCATAG CCGAATAGCC TCTCCACCCA AGCGGCCGGA

5701 GAACCTGCGT GCAATCCATC TTGTTCAATC ATGCGAAACG ATCCTCATCC

5751 TGTCTCTTGA TCAGATCTTG ATCCCCTGCG CCATCAGATC CTTGGCGGCA

5801 AGAAAGCCAT CCAGTTTACT TTGCAGGGCT TCCCAACCTT ACCAGAGGGC

5851 GCCCCAGCTG GCAATTCCGG TTCGCTTGCT GTCCATAAAA CCGCCCAGTC

5901 TAGCTATCGG CATGTAAGCC CACTGCAAGC TACCTGCTTT CTCTTTGCGC

5951 TTGCGTTTTC CCTTGTCCAG ATAGCCCAGT AGCTGACATT CATCCGGGGT

6001 CAGCACCGTT TCTGCGGACT GGCTTTCTAC GTGTTCCGCT TCCTTTAGCA

6051 GCCCTTGCGC CCTGAGTGCT TGCGGCAGCG TGAAGCTTTT TGCAAAAGCC

6101 TAGGCCTCCA AAAAGCCTC CTCACTACTT CTGGAATAGC TCAGAGGCCG

6151 AGGCGGCCTC GGCCTCTGCA TAAATAAAAA AAATTAGTCA GCCATGGGGC

6201 GGAGAATGGG CGGAACTGGG CGGAGTTAGG GGCGGGATGG GCGGAGTTAG

6251 GGGCGGGACT ATGGTTGCTG ACTAATTGAG ATGCATGCTT TGCATACTTC

6301 TGCCTGCTGG GGAGCCTGGG GACTTTCCAC ACCTGGTTGC TGACTAATTG

6351 AGATGCATGC TTTGCATACT TCTGCCTGCT GGGGAGCCTG GGGACTTTCC

6401 ACACCCTAAC TGACACACAT TCCACA
```

As described herein, the vector may comprise two, three, four, five, or more nucleic acid sequences according to the present application. In some embodiments, the vector comprises a first nucleic acid sequences encoding a first RNA-regulated fusion protein and a second nucleic acid sequence encoding a second RNA-regulated fusion protein. In other embodiments, the vector may further comprise a third nucleic acid molecule encoding a third RNA-regulated fusion protein, etc. For example, the vector may comprise 3-10 or more nucleic acid molecules, each encoding an independently selected RNA fusion protein according to the present application.

In some embodiments, where the vector encodes multiple RNA-regulated fusion proteins, each independent fusion protein may comprise a component of a metabolic pathway. In some embodiments, the metabolic pathway is glucose metabolism and the independent fusion proteins comprise insulin, glucagon, and/or protein kinase C epsilon. In other embodiments, the metabolic pathway is a GPCR signaling pathway and the independent fusion proteins are selected from the group consisting of α, β, and γ subunits of G-proteins.

In other embodiments, where the vector encodes multiple RNA-regulated fusion proteins, each RNA-regulated fusion protein comprises a distinct protein of interest. Suitable proteins of interest are described in detail above. In some embodiments, the proteins of interest comprise fluorescent proteins. In accordance with such embodiments, the fluorescent proteins have fluorescent emission spectra that do not substantially overlap with one another.

In some embodiments, the present application relates to an expression system comprising an expression vector into which is inserted a nucleic acid molecule described herein. In one embodiment, the expression system comprises a first vector encoding an RNA-regulated fusion protein and a second vector encoding a lentiviral transactivator of transcription (Tar) RNA aptamer.

Some embodiments of the present application relate to a host cell comprising a nucleic acid molecule (i.e., a nucleic acid molecule encoding an RNA-regulated fusion protein and/or a lentiviral transactivator of transcription (Tar) RNA sequence) or a vector (i.e., a vector comprising a nucleic acid molecule encoding an RNA-regulated fusion protein and/or a lentiviral transactivator of transcription (Tar) RNA sequence) described herein.

In some embodiments, the host cell is a mammalian cell. Suitable mammalian cells include, without limitation, rodent cells (i.e., mouse or rat cells), rabbit cells, guinea pig cells, feline cells, canine cells, porcine cells, equine cells, bovine cell, ovine cells, monkey cells, non-human primate, or human cells. In some embodiments, the host cell is a human cell. Suitable cells comprising the nucleic acid molecule or vector as described herein include primary or immortalized embryonic cells, fetal cells, or adult cells, at any stage of their lineage, e.g., totipotent, pluripotent, multipotent, or differentiated cells.

The nucleic acid molecules and/or vectors described herein may be introduced into cells via transformation, particularly transduction, conjugation, lipofection, protoplast fusion, mobilization, particle bombardment, microinjection, transfection, or electroporation. In some embodiments, the nucleic acid molecules described herein are incorporated into the host cell using standard cloning procedures known in the art, as described by Sambrook et al., Molecular Cloning: A Laboratory Manual, Second Edition, Cold Springs Laboratory, Cold Springs Harbor, N.Y. (1989), which is hereby incorporated by reference in its entirety.

In some embodiments, the host cell may comprise an endogenous RNA ligase. As described herein, the endogenous RNA ligase has the ability to catalyze the circularization of a ribonucleic acid molecule having a 5'-OH and a 2'-3'-cyclic phosphate. In accordance with this embodiment, the endogenous RNA ligase is RtcB.

Another aspect of the present application relates to an RNA-regulated fusion protein comprising a protein of interest and an RNA-regulated destabilization domain. Suitable proteins of interest and RNA-regulated destabilization domains are described in more detail supra.

In some embodiments, the protein of interest is a fluorescent protein, a bioluminescent protein, an enzyme, or a transcription factor. Suitable fluorescent proteins, bioluminescent proteins, enzymes, or transcription factors are described in more detail supra.

In some embodiments, the RNA-regulated destabilization domain has the consensus sequence of SEQ ID NO: 62 as follows: XXXXXXXXXXXXXXXXXx, where X at position 1 can be S or A; X at position 2 can be G or A; X at position 3 can be P or A; X at position 4 can be R or K; X at position 5 can be P, A, I, Y, K, or R; X at position 6 can be R, K, V, or Y; X at position 7 can be G, A, or R; X at position 8 can be T or A; X at position 9 can be R or K; X at position 10 can be G or A; X at position 11 can be K or A; X at position 12 can be G or A; X at position 13 can be R or K; X at position 14 can be I or A; X at position 15 can be R, K, Y, or G; X at position 16 can be R, K, V, T, or Y; X at position 17 can be any amino acid but preferably R, G, E, S, or C; and x at position 18 is optional and can be any amino acid, but preferably G, E, O, N, D, or E.

In some embodiments the RNA-regulated destabilization domain has the sequence of tDeg (SEQ ID NO: 63) as follows: SGPRPRGTRGKGRRIRRRG.

Exemplary RNA-regulated fusion proteins are identified in Table 8 below.

TABLE 8

Exemplary RNA-Regulated Fusion Proteins

| Vector | Sequence | SEQ ID NO: |
|---|---|---|
| (mNeonGreen)$_4$-tDeg | MVSKGEEDNMASLPATHELHIFGSINGVDFDMVGQGTGNPNDGYE ELNLKSTKGDLQFSPWILVPHIGYGFHQYLPYPDGMSPFQAAMVD GSGYQVHRTMQFEDGASLTVNYRYTYEGSHIKGEAQVKGTGFPAD GPVMTNSLTAADWCRSKKTYPNDKTIISTFKWSYTTGNGKRYRST ARTTYTFAKPMAANYLKNQPMYVFRKTELKHSKTELNFKEWQKAF TDVMGMDELYKGGHMGTGSTGGTGGVSKGEEDNMASLPATHELHI FGSINGVDFDMVGQGTGNPNDGYEELNLKSTKGDLQFSPWILVPH IGYGFHQYLPYPDGMSPFQAAMVDGSGYQVHRTMQFEDGASLTVN YRYTYEGSHIKGEAQVKGTGFPADGPVMTNSLTAADWCRSKKTYP NDKTIISTFKWSYTTGNGKRYRSTARTTYTFAKPMAANYLKNQPM | 80 |

TABLE 8-continued

Exemplary RNA-Regulated Fusion Proteins

| Vector | Sequence | SEQ ID NO: |
|---|---|---|
| | YVFRKTELKHSKTELNFKEWQKAFTDVMGMDELYKSGLESSGGTG GSGGVSKGEEDNMASLPATHELHIFGSINGVDFDMVGQGTGNPND GYEELNLKSTKGDLQFSPWILVPHIGYGFHQYLPYPDGMSPFQAA MVDGSGYQVHRTMQFEDGASLTVNYRYTYEGSHIKGEAQVKGTGF PADGPVMTNSLTAADWCRSKKTYPNDKTIISTFKWSYTTGNGKRY RSTARTTYTFAKPMAANYLKNQPMYVFRKTELKHSKTELNFKEWQ KAFTDVMGMDELYKGGSGTGGTASSGSGGGVSKGEEDNMASLPAT HELHIFGSINGVDFDMVGQGTGNPNDGYEELNLKSTKGDLQFSPW ILVPHIGYGFHQYLPYPDGMSPFQAAMVDGSGYQVHRTMQFEDGA SLTVNYRYTYEGSHIKGEAQVKGTGFPADGPVMTNSLTAADWCRS KKTYPNDKTIISTFKWSYTTGNGKRYRSTARTTYTFAKPMAANYL KNQPMYVFRKTELKHSKTELNFKEWQKAFTDVMGMDELYKGGRSG GGSGPRPRGTRGKGRRIRRRG<br>(GenBank Accession No. QEM23463.1 and GenBank Accession No. QEM23465.1, which are hereby incorporated by reference in their entirety) | |
| mNeonGreen-tDeg | MVSKGEEDNMASLPATHELHIFGSINGVDFDMVGQGTGNPNDGYE ELNLKSTKGDLQFSPWILVPHIGYGFHQYLPYPDGMSPFQAAMVD GSGYQVHRTMQFEDGASLTVNYRYTYEGSHIKGEAQVKGTGFPAD GPVMTNSLTAADWCRSKKTYPNDKTIISTFKWSYTTGNGKRYRST ARTTYTFAKPMAANYLKNQPMYVFRKTELKHSKTELNFKEWQKAF TDVMGMDELYKGGHMGGGSGGGSGPRPRGTRGKGRRIRRRG | 81 |
| mCherry-tDeg | MVSKGEEDNMAIIKEFMRFKVHMEGSVNGHEFEIEGEGEGRPYEG TQTAKLKVTKGGPLPFAWDILSPQFMYGSKAYVKHPADIPDYLKL SFPEGFKWERVMNFEDGGVVTVTQDSSLQDGEFIYKVKLRGTNFP SDGPVMQKKTMGWEASSERMYPEDGALKGEIKQRLKLKDGGHYDA EVKTTYKAKKPVQLPGAYNVNIKLDITSHNEDYTIVEQYERAEGR HSTGGMDELYKGGSGGGSGPRPRGTRGKGRRIRRRG | 82 |
| NanoLuc-tDeg | MVFTLEDFVGDWRQTAGYNLDQVLEQGGVSSLFQNLGVSVTPIQR IVLSGENGLKIDIHVIIPYEGLSGDQMGQIEKIFKVVYPVDDHHF KVILHYGTLVIDGVTPNMIDYFGRPYEGIAVFDGKKITVTGILWN GNKIIDERLINPDGSLLFRVTINGVTGWRLCERILAGGSHMGGSG GGSGPRPRGTRGKGRRIRRRG | 83 |
| EYFP-tDeg | MVSKGEELFTGVVPILVELDGDVNGHKFSVSGEGEGDATYGKLTL KFICTIGKLPVPWPTLVITFGYGLQCFARYPDHMKQHDFFKSAMP EGYVQERTIFFKDDGNYKTRAEVKFEGDTLVNRIELKGIDFKEDG NILGHKLEYNYNSHNVYIMADKQKNGIKVNFKIRHNIEDGSVQLA DHYQQNTPIGDGPVLLPDNHYLSYQSALSKDPNEKRDHMVLLEFV TAAGITLGMDELYKGGSGGGSGPRPRGTRGKGRRIRRRG | 84 |
| EGFP-TetR-tDeg | MVSKGEELFTGVVPILVELDGDVNGHKFSVSGEGEGDATYGKLTL KFICTTGKLPVPWPTLVTTLTYGVQCFSRYPDHMKQHDFFKSAMP EGYVQERTIFFKDDGNYKTRAEVKFEGDTLVNRIELKGIDFKEDG NILGHKLEYNYNSHNVYIMADKQKNGIKVNFKIRHNIEDGSVQLA DHYQQNTPIGDGPVLLPDNHYLSTQSKLSKDPNEKRDHMVLLEFV TAAGITLGMDELYKGTGACGTSGGRLDKSKVINSALELLNEVGIE GLTTRKLAQKLGVEQPTLYWHVKNKRALLDALAIEMLDRHHTHFC PLEGESWQDFLRNNAKSFRCALLSHRDGAKVHLGTRPTEKQYETL ENQLAFLCQQGFSLENALYALSAVGHFTLGCVLEDQEHQVAKEER ETPTTDSMPPLLRQAIELFDHQGAEPAFLFGLELIICGLEKQLKC ESGSGSGTGGIGGSGPRPRGTRGKGRRIRRRG | 85 |
| mCherry-TetR-tDeg | MVSKGEEDNMAIIKEFMRFKVHMEGSVNGHEFEIEGEGEGRPYEG TQTAKLKVTKGGPLPFAWDILSPQFMYGSKAYVKHPADIPDYLKL SFPEGFKWERVMNFEDGGVVTVTQDSSLQDGEFIYKVKLRGTNFP SDGPVMQKKTMGWEASSERMYPEDGALKGEIKQRLKLKDGGHYDA EVKTTYKAKKPVQLPGAYNVNIKLDITSHNEDYTIVEQYERAEGR HSTGGMDELYKGTGACGTSGGRLDKSKVINSALELLNEVGIEGLT TRKLAQKLGVEQPTLYWHVKNKRALLDALAIEMLDRHHTHFCPLE GESWQDFLRNNAKSFRCALLSHRDGAKVHLGTRPTEKQYETLENQ LAFLCQQGFSLENALYALSAVGHFTLGCVLEDQEHQVAKEERETP TTDSMPPLLRQAIELFDHQGAEPAFLFGLELIICGLEKQLKCESG SGSGTGGIGGSGPRPRGTRGKGRRIRRRG | 86 |
| EGFP-EZH2-tDeg | MVSKGEELFTGVVPILVELDGDVNGHKFSVSGEGEGDATYGKLTL KFICTIGKLPVPWPTLVTILTYGVQCFSRYPDHMKQHDFFKSAMP EGYVQERTIFFKDDGNYKTRAEVKFEGDTLVNRIELKGIDFKEDG NILGHKLEYNYNSHNVYIMADKQKNGIKVNFKIRHNIEDGSVQLA DHYQQNTPIGDGPVLLPDNHYLSTQSKLSKDPNEKRDHMVLLEFV TAAGITLGMDELYKGTGACGTSGGMGQTGKKSEKGPVCWRKRVKS EYMRLRQLKRFRRADEVKSMFSSNRQKILERTEILNQEWKQRRIQ | 87 |

TABLE 8-continued

Exemplary RNA-Regulated Fusion Proteins

| Vector | Sequence | SEQ ID NO: |
|---|---|---|
| | PVHILTSVSSLRGTRECSVTSDLDFPTQVIPLKTLNAVASVPIMY SWSPLQQNFMVEDETVLHNIPYMGDEVLDQDGTFIEELIKNYDGK VHGDRECGFINDEIFVELVNALGQYNDDDDDDGDDPEEREEKQK DLEDHRDDKESRPPRKFPSDKIFEAISSMFPDKGTAEELKEKYKE LTEQQLPGALPPECTPNIDGPNAKSVQREQSLHSFHTLFCRRCFK YDCFLHPFHATPNTYKRKNTETALDNKPCGPQCYQHLEGAKEFAA ALTAERIKTPPKRPGGRRRGRLPNNSSRPSTPTINVLESKDTDSD REAGTETGGENNDKEEEEKKDETSSSSEANSRCQTPIKMKPNIEP PENVEWSGAEASMFRVLIGTYYDNFCAIARLIGTKTCRQVYEFRV KESSIIAPAPAEDVDTPPRKKKRKHRLWAAHCRKIQLKKDGSSNH VYNYQPCDHPRQPCDSSCPCVIAQNFCEKFCQCSSECQNRFPGCR CKAQCNTKQCPCYLAVRECDPDLCLTCGAADHWDSKNVSCKNCSI QRGSKKHLLLAPSDVAGWGIFIKDPVQKNEFISEYCGEIISQDEA DRRGKVYDKYMCSFLFNLNNDFVVDATRKGNKIRFANHSVNPNCY AKVMMVNGDHRIGIFAKRAIQTGEELFFDYRYSQADALKYVGIER EMEIPGSGTGGIGGSGPRPRGTRGKGRRIRRRG | |
| mCherry-EZH2-tDeg | MVSKGEEDNMAIIKEFMRFKVHMEGSVNGHEFEIEGEGEGRPYEG TQTAKLKVTKGGPLPFAWDILSPQFMYGSKAYVKHPADIPDYLKL SFPEGFKWERVMNFEDGGVVTVTQDSSLQDGEFIYKVKLRGTNFP SDGPVMQKKTMGWEASSERMYPEDGALKGEIKQRLKLKDGGHYDA EVKTTYKAKKPVQLPGAYNVNIKLDITSHNEDYTIVEQYERAEGR HSTGGMDELYKGTGACGTSGGMGQTGKKSEKGPVCWRKRVKSEYM RLRQLKRFRRADEVKSMFSSNRQKILERTEILNQEWKQRRIQPVH ILTSVSSLRGTRECSVTSDLDFPTQVIPLKTLNAVASVPIMYSWS PLQQNFMVEDETVLHNIPYMGDEVLDQDGTFIEELIKNYDGKVHG DRECGFINDEIFVELVNALGQYNDDDDDDGDDPEEREEKQKDLE DHRDDKESRPPRKFPSDKIFEAISSMFPDKGTAEELKEKYKELTE QQLPGALPPECTPNIDGPNAKSVQREQSLHSFHTLFCRRCFKYDC FLHPFHATPNTYKRKNTETALDNKPCGPQCYQHLEGAKEFAAALT AERIKTPPKRPGGRRRGRLPNNSSRPSTPTINVLESKDTDSDREA GTETGGENNDKEEEEKKDETSSSEANSRCQTPIKMKPNIEPPEN VEWSGAEASMFRVLIGTYYDNFCAIARLIGTKTCRQVYEFRVKES SIIAPAPAEDVDTPPRKKKRKHRLWAAHCRKIQLKKDGSSNHVYN YQPCDHPRQPCDSSCPCVIAQNFCEKFCQCSSECQNRFPGCRCKA QCNTKQCPCYLAVRECDPDLCLTCGAADHWDSKNVSCKNCSIQRG SKKHLLLAPSDVAGWGIFIKDPVQKNEFISEYCGEIISQDEADRR GKVYDKYMCSFLFNLNNDFVVDATRKGNKIRFANHSVNPNCYAKV MMVNGDHRIGIFAKRAIQTGEELFFDYRYSQADALKYVGIEREME IPGSGTGGTGGSGPRPRGTRGKGRRIRRRG | 88 |
| EGFP-NFκB-tDeg | MVSKGEELFTGVVPILVELDGDVNGHKFSVSGEGEGDATYGKLTL KFICTIGKLPVPWPTLVTTLTYGVQCFSRYPDHMKQHDFFKSAMP EGYVQERTIFFKDDGNYKTRAEVKFEGDTLVNRIELKGIDFKEDG NILGHKLEYNYNSHNVYIMADKQKNGIKVNFKIRHNIEDGSVQLA DHYQQNTPIGDGPVLLPDNHYLSTQSKLSKDPNEKRDHMVLLEFV TAAGITLGMDELYKGGSGGSGGSGGSGGTGAEDDPYLGRPEQMFH LDPSLTHTIFNPEVFQPQMALPTADGPYLQILEQPKQRGFRFRYV CEGPSHGGLPGASSEKNKKSYPQVKICNYVGPAKVIVQLVTNGKN IHLHAHSLVGKHCEDGICTVTAGPKDMVVGFANLGILHVTKKKVF ETLEARMTEACIRGYNPGLLVHPDLAYLQAEGGGDRQLGDREKEL IRQAALQQTKEMDLSVVRLMFTAFLPDSTGSFTRRLEPVVSDAIY DSKAPNASNLKIVRMDRTAGCVTGGEEIYLLCDKVQKDDIQIRFY EEEENGGVWEGFGDFSPTDVHRQFAIVFKTPKYKDINITKPASVF VQLRRKSDLETSEPKPFLYYPEIKDKEEVQRKRQKLMPNFSDSFG GGSGAGAGGGGMFGSGGGGGGTGSTGPGYSFPHYGFPTYGGITFH PGTTKSNAGMKHGTMDTESKKDPEGCDKSDDKNTVNLFGKDPRGS LSGGTGGSGPRPRGTRGKGRRIRRRG | 89 |
| mCherry-NFκB-tDeg | MVSKGEEDNMAIIKEFMRFKVHMEGSVNGHEFEIEGEGEGRPYEG TQTAKLKVTKGGPLPFAWDILSPQFMYGSKAYVKHPADIPDYLKL SFPEGFKWERVMNFEDGGVVTVTQDSSLQDGEFIYKVKLRGTNFP SDGPVMQKKTMGWEASSERMYPEDGALKGEIKQRLKLKDGGHYDA EVKTTYKAKKPVQLPGAYNVNIKLDITSHNEDYTIVEQYERAEGR HSTGGMDELYKGGSGGSGGSGGSGGTGAEDDPYLGRPEQMFHLDP SLTHTIFNPEVFQPQMALPTADGPYLQILEQPKQRGFRFRYVCEG PSHGGLPGASSEKNKKSYPQVKICNYVGPAKVIVQLVTNGKNIHL HAHSLVGKHCEDGICTVTAGPKDMVVGFANLGILHVTKKKVFETL EARMTEACIRGYNPGLLVHPDLAYLQAEGGGDRQLGDREKELIRQ AALQQTKEMDLSVVRLMFTAFLPDSTGSFTRRLEPVVSDAIYDSK APNASNLKIVRMDRTAGCVTGGEEIYLLCDKVQKDDIQIRFYEEE ENGGVWEGFGDFSPTDVHRQFAIVFKTPKYKDINITKPASVFQL RRKSDLETSEPKPFLYYPEIKDKEEVQRKRQKLMPNFSDSFGGGS GAGAGGGGMFGSGGGGGTGSTGPGYSFPHYGFPTYGGITFHPGT TKSNAGMKHGTMDTESKKDPEGCDKSDDKNTVNLFGKDPRGSLSG | 90 |

TABLE 8-continued

Exemplary RNA-Regulated Fusion Proteins

| Vector | Sequence | SEQ ID NO: |
|---|---|---|
| | GTGGSGPRPRGTRGKGRRIRRRG | |
| EGFP-TurboID-tDeg | MVSKGEELFTGVVPILVELDGDVNGHKFSVSGEGEGDATYGKLTL KFICTIGKLPVPWPTLVTTLTYGVQCFSRYPDHMKQHDFFKSAMP EGYVQERTIFFKDDGNYKTRAEVKFEGDTLVNRIELKGIDFKEDG NILGHKLEYNYNSHNVYIMADKQKNGIKVNFKIRHNIEDGSVQLA DHYQQNTPIGDGPVLLPDNHYLSTQSKLSKDPNEKRDHMVLLEFV TAAGITLGMDELYKGTGACGTSGGMKDNTVPLKLIALLANGEFHS GEQLGETLGMSRAAINKHIQTLRDWGVDVFTVPGKGYSLPEPIPL LNAKQILGQLDGGSVAVLPVVDSTNQYLLDRIGELKSGDACIAEY QQAGRGSRGRKWFSPFGANLYLSMFWRLKRGPAAIGLGPVIGIVM AEALRKLGADKVRVKWPNDLYLQDRKLAGILVELAGITGDAAQIV IGAGINVAMRRVEESVVNQGWITLQEAGINLDRNTLAATLIRELR AALELFEQEGLAPYLPRWEKLDNFINRPVKLIIGDKEIFGISRGI DKQGALLLEQDGVIKPWMGGEISLRSAEKGSGTGGTGGSGPRPRG TRGKGRRIRRRG | 91 |
| EGFP-APEX-tDeg | MVSKGEELFTGVVPILVELDGDVNGHKFSVSGEGEGDATYGKLTL KFICTTGKLPVPWPTLVTTLTYGVQCFSRYPDHMKQHDFFKSAMP EGYVQERTIFFKDDGNYKTRAEVKFEGDTLVNRIELKGIDFKEDG NILGHKLEYNYNSHNVYIMADKQKNGIKVNFKIRHNIEDGSVQLA DHYQQNTPIGDGPVLLPDNHYLSTQSKLSKDPNEKRDHMVLLEFV TAAGITLGMDELYKGTGACGTSGKSYPTVSADYQDAVEKAKKKLR GFIAEKRCAPLMLRLAFHSAGTFDKGTKTGGPFGTIKHPAELAHS ANNGLDIAVRLLEPLKAEFPILSYADFYQLAGVVAVEVTGGPKVP FHPGREDKPEPPPEGRLPDPTKGSDHLRDVFGKAMGLTDQDIVAL SGGHTIGAAHKERSGFEGPWTSNPLIFDNSYFTELLSGEKEGLLQ LPSDKALLSDPVFRPLVDKYAADEDAFFADYAEAHQKLSELGFAD AGSGTGGTGGSGPRPRGTRGKGRRIRRRG | 92 |

Yet another aspect of the disclosure relates to a molecular complex comprising an RNA-regulated fusion protein comprising (i) a protein of interest and (ii) an RNA-regulated destabilization domain and an RNA aptamer bound specifically to the RNA-regulated destabilization domain.

In some embodiments, the protein of interest is a fluorescent protein, a bioluminescent protein, an enzyme, or a transcription factor. Suitable fluorescent proteins, bioluminescent proteins, enzymes, and transcription factors are described in detail supra.

In some embodiments, the RNA-regulated destabilization domain has the sequence of SEQ ID NO: 62, where X at position 1 is S or A; X at position 2 is G or A; X at position 3 is P or A; X at position 4 is R or K; X at position 5 is P, A, I, Y, K, or R; X at position 6 is R, K, V, or Y; X at position 7 is G, A, or R; X at position 8 is T or A; X at position 9 is R or K; X at position 10 is G or A; X at position 11 is K or A; X at position 12 is G or A; X at position 13 is R or K; X at position 14 is I or A; X at position 15 is R, K, Y, or G; X at position 16 is R, K, V, T, or Y; X at position 17 is any amino acid; and x at position 18 is optional and can be any amino acid. For example, the RNA-regulated destabilization domain may be tDeg (SEQ ID NO: 63).

Suitable RNA aptamer sequences are described in detail supra. In some embodiments, the RNA aptamer comprises the consensus sequence of SEQ ID NO: 56, SEQ ID NO: 58, or SEQ ID NO: 60, wherein N can be A, C, G, or U; S can be C or G; H can be A, C, or U; Y can be C or U; W can be A or U; B can be C, G, or U; M can be A or C; and D can be A, G, or U. For example, the RNA aptamer may comprise the sequence of wild-type TAR RNA (SEQ ID NO: 57), TAR Variant-1 (SEQ ID NO: 59), or TAR Variant-2 (Pepper; SEQ ID NO: 61).

Additional exemplary RNA aptamers may be selected from the group consisting of SEQ ID NO: 70, SEQ ID NO: 71, SEQ ID NO: 72, and SEQ ID NO: 73.

Some embodiments of the present application relate to a host cell comprising a molecular complex described herein (i.e., a molecular complex comprising an RNA-regulated fusion protein and an RNA aptamer bound specifically to the RNA-regulated destabilization domain). Suitable host cells are described in detail supra.

In some embodiments, the host cell is a mammalian cell. As described herein above, suitable mammalian cells include, without limitation, rodent cells (i.e., mouse or rat cells), rabbit cells, guinea pig cells, feline cells, canine cells, porcine cells, equine cells, bovine cell, ovine cells, monkey cells, non-human primate, or human cells. In some embodiments, the host cell is a human cell.

Another aspect of the invention relates to a method of imaging RNA in a cell. This method involves providing a first vector encoding an RNA-regulated fusion protein, wherein the RNA-regulated fusion protein comprises a fluorescent protein, a bioluminescent protein, or an enzyme fused to an RNA-regulated destabilization domain; providing second vector encoding an RNA molecule comprising (i) an RNA sequence of interest and (ii) an RNA aptamer sequence, where the RNA-regulated destabilization domain specifically binds to the RNA aptamer sequence; transfecting a host cell with the first vector and the second vector; and imaging said contacted cells.

Suitable vectors for carrying out the methods of imaging RNA in a cell are described in more detail supra and include, e.g., a plasmid (e.g., an expression vector) and a viral vector (e.g., a lentiviral or adenoviral vector).

Suitable RNA-regulated fusion proteins for carrying out the methods of the present application are described in more detail supra. In some embodiments of the methods described herein, the RNA-regulated fusion protein is a fluorescent protein selected from the group consisting of Green Fluorescent Protein, Enhanced Green Fluorescent Protein (EGFP), Enhanced Yellow Fluorescent Protein (EYFP), Venus, mVenus, Citrine, mCitrine, Cerulean, mCerulean, Orange Fluorescent Protein (OFP), mNeonGreen, moxNeonGreen, mCherry, mTagBFP, Venus, mVenus, mTurquoise, mScarlet, mWasabi, mOrange, and dTomato.

In other embodiments of the methods described herein, the RNA-regulated fusion protein is a bioluminescent protein selected from the group consisting of luciferase, β-galactosidase, β-lactamase, peroxidase, alkaline phosphatase, β-glucuronidase, and β-glucosidase. In some embodiments, the bioluminescent protein is a luciferase selected from the group consisting of Nanoluc luciferase (Nluc), Firefly luciferase, and *Renilla* luciferase (Rluc).

In further embodiments of the methods described herein, the RNA-regulated fusion protein is an enzyme, wherein the enzyme is a biotin ligase. Suitable biotin ligases are described in detail supra and include, e.g., TurboID, miniTurbo, or *E. coli* BirA.

As described in more detail supra, the RNA-regulated destabilization domain may comprise a bifunctional peptide having a lentiviral transactivator of transcription (Tat) peptide and a degron peptide. Lentiviral transactivator of transcription (Tat) peptides and a degron peptides are described in more detail supra.

In some embodiments of the methods described herein, the RNA-regulated destabilization domain comprises the consensus sequence of SEQ ID NO: 62, where X at position 1 is S or A; X at position 2 is G or A; X at position 3 is P or A; X at position 4 is R or K; X at position 5 is P, A, I, Y, K, or R; X at position 6 is R, K, V, or Y; X at position 7 is G, A, or R; X at position 8 is T or A; X at position 9 is R or K; X at position 10 is G or A; X at position 11 is K or A; X at position 12 is G or A; X at position 13 is R or K; X at position 14 is I or A; X at position 15 is R, K, Y, or G; X at position 16 is R, K, V, T, or Y; X at position 17 is any amino acid; and x at position 18 is optional and can be any amino acid. Thus, in some embodiments, the RNA-regulated destabilization domain is tDeg (SEQ ID NO: 63).

As used herein, an RNA of interest is an RNA molecule that is desired and/or is being assessed. The RNA of interest may be a messenger RNA (mRNA) or a noncoding RNA (ncRNA). A messenger RNA or "mRNA" refers to a single-stranded RNA molecule that specifies the amino acid sequence of a protein. The mRNA molecule may comprise a 5' untranslated region (5' UTR), a coding region, and a 3' untranslated region (3' UTR). A 5' UTR is an untranslated nucleotide segment in an RNA molecule immediately preceding the AUG start codon. A 3' UTR is an untranslated nucleotide segment in an RNA molecule immediately following the translation termination codon.

In some embodiments, the RNA of interest is an mRNA and the RNA aptamer is located within a coding region of the mRNA. In other embodiment, the RNA of interest is a mRNA and the RNA aptamer is located upstream of the 5' UTR, within the 5' UTR, within the 3' UTR, or downstream of the 3' UTR.

In other embodiments, the RNA of interest is a noncoding RNA (ncRNA). As described herein, a noncoding RNA refers to a functional RNA molecule that is not translated into a protein. The RNA of interest may be a noncoding RNA selected from the group consisting of ribosomal RNA (rRNA), transfer RNA (tRNA), heterogeneous nuclear RNA (hnRNA), small cytoplasmic RNA (scRNA), small nuclear (snRNA), small nucleolar (snoRNA), ribozymes, and regulatory RNA (e.g., siRNA, miRNA, microRNA, etc.).

In some embodiments, the RNA of interest is an artificial, engineered synthetic RNA.

Suitable RNA aptamers are described in detail supra. In some embodiments of the methods described herein, the RNA aptamer comprises the consensus sequence of SEQ ID NO: 56, SEQ ID NO: 58, or SEQ ID NO: 60, where N can be A, C, G, or U; S can be C or G; H can be A, C, or U; Y can be C or U; W can be A or U; B can be C, G, or U; M can be A or C; and D can be A, G, or U. For example, the RNA aptamer may comprise the sequence of wild-type TAR RNA (SEQ ID NO: 57), TAR Variant-1 (SEQ ID NO: 59), or TAR Variant-2 (Pepper; SEQ ID NO: 61). In some embodiments of the methods described herein, the RNA aptamer comprises the sequence of SEQ ID NO: 70, SEQ ID NO: 71, SEQ ID NO: 72, or SEQ ID NO: 73.

Methods of transfecting a host cell are well known in the art and described in more detail supra. According to some embodiments of the methods described herein, transfecting the host cell with the first vector and the second vector is carried out simultaneously. In other embodiments, transfecting the host cell with the first vector and the second vector is carried out sequentially.

Methods of imaging cells are well known in the art. In some embodiments, imaging said transfected cells is carried out by fluorescence microscopy or imaging flow cytometry (see, e.g., Wu et al., "Live Imaging of mRNA Using RNA-Stabilized Fluorogenic Proteins," *Nature Methods* 16:862-565 (2019) and Wu & Jaffrey, Live Imaging of mRNA Using Pepper RNA-Stabilized Fluorgenic Proteins," *Nature Methods*, DOI: 10.21203/rs.2.11494/v1 (2019), which are hereby incorporated by reference in their entirety).

Yet another aspect of the invention relates to a method of imaging RNA in a cell. This method involves providing a vector encoding an RNA-regulated fusion protein, where the RNA-regulated fusion protein comprises a fluorescent protein, a bioluminescent protein, or an enzyme fused to an RNA-regulated destabilization domain; transfecting a host cell with the first vector; contacting said transfected cell with an RNA molecule comprising (i) an RNA sequence of interest and (ii) an RNA aptamer sequence, where the RNA-regulated destabilization domain specifically binds to the RNA aptamer sequence; and imaging said contacted cells.

Suitable vectors for carrying out the methods of imaging RNA in a cell are described in more detail supra and include, e.g., a plasmid (e.g., an expression vector) and a viral vector (e.g., a lentiviral or adenoviral vector).

Suitable RNA-regulated fusion proteins for carrying out the methods of the present application are described in more detail supra. In some embodiments of the methods described herein, the RNA-regulated fusion protein is a fluorescent protein selected from the group consisting of Green Fluorescent Protein, Enhanced Green Fluorescent Protein (EGFP), Enhanced Yellow Fluorescent Protein (EYFP), Venus, mVenus, Citrine, mCitrine, Cerulean, mCerulean, Orange Fluorescent Protein (OFP), mNeonGreen, moxNeonGreen, mCherry, mTagBFP, Venus, mVenus, mTurquoise, mScarlet, mWasabi, mOrange, and dTomato.

In other embodiments of the methods described herein, the RNA-regulated fusion protein is a bioluminescent protein selected from the group consisting of luciferase, β-galactosidase, β-lactamase, peroxidase, alkaline phosphatase, β-glucuronidase, and β-glucosidase. In some embodiments, the bioluminescent protein is a luciferase selected from the group consisting of Nanoluc luciferase (Nluc), Firefly luciferase, and *Renilla* luciferase (Rluc).

In further embodiments of the methods described herein, the RNA-regulated fusion protein is an enzyme, wherein the enzyme is a biotin ligase. Suitable biotin ligases are described in detail supra and include, e.g., TurboID, miniTurbo, or *E. coli* BirA.

As described in more detail supra, the RNA-regulated destabilization domain may comprise a bifunctional peptide having a lentiviral transactivator of transcription (Tat) peptide and a degron peptide. Lentiviral transactivator of transcription (Tat) peptides and a degron peptides are described in more detail supra.

In some embodiments of the methods described herein, the RNA-regulated destabilization domain comprises the consensus sequence of SEQ ID NO: 62, where X at position 1 is S or A; X at position 2 is G or A; X at position 3 is P or A; X at position 4 is R or K; X at position 5 is P, A, I, Y, K, or R; X at position 6 is R, K, V, or Y; X at position 7 is G, A, or R; X at position 8 is T or A; X at position 9 is R or K; X at position 10 is G or A; X at position 11 is K or A; X at position 12 is G or A; X at position 13 is R or K; X at position 14 is I or A; X at position 15 is R, K, Y, or G; X at position 16 is R, K, V, T, or Y; X at position 17 is any amino acid; and x at position 18 is optional and can be any amino acid. Thus, in some embodiments, the RNA-regulated destabilization domain is tDeg (SEQ ID NO: 63).

In some embodiments, the RNA of interest is a mRNA and the RNA aptamer is located within a coding region of the mRNA. In other embodiment, the RNA of interest is a mRNA and the RNA aptamer is located upstream of the 5' UTR, within the 5' UTR, within the 3' UTR, or downstream of the 3' UTR.

In other embodiments, the RNA of interest is a noncoding RNA (ncRNA). As described herein, the term "noncoding RNA" refers to a functional RNA molecule that is not translated into a protein. The RNA of interest may be a noncoding RNA selected from the group consisting of ribosomal RNA (rRNA), transfer RNA (tRNA), heterogeneous nuclear RNA (hnRNA), small cytoplasmic RNA (scRNA), small nuclear (snRNA), small nucleolar (snoRNA), ribozymes, and regulatory RNA (e.g., siRNA, miRNA, microRNA, etc.).

Suitable RNA aptamers are described in detail supra. In some embodiments of the methods described herein, the RNA aptamer comprises the consensus sequence of SEQ ID NO: 56, SEQ ID NO: 58, or SEQ ID NO: 60, wherein N can be A, C, G, or U; S can be C or G; H can be A, C, or U; Y can be C or U; W can be A or U; B can be C, G, or U; M can be A or C; and D can be A, G, or U. For example, the RNA aptamer may comprise the sequence of wild-type TAR RNA (SEQ ID NO: 57), TAR Variant-1 (SEQ ID NO: 59), or TAR Variant-2 (Pepper; SEQ ID NO: 61). In some embodiments of the methods described herein, the RNA aptamer comprises the sequence of SEQ ID NO: 70, SEQ ID NO: 71, SEQ ID NO: 72, or SEQ ID NO: 73.

The RNA molecule comprising the (i) RNA sequence of interest and (ii) the RNA aptamer sequence may be a circular RNA molecule or a linear RNA molecule.

Methods of transfecting a host cell are well known in the art and described in more detail supra.

Contacting the transfected cell may be carried out by allowing the RNA molecule comprising the (i) RNA sequence of interest and (ii) the RNA aptamer sequence may be a circular RNA molecule or a linear RNA molecule to diffuse into the cell.

Methods of imaging cells are well known in the art. In some embodiments, imaging said contacted cells is carried out by fluorescence microscopy or imaging flow cytometry.

A further aspect of the invention relates to a method of selectively modifying an RNA-binding protein. This method involves providing a first expression vector encoding a RNA-regulated fusion protein, where the RNA-regulated fusion protein comprises an enzyme fused to an RNA-regulated destabilization domain; providing a second expression vector encoding (i) an RNA sequence of interest and (ii) an RNA aptamer sequence, where the RNA-regulated destabilization domain specifically binds to the RNA aptamer sequences; transfecting a host cell with the first and second expression vectors; and allowing the enzyme to be expressed, wherein the expressed enzyme selectively modifies a protein that binds to the RNA sequence of interest.

Suitable enzymes are described in more detail supra. In some embodiments, the enzyme is selected from the group consisting of a ligase, a peroxidase, and a methyltransferase.

In some embodiments of the methods described herein, the enzyme is a biotin ligase selected from the group consisting of TurboID, miniTurbo, and *E. coli* BirA.

In some embodiments of the methods described herein, the enzyme is a peroxidase selected from the group consisting of an ascorbate peroxidase and a horseradish peroxidase. The ascorbate peroxidase may be APEX2.

As described in more detail supra, the RNA-regulated destabilization domain may comprise a bifunctional peptide having a lentiviral transactivator of transcription (Tat) peptide and a degron peptide. Lentiviral transactivator of transcription (Tat) peptides and a degron peptides are described in more detail supra.

In some embodiments of the methods described herein, the RNA-regulated destabilization domain comprises the consensus sequence of SEQ ID NO: 62, where X at position 1 is S or A; X at position 2 is G or A; X at position 3 is P or A; X at position 4 is R or K; X at position 5 is P, A, I, Y, K, or R; X at position 6 is R, K, V, or Y; X at position 7 is G, A, or R; X at position 8 is T or A; X at position 9 is R or K; X at position 10 is G or A; X at position 11 is K or A; X at position 12 is G or A; X at position 13 is R or K; X at position 14 is I or A; X at position 15 is R, K, Y, or G; X at position 16 is R, K, V, T, or Y; X at position 17 is any amino acid; and x at position 18 is optional and can be any amino acid. Thus, in some embodiments, the RNA-regulated destabilization domain is tDeg (SEQ ID NO: 63).

In some embodiments, the RNA of interest is a mRNA and the RNA aptamer is located within a coding region of the mRNA. In other embodiment, the RNA of interest is a mRNA and the RNA aptamer is located upstream of the 5' UTR, within the 5' UTR, within the 3' UTR, or downstream of the 3' UTR.

In other embodiments, the RNA of interest is a noncoding RNA (ncRNA). As described herein, the term "noncoding RNA" refers to a functional RNA molecule that is not translated into a protein. The RNA of interest may be a noncoding RNA selected from the group consisting of ribosomal RNA (rRNA), transfer RNA (tRNA), heterogeneous nuclear RNA (hnRNA), small cytoplasmic RNA (scRNA), small nuclear (snRNA), small nucleolar (snoRNA), ribozymes, and regulatory RNA (e.g., siRNA, miRNA, microRNA, etc.).

Suitable RNA aptamers are described in detail supra. In some embodiments of the methods described herein, the RNA aptamer comprises the consensus sequence of SEQ ID NO: 56, SEQ ID NO: 58, or SEQ ID NO: 60, wherein N can be A, C, G, or U; S can be C or G; H can be A, C, or U; Y can be C or U; W can be A or U; B can be C, G, or U; M can be A or C; and D can be A, G, or U. For example, the RNA aptamer may comprise the sequence of wild-type TAR RNA (SEQ ID NO: 57), TAR Variant-1 (SEQ ID NO: 59), or TAR Variant-2 (Pepper; SEQ ID NO: 61). In some embodiments of the methods described herein, the RNA aptamer comprises the sequence of SEQ ID NO: 70, SEQ ID NO: 71, SEQ ID NO: 72, or SEQ ID NO: 73.

In some embodiments of the methods of selectively modifying an RNA-binding protein described herein, the method further involves identifying a protein that is selectively modified by the enzyme within the transfected cells. See, e.g., Ramanathan et al., "RNA-Protein Interaction Detection in Living Cells," *Nature Methods* 15:207-212 (2018), which is hereby incorporated by reference in its entirety.

Another aspect relates to a method of regulating expression of an RNA-stabilized protein of interest. This method involves providing a first vector encoding an RNA-regulated fusion protein, where the RNA-regulated fusion protein comprises a protein of interest fused to an RNA-regulated destabilization domain; providing a second vector encoding an RNA aptamer sequence, where the RNA-regulated destabilization domain specifically binds to the RNA aptamer sequence; providing a host cell comprising a functional ubiquitination system; transfecting the host cell with the first and second expression vectors; and expressing the first and second expression vectors within the host cell, where said expressing the first and second expression vectors regulates proteomic stability of the RNA-regulated fusion protein; and where, in the absence of any expressed RNA aptamer sequence in the host cell, the RNA-regulated destabilization domain promotes degradation of the RNA-regulated fusion protein by the ubiquitination system; and where the RNA-regulated fusion protein is stabilized by the expressed RNA aptamer sequence.

Another aspect of the invention relates to a method of regulating expression of an RNA-stabilized protein of interest. This method involves providing a first vector encoding an RNA-regulated fusion protein, where the RNA-regulated fusion protein comprises a protein of interest fused to an RNA-regulated destabilization domain; providing a second vector encoding an RNA aptamer sequence, where the RNA-regulated destabilization domain specifically binds to the RNA aptamer sequence; providing a mammalian cell lysate or solution comprising (i) a ubiquitin ligase, (ii) proteosomal degradation machinery, (iii) transcriptional machinery, and (iv) translational machinery; contacting the mammalian cell lysate or solution with the first and second expression vectors; and expressing the first and second expression vectors, where said expressing the first and second expression vectors regulates proteomic stability of the RNA-regulated fusion protein; and where, in the absence of any expressed RNA aptamer sequence in the cell lysate or solution, the RNA-regulated destabilization domain promotes degradation of the RNA-regulated fusion protein by the proteosomal degradation system; and where the RNA-regulated fusion protein is stabilized by the expressed RNA aptamer sequence.

Suitable proteins of interest for use in the methods described herein are described in more detail supra. In some embodiments, the protein of interest is a fluorescent protein, a bioluminescent protein, an enzyme, or a transcription factor. In other embodiments, the protein of interest is selected from the group consisting of a G-protein coupled receptor (GPCR), a nuclear receptor, a voltage gated ion channel, a ligand gated channel, a receptor tyrosine kinase, a growth factor, a phosphatase, a protein kinase, a viral regulator, a bacterial cell division protein, a scaffold protein, a DNA repair protein, a cytoskeletal protein, a ribosome, a histone deacetylase, an apoptosis regulator, a chaperone protein, a kinase, a phosphorylase, a phosphatase, deacetylase, a cytoskeletal protein (e.g., myosin, actin, dynein, kinesin, and tubulin).

Suitable expression vectors encoding RNA-regulated fusion proteins and vectors encoding an RNA aptamer sequence for use in the methods described herein are described in detail supra and include, e.g., a plasmid (e.g., an expression vector) and a viral vector (e.g., a lentiviral or adenoviral vector).

As described in more detail supra, the RNA-regulated destabilization domain may comprise a bifunctional peptide having a lentiviral transactivator of transcription (Tat) peptide and a degron peptide. Lentiviral transactivator of transcription (Tat) peptides and a degron peptides are described in more detail supra.

In some embodiments of the methods described herein, the RNA-regulated destabilization domain comprises the consensus sequence of SEQ ID NO: 62, where X at position 1 is S or A; X at position 2 is G or A; X at position 3 is P or A; X at position 4 is R or K; X at position 5 is P, A, I, Y, K, or R; X at position 6 is R, K, V, or Y; X at position 7 is G, A, or R; X at position 8 is T or A; X at position 9 is R or K; X at position 10 is G or A; X at position 11 is K or A; X at position 12 is G or A; X at position 13 is R or K; X at position 14 is I or A; X at position 15 is R, K, Y, or G; X at position 16 is R, K, V, T, or Y; X at position 17 is any amino acid; and x at position 18 is optional and can be any amino acid. Thus, in some embodiments, the RNA-regulated destabilization domain is tDeg (SEQ ID NO: 63).

Suitable RNA aptamer sequences for use in the methods described herein are described in more detail supra. In some embodiments, the RNA aptamer comprises the consensus sequence of SEQ ID NO: 56, SEQ ID NO: 58, or SEQ ID NO: 60, wherein N can be A, C, G, or U; S can be C or G; H can be A, C, or U; Y can be C or U; W can be A or U; B can be C, G, or U; M can be A or C; and D can be A, G, or U. For example, the RNA aptamer may comprises the sequence of wild-type TAR RNA (SEQ ID NO: 57), TAR Variant-1 (SEQ ID NO: 59), or TAR Variant-2 (Pepper; SEQ ID NO: 61). In other embodiments, the RNA aptamer comprises the sequence of SEQ ID NO: 70, SEQ ID NO: 71, SEQ ID NO: 72, or SEQ ID NO: 73.

Suitable host cells for use in the methods described herein are described in more detail supra. In some embodiments, the host cell is a mammalian cell.

Suitable mammalian cell lysates include, for example and without limitation, human cell lysates, non-human primate cell lysates, feline cell lysates, canine cell lysates, ovine cell lysates, hircine cell lysates, bovine cell lysates, equine cell lysates, porcine cell lysates, leporine cell lysates, and murine cell lysates.

Suitable solutions comprising (i) a ubiquitin ligase, (ii) proteosomal degradation machinery, (iii) transcriptional machinery, and (iv) translational machinery are well known in the art.

Exemplary ubiquitin ligases include, without limitation, ubiquitin E3 ligases (Li et al., "Genome-Wide and Functional Annotation of Human E3 Ubiquitin Ligases Identifies MULAN, A Mitochondrial E3 that Regulates the Organelle's Dynamics and Signaling," *PLoS One* 3(1):e1487 (2008); Berndsen & Wolberger, "New Insights into Ubiquitin E3 Ligase Mechanism," *Nat. Struct. Mol. Biol.* 21(4): 301-307 (2014), which are hereby incorporated by reference in their entirety). In some embodiments, the ubiquitin E3 ligase is selected form the group consisting of Really Interesting New Gene/U-box (RING) E3 ligase, Homologous to E6AP C-Terminus (HECT) E3 ligase, and RING between RING (RBR) E3 ligase (see, e.g., Metzger et al., "RING-Type E3 Ligases: Master Manipulators of E2 Ubiquitin-Conjugating Enzymes and Ubiquitination," Biochim. Biophys. Acta. 1843(1):47-60 (2014); Rotin & Kumar, "Physiological Functions of the HECT Family of Ubiquitin Ligases," Nat. Rev. Mol. Cell. Biol. 10(6):398-409 (2009); Sluimer & Distel, "Regulating the Human HECT E3 Ligases," Cell Mol. Life Sci. 75(17):3121-3141 (2018); Reiter & Klevit, "Characterization of RING-Between-RING E3 Ubiquitin Transfer Mechanisms," Methods. Mol. Biol. 1844:3-17 (2018); and Dove & Klevit, "RING-Between-RING E3 Ligases: Emerging Themes Amid the Variations," J. Mol. Biol. 429(22):3363-3375 (2017), which are hereby incorporated by reference in their entirety).

Methods of transfecting cells are well known in the art and described in more detail supra.

Another aspect of the present application relates to a treatment method. This method involves contacting a cell with an RNA aptamer, where upon said contacting, the aptamer interacts with an RNA-regulated destabilization domain fused to a protein of interest in the cell to stabilize the protein of interest in the cell.

According to one embodiment, this and other treatment methods described herein are effective to treat a cell, e.g., a cell under a stress or disease condition. Exemplary cell stress conditions may include, without limitation, exposure to a toxin; exposure to chemotherapeutic agents, irradiation, or environmental genotoxic agents such as polycyclic hydrocarbons or ultraviolet (UV) light; exposure of cells to conditions such as glucose starvation, inhibition of protein glycosylation, disturbance of Ca2+ homeostasis and oxygen; exposure to elevated temperatures, oxidative stress, or heavy metals; and exposures to a pathological disease state (e.g., diabetes, Parkinson's disease, cardiovascular disease (e.g., myocardial infarction, end-stage heart failure, arrhythmogenic right ventricular dysplasia, and Adriamycin-induced cardiomyopathy), and various cancers (Fulda et al., "Cellular Stress Responses: Cell Survival and Cell Death," Int. J Cell Biol. (2010), which is hereby incorporated by reference in its entirety).

In some embodiments, contacting a cell with an RNA molecule (aptamer) of the present application involves introducing an RNA molecule into a cell. Suitable methods of introducing RNA molecules into cells are well known in the art and include, but are not limited to, the use of transfection reagents, electroporation, microinjection, or via viruses.

The cell may be a eukaryotic cell. Exemplary eukaryotic cells include a yeast cell, an insect cell, a fungal cell, a plant cell, and an animal cell (e.g., a mammalian cell). Suitable mammalian cells include, for example without limitation, human, non-human primate, cat, dog, sheep, goat, cow, horse, pig, rabbit, and rodent cells.

The RNA molecule of the present invention may be isolated or present in in vitro conditions for extracellular expression and/or processing. According to this embodiment, the RNA molecule is contacted by an RNA ligase (e.g., RtcB) in vitro, purified, circularized, and then the circularized RNA molecule is administered to a cell or subject for treatment.

Treating cells also includes treating the organism in which the cells reside. Thus, by this and the other treatment methods of the present invention, it is contemplated that treatment of a cell includes treatment of a subject in which the cell resides.

In some embodiments, the treatment method further comprises introducing the protein of interest into the cell prior to said contacting.

In some embodiments, the cell is in a patient.

In some embodiments, introducing is carried out by any one or more of injecting mRNA encoding for the protein of interest into the patient, injecting a plasmid encoding for the protein of interest into the patient, injecting the protein of interest into the patient, or systemically delivering the protein of interest into the patient.

In some embodiments, the patient is a human.

Another aspect of the present application relates to a treatment method. This method involves contacting a cell with a vector according to the present application under conditions effective to express an RNA molecule as described herein to treat the cell.

A further aspect of the present application relates to a kit comprising a vector encoding an RNA-regulated destabilization domain and a vector encoding an RNA aptamer that specifically binds to said RNA-regulated destabilization domain. Suitable RNA-regulated destabilization domains and RNA aptamers are described in detail supra.

In some embodiments, the kit comprises a vector encoding tDeg and vector encoding a Pepper aptamer.

EXAMPLES

The following examples are provided to illustrate embodiments of the present invention but they are by no means intended to limit its scope.

Materials and Methods for Examples 1-5

General methods and materials. Single stranded synthetic DNA oligonucleotides for PCR were purchased from Integrated DNA Technologies. Phusion® High-Fidelity DNA Polymerase (NEB M0530) was used for routine PCR amplifications. PCR products were run on 1% TAE agarose gels. PCR products with correct size were then excised and purified with the Qiaquick Gel Extraction kit (Qiagen 28704). Restriction endonucleases used for restriction digest were purchased from New England Biolabs, and used according to the manufacturer's recommended protocol. DNA ligation reactions were carried out using the Quick Ligation™ Kit (NEB M2200L). DNA plasmids were propagated using chemically competent E. coli (Agilent 200314). The QIAprep Spin Plasmid Miniprep Kit (Qiagen 27106) was used for DNA plasmid extraction and purification from E. coli. DNA sequencing (GENEWIZ) was used to verify the inserted gene sequences.

Cell culture and transfection. HEK293T/17 (ATCC CRL-11268), U2OS (ATCC HTB-96), COS-7 (ATCC CRL-1651), and HeLa (ATCC CCL-2) cells were cultured in DMEM (Thermo Fisher Scientific 11995-065) supplemented with 10% fetal bovine serum (Corning 35-010-CV), 100 U ml$^{-1}$ penicillin and 100 μg ml$^{-1}$ of streptomycin (Thermo Fisher Scientific 15140122) under 37° C. with 5% $CO_2$. TrypLE Express (Thermo Fisher Scientific 12604013) was used for detaching cells from culture flasks during cell passage. All cell lines used in this study were transfected using FuGENE HD (Promega 2311) according to the manufacturer's instructions. Prior to live-cell imaging, cells were changed to imaging media: phenol red-free DMEM (Thermo Fisher Scientific 31053-028) supplemented with 10% fetal bovine serum (Corning 35-010-CV), 100 U ml$^{-1}$ penicillin and 100 μg ml$^{-1}$ of streptomycin (Thermo Fisher Scientific 15140122), 1× GlutaMAX™ (Thermo Fisher Scientific 35050-061), and 1 mM sodium pyruvate (Thermo Fisher Scientific 11360-070).

Fluorescence and bioluminescence imaging of tDeg-tagged proteins. To construct an expression vector for EYFP, EYFP-tDeg, mNeonGreen-tDeg, mCherry-tDeg, NanoLuctDeg, EGFP-TetR-tDeg, EGFP-EZH2-tDeg, or mCherry-NF-κB-tDeg, a pcDNA3.1(+) vector was digested by MluI and XbaI and ligated to an insert comprising a miniCMV promoter (5'-GGTAGGCGTGTACGGTGGGAGGCC-TATATAAGCAG AGCT-3' (SEQ ID NO: 93), a HindIII restriction site, a Kozak sequence (5'-GCCACC-3'), and the gene encoding EYFP, EYFP, mNeonGreen, mCherry, Nano-Luc, EGFP-TetR, EGFP-EZH2, or mCherry-NF-κB, respectively, fused with tDeg. These expression vectors were called miniCMV-EYFP, miniCMV-EYFP-tDeg, miniCMV-mNeonGreen-tDeg, miniCMV-mCherry-tDeg, miniCMV-NanoLuc-tDeg, miniCMV-EGFP-TetR-tDeg, miniCMV-EGFP-EZH2-tDeg, and miniCMV-mCherry-NF-κB-tDeg respectively. For control constructs of miniCMV-EGFP-TetR, miniCMV-EGFP-EZH2, and miniCMV-mCherry-NF-κB, a stop codon was inserted on the immediate upstream of the coding sequence of tDeg using QuikChange Site-Directed Mutagenesis Kits (Agilent).

To construct an expression vector for different circular RNAs, the Tornado expression plasmid (Litke et al., Highly Efficient Expression of Circular RNA Aptamers in Cells using Autocatalytic Transcripts," Nat. Biotechnol. 37:667-675 (2019), which is hereby incorporated by reference in is entirety) containing an F30 scaffold was digested, then ligated to inserts encoding the following sequences, respectively: wild-type TAR RNA (5'-GGCTCGTGTAGCTCATT-AGCTCCGAGCC-3' (SEQ ID NO: 65)), TAR Variant-1 (5'-GGCTCGTCTGAGCTCATTAGCTCCGAGCC-3'(SEQ ID NO: 67)), Pepper (TAR Variant-2) (5'-GGCTCGTT-GAGCTCATTAGCTCCGAGCC-3'(SEQ ID NO: 69), or a control RNA, the MS2 hairpin (5'-ACATGAGGATCACC-CATGT-3'(SEQ ID NO: 94)). These vectors were called: U6+27-tnd-wildtype TAR, TAR Variant-1, Pepper (TAR Variant-2), control RNA, respectively.

For live-cell imagining experiments with HEK293T cells, HEK293T cells were seeded into 12-well flat bottom cell culture plates (Corning™ 3513) with 2×10$^5$ cells per well, and were cultured overnight. On the next day, cells were transfected using FuGENE HD (Promega 2311) according to the manufacturer's instructions. Specifically, for imaging experiments in FIGS. 1A-C, 550 ng of miniCMV-EYFP-tDeg were cotransfected with 550 ng of U6+27-tnd-wildtype TAR, TAR Variant-1, Pepper (TAR Variant-2), or control RNA, respectively. In the case of EYFP, 550 ng of miniCMV-EYFP was transfected with 550 ng of diluent DNA (pUC19 plasmid) to maintain 1.1 µg of total plasmid DNA per well. For imaging experiments in FIGS. 6A-6G and FIGS. 7A-7G, 550 ng of miniCMV-protein X-tDeg (protein X=mNeonGreen, mCherry, NanoLuc, EGFP-TetR, EGFP-EZH2, or mCherry-NF-κB) was cotransfected with 550 ng of circular Pepper (TAR Variant-2) or with 550 ng of diluent DNA (pUC19 plasmid). At 24 hours after transfection, cells were subcultured into 35 mm imaging dishes precoated with poly-D-lysine (Mattek Corporation P35GC-1.5-14C) and mouse laminin I (Cultrex® 3401-010-02) in culture media. Cells were then cultured overnight. Cell culture media was changed imaging media prior to fluorescence or bioluminescence live-cell imaging.

Figure 4A:
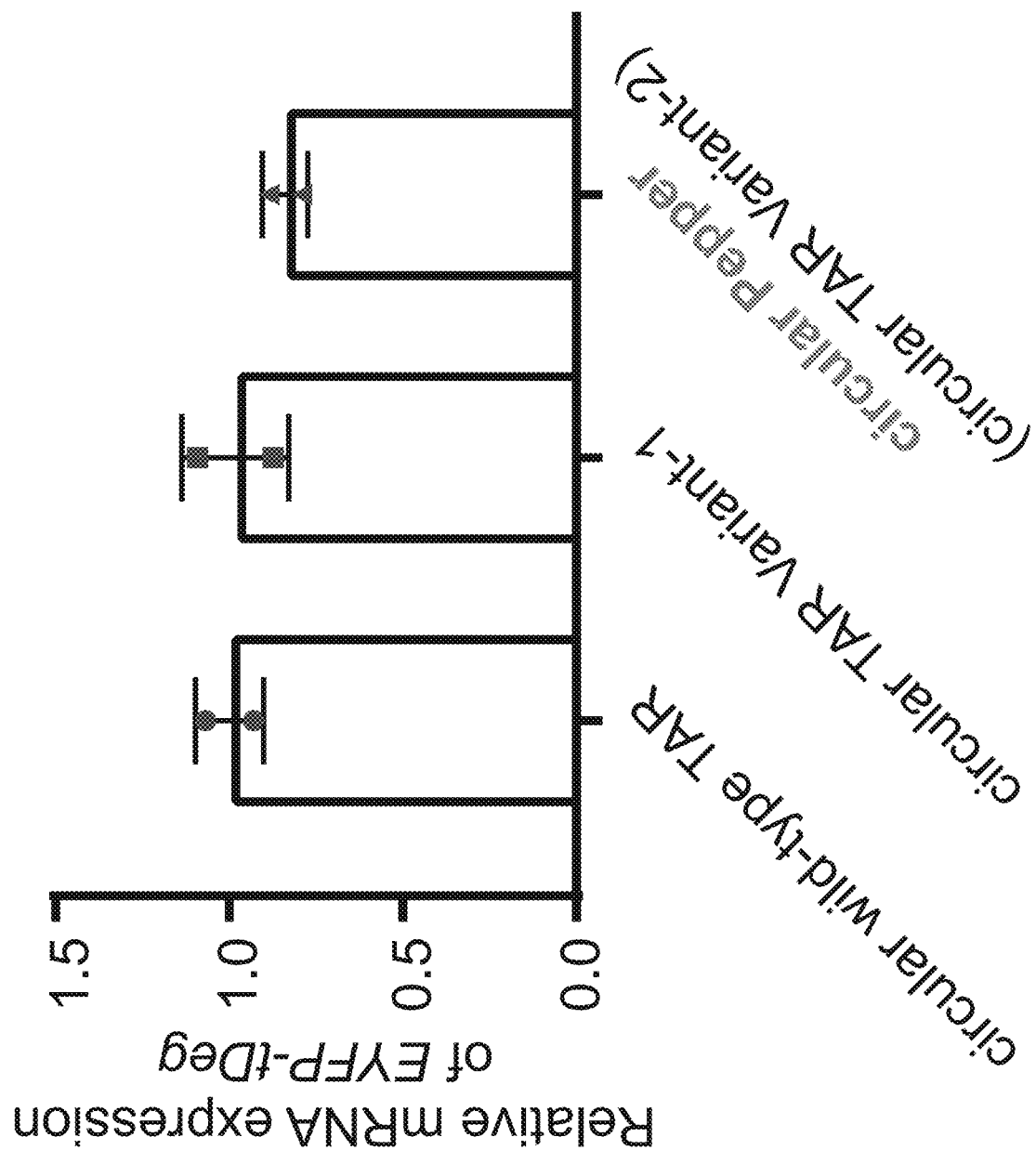
FIGS. 4A-4B demonstrate that engineered TAR variants' higher efficiency in stabilizing EYFP-tDeg proteins is not due to expression differences in EYFP-tDeg mRNA or the circular TAR RNAs.
Figure 4B:
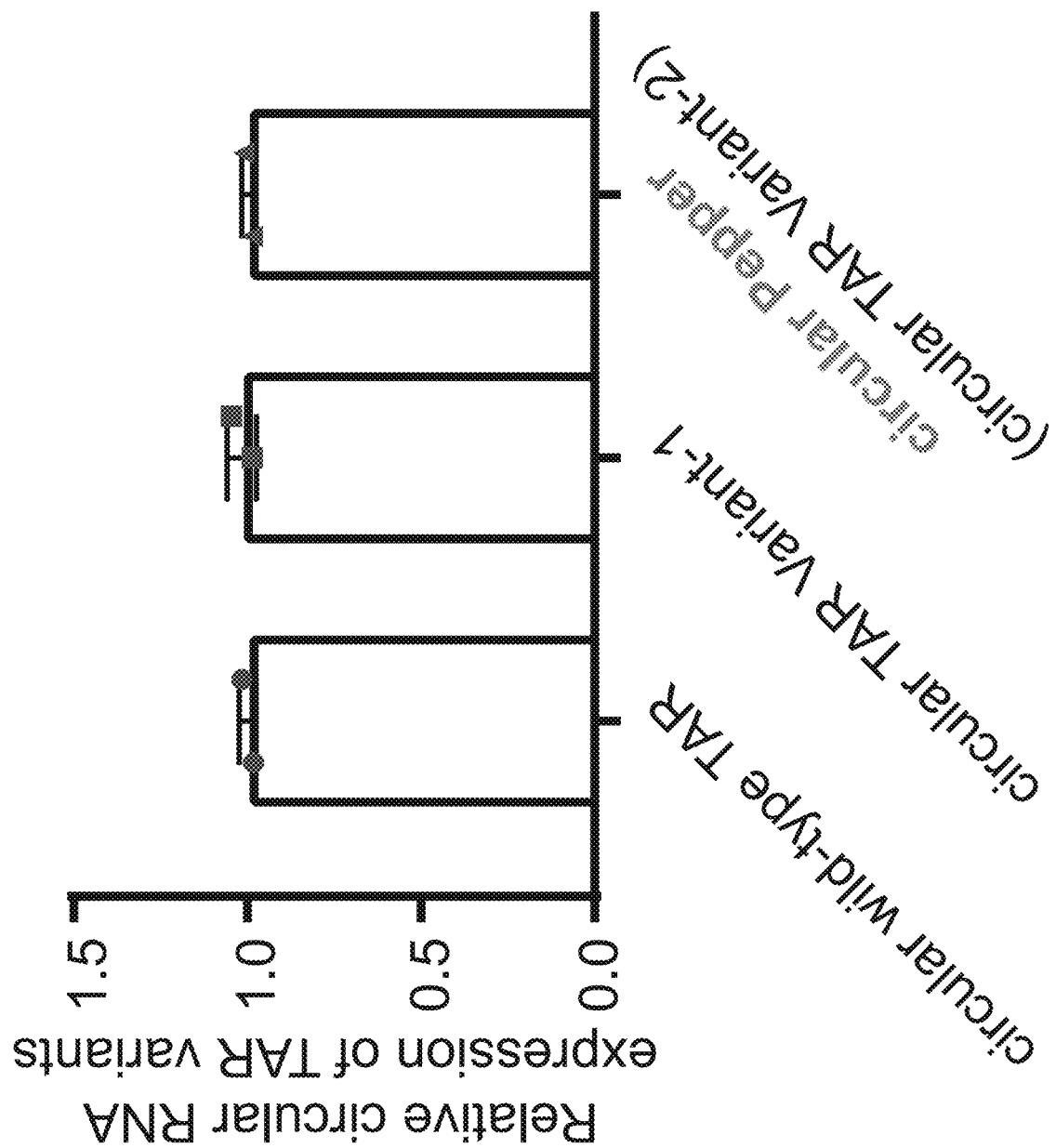
Figure 5E:
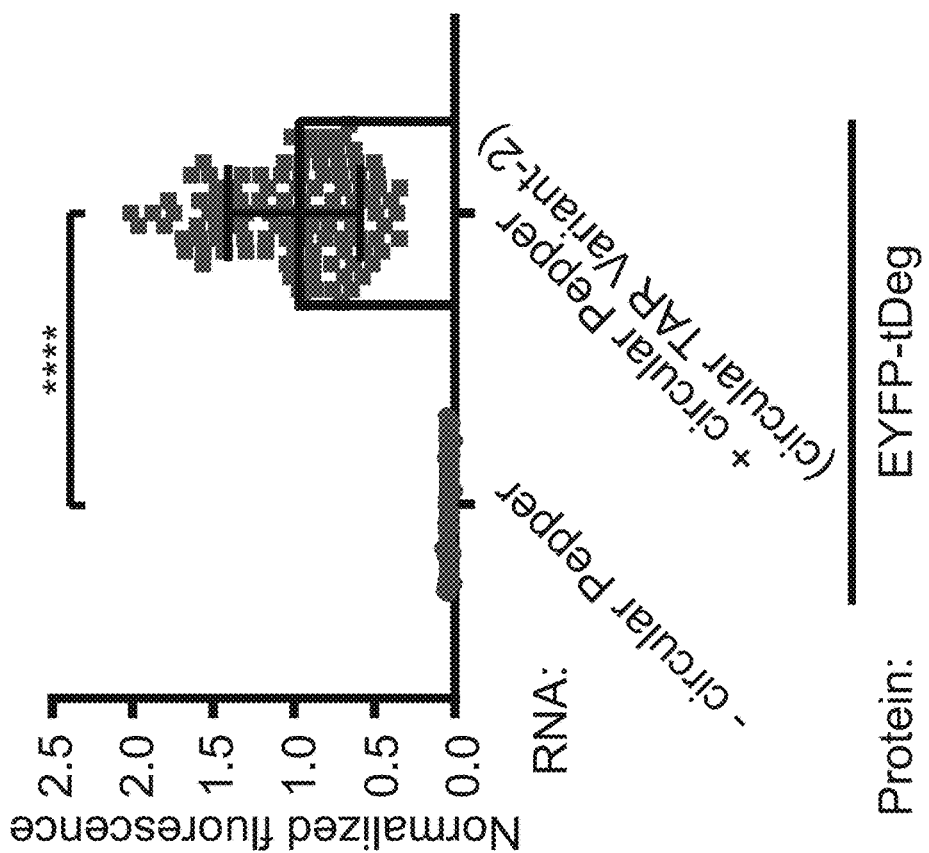
Figure 5F:
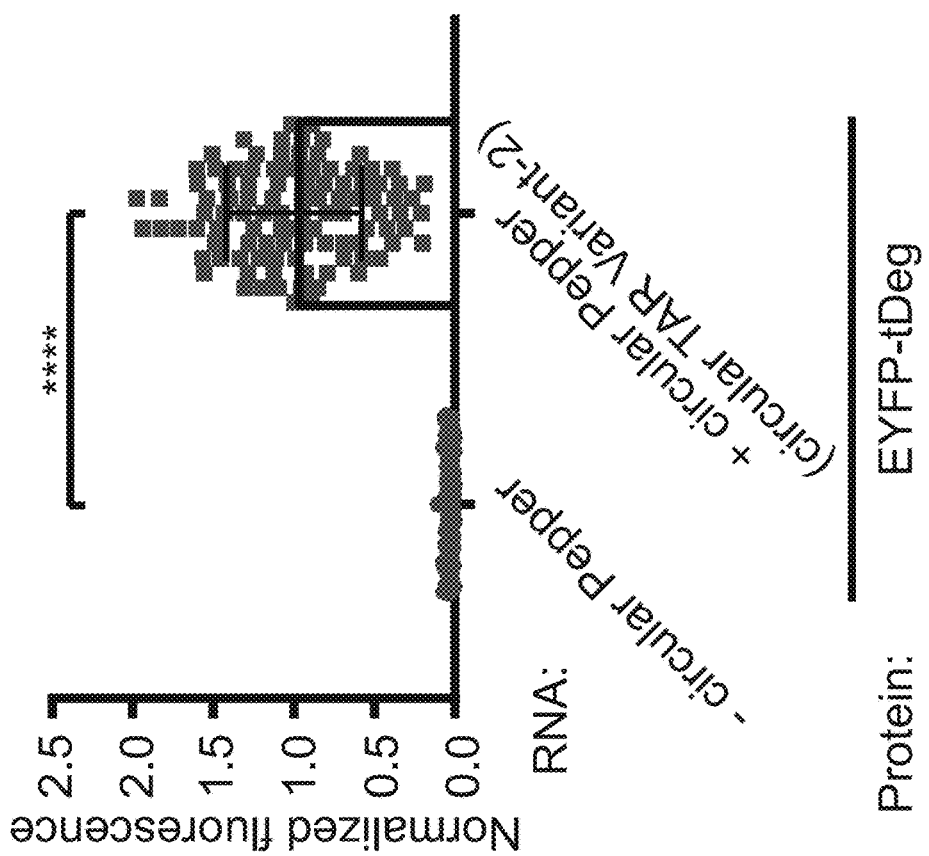
Figure 5G:
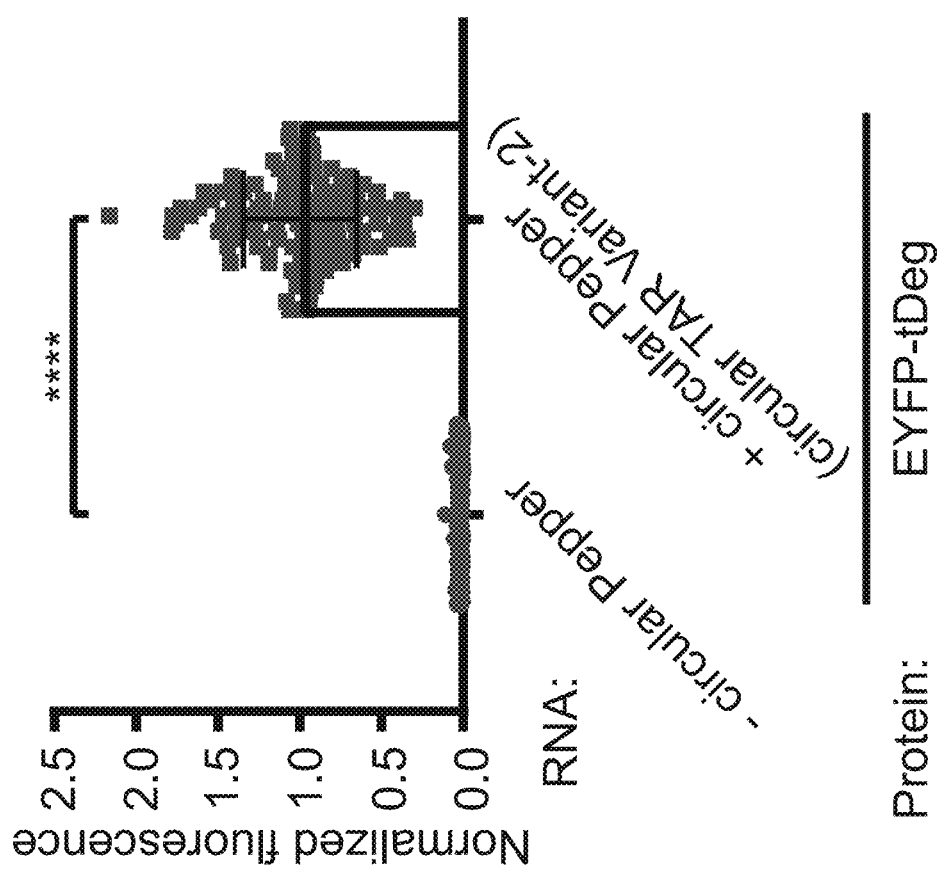
Figure 6F:
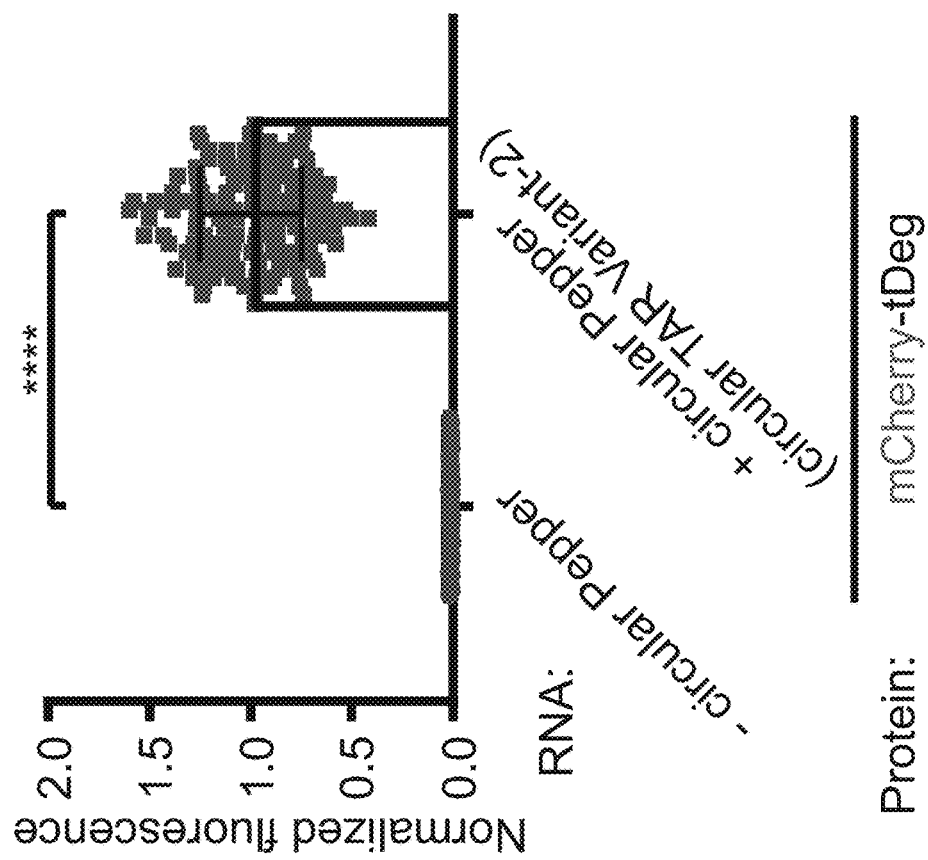
Figure 6E:
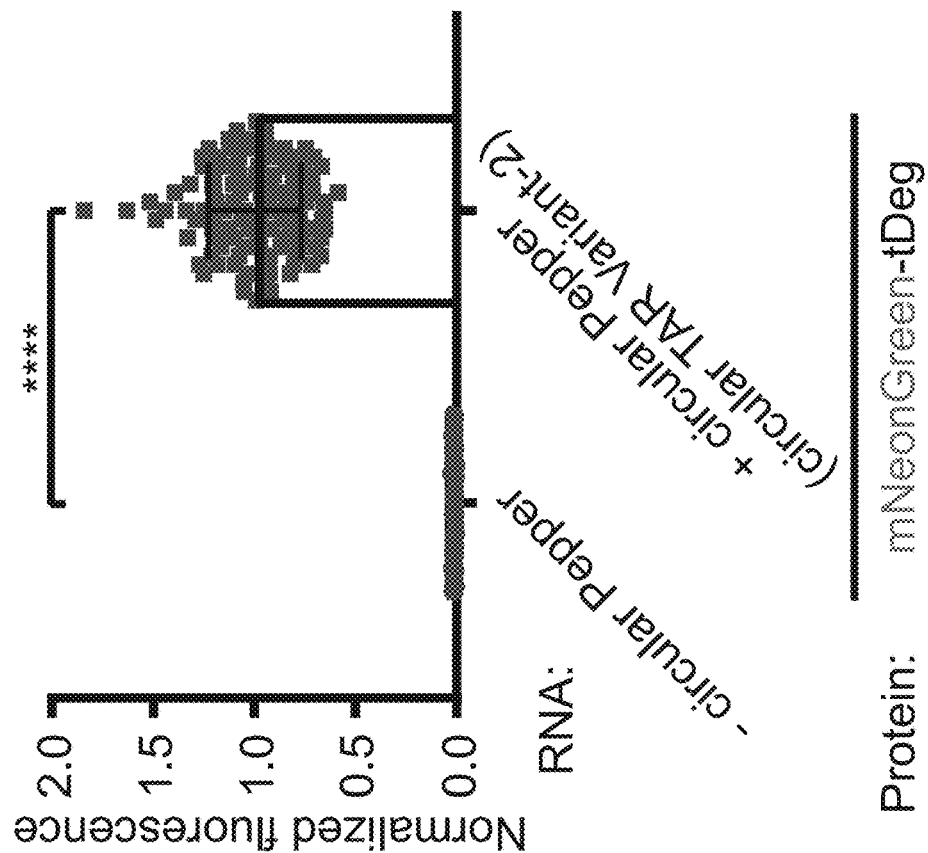
Figure 6G:
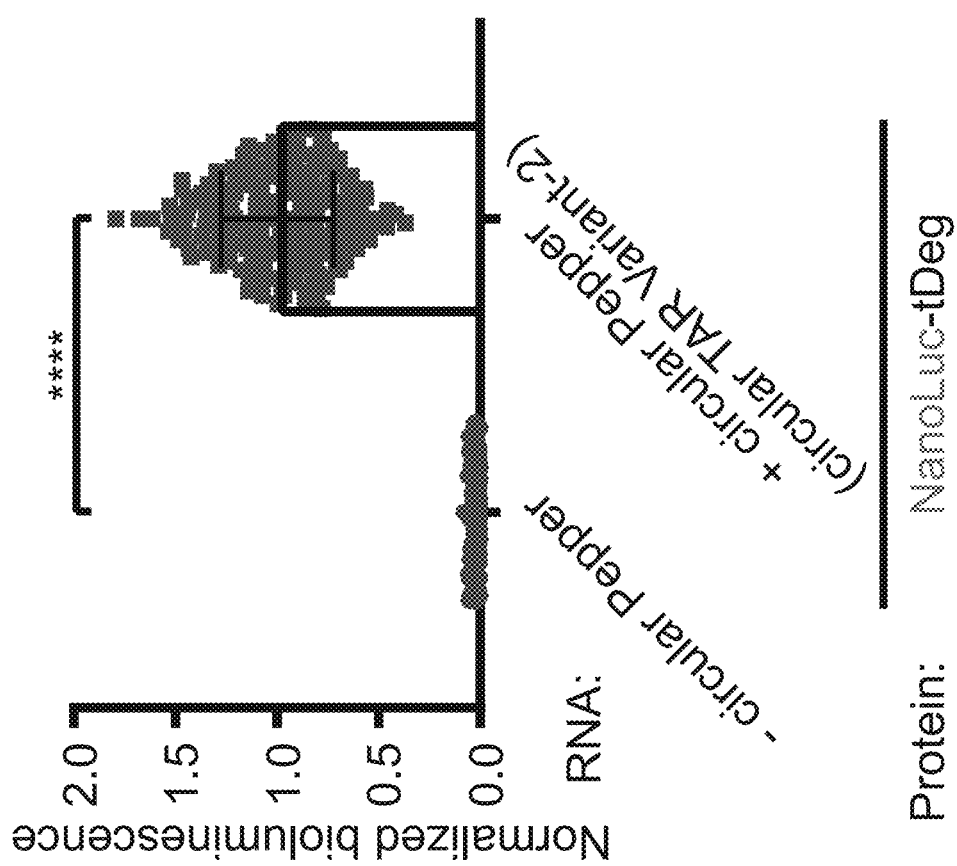
Figures 7E, 7F:
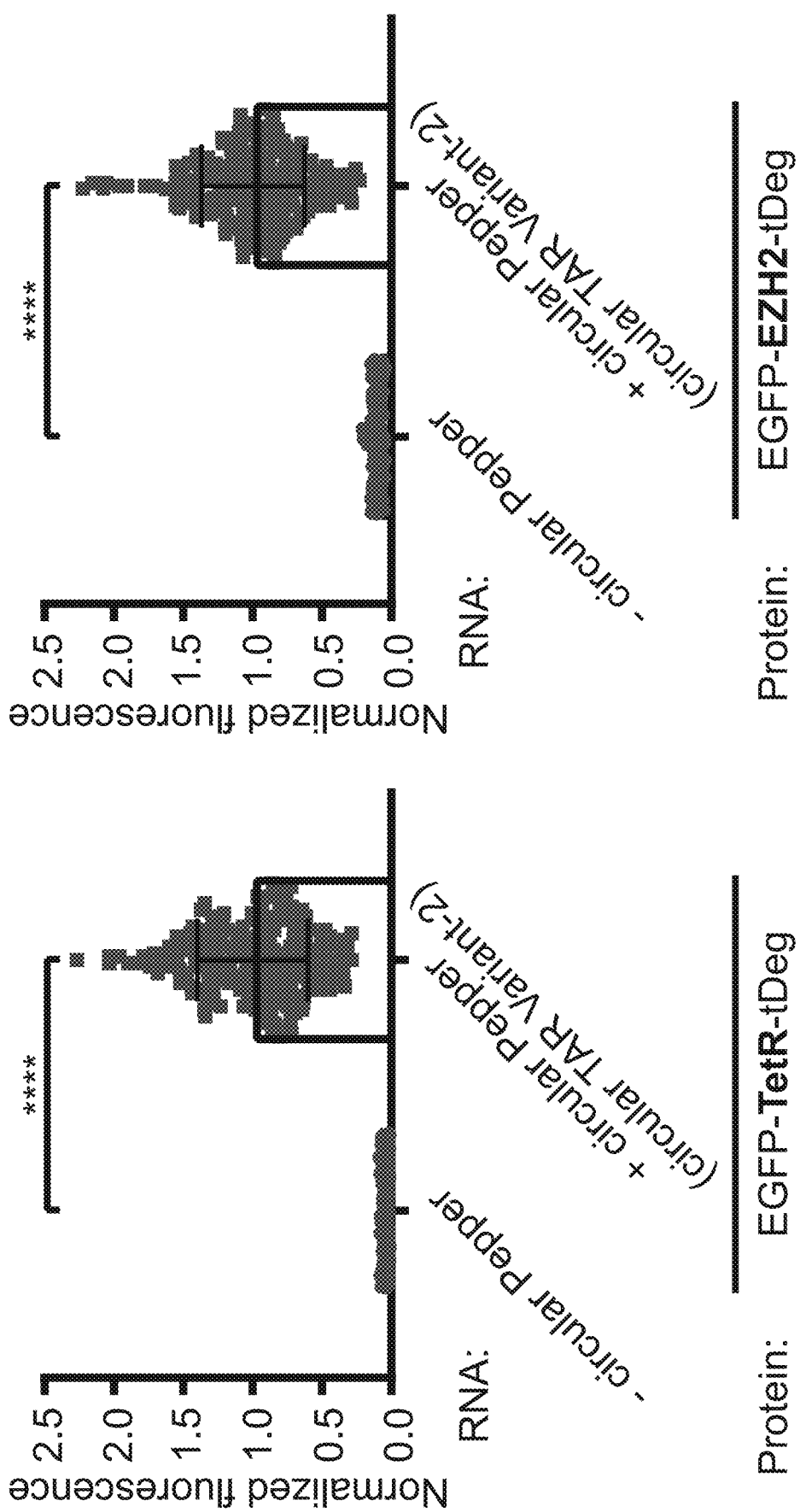
Figure 7G:
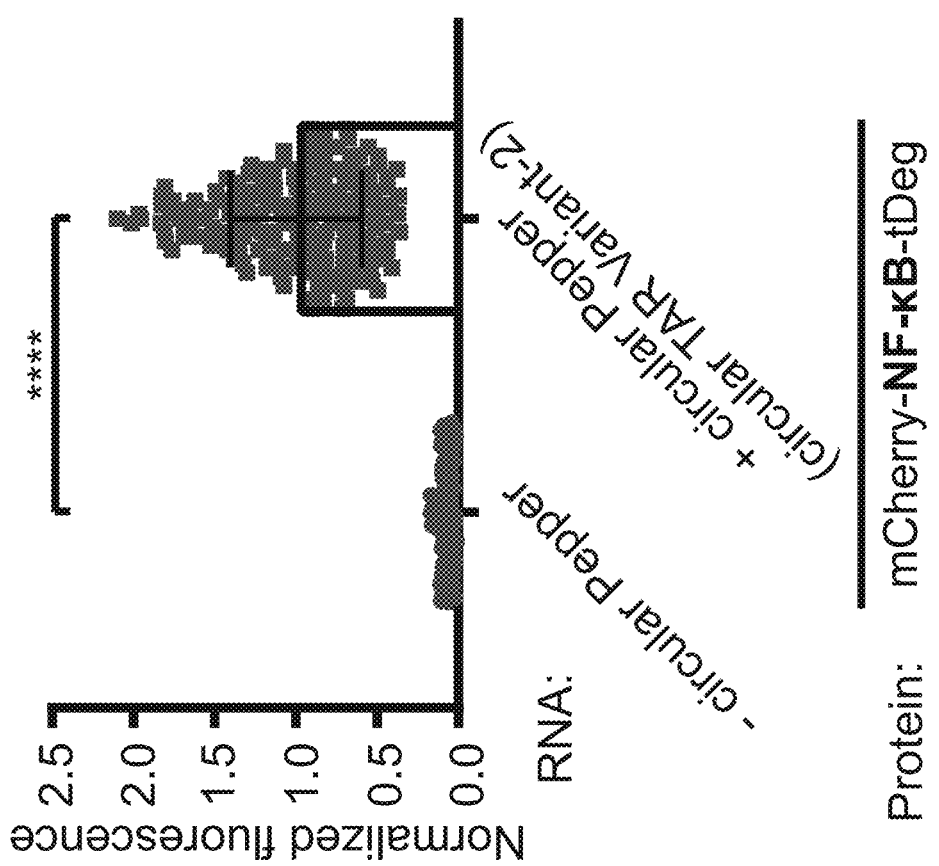

For live-cell imagining experiments in FIGS. 4A-4B, U2OS cells, COS-7 cells, or HeLa cells were seeded into 35 mm imaging dishes precoated with poly-D-lysine (Mattek Corporation P35GC-1.5-14C) with 2×10$^5$ cells per dish, respectively. On the next day, cells were transfected using FuGENE HD (Promega 2311) according to the manufacturer's instructions. Specifically, 1.4 µg of miniCMV-EYFP-tDeg was cotransfected with 1.4 µg of circular Pepper (TAR Variant-2) or 1.4 µg of diluent DNA (pUC19 plasmid). At 48 hours after transfection, cell culture media was changed imaging media prior to fluorescence live-cell imaging.

Prior to live-cell fluorescence or bioluminescence imaging, 1 µL of Hoechst 33342 (Thermo Fisher Scientific H3570) per 2 ml of imaging media was added to the cells. In the case of proteasome inhibitor treatment, cells were treated with either DMSO or 10 µM (final concentration in the media) MG132 for 7 hours prior to live-cell imaging. In the case of bioluminescence imaging of NanoLuc, 20 µL of furimazine (Promega Nano-Glo® Luciferase Assay System) per 2 ml of imaging media was added to the cells prior to bioluminescence imaging.

For live-cell fluorescence or bioluminescence imaging, an epifluorescence inverted microscope (Nikon Eclipse TE2000-E) equipped with a CoolSnap HQ2 CCD camera and a 130-W Nikon mercury lamp was used. The NIS-Elements Advanced Research software (Nikon) was used to control the microscope and camera. Cells were imaged with a 20×/0.75-NA (numerical aperture) or a 40×/0.75-NA air objective (Nikon) at 37° C. A FITC filter cube (with excitation filter 470±20 nm, dichroic mirror 495 nm (long pass), and emission filter 525±25 nm) was used for detecting EGFP-TetR-tDeg or EGFP-EZH2-tDeg with an exposure time of 500 msec. A YFP filter cube (with excitation filter 500±12 nm, dichroic mirror 520 nm (long pass), and emission filter 542±13.5 nm) was used for detecting EYFP, EYFP-tDeg, or mNeonGreen-tDeg with an exposure time of 500 msec. A TRITC filter cube (with excitation filter 560±20 nm, dichroic mirror 585 nm (long pass), and emission filter 630±37.5 nm) was used for detecting mCherry-tDeg, or mCherry-NF-κB-tDeg with an exposure time of 500 msec. A filter cube (with emission filter 460±25 nm) was used for detecting the bioluminescence of NanoLuc with an exposure time of 3 minutes. A DAPI filter cube (with 350±25 nm excitation filter, 400 nm (long pass) dichroic mirror, and 460±25 nm emission filter) was used for detecting the Hoechst-stained nuclei in cells with an exposure time of 100-500 msec. All filters used in these filter cubes are purchased from Chroma Technology. Cell fluorescence/bioluminescence was calculated using ImageJ by measuring the mean fluorescence/bioluminescence signal in a cell's area and subtracting background based on average signal of culture media. Normalized fluorescence/bioluminescence was calculated by dividing the cell fluorescence/bioluminescence intensity of each cell to the averaged cell fluorescence/bioluminescence of the whole cell population.

RT-qPCR. Total RNA was isolated from cells using Trizol according to the manufacturer's instruction. To remove residual DNA contaminations, the purified RNA was treated with DNaseI (Thermo-Fisher) according to the manufacturer's instructions. The same amount of DNaseI-treated RNA was reverse transcribed to cDNA using SuperScript IV First-Strand kit (Invitrogen) with random hexamers according to the manufacturer's instructions. To measure relative expression levels of the RNAs of interest, qPCR measurements were performed using the iQ SYBR Green Supermix with 0.250 ng of cDNA in the final reaction mix. For the amplification, the following protocol was used: 98° C. for 2 minutes, 40 cycles of 95° C. for 10 seconds, 60° C. for 40 seconds. Primer sets for amplifying the cDNA of EYFP and mCherry are listed in Table 9. Every primer set was tested for its efficiency. To test primer specificity, melting curves were performed at the end of the 40 cycles of amplification. In the case of mCherry quantification, an untransfected sample was added as additional negative control. Relative measurements (2^-ΔCq) of mCherry, EYFP were performed using GAPDH and RPS18 as housekeeping genes. Biological replicates were tested.

TABLE 9 ssDNA oligo probes used in RT-qPCR

| | | |
|---|---|---|
| EYFP fw | ACGTAAACGGCCACAAGTTC | SEQ ID NO: 95 |
| EYFP rv | CTTCATGTGGTCGGGGTAGC | SEQ ID NO: 96 |
| mCherry fw | CACGAGTTCGAGATCGAGGG | SEQ ID NO: 97 |
| mCherry rv | CAAGTAGTCGGGGATGTCGG | SEQ ID NO: 98 |

Gel staining. Total RNA was isolated from cells using TRIzol® according to the manufacturer's instruction. Then, 2.5 µg of isolated total RNA was separated using a precast 6% TBE-Urea Gel (Life Technologies EC68655). This gel was run at 200 V in TBE buffer until completion, and stained with SYBR Gold (ThermoFisher S11494) diluted 1:10,000 in TBE buffer for 15 minutes. After SYBR Gold staining, RNA bands were imaged on a ChemiDoc XRS+ system (Bio-Rad).

mRNA imaging using tDeg and Pepper. To construct an expression vector for RNA-regulated fluorescent fusion proteins used in mRNA imaging, a pcDNA3.1(+) vector was digested by MluI and XbaI and ligated to an insert comprising a miniCMV promoter (5'-GGTAGGCGTGTACGGTGGGAGGCC-TATATAAGCAGAG CT-3' (SEQ ID NO: 118)), a HindIII restriction site, a Kozak sequence (5'-GCCACC-3'), and the gene encoding tandem copies of mNeonGreen, mVenus, or mCherry, respectively. To construct an expression vector for an mCherry mRNA reporter containing different 3'UTR tags comprising 10 or 20 concatenated Pepper aptamers, a pcDNA3.1(+) vector was first digested by HindIII and XbaI and ligated to an insert encoding the gene of mCherry followed by XhoI after its stop codon. This vector was called CMV-mCherry. CMV-mCherry was then digested XhoI and XbaI, and ligated to different Pepper tags, respectively. All the Pepper tags were synthesized by GenScript.

U2OS cells were seeded into 35 mm imaging dishes precoated with poly-D-lysine (Mattek Corporation P35GC-1.5-14C) with $2 \times 10^5$ cells per dish. On the next day, cells were transfected using FuGENE HD (Promega 2311) according to the manufacturer's instructions. Specifically, 1.4 µg of RNA-regulated fluorescent fusion protein plasmids were cotransfected with 1.4 µg of mRNA reporter plasmids. At 48 hours after transfection, cell culture media was changed to imaging media prior to imaging experiments.

For mRNA imaging experiments, an epifluorescence inverted microscope (Olympus IX-70) equipped with a Evolve® 512 EMCCD OEM camera (Photometrics) and an Insight SSI 7 color solid state illumination system (Applied Precision) was used. The Resolve3D softWoRx-Acquire Version: 6.5.2 was used to control the microscope and camera. Cells were imaged with a 100×/1.4-NA oil objective at 37° C., with N=1.520 immersion oil (Applied Precision). A FITC filter cube (with excitation filter 475±14 nm, dichroic mirror with a reflection band of 481-502 nm, and a transmission band of 506-543 nm), and emission filter 525±25 nm) was used for detecting mNeonGreen with an exposure time of 50 msec. A YFP filter cube (with excitation filter 513±8.5 nm, dichroic mirror with a reflection band of 496-528 nm, and a transmission band of 537-550 nm, and emission filter 559±19 nm) was used for detecting mVenus with an exposure time of 100 msec. A TRITC filter cube (with excitation filter 542±13.5 nm, dichroic mirror with a reflection band of 547-565 nm, and a transmission band of 576-630 nm, and emission filter 594±22.5 nm) was used for detecting reporter plasmids encoding mCherry with an exposure time of 10-100 msec. Signal-to-noise ratio of the fluorescent puncta was calculated by the mean fluorescence intensity of each mRNA puncta divided by the mean fluorescence intensity of the adjacent cytosolic background fluorescence.

Northern blot. HEK293T cells were seeded into 10 cm culture dish with $3 \times 10^6$ cells per dish. On the next day, cells were cotransfected with CMV-mCherry-(F30-2×Pepper)$_{10}$ and miniCMV-(mNeonGreen)$_4$-tDeg or pUC19, respectively. A total amount of 19 µg plasmid DNA was used for each culture dish, and pUC19 vector was used here as a diluent DNA to ensure the same amount of plasmid DNA transfected to the cells. All transfections were performed using FuGENE HD (Promega 2311) according to the manufacturer's instructions. Cells were harvested after 48 hours of transfection. Total RNA was extracted with TRIzol® (Thermo Fisher Scientific 15596026) followed by isopropanol precipitation. The purified total RNA was then subjected to RNase-free DNase I (Thermo Fisher Scientific AM2224) digestion at 37° C. for 1 hour. After digestion, the RNA was subjected to phenol-chloroform (Thermo Fisher Scientific AM9720) extraction and ethanol purification.

For gel electrophoresis, a 1.5% agarose/formaldehyde gel (20 mM MOPS, 5 mM sodium acetate, 1 mM EDTA, 1.5% w/v agarose, 2% formaldehyde) was used. 20 µg of total RNA was loaded in each lane. The RNA was resuspended in 20 µL of RNA sample buffer (20 mM MOPS, 5 mM sodium acetate, 1 mM EDTA, 50% v/v formamide, 3.7% formaldehyde). The RNA samples were heated at 70° C. for 10 minutes, and then chilled on ice for more than 1 minute. Before loading the RNA samples into the gel, the RNA samples were mixed with 2 µL of loading buffer (50% glycerol, 5 mM EDTA, 0.4% bromophenol blue, 0.4% xylene cyanol). The gel was run at 70 V for 2 hours. After electrophoresis, the gel was stained with 1×SYBR™ Gold Nucleic Acid Gel Stain (Thermo Fisher Scientific S11494) to assess the quality of the RNA and check for separation. All solutions mentioned above were made in diethylpyrocarbonate (DEPC)-treated water.

After electrophoresis, the RNA was transferred to Amersham Hybond-N+ nylon membrane (GE Healthcare Life Sciences RPN203B) using the VacuGene XL Vacuum Blotting System (GE Healthcare Life Sciences) according to the manufacturer's instructions. The RNA was then UV crosslinked to the nylon membrane. The membrane was washed with NorthernMax® Prehybridization/Hybridization Buffer (Thermo Fisher Scientific AM8677) at 42° C. for at least 30 minutes. Biotinylated (at 5') single-stranded DNA probes (Integrated DNA Technologies) as shown in Table 10 were mixed with NorthernMax® Prehybridization/Hybridization Buffer and incubated with the membrane at 42° C. overnight. On the following day, the membrane was washed in 50 mL of wash buffer 1 (2×SSC, 0.1% SDS) twice at 42° C. for 10 minutes each time, and then washed with wash buffer 2 (0.1×SSC, 0.1% SDS) twice at 42° C. for 15 minutes. The membrane was visualized by Chemiluminescent Nucleic Acid Detection Module Kit (Thermo Fisher Scientific 89880).

Figure 12A:
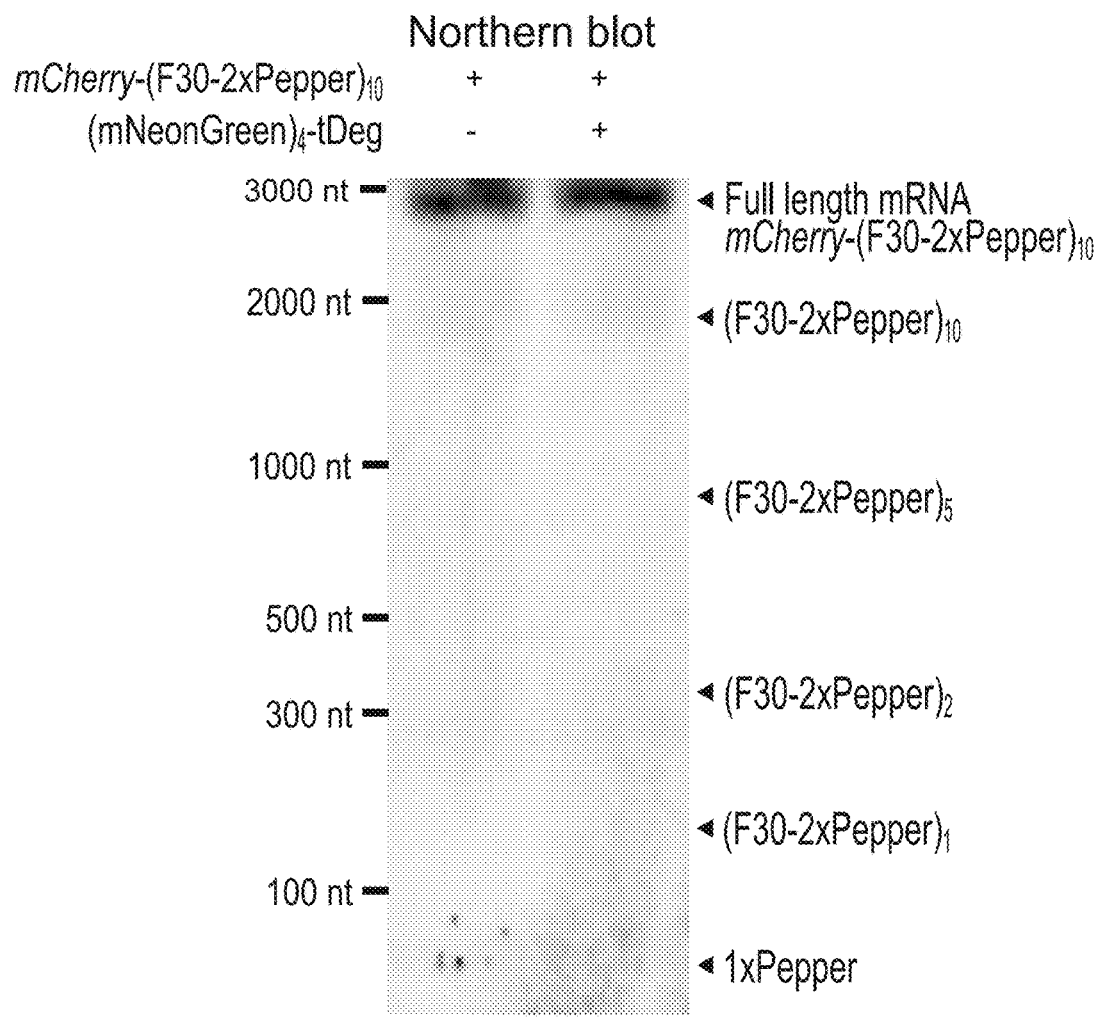

TABLE 10 ssDNA oligo probes used in FIG. 12A

| Probe-1  | GTTGAGTGATTAGCGATTGATTCCGGCC    | SEQ ID NO: 99  |
|----------|---------------------------------|----------------|
| Probe-2  | GTCGGATGATTTTCGTAATAGATTGCGCTG  | SEQ ID NO: 100 |
| Probe-3  | TTGACGTGATTTTGTGAGATTTTCCGCAG   | SEQ ID NO: 101 |
| Probe-4  | TGCCTGATTGTAAGTATGTGGATTATCGG   | SEQ ID NO: 102 |
| Probe-5  | GGATAGGTATGGAGGAAGTAGCTTGGA     | SEQ ID NO: 103 |
| Probe-6  | ACAATATCTTGCGCCGTTCGATCTTG      | SEQ ID NO: 104 |
| Probe-7  | GGCCGCCAAGAAGAACGACCAA          | SEQ ID NO: 105 |
| Probe-8  | CCTAAGAACCTAACATATCTAGCGAGG     | SEQ ID NO: 106 |
| Probe-9  | TGTGCACCTTGAAGCGCATGAA          | SEQ ID NO: 107 |
| Probe-10 | CCTGGGTCACGGTCACCACG            | SEQ ID NO: 108 |
| Probe-11 | GCCCATGGTCTTCTTCTGC             | SEQ ID NO: 109 |
| Probe-12 | GGGTGCTTCACGTAGGCCTT            | SEQ ID NO: 110 |
| Probe-13 | GTCACCTTCAGCTTGGCGGTC           | SEQ ID NO: 111 |
| Probe-14 | GCCTCTGCTTGATCTCGCCCTTC         | SEQ ID NO: 112 |
| Probe-15 | GTCTTGACCTCAGCGTCGTAGTG         | SEQ ID NO: 113 |
| Probe-16 | CGGCGCGTTCGTACTGTTCC            | SEQ ID NO: 114 |
| Probe-17 | GCCGATAATCCACATACTTACAATCAGG    | SEQ ID NO: 115 |

Imaging membrane-tethered mRNA. U2OS cells were seeded 72 hours before imaging in 96-well glass bottom dishes (Matriplates, Brooks Life Science Systems) at 40% confluency. Cells were transfected with DNA plasmids that encode miniCMV-(mNeonGreen)$_4$-tDeg, PCP-3×mCherry-CAAX and the mRNA reporter 48 hours before imaging using 0.5 µl FuGENE 6 (Promega) and 200-300 ng DNA per well. The transfection mix was prepared in OptiMEM (Sigma-Aldrich) and added to the cells in a total volume 150-200 µl of medium.

Twenty-four hours prior to imaging, transcription of the reporters was induced by addition of doxycycline (1 ng/ml) (Sigma-Aldrich). Thirty minutes before imaging, the cell culture medium was replaced with pre-warmed $CO_2$-independent Leibovitz's-15 medium (Gibco) with doxycycline. Images were acquired using a Nikon TI inverted microscope with perfect focus system equipped with a Yokogawa CSU-X1 spinning disc, a 100× 1.49 NA objective and an iXon Ultra 897 EMCCD camera (Andor) and was controlled by NIS software (Nikon). During the experiment, cells were maintained at a constant temperature of 37° C. Single Z-plane images were acquired, with the bottom plasma membrane of the cell in the focal plane. Camera exposure times of 500 ms were used for both mNeonGreen and mCherry.

To determine the fluorescence intensity of mRNA foci, mean spot intensities were measured in Image J in a region of interest (ROI) 0.53×0.53 µm in size. For each spot, local background fluorescence intensity was measured in a ROI (0.53×0.53 µm in size) directly next to the spot of interest, and mean background fluorescence intensities were subtracted from the mean spot intensity. Cells with very high number of mRNAs (more than ~50) were excluded from the analysis.

Western Blotting. Cells were lysed in whole cell lysis buffer (10 mM Tris-HCl pH 7.4, 10 mM EDTA, 50 mM NaCl, 1% Triton X-100, 0.1% SDS) containing 1× protease and phosphatase inhibitor (Pierce, 78440). Lysates were cleared by centrifugation (12,000 g for 10 minutes). Protein quantification was performed using the Pierce BCA protein assay kit according to the manufacturer's instruction (Thermo Fisher Scientific, 23227). Equal quantities of proteins were mixed with loading dye, and incubated at 95° C. for 5 minutes before they were separated on 4-12% Bis-Tris gels (Invitrogen) and transferred onto a PVDF membrane at constant 350 mA at 4° C. for 1 hour. Membranes were blocked by incubation in 5% milk for 1 hour at room temperature under agitation and then incubated with the following primary antibodies: mouse anti-GAPDH (Santa Cruz) with a 1:5000 dilution in 1% milk overnight, or rabbit anti-mCherry (Abcam, ab167453) with a 1:1000 dilution in 1% milk overnight, or rabbit anti-ubiquitin (Abcam, ab19247) with a 1:1000 dilution in 1% milk overnight. After incubation with the appropriate secondary antibodies conjugated to HRP and extensive washing, blots were imaged on a ChemiDoc XRS+ system (Bio-Rad).

Imaging ER-targeting mRNA. To construct an expression vector for an ER-targeting mRNA reporter, DNA sequence that encodes the first 29 amino acids of cytochrome p450, CytERM, and a linker sequence (MDPVVVLGLCLSCLLLLSLWKQSYGGGKLGGSGG TGGSGTSGG (SEQ ID NO: 116) was cloned into the upstream of the mCherry sequence of the CMV-mCherry-(F30-2×Pepper)$_{10}$ plasmid to make CMV-CytERM-mCherry-(F30-2×Pepper)$_{10}$. To construct the plasmid that encodes the RNA-regulated fluorescent fusion protein used in this experiment, the miniCMV promoter sequence in miniCMV-(mNeonGreen)$_4$-tDeg was replaced with the human ubiquitin C promoter sequence to make UbC-(mNeonGreen)$_4$-tDeg.

U2OS cells were seeded into 35 mm imaging dishes precoated with poly-D-lysine (Mattek Corporation P35GC-1.5-14C) with 2×10$^5$ cells per dish. On the following day, cells were cotransfected with 1.4 µg of CMV-CytERM-mCherry-(F30-2×Pepper)$_{10}$, 0.28 µg of UbC-(mNeonGreen)$_4$-tDeg, and 1.12 µg of pUC19 (as a diluent DNA) using FuGENE HD (Promega 2311) according to the manufacturer's instructions. At 48 hours after transfection, cell culture media was changed to imaging media prior to imaging experiments. This imaging setup for these experiments are the same as the one used for mRNA imaging using tDeg and Pepper.

Imaging β-actin mRNA after arsenite stress. To construct an expression vector for a β-actin mRNA reporter containing a (F30-2×Pepper)$_{10}$ tag, the full length β-actin gene (from Addgene Plasmid #27123) was amplified by PCR and digested by XhoI and HindIII, and then ligated to a vector from CMV-mcherry-(F30-2×Pepper)$_{10}$ digested by the same restriction endonucleases to cut out the gene encoding mCherry. This expression vector was called CMV-O-actin-(F30-2×Pepper)$_{10}$.

U2OS cells stably expresses Halo-G3BP1 were seeded into 35 mm imaging dishes precoated with poly-D-lysine (Mattek Corporation P35GC-1.5-14C) with 2×10$^5$ cells per dish. On the following day, cells were cotransfected with 1.4 µg of miniCMV-(mNeonGreen)$_4$-tDeg with 1.4 µg of CMV- O-actin-(F30-2×Pepper)₁₀ using FuGENE HD (Promega 2311) according to the manufacturer's instructions. For control experiments, 1.4 µg of miniCMV-(mNeonGreen)₄-tDeg with 1.4 µg of U6+27-tnd-Pepper was used following the same transfection protocol. At ~40 hours after transfection, cell culture media was changed to imaging media with the HaloTag® TMRDirect™ Ligand (Promega G2991) for 5 hours. Cells were then rinsed with 1×PBS (Thermo Fisher Scientific 10010049) and incubated in imaging media prior to imaging experiments. The same microscope setup as in the above mRNA imaging experiments was used. To induce stress granule formation, 1 mL of imaging media supplemented with 1000 µM of sodium arsenite was added to the cells cultured in 1 mL of imaging media to reach a final concentration of 500 µM of sodium arsenite.

Statistical analysis. All data were expressed as means±s.d. with sample sizes (n) listed for each experiment. Statistical analyses were performed using Excel (Microsoft) and Prism (Graphpad). For different circular TAR variants' inhibition of tDeg's destabilizing effect, and optimization of the number of fluorescent mNeonGreen monomers in the RNA-regulated fluorescent fusion protein for imaging mRNA in live cells, one-way ANOVA was used to analyze significant differences between group means. For Pepper RNA-dependent regulation of protein stability, imaging green Pepper-tagged β-actin mRNA, proteasomal inhibition, imaging membrane-tethered mRNA, two tailed Student's t-tests were used to analyze significant differences between group means. P values were reported for each experiment.

Example 1—tDeg Reduces Protein Stability by Inducing Proteasomal Degradation

In order to expand fluorescent aptamer-based imaging, Applicant sought to create a new class of RNA-regulated fluorescent dyes that are genetically encoded. Fluorescent proteins are particularly useful since a diverse array of spectrally distinct proteins have been described (Rodriguez et al., "The Growing and Glowing Toolbox of Fluorescent and Photoactive Proteins," *Trends Biochem. Sci.* 42:111-129 (2017), which is hereby incorporated by reference in its entirety). However, these proteins are constitutively fluorescent. To make them dependent on RNA, Applicant considered making them rapidly degraded in cells except when bound by a specific RNA aptamer. In this way, fluorescence would be selectively associated with RNA-protein complexes, and not with unbound fluorescent protein. This would be functionally equivalent to RNA-induced fluorescence of small molecule dyes.

Figure 1B:
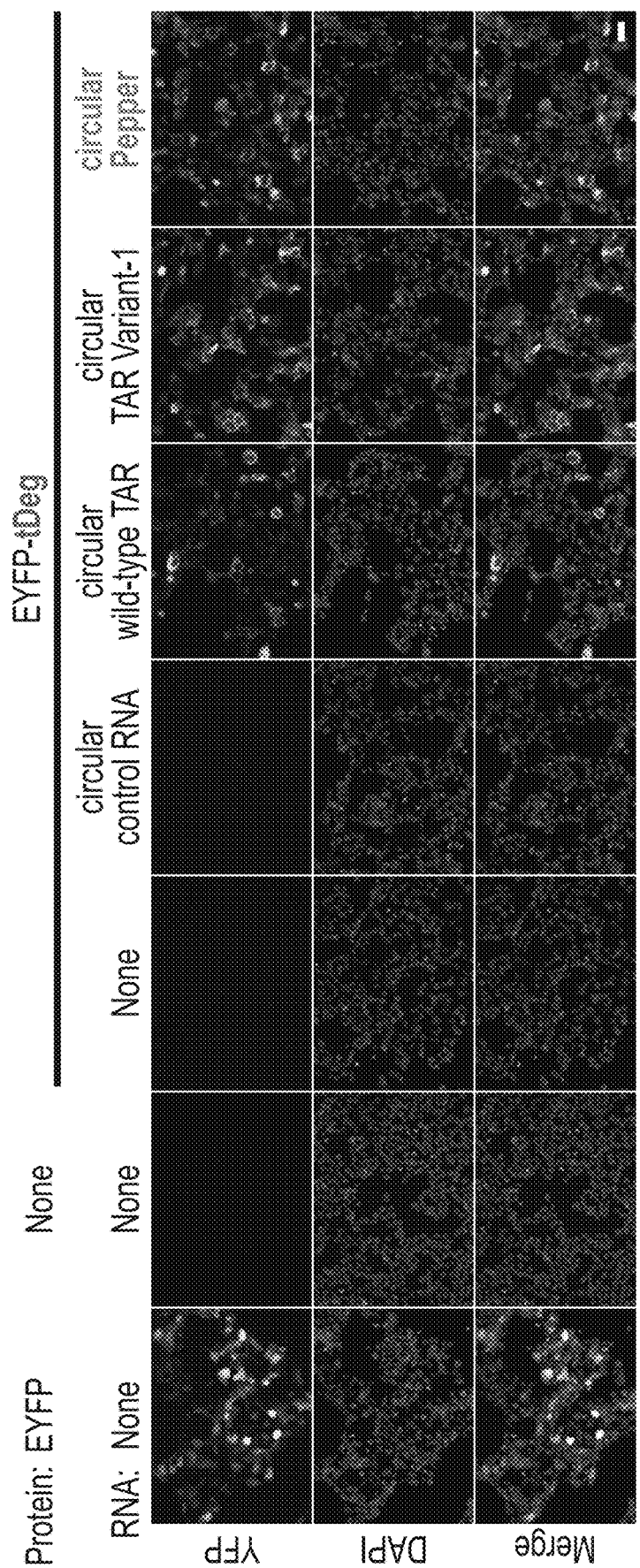
Figure 2A:
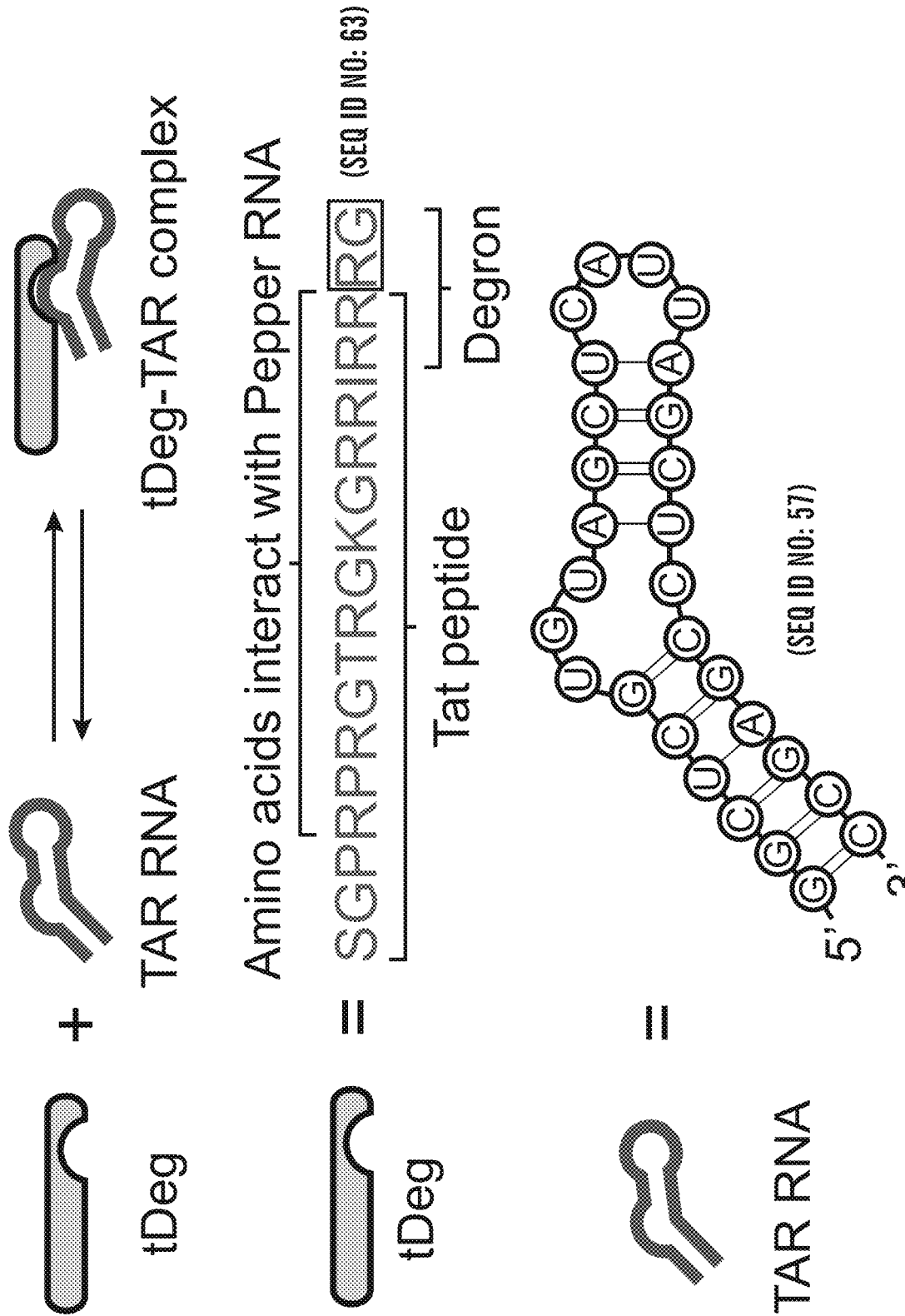
FIGS. 2A-2B are schematic illustrations showing the design of tDeg, an RNA-regulated destabilization domain. Shown is a structural representation of how TAR binds to the tDeg, and may therefore obstruct recognition of the Arg-Arg-Arg-Gly degradation-inducing signal. RNA is depicted in grey, and peptide sequence is shown letters of the polypeptide chain. A schematic representation of RNA binding to the tDeg sequence is shown in FIG. 2A. Here, a bifunctional peptide sequence, called tDeg, that functions both as a destabilization domain and as a binding site for the bovine immunodeficiency virus TAR RNA (in grey) was designed. Knowing that the TAR RNA binds to specific amino acids in the Tat peptide including the two C-terminal arginines, an Arg-Gly (highlighted in a black box) was added to the C-terminus of the Tat peptide to make the full Arg-Arg-Arg-Gly degron. When the TAR RNA binds to this bifunctional domain, it impedes the function of the destabilization domain by sterically blocking recognition of the Arg-Arg-Arg-Gly degron by proteasomal machinery. The structure model (FIG. 2B) of the Tat-TAR complex shows that the first two arginines of the Arg-Arg-Arg-Gly degron would be inaccessible to any Arg-Arg-Arg-Gly-binding protein that mediates its degradation. The additional Arg-Gly residues are modeled into the C-terminus of Tat in a black box in FIG. 2B. The structure representation in FIG. 2B is based on the NMR structure of the bovine immunodeficiency virus Tat-TAR complex (PDB entry: 1BIV) (Puglisi et al., "Solution Structure of a Bovine Immunodeficiency Virus Tat-TAR Peptide-RNA Complex," *Science* 270:1200-3 (1995), which is hereby incorporated by reference in its entirety).
Figure 2B:
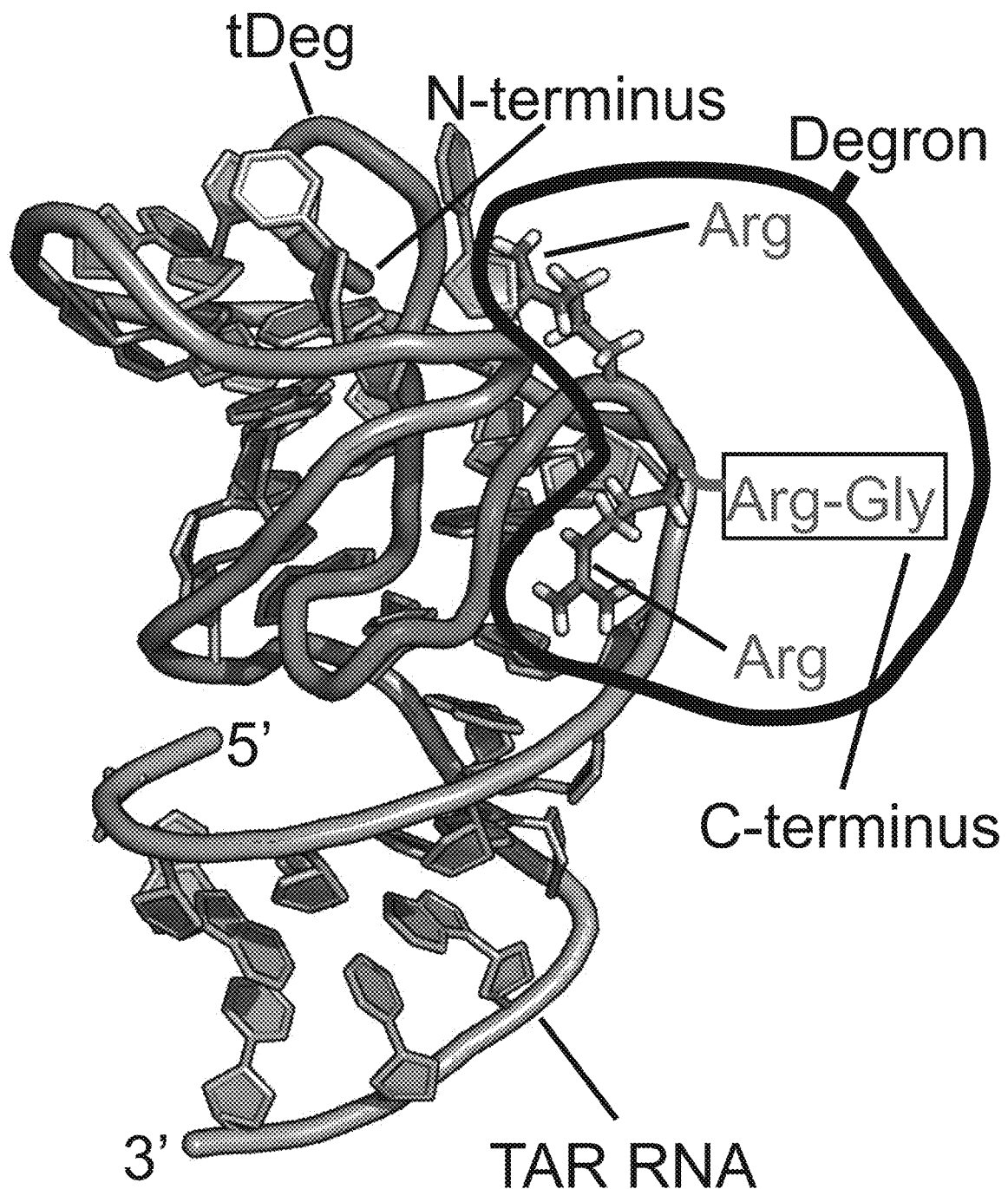

First, a "destabilization domain" that can be inhibited by an RNA aptamer was developed. Previously, the Arg-Arg-Arg-Gly (SEQ ID NO: 117) was described as a degron sequence when appended to the C-terminus of proteins (Bonger et al., "Small-Molecule Displacement of a Cryptic Degron Causes Conditional Protein Degradation," *Nat. Chem. Biol.* 7:531-537 (2011), which is hereby incorporated by reference in its entirety). This sequence is similar to the arginine-rich RNA-binding domain of the Tat protein, which contains Arg-Arg as its last two amino acids. Therefore, Arg-Gly was appended to extend this Arg-Arg sequence so that the full Arg-Arg-Arg-Gly (SEQ ID NO: 117) degron is at the C-terminus of this peptide (FIGS. 1A-1B and FIGS. 2A-2B). This 19-amino acid-long bifunctional peptide was termed "tDeg." Tat binds a 28 nt-long RNA hairpin termed TAR (Ye et al., "Molecular Recognition in the Bovine Immunodeficiency Virus Tat Peptide-TAR RNA Complex," *Chem. Biol.* 2:827-40 (1995) and Puglisi et al., "Solution Structure of a Bovine Immunodeficiency Virus Tat-TAR Peptide-RNA Complex," *Science* 270:1200-1203 (1995), which are hereby incorporated by reference in their entirety), which may shield the degron and thus prevent recruitment of the proteasomal machinery needed for proteolysis (FIG. 1A and FIGS. 2A-2B).

Figure 1C:
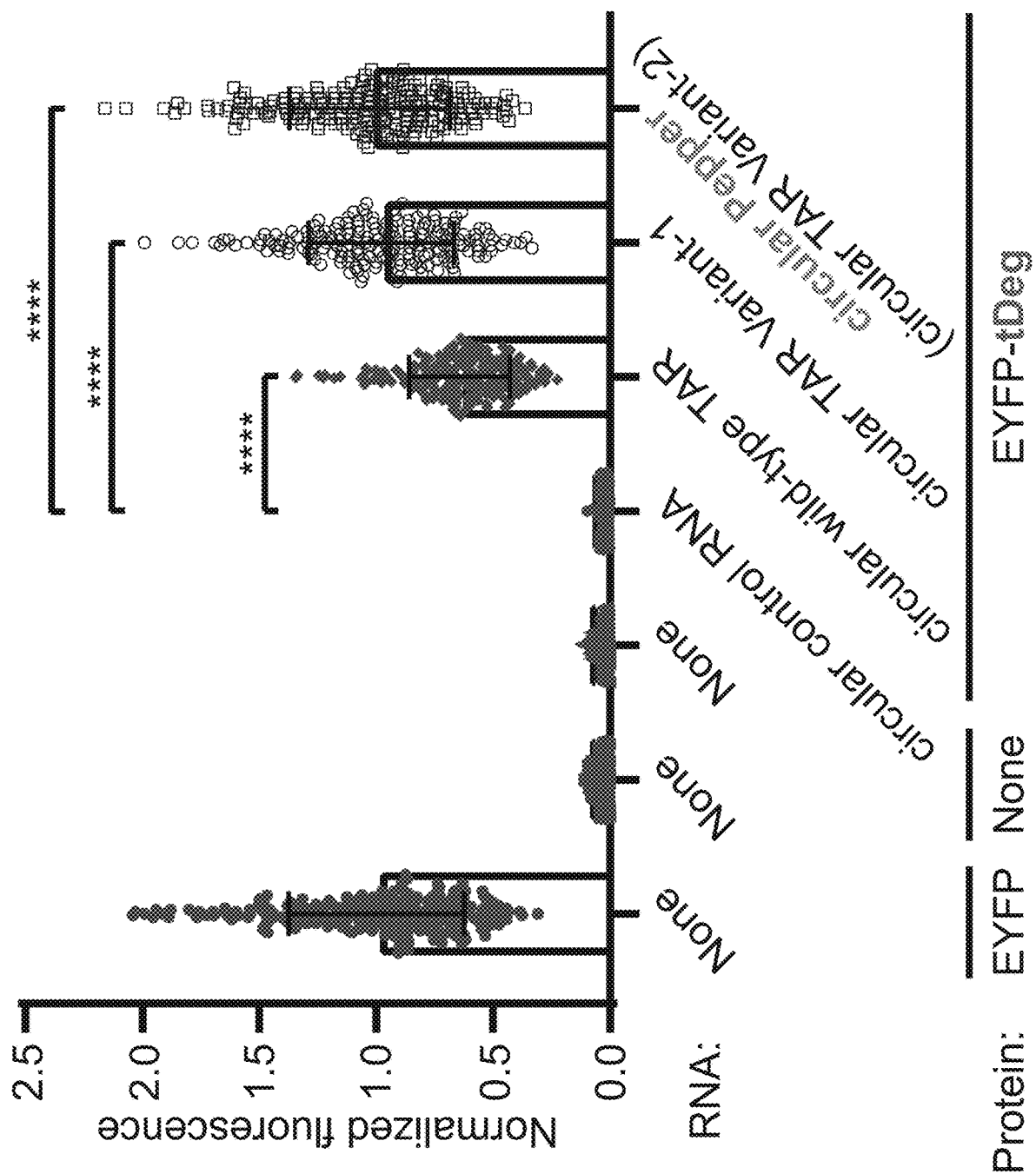
Figure 3A:
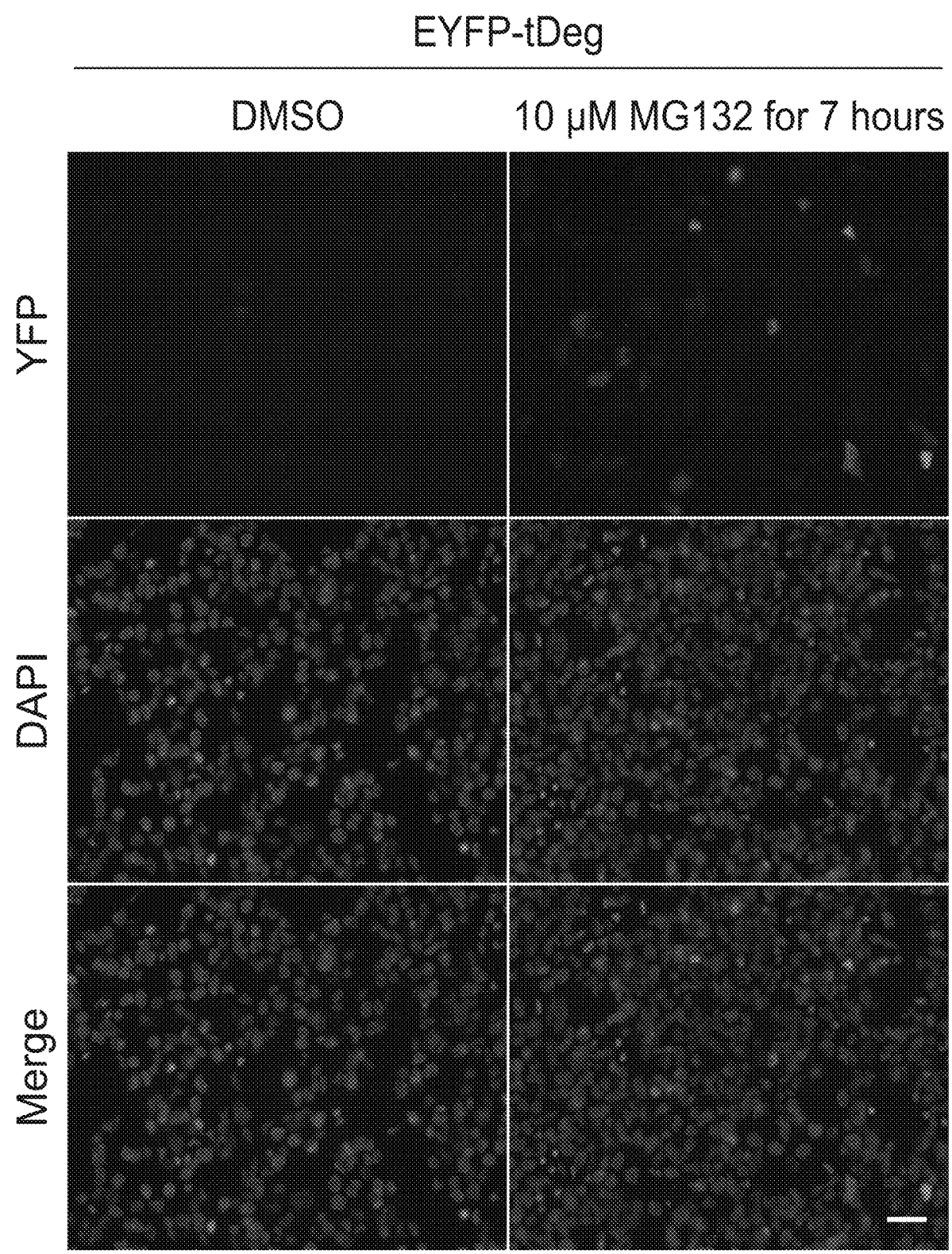
FIGS. 3A-3B demonstrate that tDeg confers protein instability to EYFP by proteasomal degradation.
Figure 3B:
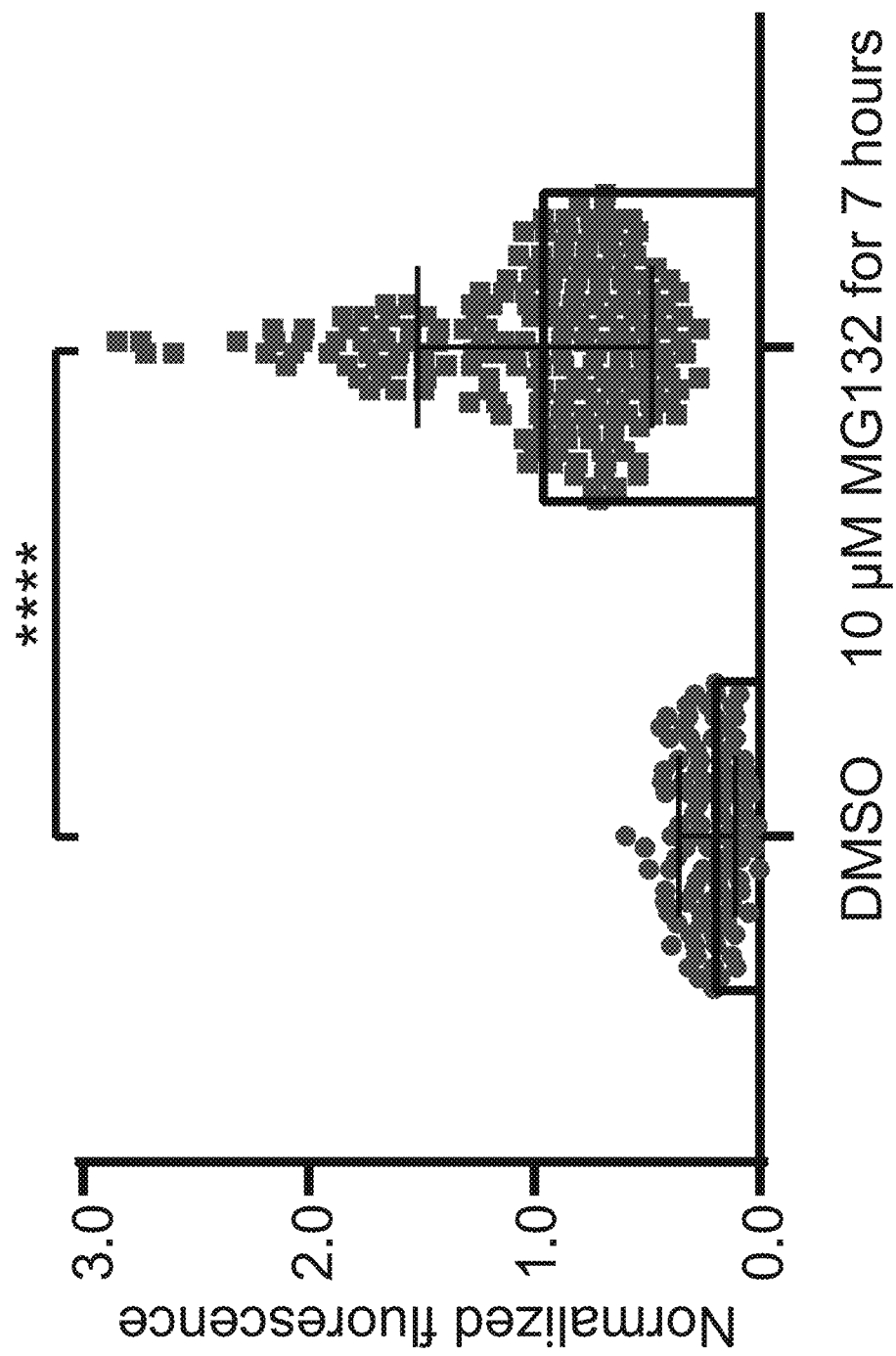

Whether tDeg confers instability to proteins was first investigated. To do so, tDeg was fused to the C-terminus of enhanced yellow fluorescent protein (EYFP), and the resulting fusion protein (EYFP-tDeg) was expressed in HEK293T cells. While EYFP was readily detectable, EYFP-tDeg was nearly undetectable (FIGS. 1B-1C). EYFP-tDeg was restored by proteasome inhibition (FIGS. 3A-3B) indicated that tDeg reduces protein stability by inducing proteasomal degradation.

Example 2—tDeg is Regulated by TAR RNA and TAR RNA Variants

Whether the tDeg can be regulated by the TAR RNA was next investigated. The TAR RNA was expressed as a circular RNA using the Tornado ribozyme-assisted circularization approach to achieve high expression in mammalian cells (Litke & Jaffrey, "Highly Efficient Expression of Circular RNA Aptamers in Cells Using Autocatalytic Transcripts," *Nat. Biotechnol.* 37:667-675 (2019), which is hereby incorporated by reference in its entirety). When TAR was expressed, EYFP-tDeg-expressing cells exhibited a 24-fold increase of fluorescence relative to control RNA (FIGS. 1B-1C). TAR variants that bind Tat with higher affinity, Variant-1 and Variant-2 (Smith et al., "Altering the Context of an RNA Bulge Switches the Binding Specificities of Two Viral Tat Proteins," *Biochemistry* 37:10808-10814 (1998), which is hereby incorporated by reference in its entirety), were even more efficient at inducing EYFP-tDeg, with Variant-2 exhibiting a 38-fold increase in cellular fluorescence (FIGS. 1B-1C; FIGS. 4A-4B). Expression of Variant-2 induced EYFP-tDeg cellular fluorescence levels similar to levels in cells expressing EYFP without the tDeg (FIG. 1C). Furthermore, Variant-2 induced EYFP-tDeg fluorescence in diverse cell types (FIGS. 5A-5G). Thus, the EYFP-tDeg is a RNA-regulated fluorescent fusion protein that is regulated by TAR.

Because the TAR Variant-2 aptamer can control the expression of different colored fluorescent proteins, as described infra, this aptamer was named after the multicolored vegetable Pepper, in keeping with the vegetable nomenclature system used previously for fluorogenic RNA aptamers.

Example 3—tDeg Tag is a Versatile Tag for Pepper-Dependent Protein Stabilization Whether the expression level of other proteins could be controlled by the Pepper RNA was next investigated. Addition of tDeg to the C-terminus of mNeonGreen, mCherry, NanoLuc, tetracycline repressor protein (TetR), EZH2, and NF-κB, resulted in minimal or undetectable protein levels in control cells and clear induction in circular Pepper-expressing cells (FIGS. 6A-6G and FIGS. 7A-7G). Taken together, these data indicate that the tDeg tag is a versatile tag for RNA-dependent protein stabilization.

Example 4—Intracellular Imaging Using Pepper-Modified mRNA mRNAs are commonly imaged using tethered fluorescent proteins. For example, a GFP fusion with MS2 phage coat protein (MCP) can be recruited to mRNAs containing 24-48 consecutive MS2 RNA hairpins in their 3'UTRs (Bertrand et al., "Localization of ASH1 mRNA Particles in Living Yeast," *Mol. Cell* 2:437-45 (1998), which is hereby incorporated by reference in its entirety). In this way, many GFPs are recruited to single mRNAs resulting in an aggregate fluorescence that can be detected by fluorescence microscopy. Typically nuclear localization elements are added to the GFP-MCP fusion to remove the unbound fluorescent protein from the cytoplasm into the nucleus (Bertrand et al., "Localization of ASH1 mRNA Particles in Living Yeast," *Mol. Cell* 2:437-45 (1998), which is hereby incorporated by reference in its entirety). This can reduce the fluorescence background in the cytosol, facilitating mRNA detection. However, this may introduce a potential artifact since the MS2-tagged mRNAs will contain dozens of nuclear localization sequences due to the recruited fluorescent proteins (Tyagi, S., "Imaging Intracellular RNA Distribution and Dynamics in Living Cells," *Nat. Methods* 6:331-338 (2009), which is hereby incorporated by reference in its entirety). The RNA aptamers described herein do not introduce a cellular trafficking element and may therefore bypass this concern.

Figure 8A:
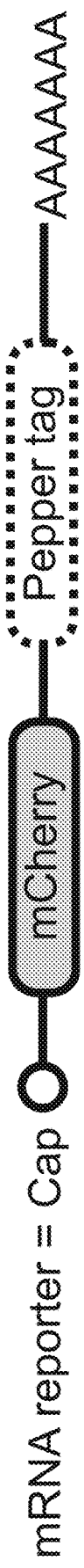
FIGS. 8A-8B demonstrate the optimization of a concatenated Pepper tag to image mRNAs in live cells. Pepper RNA-regulated fluorescent proteins were used to fluorescently tag mRNAs in live cells. As a first step, the best way to incorporate the Pepper aptamers in the 3'UTR of a transcript of interest was determined. In these experiments, a fluorescent protein (mNeonGreen)$_2$-tDeg and an mCherry mRNA reporter (FIG. 8A) containing 3'UTR tags comprising 10 or 20 concatenated Pepper aptamers with and without a folding scaffold, F30, were expressed respectively. In the case of the (Pepper)$_{20}$ and (F30-2×Pepper)$_{10}$ tags, mobile green fluorescent puncta in the cytosol were observed (FIG. 8B). A signal to noise ratio was evident when the (F30-2× Pepper)$_{10}$ tag (signal to noise ratio=1.8) was used, compared to the (Pepper)$_{20}$ tag (signal to noise ratio=1.5). However, puncta were not readily detectable with either the (Pepper)$_{10}$ tag or the (F30-1×Pepper)$_{10}$ tag. Therefore, the (F30-2× Pepper)$_{10}$ tag was used to image mRNAs in the subsequent experiments. Scale bar, 20 µm. This experiment was performed three times with similar results.
Figure 8B:
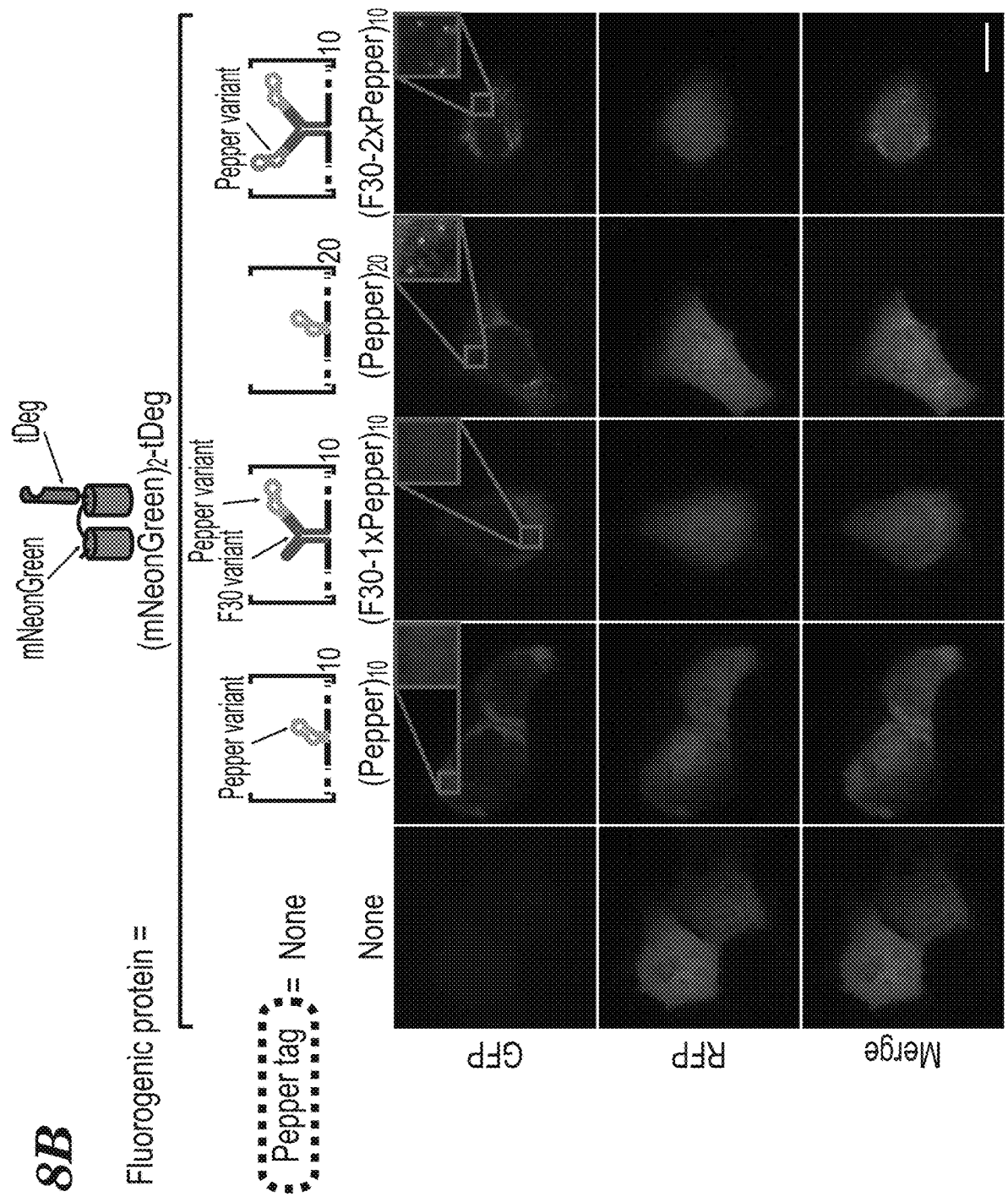
Figure 9B:
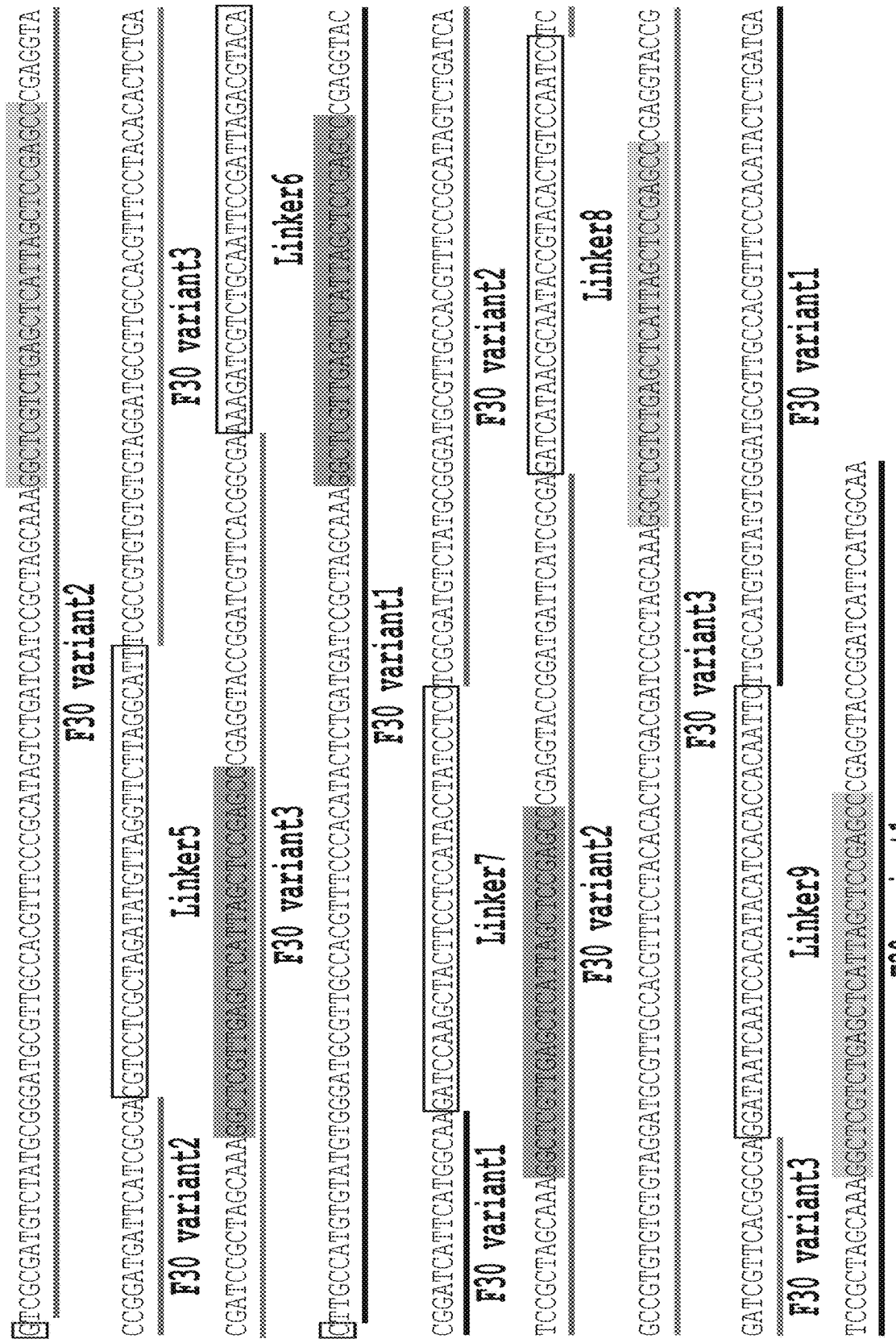
Figure 9C:
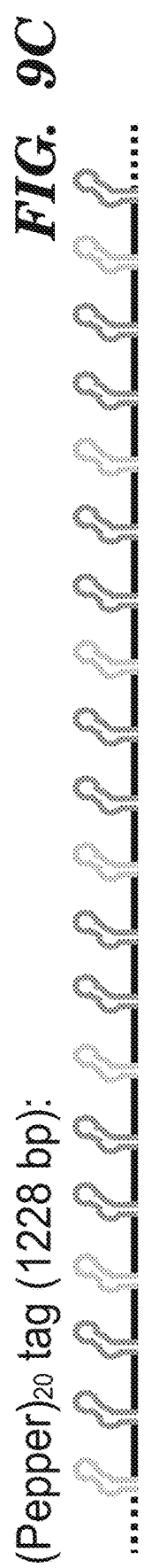
Figure 9C:
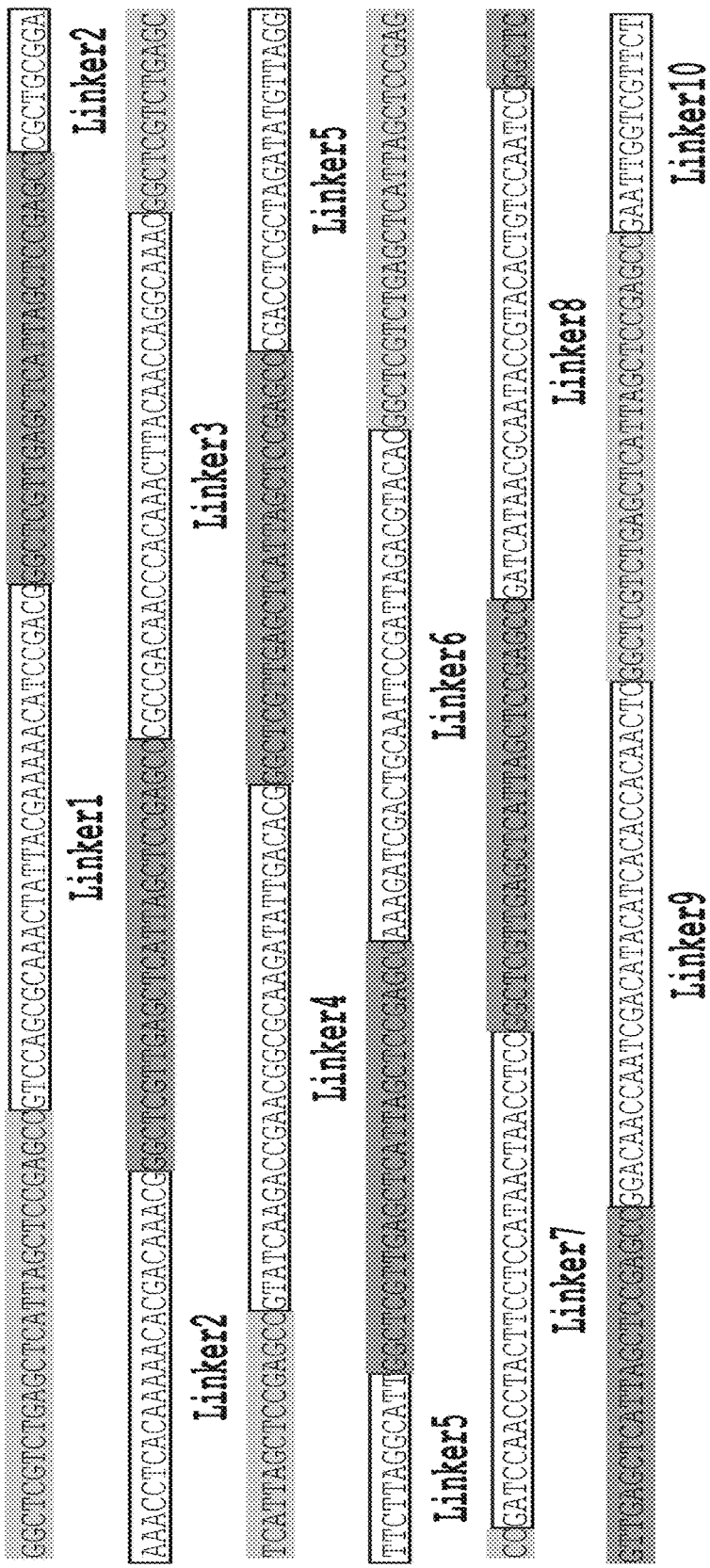
Figure 9C:
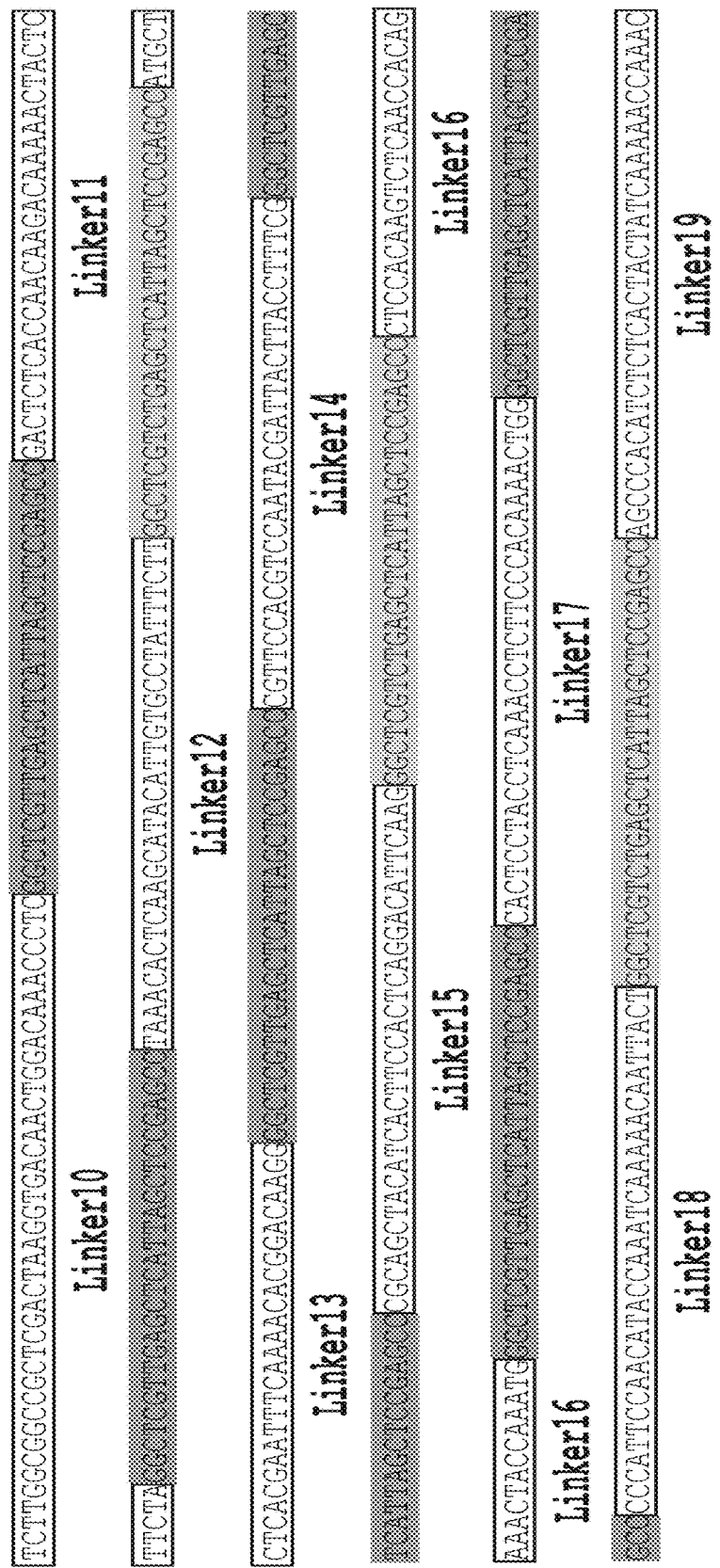
Figure 9D:
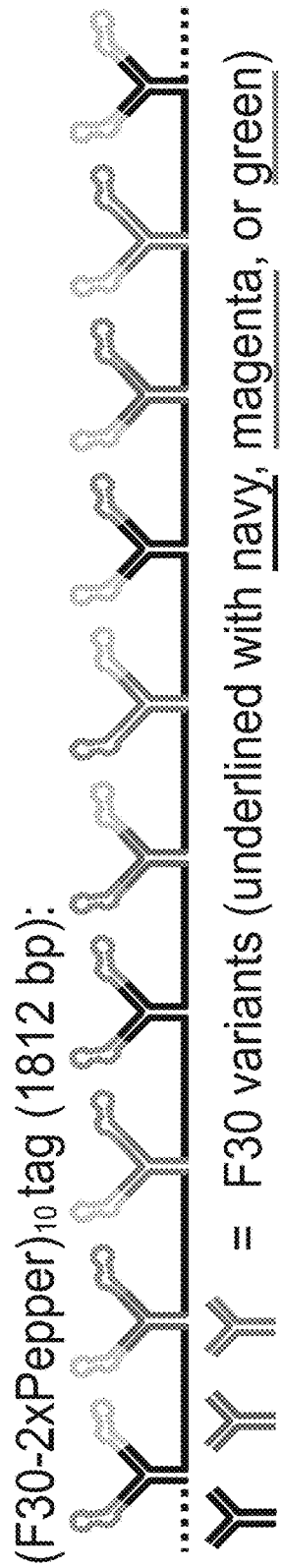
Figure 9D:
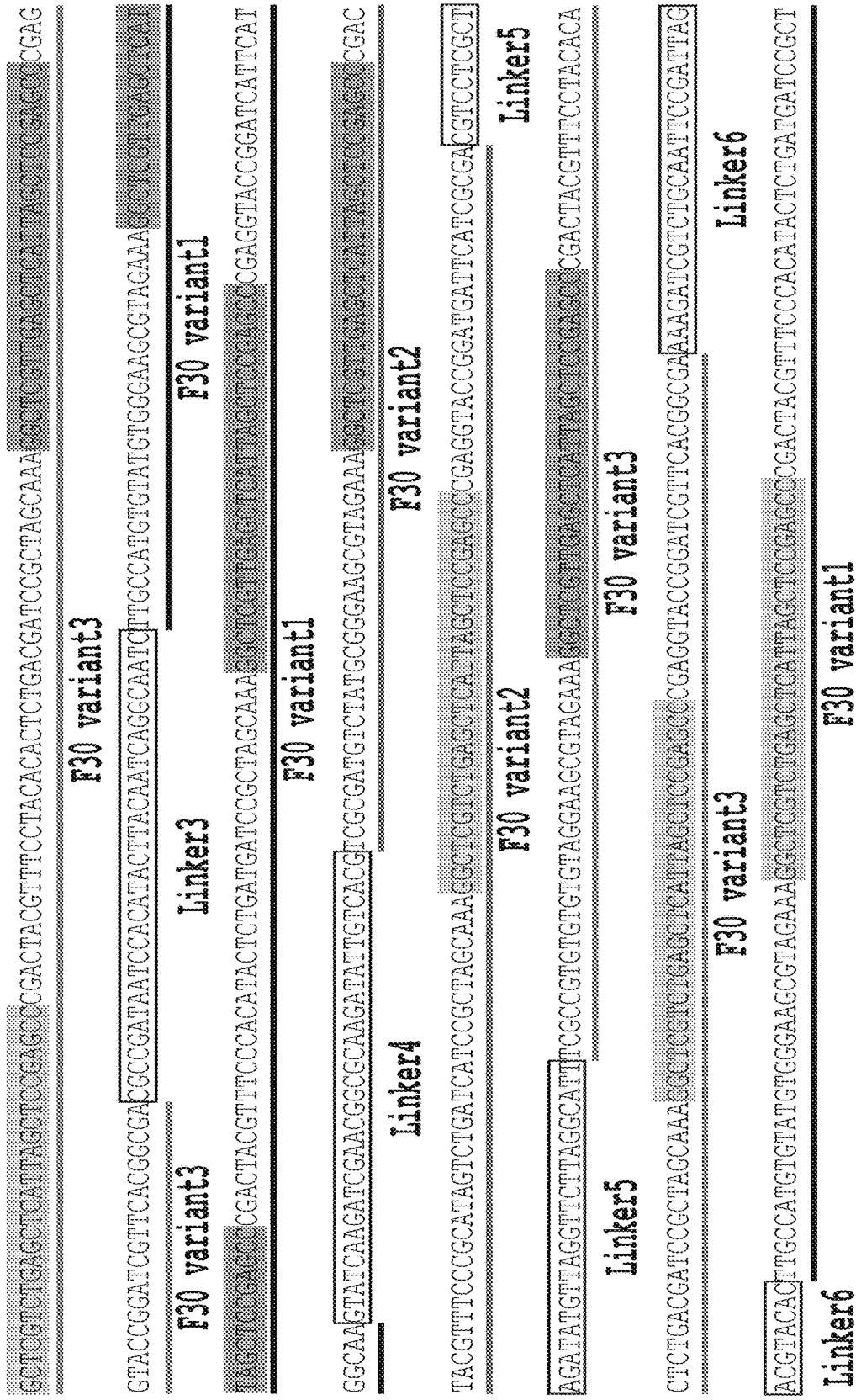
Figure 9D:
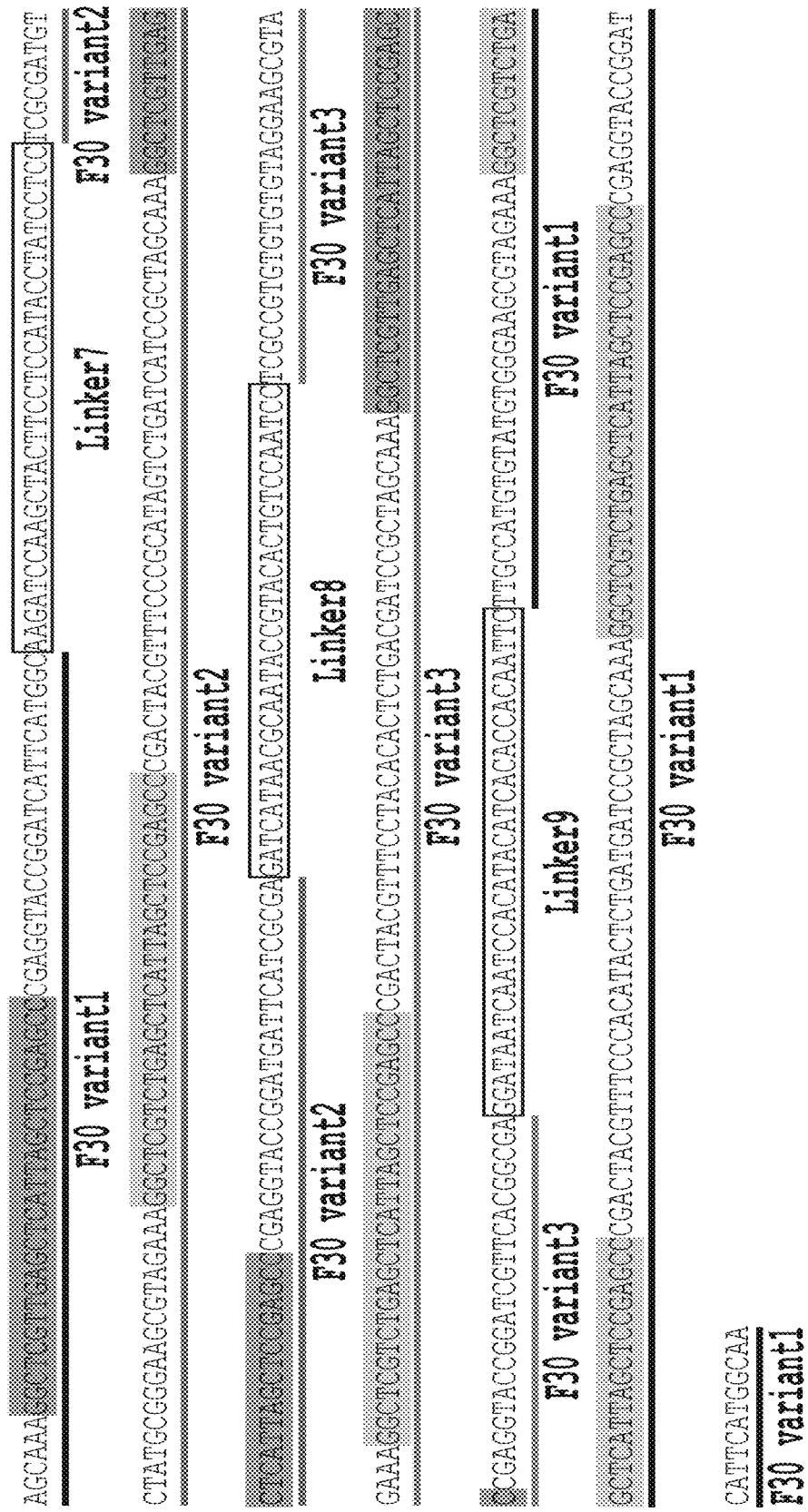
Figure 10A:
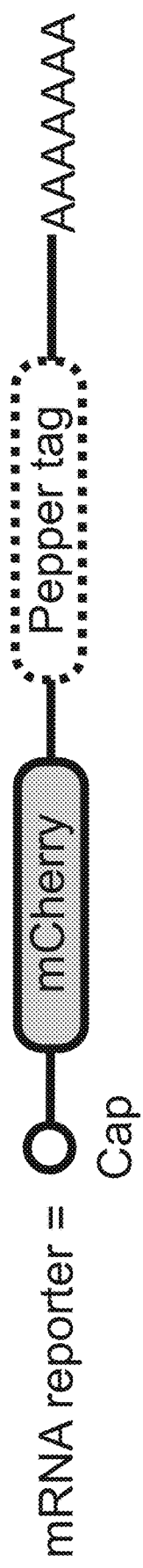
FIGS. 10A-10C demonstrate the optimization of the number of fluorescent mNeonGreen monomers in the fluorescent protein for imaging mRNA in live cells.
Figure 10B:
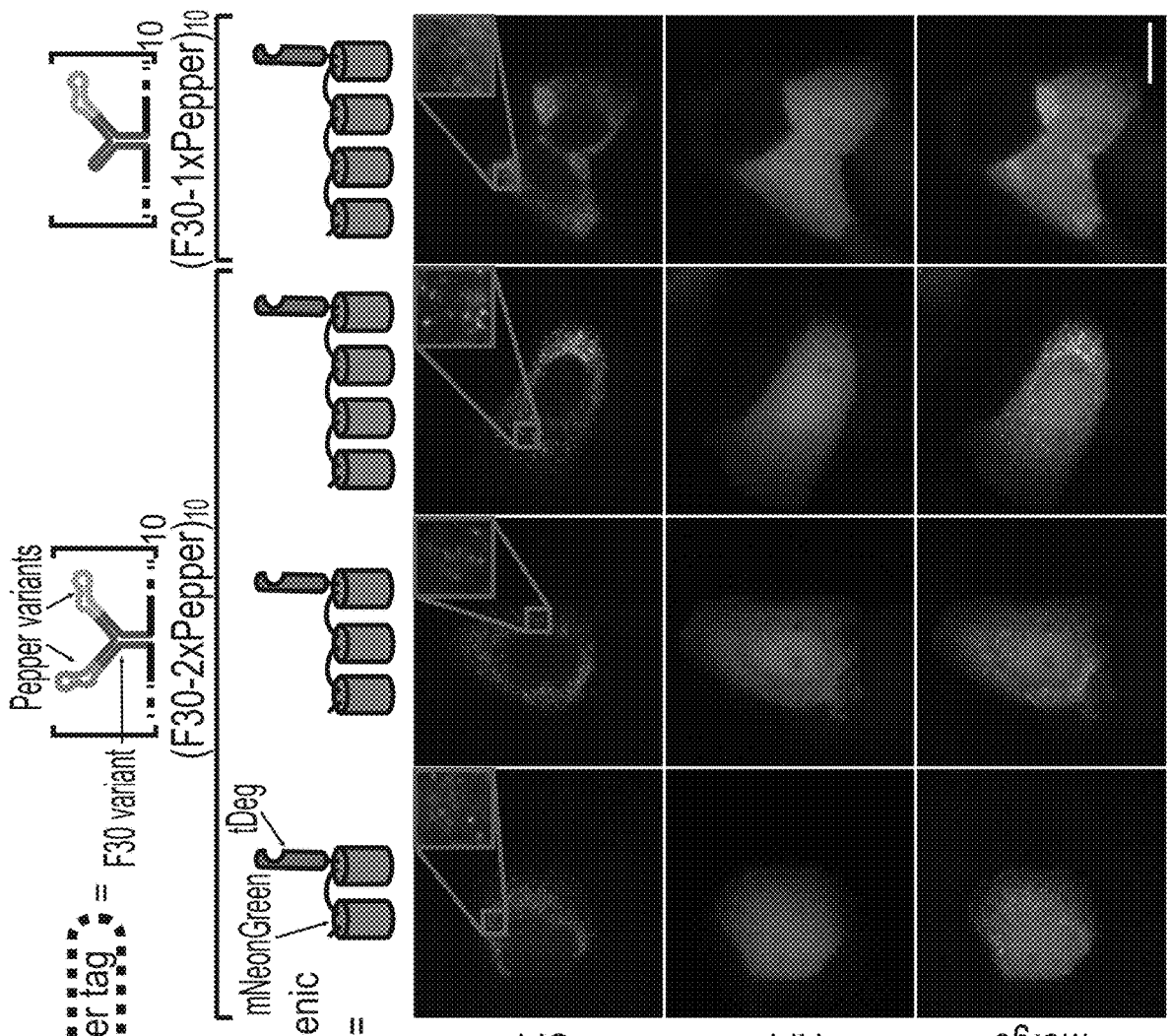
Figure 10C:
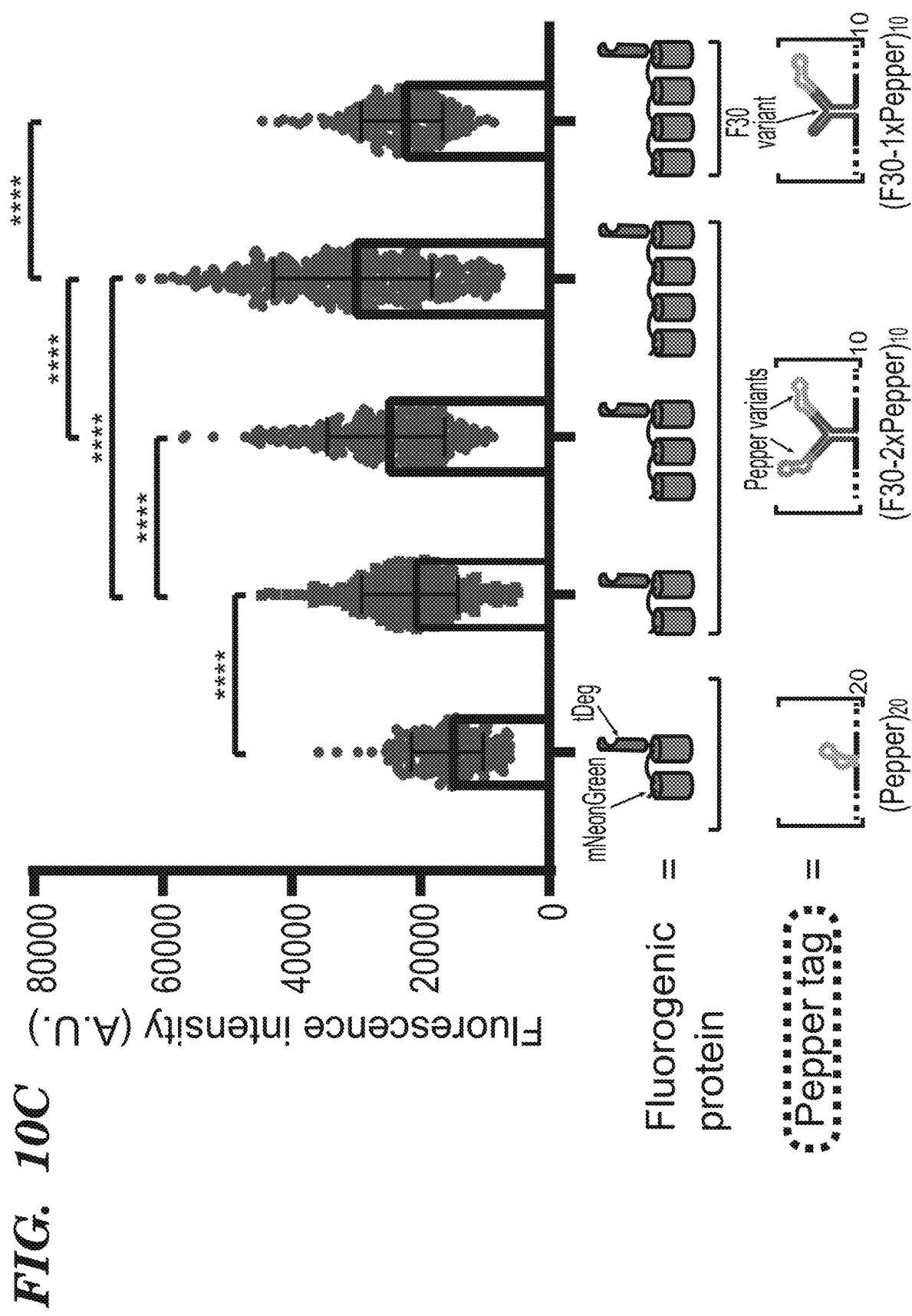
Figure 11A:
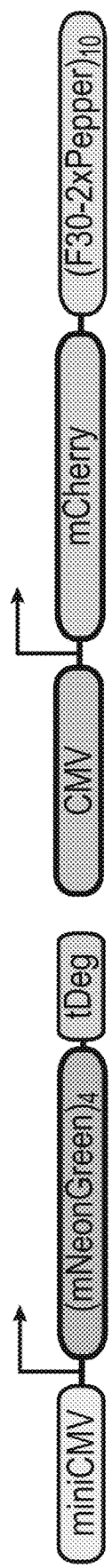
FIGS. 11A-11C demonstrate that Pepper tag enables visualization of both nuclear and cytosolic mRNAs.
Figure 11B:
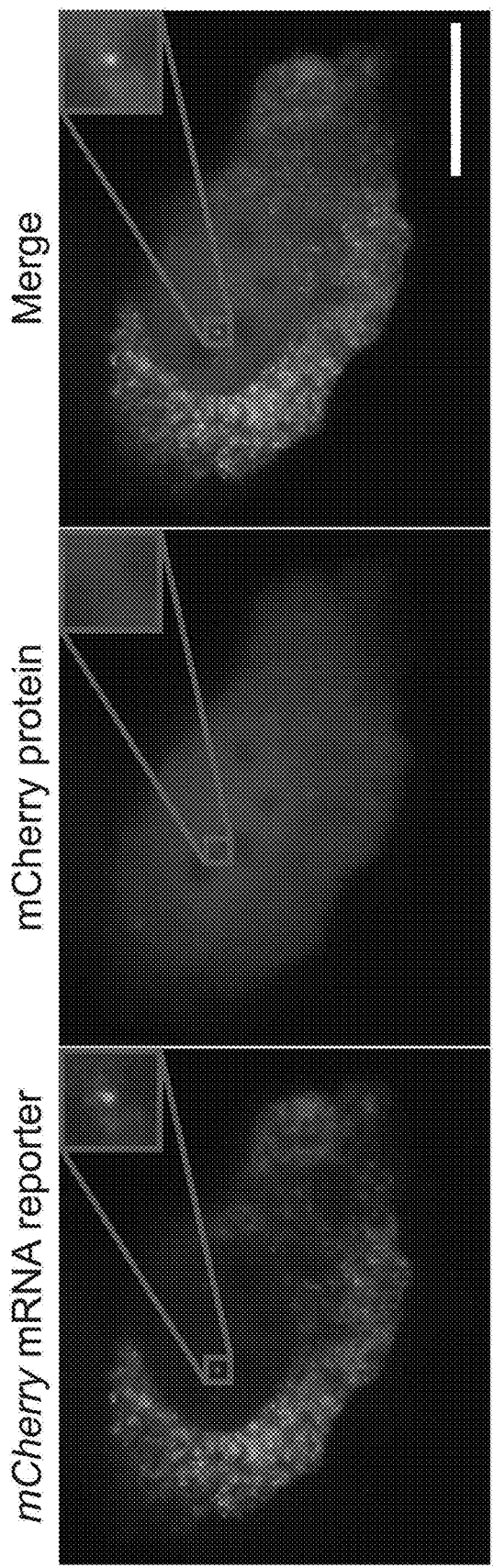
Figure 11C:
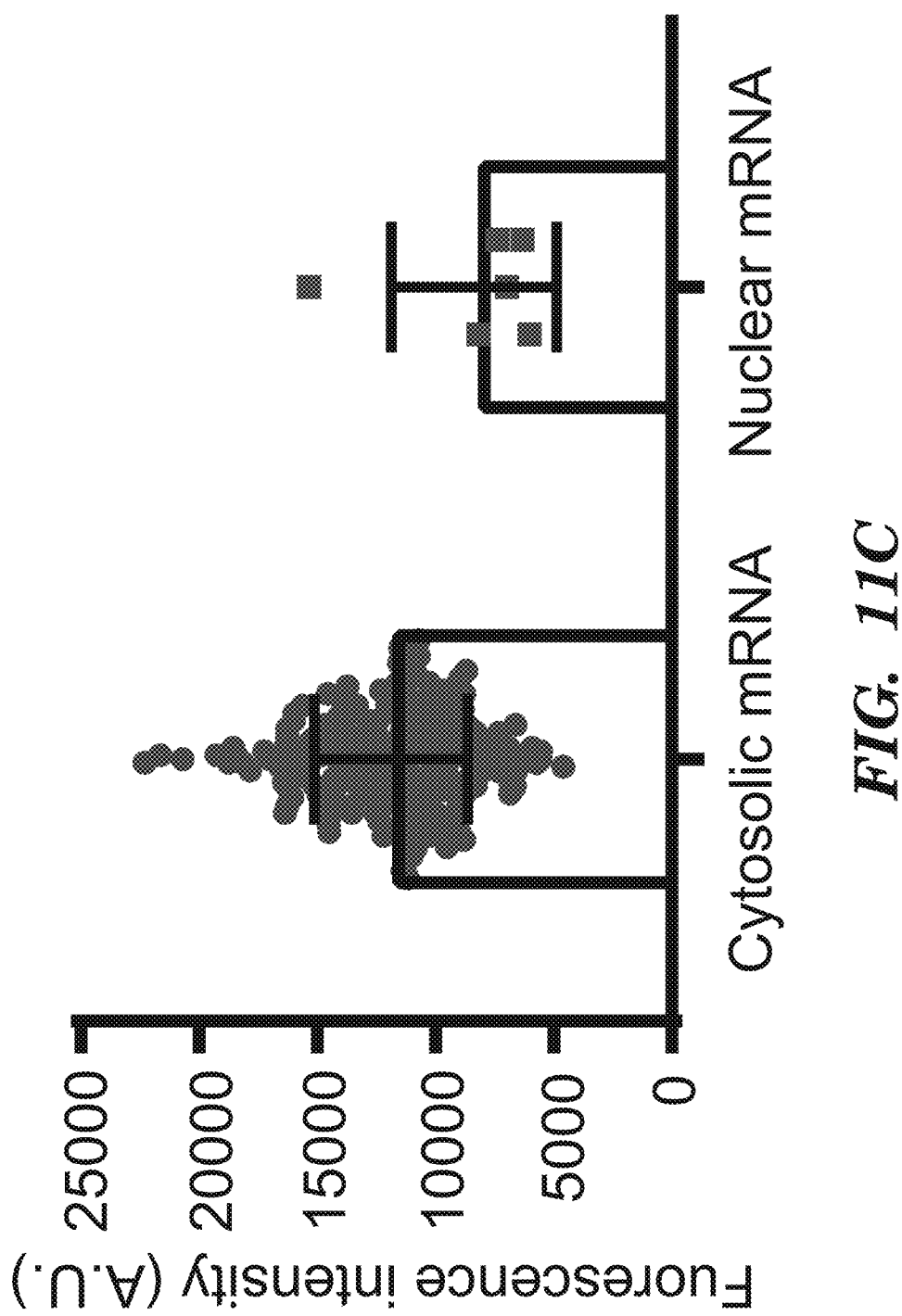

To investigate the use of RNA aptamers in intracellular imaging, a tag for mRNA imaging consisting of consecutive Pepper aptamers was next generated. In optimization experiments, an mCherry mRNA reporter containing different 3'UTR tags comprising 10 or 20 concatenated Pepper aptamers and Pepper aptamers that were inserted into an RNA three-way junction sequence termed F30 were imaged. Aptamers inserted within the F30 show improved folding (Filonov et al., "In-Gel Imaging of RNA Processing Using Broccoli Reveals Optimal Aptamer Expression Strategies," *Chem. Biol.* 22:649-60 (2015), which is hereby incorporated by reference in its entirety). mCherry mRNA was readily detectable as mobile fluorescent puncta in the cytoplasm when the tag contained 20 Pepper aptamers. The brightest puncta were seen when using the (F30-2×Pepper)$_{10}$ tag, which comprises 10 consecutive F30 sequences, with each of the two arms of F30 containing one Pepper aptamer (FIGS. 8A—B; FIGS. 9A-9D; and FIGS. 10A-10C).

mRNA imaging using RNA-regulated fluorescent fusion proteins of different brightness was also investigated. These proteins comprised 2, 3, or 4 tandem mNeonGreen monomers with a C-terminal tDeg. In these experiments, a RNA-regulated fluorescent fusion protein comprising four mNeonGreens provided the highest signal-to-noise ratio for imaging mRNAs (FIGS. 10A-10C). Although most fluorescent puncta were detected in the cytoplasm, occasional puncta were detected in the nucleus, potentially reflecting mRNAs prior to nuclear export (FIGS. 11A-11C).

Figure 12B:
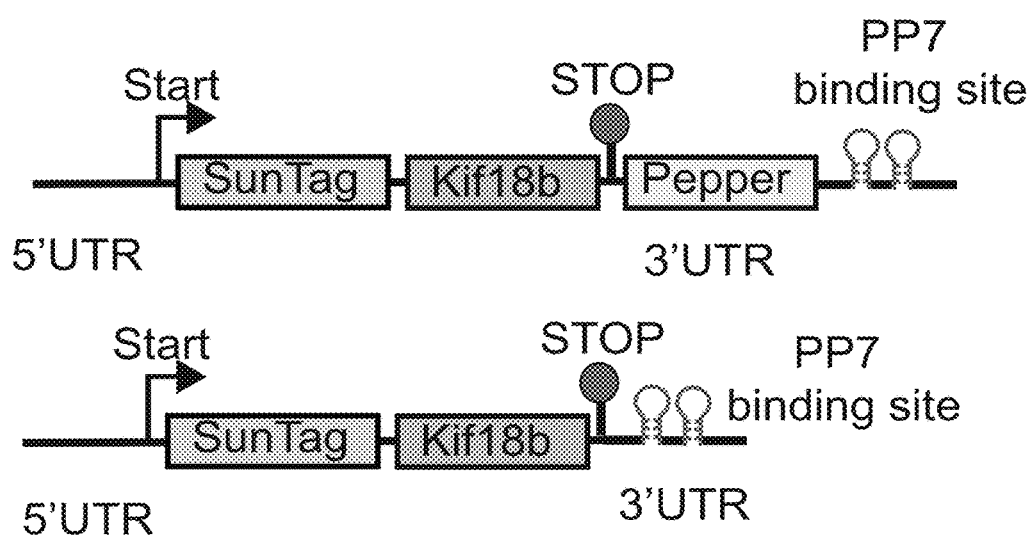

Cellular puncta likely reflect single mRNA molecules rather than Pepper-containing mRNA fragments since northern blotting of total cellular RNA derived from cells expressing (F30-2×Pepper)$_{10}$-tagged mRNA, either with or without coexpression of the (mNeonGreen)$_4$-tDeg showed mostly full-length transcripts (FIG. 12A). Furthermore, puncta derived from mRNAs tagged with (F30-2×Pepper)$_{10}$ were the same size and intensity as mRNAs tagged using the PP7 fluorescent protein recruitment system, which was previously shown to reflect single mRNA molecules (Yan et al., "Dynamics of Translation of Single mRNA Molecules In Vivo," *Cell* 165:976-989 (2016), which is hereby incorporated by reference in its entirety) (FIGS. 12B-12D).

Figure 13B:
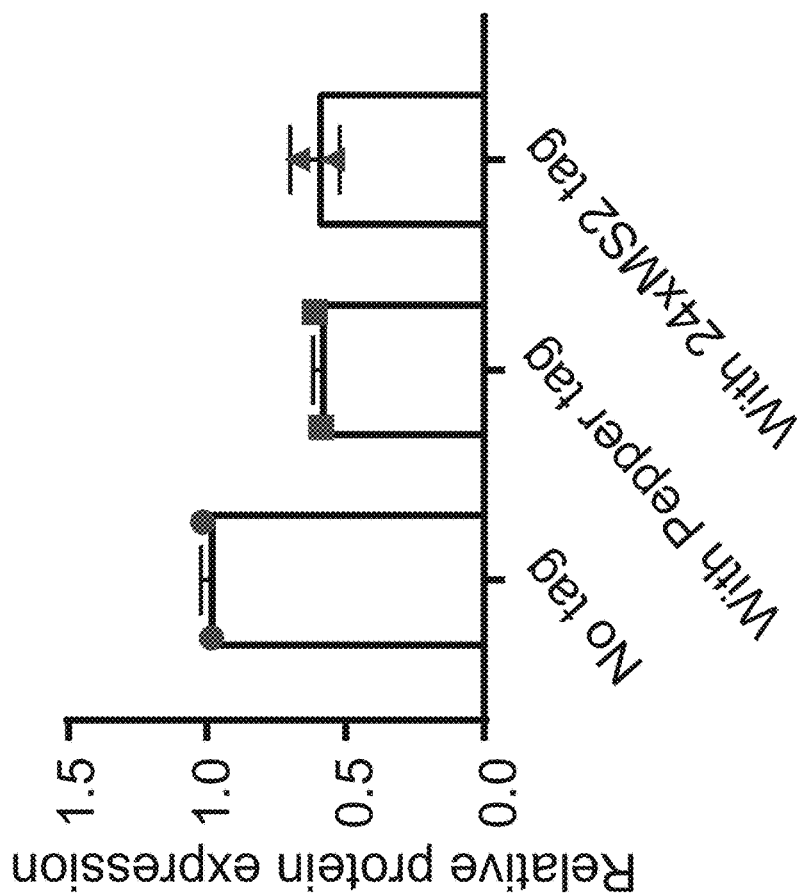
FIGS. 13A-13E demonstrate that Pepper tag and fluorescent fusion protein do not have observable effects on mRNA turnover kinetics, mRNA translation efficiency, or proteasome activity in cells. To test whether adding the Pepper tag to an mRNA transcript affects its stability, reporter plasmids expressing mCherry transcripts with and without the (F30-2×Pepper)$_{10}$ tag were constructed. HEK293T cells were transfected with these two reporter plasmids, respectively. In each case, the same cells were cotransfected with the (mNeonGreen)$_4$-tDeg fluorescent fusion protein. The cells were treated with 5 µg/mL actinomycin D to inhibit new transcription. The amount of reporter mRNA transcripts remaining at each time point was quantified by RT-qPCR at t=0, 1, 2, 4, and 6 hours of actinomycin D treatment. The results showed that fusing the Pepper tag to the reporter mRNA (half-life=5.9 hours) does not significantly affect its turnover rate compared to its untagged counterpart (half-life=6.0 hours) (FIG. 13A). Thus, these data suggest that Pepper-tagged mRNA transcripts have similar turnover kinetics as mRNAs without the Pepper tag. Data were collected from 2 independent cell cultures. Values are means±s.d. To test whether adding the Pepper tag to an mRNA transcript affects its protein translation efficiency, the protein translation efficiency of an mCherry mRNA was compared with and without the (F30-2×Pepper)$_{10}$ Pepper tag. HEK293T cells expressing mCherry mRNA or mCherry-(F30-2×Pepper)$_{10}$ mRNA were harvested. The amount of mCherry protein and mCherry mRNA was quantified by western blotting and RT-qPCR, respectively. A slight decrease of mRNA levels in the Pepper-tagged mCherry mRNA was observed compared to its untagged counterpart (FIG. 13C). The same phenomenon was also observed in the mCherry mRNA tagged with the 24×MS2 hairpins (Wu et al., "Synonymous Modification results in High-Fidelity Gene Expression of Repetitive Protein and Nucleotide Sequences," *Genes Dev.* 29:876-86 (2015), which is hereby incorporated by reference in its entirety). This may due to the longer transcript length associate with 3'UTR-tagged mRNAs. Protein translation efficiency was calculated by normalizing the amount of mCherry protein to the amount of mCherry mRNA (FIGS. 13B-13D). No significant difference in protein translation efficiency was found between the untagged mCherry mRNA transcript and the Pepper-tagged mCherry mRNA transcript (FIG. 13D). These results suggest that Pepper tag does not significantly affect protein translation of these mRNA reporter transcripts. Data were collected from 2 independent cell cultures. Values are means±s.d. Since the degradation mechanism of the fluorescent RNA-regulated fusion proteins described herein relies on ubiquitination and subsequent proteasomal degradation, expression of fluorescent RNA-regulated fusion proteins could lead to the overload of proteasome activity in cells. To test whether the expression of fluorescent RNA-regulated fusion proteins overloads proteasome activity, a RNA-regulated fluorescent fusion protein, (mNeonGreen)$_4$-tDeg was expressed in HEK293T cells. If the expression of (mNeonGreen)$_4$-tDeg overloads the activity of the proteasome, an accumulation of the ubiquitinated protein in cells would be expected.
Figure 13A:
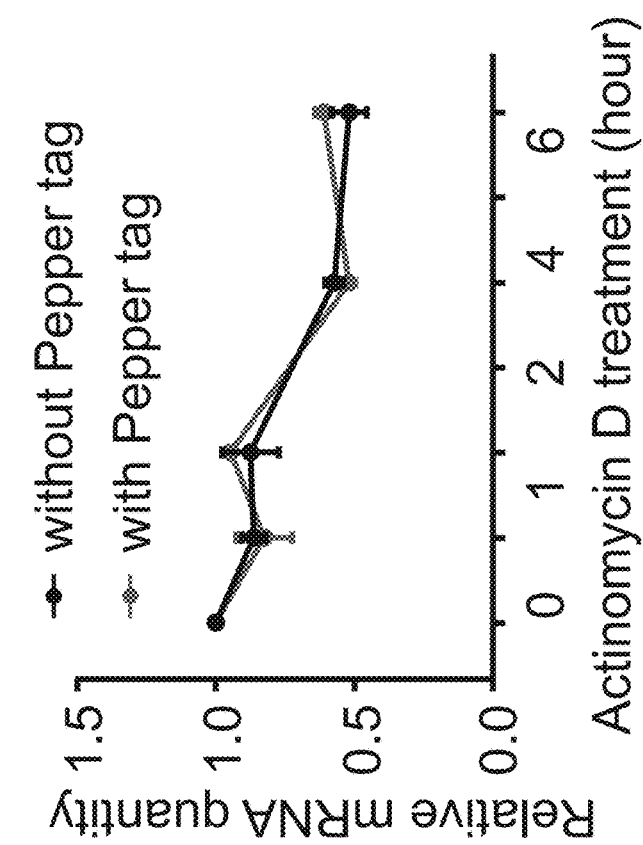
Figures 13C, 13D:
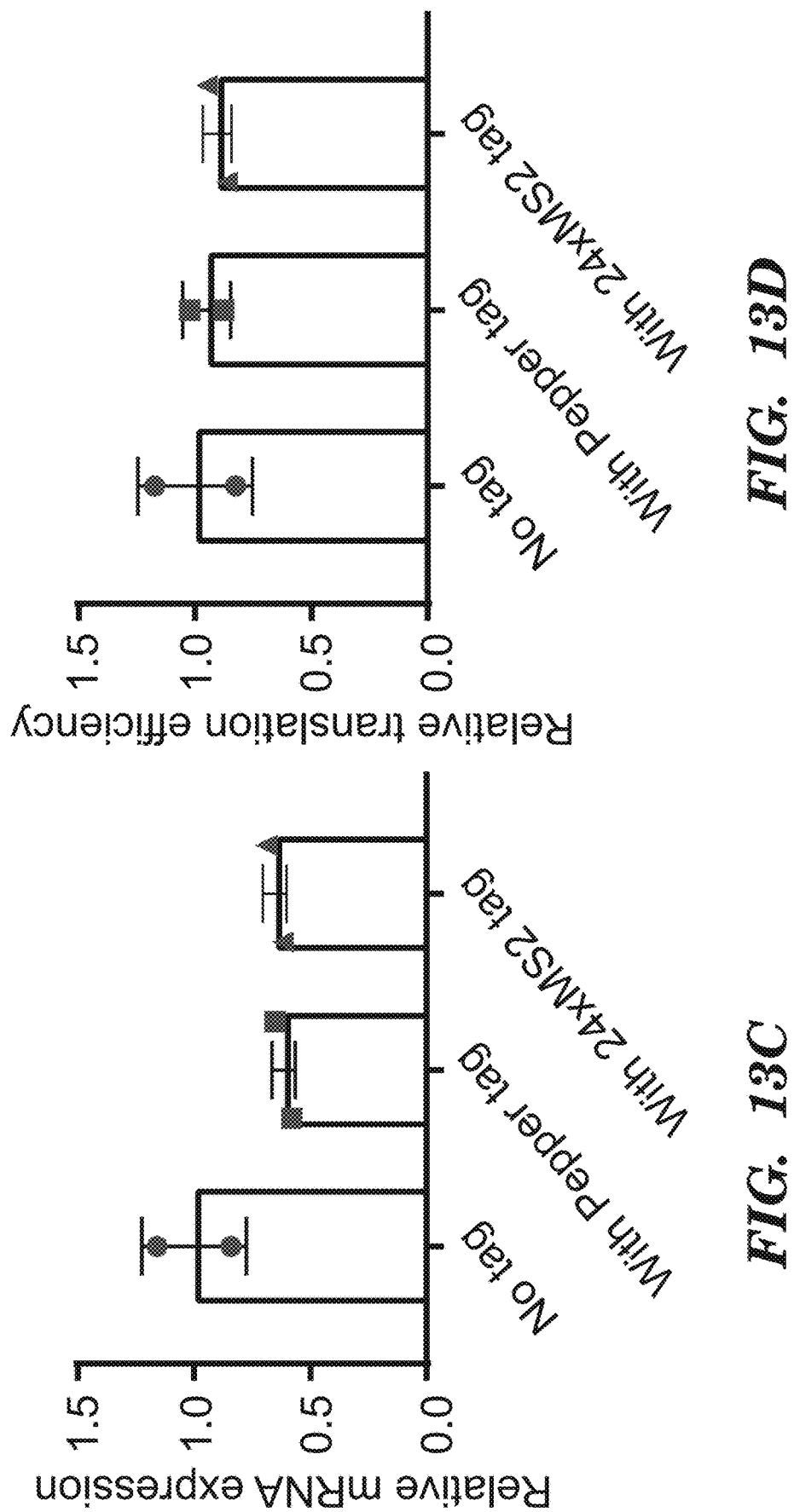
Figure 13E:
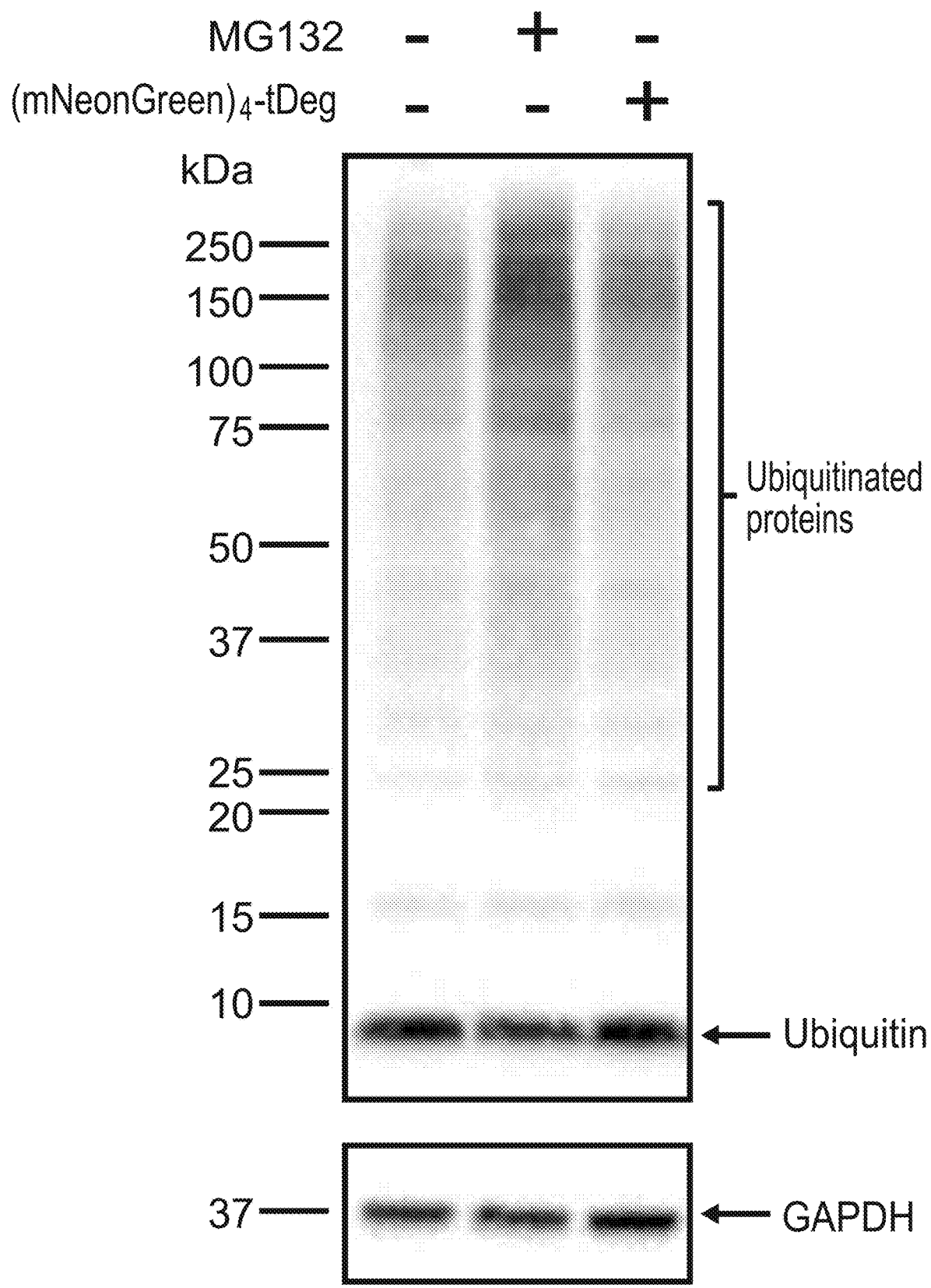
Figure 14A:
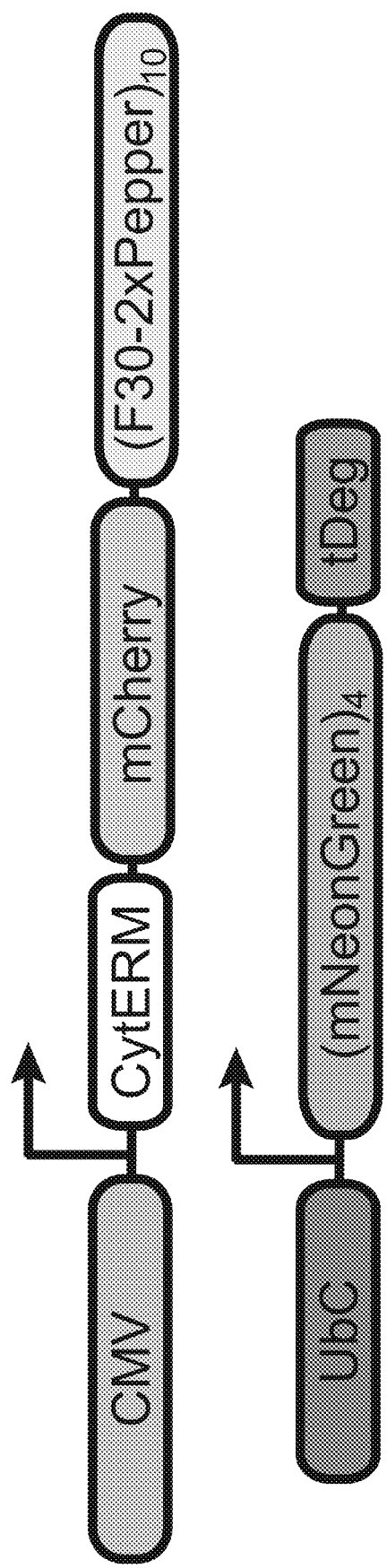
FIGS. 14A-14D demonstrate that Pepper tag does not disrupt the localization of mRNAs. To determine whether the Pepper tag disrupts an mRNA's proper cellular localization, an ER-targeting reporter mRNA was chosen, and its localization in cells was imaged using the (F30-2×Pepper)$_{10}$ Pepper tag and the (mNeonGreen)$_4$-tDeg fluorescent fusion protein (FIG. 14A). This ER-targeting reporter mRNA encodes the first 29 amino acids of cytochrome p450, CytERM, and the encoding sequence of mCherry followed by (F30-2×Pepper)$_{10}$ in the 3'UTR (FIG. 14A). During protein translation, the CytERM peptide will direct this reporter mRNA to the outer ER membrane, and confine the mRNA's mobility. Indeed, green fluorescent puncta with low mobility were observed (FIGS. 14B, 14D), suggesting that the reporter mRNA is localized to the outer ER membrane. To further validate the localization of the ER-targeting reporter mRNA, the cells were treated with a translation inhibitor (100 μg/mL, puromycin) to liberate the reporter mRNA from the ER into the cytosol. A significant mobility increase of the green fluorescent puncta was observed (FIG. 14C, FIG. 14D), reflecting the dissociation of the reporter mRNA from the ER. Together, these results confirmed that the Pepper tag does not disrupt the localization of mRNAs. Scale bar in (FIG. 14B, FIG. 14C), 10 μm. Relative diffusion coefficient of mRNA puncta is plotted (n=2 independent cell cultures). Values are means±s.d. ****P=2.7×10$^{-6}$ by unpaired two-tailed Student's t-test.
Figures 14B, 14C:
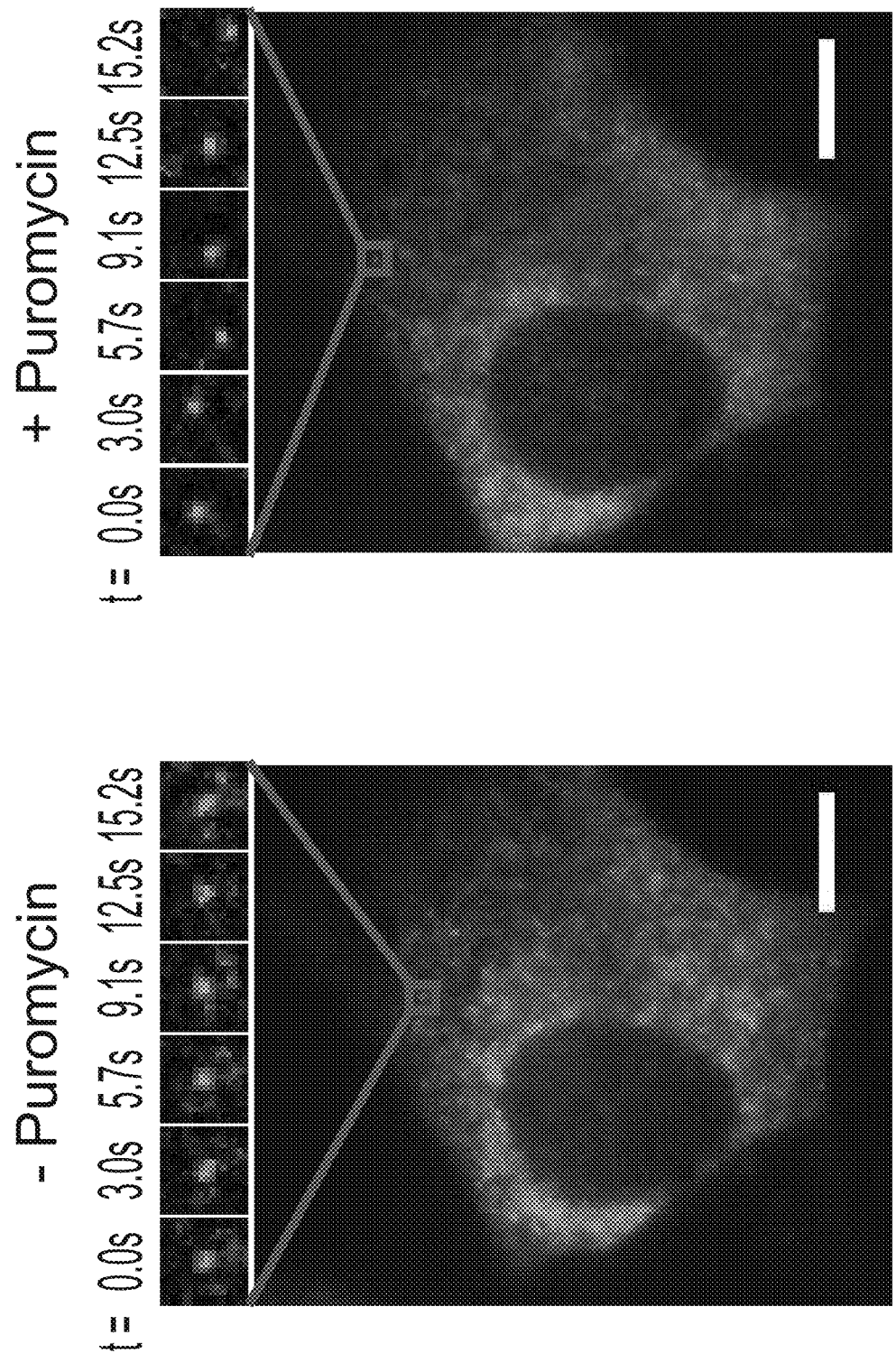
Figure 14D:
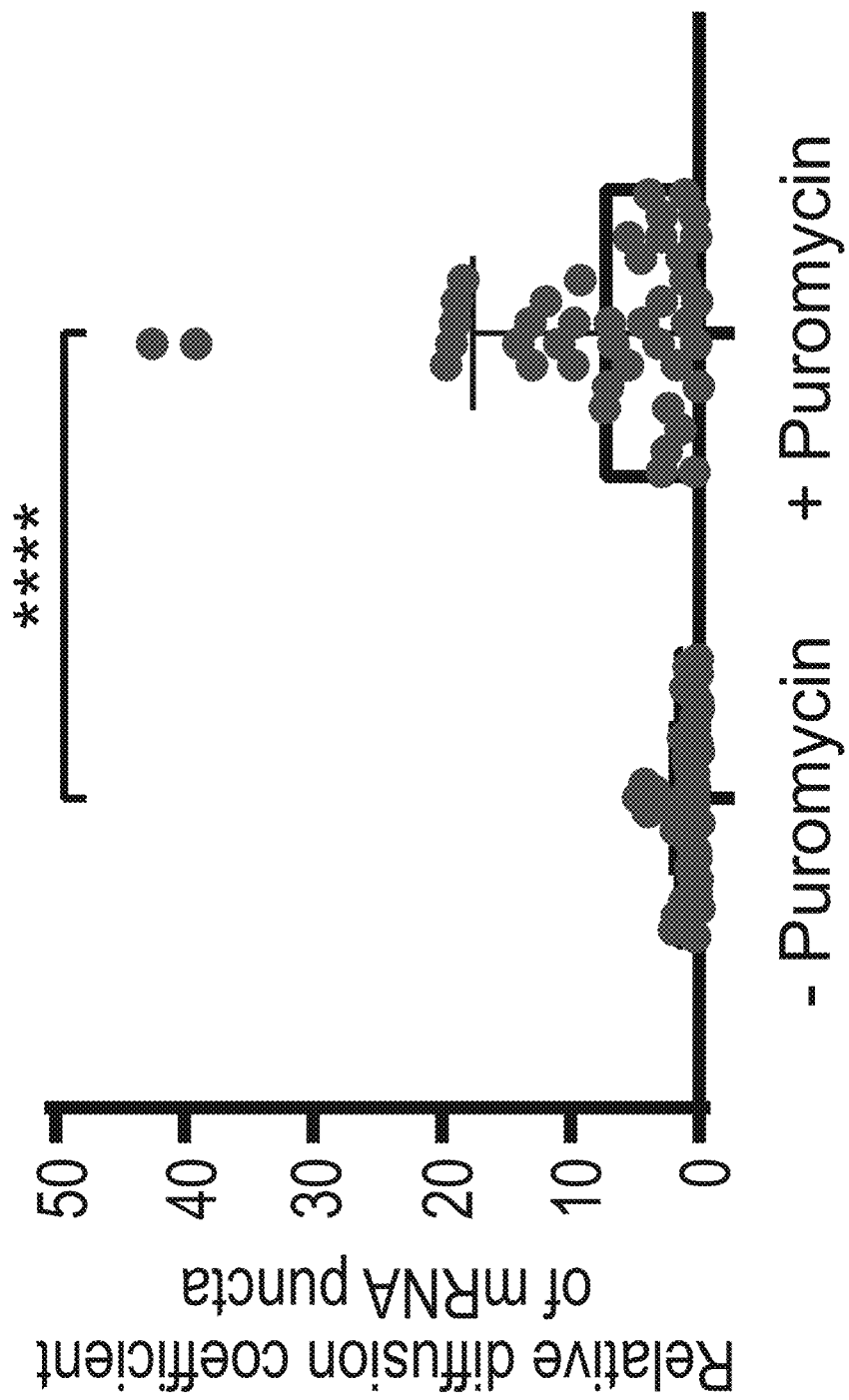
Figure 15C:
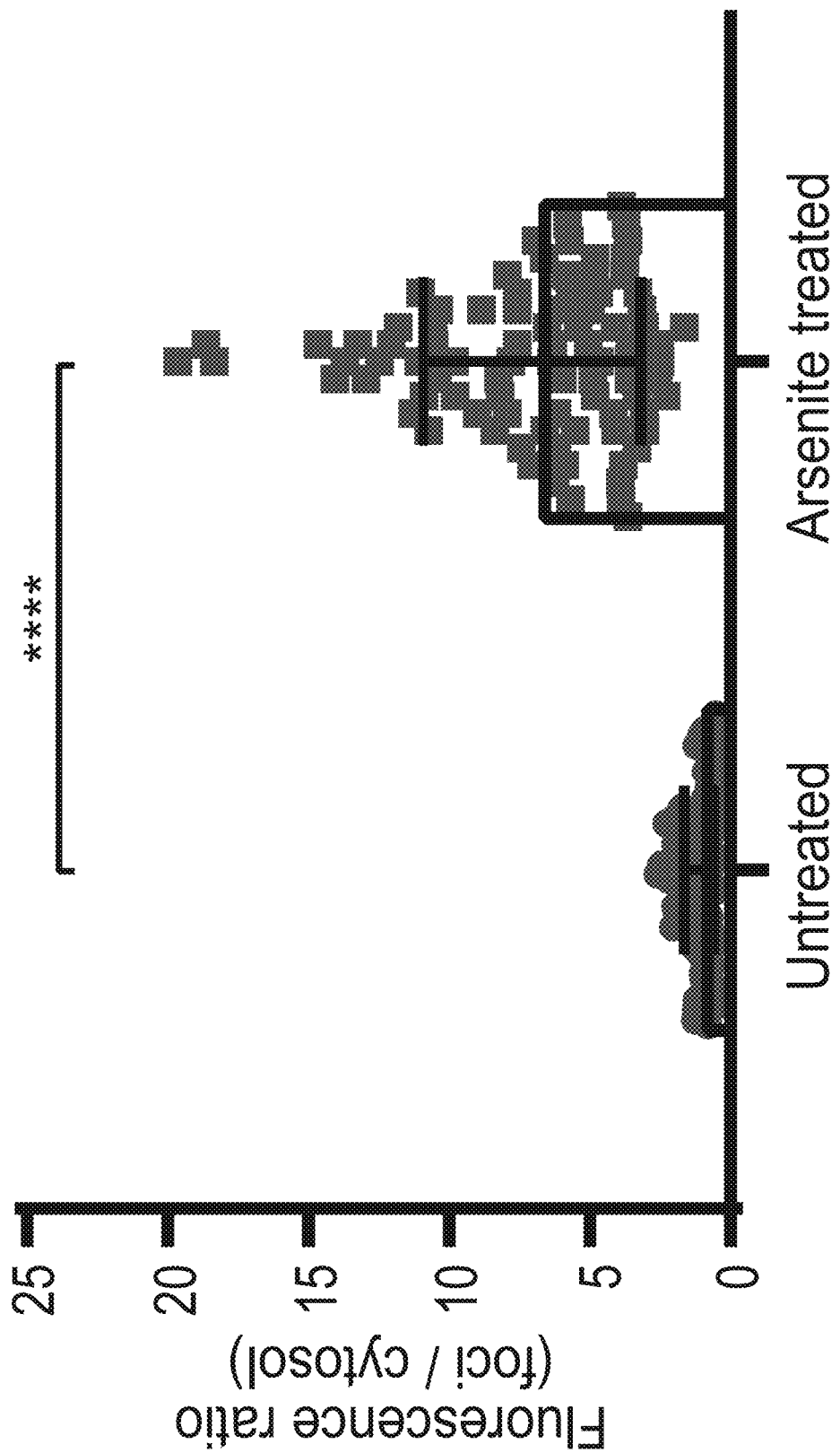
Figure 16A:
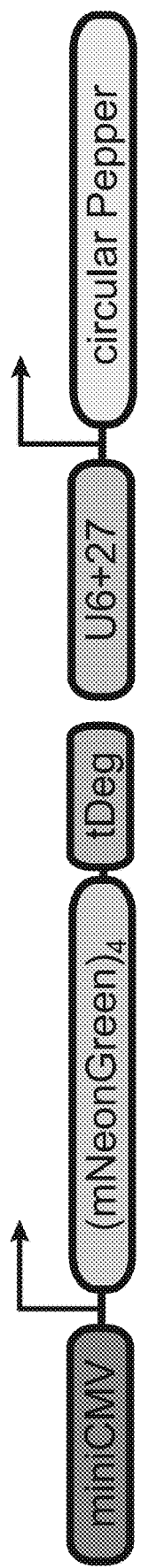
FIGS. 16A-16B demonstrate that (mNeonGreen)$_4$-tDeg without the Pepper-tagged β-actin mRNA does not accumulate in stress granules upon arsenite treatment.
Figure 16B:
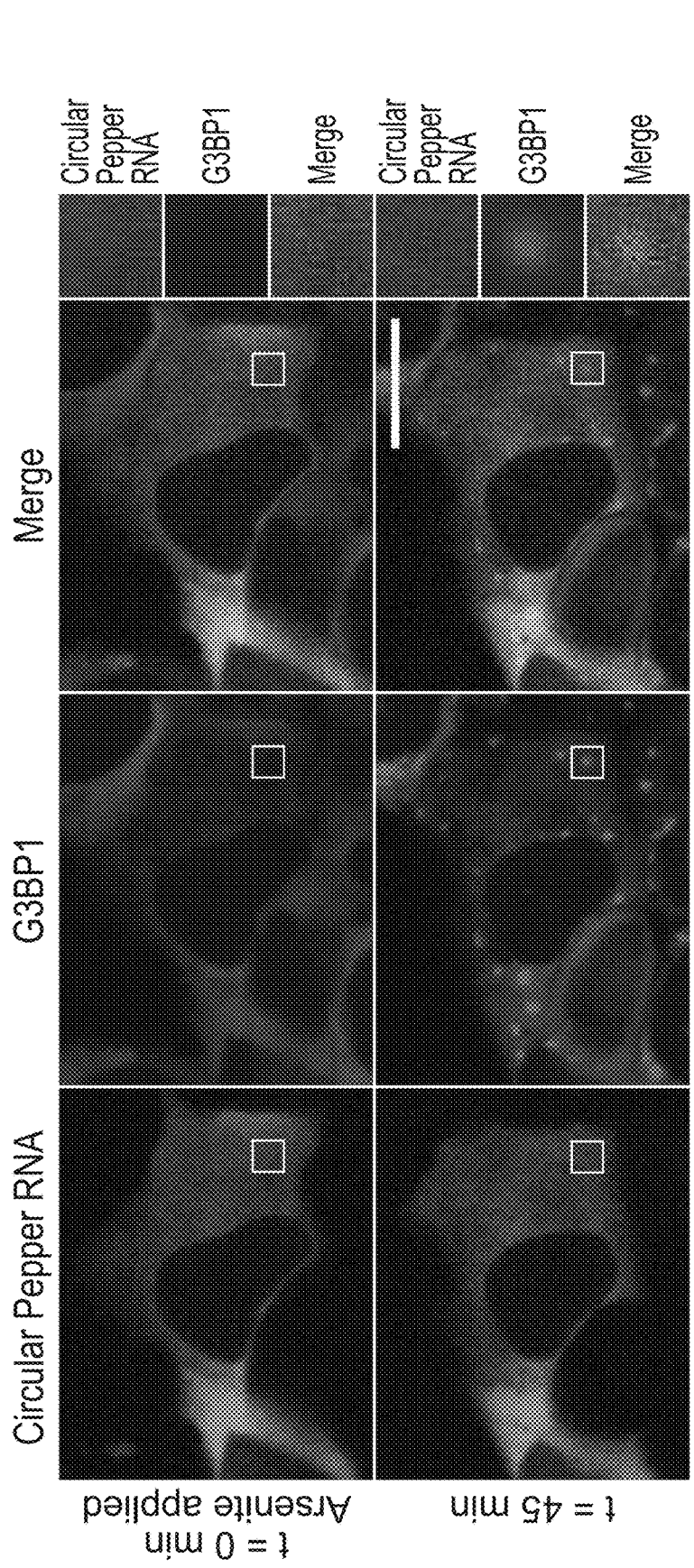

Adding the Pepper tag to an mRNA could adversely affect mRNA fate. However, the (F30-2×Pepper)$_{10}$ Pepper tag was not found to substantially alter the stability of the mCherry transcript (FIG. 13A). Similarly, a significant difference in protein translation between the untagged and Pepper-tagged mCherry mRNA transcript was not observed (FIGS. 13B-13D). Lastly, expression of RNA-regulated fluorescent fusion proteins did not significantly affect total cellular proteasome activity (FIG. 13E).

mRNAs that exhibit specific subcellular localizations were next imaged. mRNA localization to the endoplasmic reticulum (ER) was imaged using an ER-targeted reporter mRNA that encodes the first 29 amino acids of cytochrome P450, CytERM (cytoplasmic end of an endoplasmic reticulum signal-anchor membrane protein) (Costantini et al., "Assessing the Tendency of Fluorescent Proteins to Oligomerize Under Physiologic Conditions," *Traffic* 13:643-649 (2012), which is hereby incorporated by reference in its entirety). This sequence tethers the mRNA to the outer ER membrane during protein translation, and restricts the mRNA's mobility. Indeed, fluorescent puncta with low mobility were observed when this mRNA was expressed with a 3'UTR (F30-2×Pepper)$_{10}$ Pepper tag (FIGS. 14A-14D). Treatment with puromycin, which disrupts the ribosome and dissociates the mRNA from the nascent peptide, significantly increased puncta mobility, consistent with dissociation of the reporter mRNA from the ER (FIGS. 14A-14D).

Next, β-actin mRNA containing a 3'UTR (F30-2×Pepper)$_{10}$ tag was expressed and its localization was imaged in response to arsenite treatment, which induces stress granule formation (Tourrière et al., "The RasGAP-Associated Endoribonuclease G3BP Assembles Stress Granules," *J. Cell Biol.* 160:823-831 (2003), which is hereby incorporated by reference in its entirety). Upon application of 500 µM arsenite, the individual fluorescent puncta rapidly accumulated to form stress granules as evidenced by coexpression of Halo-tagged G3BP1 to label stress granules (FIGS. 15A-C and FIGS. 16A-B).

Example 5—Imaging of Pepper-Regulated mVenus and Pepper-Regulated mCherry

Figure 17B:
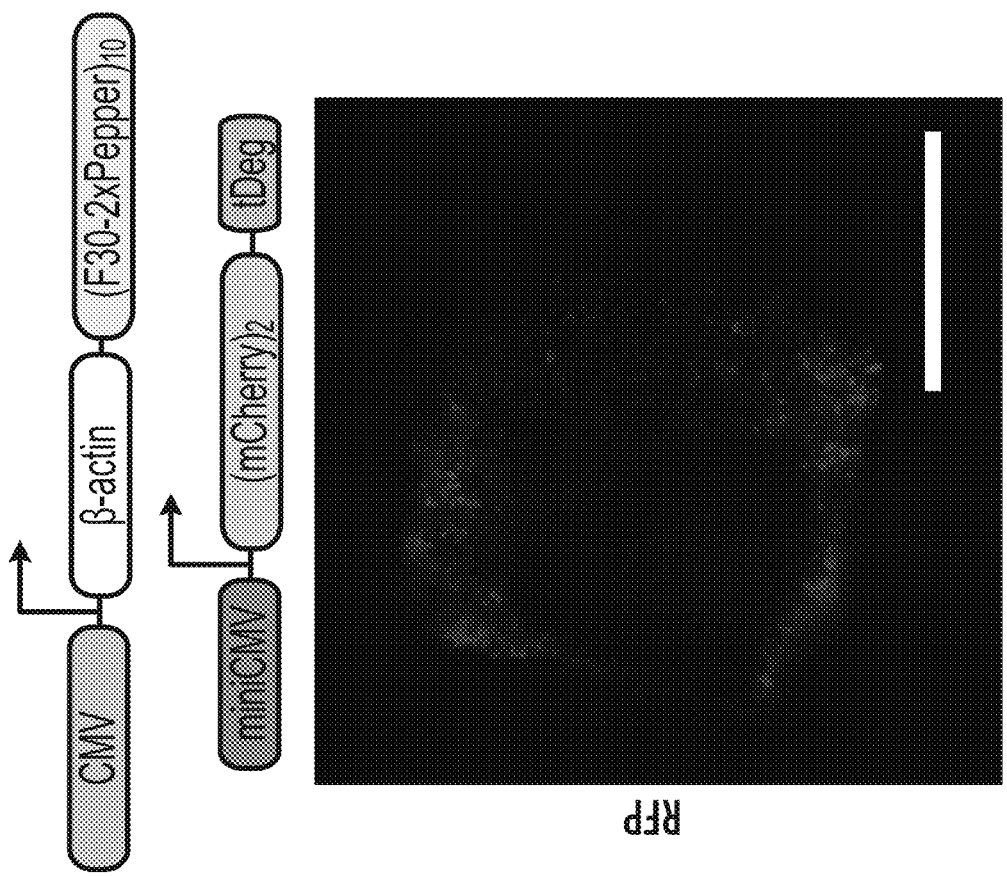
FIGS. 17A-17B demonstrate imaging of mRNAs using Pepper RNA-regulated fluorescent fusion proteins with different hues. So far, mRNA imaging using the green Pepper RNA tag, comprising the Pepper aptamer and a Pepper-regulated fluorescent mNeonGreen fusion protein has been described herein. To further expand the color palette for mRNA imaging, (mVenus)$_2$-tDeg and (mCherry)$_2$-tDeg were expressed to generate yellow Pepper and red Pepper complexes on mRNA. In these experiments, (mVenus)$_2$-tDeg was used to image an mCherry mRNA reporter tagged with (F30-2×Pepper)$_{10}$ (FIG. 17A), and (mCherry)$_2$-tDeg was used to image a β-actin mRNA reporter tagged with (F30-2×Pepper)$_{10}$ (FIG. 17B), respectively. In both cases, mobile fluorescent puncta were observed in cells. This experiment was performed twice with similar results. Scale bar, 20 μm.
Figure 17A:
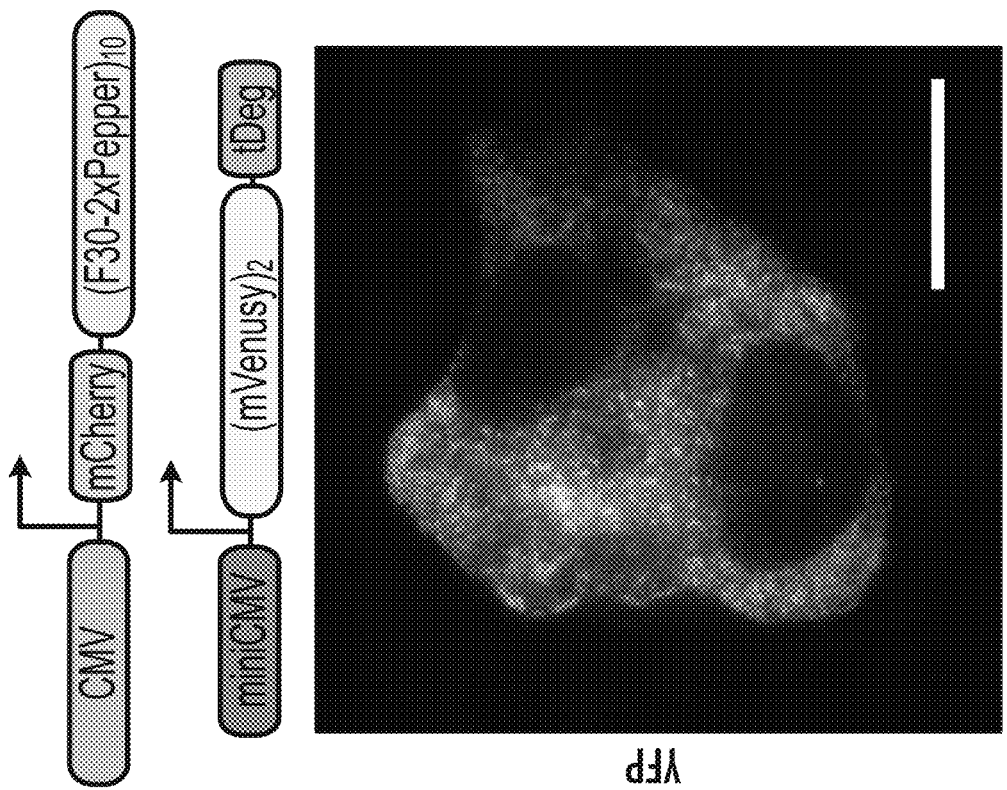

To expand the color palette of RNA-regulated fluorescent fusion proteins, two tandem copies of mVenus and two tandem copies of mCherry were fused with a C-terminal tDeg tag to convert them into RNA-regulated fluorescent fusion proteins, respectively, for imaging mRNAs. In both cases, fluorescent puncta were detected in the yellow and red fluorescence channels, respectively (FIGS. 17A-17B). Together, these data show that Pepper-tagged mRNAs can be imaged in different colors using different fluorogenic proteins.

Discussion of Examples 1-5

The studies described infra demonstrate how constitutively fluorescent proteins can be converted to fluorescent proteins that are regulated by RNA aptamers. RNA-regulation was conferred to a protein by making its proteomic stability controlled by an RNA aptamer, Pepper. In this way, unbound RNA-regulated fluorescent fusion protein is rapidly degraded, but the RNA-regulated fluorescent fusion-protein bound to an specific RNA aptamer (e.g., Pepper) remains stable. Thus, these Pepper-regulated fluorescent fusion proteins are functionally analogous to RNA-regulated fluorogenic dyes. This system has the advantage of being able to use diverse fluorescent proteins with diverse spectral properties. Additionally, unlike the Spinach system (Paige et al., RNA Mimics of Green Fluorescent Protein," *Science* 333:642-646 (2011), which is hereby incorporated by reference in its entirety), the fluorescent system described herein is fully genetically encoded.

Fluorophore maturation kinetics may also contribute to the low fluorescence of the Pepper system. Since the tDeg tag is highly efficient, it is possible that newly synthesized mNeonGreen is degraded prior to chromophore maturation. mNeonGreen that is bound to the RNA may persist for a sufficiently long time to mature to a fluorescent form while bound to RNA. This may further contribute to the low background fluorescence in cells.

Unlike previous mRNA imaging systems, no nuclear localization elements are added to fluorescent proteins to lower cytosolic background fluorescence. Instead, low background fluorescence is achieved by the highly efficient degradation of the unbound RNA-regulated fluorescent fusion protein. The simplicity of this system should simplify mRNA imaging.

An important question is whether the tagged mRNA faithfully recapitulates behavior of the endogenous mRNA. The Pepper tag did not substantially affect the stability, translation, and localization of the specific mRNAs described herein. Nevertheless, imaging tags are best used when comparing two mRNAs that differ by a single sequence alteration, or the same mRNA compared in two different conditions. In this way the role of a putative functional RNA element or RNA-regulatory pathway can be inferred and then validated with the endogenous mRNA.

Although the RNA-regulated destabilization domains were used to create fluorescent fusion proteins for RNA imaging, the ability to control protein expression levels through the Pepper aptamer can potentially enable novel synthetic biology applications. For these applications, Pepper can be expressed on its own, rather than part of an mRNA. By expressing tDeg-tagged proteins, diverse types of protein functions can be regulated by RNA aptamer expression levels.

Example 6—the tDeg-Pepper System can be Used to Selectively Modify RNA-Binding Proteins RNA-binding proteins (RBPs) bind to RNA molecules to orchestrate most biological functions in the cell. A major way to uncover previously unknown biological functions is to discover the RBPs involved in these processes. Current methods for discovering RBPs have low sensitivity. This is because current methods rely on recruiting a biotin ligase or a peroxidase to an RNA of interest to biotinylate any RBPs that are bound to this RNA. The major problem of these methods is the promiscuous activity of the biotin ligase or peroxidase would also nonspecifically biotinylate irrelevant proteins in the cytosol.

Figure 18B:
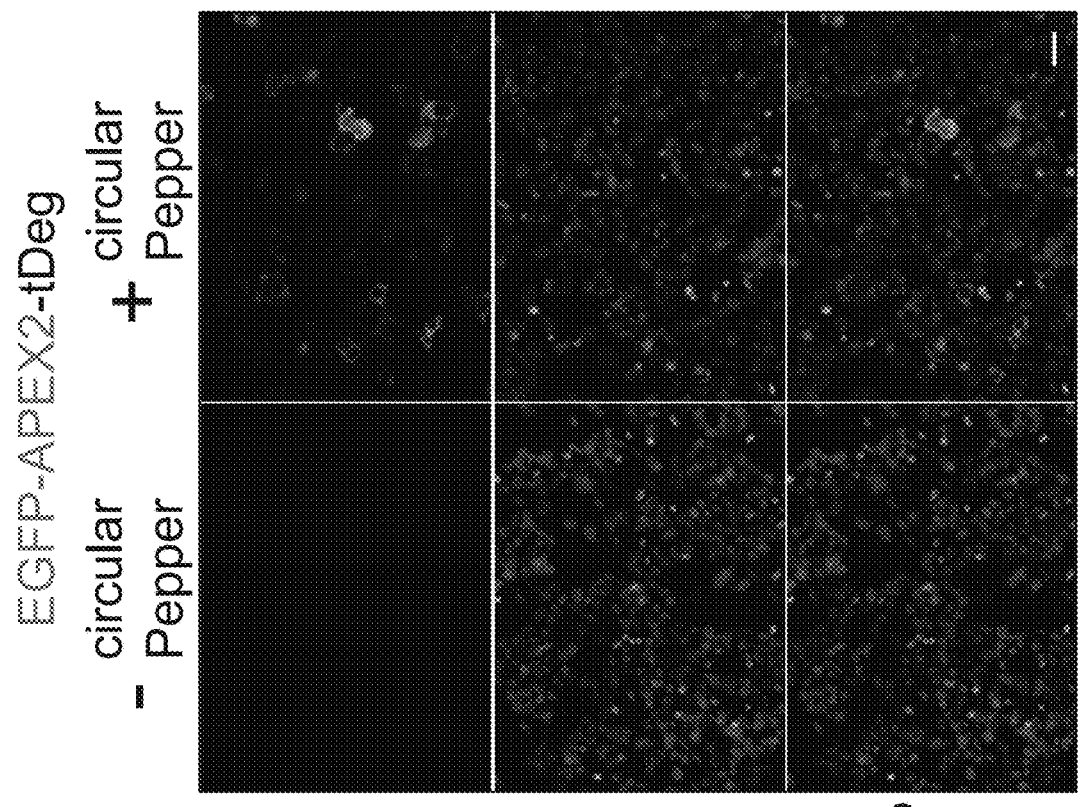
FIGS. 18A-18D demonstrate the use of the tDeg-Pepper system to selectively biotinylate RNA-binding protein. tDeg was first shown to confer Pepper RNA-dependent regulation of a biotin ligase, TurboID, and a peroxidase, APEX2. HEK293T cells transiently expressed EGFP-TurboID-tDeg (FIG. 18A), and EGFP-APEX2-tDeg (FIG. 18B), with and without the Pepper RNA aptamer, respectively. In each case, proteins were nearly undetectable unless coexpressed with the Pepper RNA.
Figure 18A:
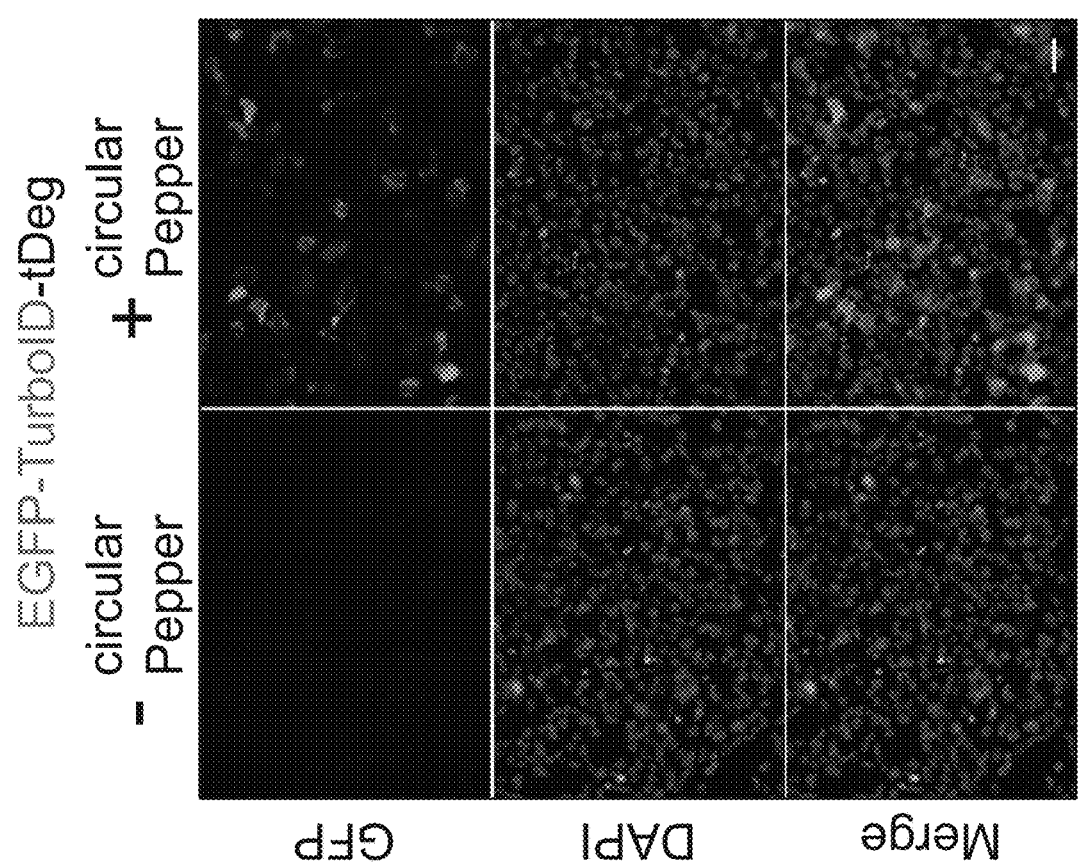
Figure 18C:
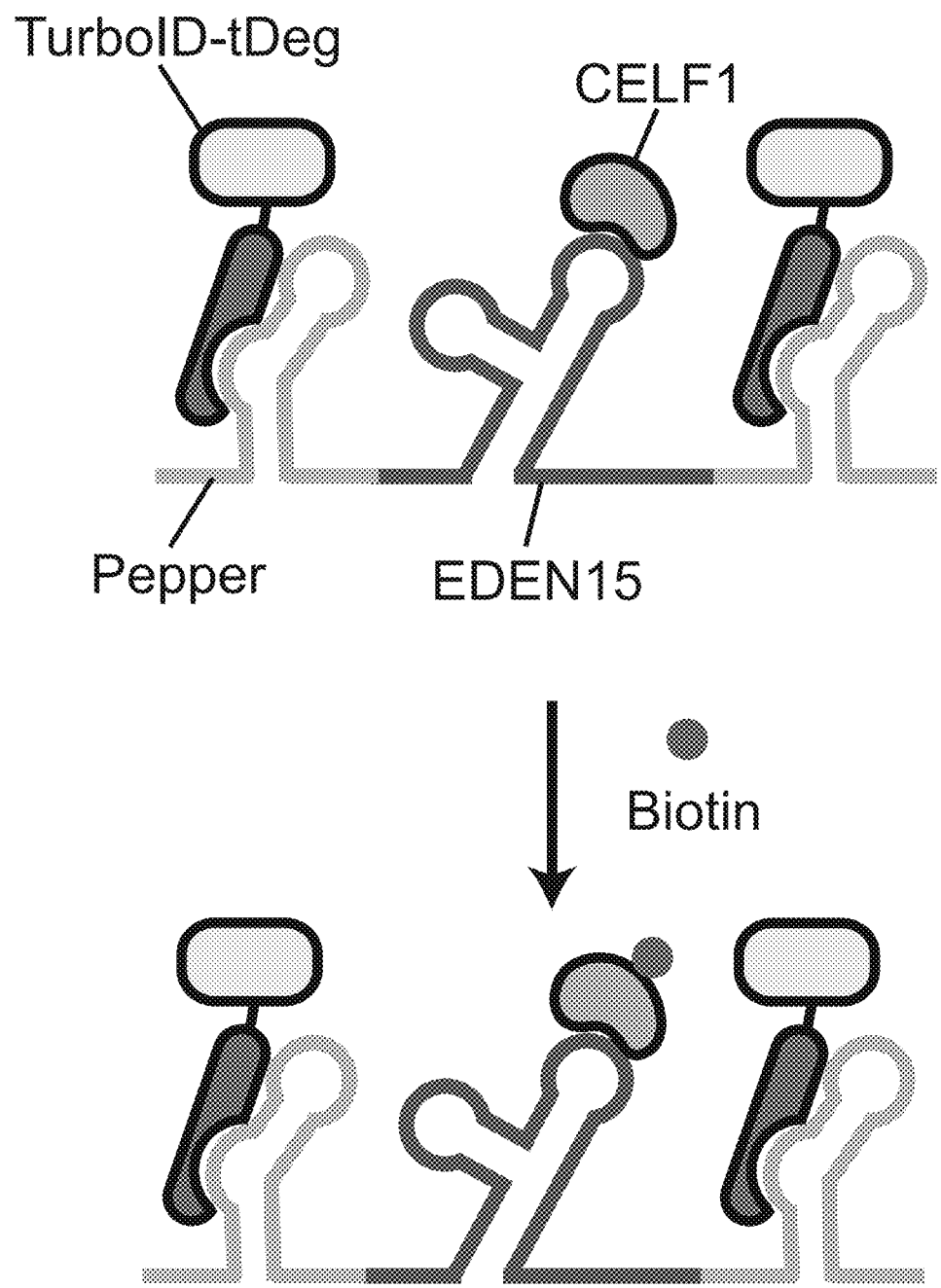
Figure 18D:
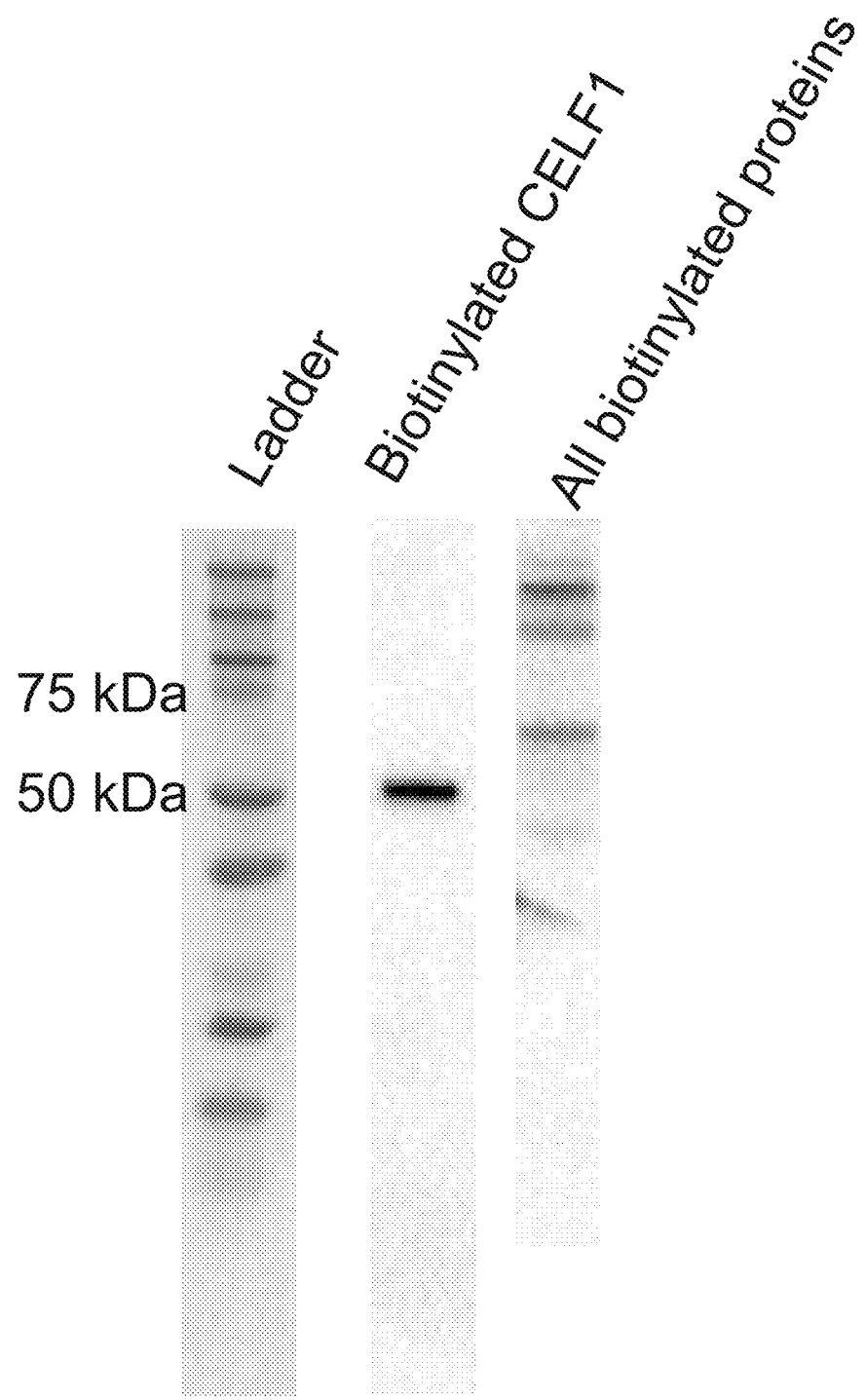

To address this problem, new method for identifying RBPs with high sensitivity was developed. In this method, a biotin ligase and a peroxidase, whose activity is only turned on when it binds to the RNA target, was engineered. To achieve this, tDeg was fused to a biotin ligase, called TurboID, and an engineered peroxidase, called APEX2, respectively. The stability of these two proteins can be regulated by the Pepper RNA. This method drastically decreases the nonspecific biotinylation due to the promiscuous activity of this biotin ligase and peroxidase, thereby enabling the discovery of RBPs in living cells with high sensitivity.

tDeg confers Pepper RNA-dependent regulation of a biotin ligase, TurboID, and a peroxidase, APEX2. FIG. 18A-18B show that HEK293T cells transiently express EGFP-TurboID-tDeg (FIG. 18A), and EGFP-APEX2-tDeg (FIG. 18B), with and without the Pepper RNA aptamer, respectively. In each case, proteins were nearly undetectable unless coexpressed with the Pepper RNA. FIG. 18C provides a schematic showing that a selectively activated biotin ligase (TurboID-tDeg) specifically biotinylates an RNA-binding protein (CELF1) that bind to the RNA sequence of interest (EDEN15). FIG. 18 D shows that TurboID-tDeg enables selective biotinylation of CELF1, while minimizing nonspecific biotinylation of proteins that do not bind to the RNA of interest (EDEN15). These results demonstrate that the tDeg-Pepper system can be used to selectively modify RNA-binding proteins.

Example 7—Tat-GG Confers Pepper RNA-Dependent Regulation

Figure 19:
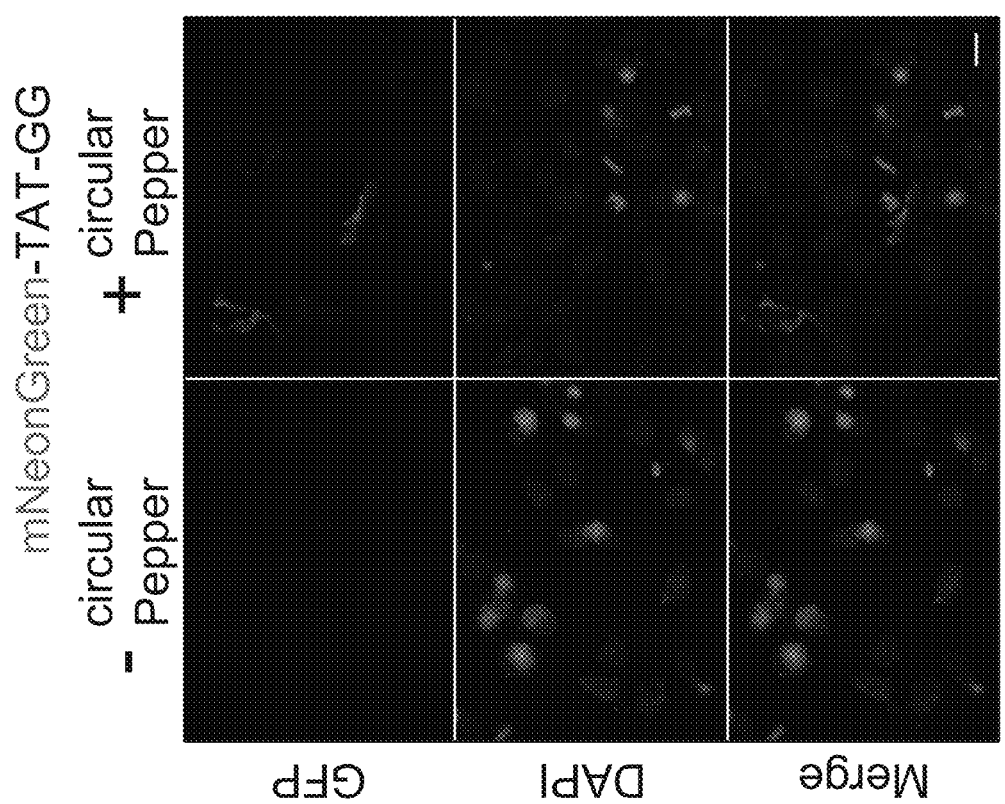
FIG. 19 demonstrates that Tat-GG confers Pepper RNA-dependent Regulation. In these experiments, U2OS cells transiently expressed mNeonGreen-Tat-GG fusion protein with and without the circular Pepper RNA aptamer, respectively. mNeonGreen was nearly undetectable (left panels) unless coexpressed with circular Pepper RNA (right panels). All cells were stained with Hoechst dye. Scale bar, 20 μm.

Next, whether a variant of tDeg, Tat-GG, can be regulated by the Pepper RNA aptamer was examined. In these experiments, U2OS cells transiently expressed mNeonGreen-Tat-GG fusion protein with and without the circular Pepper RNA aptamer, respectively. Cells showed undetectable levels of green fluorescence without the circular Pepper RNA aptamer (FIG. 19). The green fluorescence of mNeonGreen-Tat-GG was only restored when the circular Pepper RNA aptamer was coexpressed (FIG. 19). Thus, these results confirm that the tDeg variant Tat-GG can be regulated by the Pepper RNA aptamer.

Example 8—HIV Tat-RRRG Confers HIV TAR-Dependent Regulation

Figure 20:
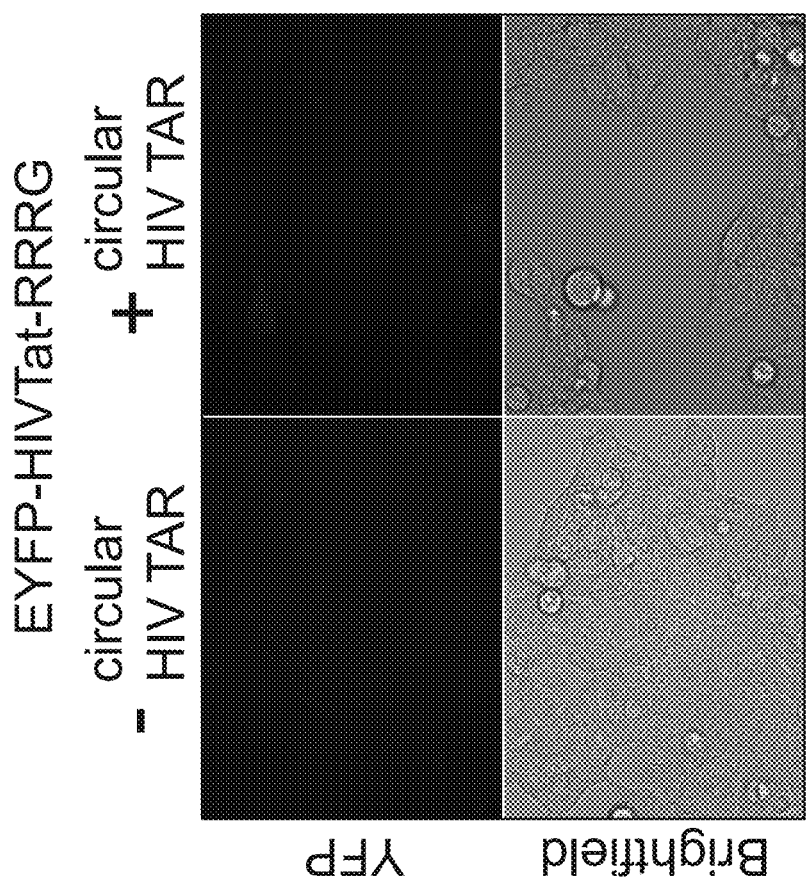
FIG. 20 demonstrate that HIV Tat-RRRG (SEQ ID NO: 127) confers HIV TAR RNA-dependent regulation. In these experiments, cells transiently expressed YFP-HIV Tat-RRRG fusion protein with and without the circular HIV TAR RNA aptamer, respectively. YFP was nearly undetectable (top left panel) unless coexpressed with circular HIV TAR RNA aptamer (right panel). Bottom panels show brightfield microscopy of cells transfected with EYFP-HIV Tat-RRRG in the absence (left panel) or presence (right panel) of circular HIV TAR RNA (SEQ ID NO: 128).

Next, whether HIV Tat-RRRG (RKKRRQRRRG; SEQ ID NO: 127) can be regulated by the HIV TAR sequence ACGAAGCUUGAUCCCGUUUGCCGGUCGAU CGCUUCGA (SEQ ID NO: 128) was examined. In these experiments, cells transiently expressed YFP-HIV Tat-RRRG fusion protein with and without the circular HIV TAR RNA aptamer, respectively. Cells showed undetectable levels of yellow fluorescence without the circular HIV TAR RNA aptamer (FIG. 20). The yellow fluorescence of YFP-HIV Tat-RRRG was restored when the circular HIV TAR RNA aptamer was coexpressed (FIG. 20). Thus, these results confirm that HIV Tat-RRRG can be regulated by the HIV TAR RNA aptamer.

What is claimed:

1. A nucleic acid molecule encoding an RNA-regulated fusion protein, said nucleic acid molecule comprising:
   a first nucleic acid sequence encoding a protein of interest and a second nucleic acid sequence encoding an RNA-regulated destabilization domain,
   wherein the second nucleic acid sequence is operably coupled to the first nucleic acid sequence,
   wherein the RNA-regulated destabilization domain is a bifunctional peptide comprising:
   a lentiviral transactivator of transcription (Tat) peptide and
   a degron peptide,
   wherein an RNA aptamer interacts with the RNA-regulated destabilization domain to stabilize the protein of interest, and
   wherein the RNA-regulated destabilization domain is tDeg as set forth in SEQ ID NO: 63.

2. The nucleic acid molecule according to claim 1, wherein the protein of interest is a fluorescent protein, a bioluminescent protein, an enzyme, or a transcription factor.

3. The nucleic acid molecule according to claim 1, wherein the lentiviral transactivator of transcription (Tat) peptide comprises an RNA binding site corresponding to or amino acid residues 4-17 of SEQ ID NO: 55.

4. The nucleic acid molecule according to claim 1 further comprising:
   a third nucleic acid sequence encoding a second protein of interest, wherein the third nucleic acid sequence is located between the first nucleic acid sequence and second nucleic acid sequence.

5. A vector comprising the nucleic acid molecule according to claim 1.

6. An expression system comprising an expression vector into which is inserted the nucleic acid molecule according to claim 1.

7. A host cell comprising the nucleic acid molecule of according to claim 1.

8. An RNA-regulated fusion protein encoded by the nucleic acid molecule according to claim 1.

9. A molecular complex comprising:
   an RNA-regulated fusion protein encoded by the nucleic acid molecule according to claim 1 comprising
      (i) a protein of interest and
      (ii) an RNA-regulated destabilization domain; and
   an RNA aptamer bound specifically to the RNA-regulated destabilization domain.

10. A host cell containing the molecular complex according to claim 9.

* * * * *

SEQUENCE LISTING

```
<160> NUMBER OF SEQ ID NOS: 130

<210> SEQ ID NO 1
<211> LENGTH: 238
<212> TYPE: PRT
<213> ORGANISM: Artificial
<220> FEATURE:
<223> OTHER INFORMATION: Green Fluorescent Protein
```

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 2
<211> LENGTH: 239
<212> TYPE: PRT
<213> ORGANISM: Artificial
<220> FEATURE:
<223> OTHER INFORMATION: Enhanced Green Fluorescent Protein

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235
```

<210> SEQ ID NO 3
<211> LENGTH: 239
<212> TYPE: PRT
<213> ORGANISM: Artificial
<220> FEATURE:
<223> OTHER INFORMATION: Enhanced Yellow Fluorescent Protein

<400> SEQUENCE: 3

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235
```

```
<210> SEQ ID NO 4
<211> LENGTH: 239
<212> TYPE: PRT
<213> ORGANISM: Artificial
<220> FEATURE:
<223> OTHER INFORMATION: Venus

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 5
<211> LENGTH: 239
<212> TYPE: PRT
<213> ORGANISM: Artificial
<220> FEATURE:
<223> OTHER INFORMATION: mVenus

<400> SEQUENCE: 5

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80
```

```
Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 6
<211> LENGTH: 239
<212> TYPE: PRT
<213> ORGANISM: Artificial
<220> FEATURE:
<223> OTHER INFORMATION: Citrine

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205
```

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 7
<211> LENGTH: 239
<212> TYPE: PRT
<213> ORGANISM: Artificial
<220> FEATURE:
<223> OTHER INFORMATION: mCitrine

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Met Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 8
<211> LENGTH: 239
<212> TYPE: PRT
<213> ORGANISM: Artificial
<220> FEATURE:
<223> OTHER INFORMATION: Cerulean

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile

```
            35                  40                  45
Cys Thr Thr Gly Lys Leu Pro Val Pro Trp Pro Thr Leu Val Thr Thr
 50                  55                  60

Leu Thr Trp Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
        130                 135                 140

Asn Ala Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 9
<211> LENGTH: 239
<212> TYPE: PRT
<213> ORGANISM: Artificial
<220> FEATURE:
<223> OTHER INFORMATION: mCerulean

<400> SEQUENCE: 9

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
 50                  55                  60

Leu Thr Trp Gly Val Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
        130                 135                 140

Asn Ala Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
```

```
              165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys
225                 230                 235

<210> SEQ ID NO 10
<211> LENGTH: 222
<212> TYPE: PRT
<213> ORGANISM: Artificial
<220> FEATURE:
<223> OTHER INFORMATION: Orange Fluorescent Protein

<400> SEQUENCE: 10

Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Asp Pro
            20                  25                  30

Tyr Thr Gly Lys Tyr Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
        115                 120                 125

Pro Val Met Lys Asn Glu Ile Val Met Glu Glu Pro Thr Glu Glu Thr
    130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 11
<211> LENGTH: 236
<212> TYPE: PRT
<213> ORGANISM: Artificial
<220> FEATURE:
<223> OTHER INFORMATION: mNeon Green

<400> SEQUENCE: 11

Met Val Ser Lys Gly Glu Glu Asp Asn Met Ala Ser Leu Pro Ala Thr
1               5                   10                  15
```

His Glu Leu His Ile Phe Gly Ser Ile Asn Gly Val Asp Phe Asp Met
                20                  25                  30

Val Gly Gln Gly Thr Gly Asn Pro Asn Asp Gly Tyr Glu Glu Leu Asn
            35                  40                  45

Leu Lys Ser Thr Lys Gly Asp Leu Gln Phe Ser Pro Trp Ile Leu Val
        50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 12
<211> LENGTH: 236
<212> TYPE: PRT
<213> ORGANISM: Artificial
<220> FEATURE:
<223> OTHER INFORMATION: moxNeon Green

<400> SEQUENCE: 12

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
                20                  25                  30

Val Gly Gln Gly Thr Gly Asn Pro Asn Asp Gly Tyr Glu Glu Leu Asn
            35                  40                  45

Leu Lys Ser Thr Lys Gly Asp Leu Gln Phe Ser Pro Trp Ile Leu Val
        50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

```
Ala Ala Asp Trp Ser Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
            195                 200                 205

Leu Lys His Ser Lys Thr Glu Leu Asn Phe Lys Glu Trp Gln Lys Ala
            210                 215                 220

Phe Thr Asp Val Met Gly Met Asp Glu Leu Tyr Lys
225                 230                 235
```

<210> SEQ ID NO 13
<211> LENGTH: 236
<212> TYPE: PRT
<213> ORGANISM: Artificial
<220> FEATURE:
<223> OTHER INFORMATION: mCherry

<400> SEQUENCE: 13

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys
225                 230                 235
```

<210> SEQ ID NO 14
<211> LENGTH: 237
<212> TYPE: PRT
<213> ORGANISM: Artificial
<220> FEATURE:

<223> OTHER INFORMATION: mTagBFP

<400> SEQUENCE: 14

Met Val Ser Lys Gly Glu Glu Leu Ile Lys Glu Asn Met His Met Lys
1               5                   10                  15

Leu Tyr Met Glu Gly Thr Val Asp Asn His His Phe Lys Cys Thr Ser
            20                  25                  30

Glu Gly Glu Gly Lys Pro Tyr Glu Gly Thr Gln Thr Met Arg Ile Lys
        35                  40                  45

Val Val Glu Gly Gly Pro Leu Pro Phe Ala Phe Asp Ile Leu Ala Thr
    50                  55                  60

Ser Phe Leu Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Thr Ser Asn Gly Pro Val Met Gln Lys Lys Thr Leu Gly Trp
    130                 135                 140

Glu Ala Phe Thr Glu Thr Leu Tyr Pro Ala Asp Gly Gly Leu Glu Gly
145                 150                 155                 160

Arg Asn Asp Met Ala Leu Lys Leu Val Gly Gly Ser His Leu Ile Ala
                165                 170                 175

Asn Ala Lys Thr Thr Tyr Arg Ser Lys Lys Pro Ala Lys Asn Leu Lys
            180                 185                 190

Met Pro Gly Val Tyr Tyr Val Asp Tyr Arg Leu Glu Arg Ile Lys Glu
        195                 200                 205

Ala Asn Asn Glu Thr Tyr Val Glu Gln His Glu Val Ala Val Ala Arg
    210                 215                 220

Tyr Cys Asp Leu Pro Ser Lys Leu Gly His Lys Leu Asn
225                 230                 235

<210> SEQ ID NO 15
<211> LENGTH: 239
<212> TYPE: PRT
<213> ORGANISM: Artificial
<220> FEATURE:
<223> OTHER INFORMATION: Venus

<400> SEQUENCE: 15

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

```
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 16
<211> LENGTH: 239
<212> TYPE: PRT
<213> ORGANISM: Artificial
<220> FEATURE:
<223> OTHER INFORMATION: mVenus

<400> SEQUENCE: 16

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 17
<211> LENGTH: 239
<212> TYPE: PRT
<213> ORGANISM: Artificial
<220> FEATURE:
<223> OTHER INFORMATION: mTurquoise

<400> SEQUENCE: 17

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Ser Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 18
<211> LENGTH: 232
<212> TYPE: PRT
<213> ORGANISM: Artificial
<220> FEATURE:
<223> OTHER INFORMATION: mScarlet

<400> SEQUENCE: 18

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
                20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ser Trp Asp Ile Leu Ser Pro
        50                  55                  60

Gln Phe Met Tyr Gly Ser Arg Ala Phe Thr Lys His Pro Ala Asp Ile

```
                   65                  70                  75                  80
Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Gly Met Asp Glu Leu Tyr Lys
225                 230

<210> SEQ ID NO 19
<211> LENGTH: 236
<212> TYPE: PRT
<213> ORGANISM: Artificial
<220> FEATURE:
<223> OTHER INFORMATION: mWasabi

<400> SEQUENCE: 19

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
                20                  25                  30

Val Ile Glu Gly Glu Gly Glu Gly Lys Pro Tyr Asp Gly Thr Asn Thr
            35                  40                  45

Ile Asn Leu Glu Val Lys Glu Gly Ala Pro Leu Pro Phe Ser Tyr Asp
        50                  55                  60

Ile Leu Thr Thr Ala Phe Ser Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125

Leu Lys Gly Glu Asn Phe Pro Pro Asn Gly Pro Val Met Gln Lys Glu
    130                 135                 140

Thr Thr Gly Trp Asp Ala Ser Thr Glu Arg Met Tyr Val Arg Asp Gly
145                 150                 155                 160

Val Leu Lys Gly Asp Val Lys Met Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
```

```
              195                 200                 205
His Asp Lys Asp Tyr Asn Lys Val Thr Val Tyr Glu Ile Ala Val Ala
    210                 215                 220

Arg Asn Ser Thr Asp Gly Met Asp Glu Leu Tyr Lys
225                 230                 235

<210> SEQ ID NO 20
<211> LENGTH: 236
<212> TYPE: PRT
<213> ORGANISM: Artificial
<220> FEATURE:
<223> OTHER INFORMATION: mOrange

<400> SEQUENCE: 20

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 21
<211> LENGTH: 234
<212> TYPE: PRT
<213> ORGANISM: Artificial
<220> FEATURE:
<223> OTHER INFORMATION: dTomato

<400> SEQUENCE: 21

Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
            20                  25                  30
```

```
Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
 50                  55                  60

Gln Phe Met Tyr Gly Ser Lys Ala Tyr Val Lys His Pro Ala Asp Ile
 65                  70                  75                  80

Pro Asp Tyr Lys Lys Leu Ser Phe Pro Glu Gly Phe Lys Trp Glu Arg
                 85                  90                  95

Val Met Asn Phe Glu Asp Gly Gly Leu Val Thr Val Thr Gln Asp Ser
            100                 105                 110

Ser Leu Gln Asp Gly Thr Leu Ile Tyr Lys Val Lys Met Arg Gly Thr
            115                 120                 125

Asn Phe Pro Pro Asp Gly Pro Val Met Gln Lys Lys Thr Met Gly Trp
130                 135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
            195                 200                 205

Tyr Thr Ile Val Glu Gln Tyr Glu Arg Ser Glu Gly Arg His His Leu
            210                 215                 220

Phe Leu Tyr Gly Met Asp Glu Leu Tyr Lys
225                 230

<210> SEQ ID NO 22
<211> LENGTH: 171
<212> TYPE: PRT
<213> ORGANISM: Artificial
<220> FEATURE:
<223> OTHER INFORMATION: Nanoluc luciferase

<400> SEQUENCE: 22

Met Val Phe Thr Leu Glu Asp Phe Val Gly Asp Trp Arg Gln Thr Ala
 1               5                  10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
            35                  40                  45

Ser Gly Glu Asn Gly Leu Lys Ile Asp Ile His Val Ile Ile Pro Tyr
 50                  55                  60

Glu Gly Leu Ser Gly Asp Gln Met Gly Gln Ile Glu Lys Ile Phe Lys
 65                  70                  75                  80

Val Val Tyr Pro Val Asp Asp His His Phe Lys Val Ile Leu His Tyr
                 85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160
```

```
Thr Gly Trp Arg Leu Cys Glu Arg Ile Leu Ala
            165                 170
```

<210> SEQ ID NO 23
<211> LENGTH: 550
<212> TYPE: PRT
<213> ORGANISM: Artificial
<220> FEATURE:
<223> OTHER INFORMATION: Firefly luciferase

<400> SEQUENCE: 23

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350
```

```
Pro Glu Gly Asp Asp Lys Pro Gly Ala Val Gly Lys Val Pro Phe
            355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ser Lys Leu
545                 550

<210> SEQ ID NO 24
<211> LENGTH: 311
<212> TYPE: PRT
<213> ORGANISM: Artificial
<220> FEATURE:
<223> OTHER INFORMATION: Renilla luciferase

<400> SEQUENCE: 24

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160
```

-continued

```
Glu Asp Ile Ala Leu Ile Lys Ser Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

```
<210> SEQ ID NO 25
<211> LENGTH: 185
<212> TYPE: PRT
<213> ORGANISM: Artificial
<220> FEATURE:
<223> OTHER INFORMATION: Gaussia luciferase

<400> SEQUENCE: 25
```

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185
```

```
<210> SEQ ID NO 26
<211> LENGTH: 1015
```

```
<212> TYPE: PRT
<213> ORGANISM: Artificial
<220> FEATURE:
<223> OTHER INFORMATION: Beta-galactosidase

<400> SEQUENCE: 26
```

| | | | | | | | | | | | | | | |
|---|---|---|---|---|---|---|---|---|---|---|---|---|---|---|
| Val | Val | Leu | Gln | Arg | Arg | Asp | Trp | Glu | Asn | Pro | Gly | Val | Thr | Gln | Leu |
| 1 | | | | 5 | | | | | 10 | | | | | 15 | |
| Asn | Arg | Leu | Ala | Ala | His | Pro | Pro | Phe | Ala | Ser | Trp | Arg | Asn | Ser | Glu |
| | | | 20 | | | | | 25 | | | | | 30 | | |
| Glu | Ala | Arg | Thr | Asp | Arg | Pro | Ser | Gln | Gln | Leu | Arg | Ser | Leu | Asn | Gly |
| | | | 35 | | | | | 40 | | | | | 45 | | |
| Glu | Trp | Arg | Phe | Ala | Trp | Phe | Pro | Ala | Pro | Glu | Ala | Val | Pro | Glu | Ser |
| | 50 | | | | | 55 | | | | | 60 | | | | |
| Trp | Leu | Glu | Cys | Asp | Leu | Pro | Glu | Ala | Asp | Thr | Val | Val | Pro | Ser | |
| 65 | | | | | 70 | | | | | 75 | | | | | 80 |
| Asn | Trp | Gln | Met | His | Gly | Tyr | Asp | Ala | Pro | Ile | Tyr | Thr | Asn | Val | Thr |
| | | | | 85 | | | | | 90 | | | | | 95 | |
| Tyr | Pro | Ile | Thr | Val | Asn | Pro | Pro | Phe | Val | Pro | Thr | Glu | Asn | Pro | Thr |
| | | | 100 | | | | | 105 | | | | | 110 | | |
| Gly | Cys | Tyr | Ser | Leu | Thr | Phe | Asn | Val | Asp | Glu | Ser | Trp | Leu | Gln | Glu |
| | | | | 115 | | | | | 120 | | | | | 125 | |
| Gly | Gln | Thr | Arg | Ile | Ile | Phe | Asp | Gly | Val | Asn | Ser | Ala | Phe | His | Leu |
| | | | 130 | | | | | 135 | | | | | 140 | | |
| Trp | Cys | Asn | Gly | Arg | Trp | Val | Gly | Tyr | Gly | Gln | Asp | Ser | Arg | Leu | Pro |
| 145 | | | | | 150 | | | | | 155 | | | | | 160 |
| Ser | Glu | Phe | Asp | Leu | Ser | Ala | Phe | Leu | Arg | Ala | Gly | Glu | Asn | Arg | Leu |
| | | | | 165 | | | | | 170 | | | | | 175 | |
| Ala | Val | Met | Val | Leu | Arg | Trp | Ser | Asp | Gly | Ser | Tyr | Leu | Glu | Asp | Gln |
| | | | 180 | | | | | 185 | | | | | 190 | | |
| Asp | Met | Trp | Arg | Met | Ser | Gly | Ile | Phe | Arg | Asp | Val | Ser | Leu | Leu | His |
| | | | 195 | | | | | 200 | | | | | 205 | | |
| Lys | Pro | Thr | Thr | Gln | Ile | Ser | Asp | Phe | His | Val | Ala | Thr | Arg | Phe | Asn |
| | | | 210 | | | | | 215 | | | | | 220 | | |
| Asp | Asp | Phe | Ser | Arg | Ala | Val | Leu | Glu | Ala | Glu | Val | Gln | Met | Cys | Gly |
| 225 | | | | | 230 | | | | | 235 | | | | | 240 |
| Glu | Leu | Arg | Asp | Tyr | Leu | Arg | Val | Thr | Val | Ser | Leu | Trp | Gln | Gly | Glu |
| | | | | 245 | | | | | 250 | | | | | 255 | |
| Thr | Gln | Val | Ala | Ser | Gly | Thr | Ala | Pro | Phe | Gly | Gly | Glu | Ile | Ile | Asp |
| | | | 260 | | | | | 265 | | | | | 270 | | |
| Glu | Arg | Gly | Gly | Tyr | Ala | Asp | Arg | Val | Thr | Leu | Arg | Leu | Asn | Val | Glu |
| | | | 275 | | | | | 280 | | | | | 285 | | |
| Asn | Pro | Lys | Leu | Trp | Ser | Ala | Glu | Ile | Pro | Asn | Leu | Tyr | Arg | Ala | Val |
| | | | 290 | | | | | 295 | | | | | 300 | | |
| Val | Glu | Leu | His | Thr | Ala | Asp | Gly | Thr | Leu | Ile | Glu | Ala | Glu | Ala | Cys |
| 305 | | | | | 310 | | | | | 315 | | | | | 320 |
| Asp | Val | Gly | Phe | Arg | Glu | Val | Arg | Ile | Glu | Asn | Gly | Leu | Leu | Leu | Leu |
| | | | | 325 | | | | | 330 | | | | | 335 | |
| Asn | Gly | Lys | Pro | Leu | Leu | Ile | Arg | Gly | Val | Asn | Arg | His | Glu | His | His |
| | | | 340 | | | | | 345 | | | | | 350 | | |
| Pro | Leu | His | Gly | Gln | Val | Met | Asp | Glu | Gln | Thr | Met | Val | Gln | Asp | Ile |
| | | | 355 | | | | | 360 | | | | | 365 | | |
| Leu | Leu | Met | Lys | Gln | Asn | Asn | Phe | Asn | Ala | Val | Arg | Cys | Ser | His | Tyr |
| | | | 370 | | | | | 375 | | | | | 380 | | |

```
Pro Asn His Pro Leu Trp Tyr Thr Leu Cys Asp Arg Tyr Gly Leu Tyr
385                 390                 395                 400

Val Val Asp Glu Ala Asn Ile Glu Thr His Gly Met Val Pro Met Asn
            405                 410                 415

Arg Leu Thr Asp Asp Pro Arg Trp Leu Pro Ala Met Ser Glu Arg Val
            420                 425                 430

Thr Arg Met Val Gln Arg Asp Arg Asn His Pro Ser Val Ile Ile Trp
            435                 440                 445

Ser Leu Gly Asn Glu Ser Gly His Gly Ala Asn His Asp Ala Leu Tyr
450                 455                 460

Arg Trp Ile Lys Ser Val Asp Pro Ser Arg Pro Val Gln Tyr Glu Gly
465                 470                 475                 480

Gly Gly Ala Asp Thr Thr Ala Thr Asp Ile Ile Cys Pro Met Tyr Ala
            485                 490                 495

Arg Val Asp Glu Asp Gln Pro Phe Pro Ala Val Pro Lys Trp Ser Ile
            500                 505                 510

Lys Lys Trp Leu Ser Leu Pro Gly Glu Thr Arg Pro Leu Ile Leu Cys
            515                 520                 525

Glu Tyr Ala His Ala Met Gly Asn Ser Leu Gly Gly Phe Ala Lys Tyr
530                 535                 540

Trp Gln Ala Phe Arg Gln Tyr Pro Arg Leu Gln Gly Gly Phe Val Trp
545                 550                 555                 560

Asp Trp Val Asp Gln Ser Leu Ile Lys Tyr Asp Glu Asn Gly Asn Pro
            565                 570                 575

Trp Ser Ala Tyr Gly Gly Asp Phe Gly Asp Thr Pro Asn Asp Arg Gln
            580                 585                 590

Phe Cys Met Asn Gly Leu Val Phe Ala Asp Arg Thr Pro His Pro Ala
            595                 600                 605

Leu Thr Glu Ala Lys His Gln Gln Phe Phe Gln Phe Arg Leu Ser
610                 615                 620

Gly Gln Thr Ile Glu Val Thr Ser Glu Tyr Leu Phe Arg His Ser Asp
625                 630                 635                 640

Asn Glu Leu Leu His Trp Met Val Ala Leu Asp Gly Lys Pro Leu Ala
            645                 650                 655

Ser Gly Glu Val Pro Leu Asp Val Ala Pro Gln Gly Lys Gln Leu Ile
            660                 665                 670

Glu Leu Pro Glu Leu Pro Gln Pro Glu Ser Ala Gly Gln Leu Trp Leu
            675                 680                 685

Thr Val Arg Val Val Gln Pro Asn Ala Thr Ala Trp Ser Glu Ala Gly
            690                 695                 700

His Ile Ser Ala Trp Gln Gln Trp Arg Leu Ala Glu Asn Leu Ser Val
705                 710                 715                 720

Thr Leu Pro Ala Ala Ser His Ala Ile Pro His Leu Thr Thr Ser Glu
            725                 730                 735

Met Asp Phe Cys Ile Glu Leu Gly Asn Lys Arg Trp Gln Phe Asn Arg
            740                 745                 750

Gln Ser Gly Phe Leu Ser Gln Met Trp Ile Gly Asp Lys Lys Gln Leu
            755                 760                 765

Leu Thr Pro Leu Arg Asp Gln Phe Thr Arg Ala Pro Leu Asp Asn Asp
            770                 775                 780

Ile Gly Val Ser Glu Ala Thr Arg Ile Asp Pro Asn Ala Trp Val Glu
785                 790                 795                 800

Arg Trp Lys Ala Ala Gly His Tyr Gln Ala Glu Ala Ala Leu Leu Gln
```

```
                    805                 810                 815
Cys Thr Ala Asp Thr Leu Ala Asp Ala Val Leu Ile Thr Thr Ala His
                820                 825                 830
Ala Trp Gln His Gln Gly Lys Thr Leu Phe Ile Ser Arg Lys Thr Tyr
            835                 840                 845
Arg Ile Asp Gly Ser Gly Gln Met Ala Ile Thr Val Asp Val Glu Val
        850                 855                 860
Ala Ser Asp Thr Pro His Pro Ala Arg Ile Gly Leu Asn Cys Gln Leu
865                 870                 875                 880
Ala Gln Val Ala Glu Arg Val Asn Trp Leu Gly Leu Gly Pro Gln Glu
                885                 890                 895
Asn Tyr Pro Asp Arg Leu Thr Ala Ala Cys Phe Asp Arg Trp Asp Leu
            900                 905                 910
Pro Leu Ser Asp Met Tyr Thr Pro Tyr Val Phe Pro Ser Glu Asn Gly
        915                 920                 925
Leu Arg Cys Gly Thr Arg Glu Leu Asn Tyr Gly Pro His Gln Trp Arg
    930                 935                 940
Gly Asp Phe Gln Phe Asn Ile Ser Arg Tyr Ser Gln Gln Gln Leu Met
945                 950                 955                 960
Glu Thr Ser His Arg His Leu Leu His Ala Glu Gly Thr Trp Leu
                965                 970                 975
Asn Ile Asp Gly Phe His Met Gly Ile Gly Asp Asp Ser Trp Ser
            980                 985                 990
Pro Ser Val Ser Ala Glu Phe Gln Leu Ser Ala Gly Arg Tyr His Tyr
        995                1000                1005
Gln Leu Val Trp Cys Gln Lys
    1010                1015

<210> SEQ ID NO 27
<211> LENGTH: 286
<212> TYPE: PRT
<213> ORGANISM: Artificial
<220> FEATURE:
<223> OTHER INFORMATION: Beta-lactamase

<400> SEQUENCE: 27

Met Ser Ile Gln His Phe Arg Val Ala Leu Ile Pro Phe Phe Ala Ala
1               5                   10                  15
Phe Cys Leu Pro Val Phe Ala His Pro Glu Thr Leu Val Lys Val Lys
                20                  25                  30
Asp Ala Glu Asp Gln Leu Gly Ala Arg Val Gly Tyr Ile Glu Leu Asp
            35                  40                  45
Leu Asn Ser Gly Lys Ile Leu Glu Ser Phe Arg Pro Glu Glu Arg Phe
        50                  55                  60
Pro Met Met Ser Thr Phe Lys Val Leu Leu Cys Gly Ala Val Leu Ser
65                  70                  75                  80
Arg Ile Asp Ala Gly Gln Glu Gln Leu Gly Arg Arg Ile His Tyr Ser
                85                  90                  95
Gln Asn Asp Leu Val Glu Tyr Ser Pro Val Thr Glu Lys His Leu Thr
            100                 105                 110
Asp Gly Met Thr Val Arg Glu Leu Cys Ser Ala Ala Ile Thr Met Ser
        115                 120                 125
Asp Asn Thr Ala Ala Asn Leu Leu Leu Thr Thr Ile Gly Gly Pro Lys
    130                 135                 140
Glu Leu Thr Ala Phe Leu His Asn Met Gly Asp His Val Thr Arg Leu
```

```
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
                195                 200                 205

Met Glu Ala Asp Lys Val Ala Gly Pro Leu Leu Arg Ser Ala Leu Pro
            210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
                275                 280                 285

<210> SEQ ID NO 28
<211> LENGTH: 250
<212> TYPE: PRT
<213> ORGANISM: Artificial
<220> FEATURE:
<223> OTHER INFORMATION: Ascorbate peroxidase 1, cytosolic

<400> SEQUENCE: 28

Met Gly Lys Ser Tyr Pro Thr Val Ser Ala Asp Tyr Gln Lys Ala Val
1               5                   10                  15

Glu Lys Ala Lys Lys Lys Leu Arg Gly Phe Ile Ala Glu Lys Arg Cys
            20                  25                  30

Ala Pro Leu Met Leu Arg Leu Ala Trp His Ser Ala Gly Thr Phe Asp
        35                  40                  45

Lys Gly Thr Lys Thr Gly Gly Pro Phe Gly Thr Ile Lys His Pro Ala
    50                  55                  60

Glu Leu Ala His Ser Ala Asn Asn Gly Leu Asp Ile Ala Val Arg Leu
65                  70                  75                  80

Leu Glu Pro Leu Lys Ala Glu Phe Pro Ile Leu Ser Tyr Ala Asp Phe
                85                  90                  95

Tyr Gln Leu Ala Gly Val Val Ala Val Glu Val Thr Gly Gly Pro Glu
            100                 105                 110

Val Pro Phe His Pro Gly Arg Glu Asp Lys Pro Glu Pro Pro Pro Glu
        115                 120                 125

Gly Arg Leu Pro Asp Ala Thr Lys Gly Ser Asp His Leu Arg Asp Val
    130                 135                 140

Phe Gly Lys Ala Met Gly Leu Thr Asp Gln Asp Ile Val Ala Leu Ser
145                 150                 155                 160

Gly Gly His Thr Ile Gly Ala Ala His Lys Glu Arg Ser Gly Phe Glu
                165                 170                 175

Gly Pro Trp Thr Ser Asn Pro Leu Ile Phe Asp Asn Ser Tyr Phe Thr
            180                 185                 190

Glu Leu Leu Ser Gly Glu Lys Glu Gly Leu Leu Gln Leu Pro Ser Asp
        195                 200                 205

Lys Ala Leu Leu Ser Asp Pro Val Phe Arg Pro Leu Val Asp Lys Tyr
    210                 215                 220

Ala Ala Asp Glu Asp Ala Phe Phe Ala Asp Tyr Ala Glu Ala His Gln
```

```
<210> SEQ ID NO 29
<211> LENGTH: 250
<212> TYPE: PRT
<213> ORGANISM: Arabidopsis thaliana

<400> SEQUENCE: 29

Met Thr Lys Asn Tyr Pro Thr Val Ser Glu Asp Tyr Lys Lys Ala Val
1               5                   10                  15

Glu Lys Cys Arg Arg Lys Leu Arg Gly Leu Ile Ala Glu Lys Asn Cys
            20                  25                  30

Ala Pro Ile Met Val Arg Leu Ala Trp His Ser Ala Gly Thr Phe Asp
        35                  40                  45

Cys Gln Ser Arg Thr Gly Gly Pro Phe Gly Thr Met Arg Phe Asp Ala
    50                  55                  60

Glu Gln Ala His Gly Ala Asn Ser Gly Ile His Ile Ala Leu Arg Leu
65                  70                  75                  80

Leu Asp Pro Ile Arg Glu Gln Phe Pro Thr Ile Ser Phe Ala Asp Phe
                85                  90                  95

His Gln Leu Ala Gly Val Val Ala Val Glu Val Thr Gly Gly Pro Asp
            100                 105                 110

Ile Pro Phe His Pro Gly Arg Glu Asp Lys Pro Gln Pro Pro Pro Glu
        115                 120                 125

Gly Arg Leu Pro Asp Ala Thr Lys Gly Cys Asp His Leu Arg Asp Val
    130                 135                 140

Phe Ala Lys Gln Met Gly Leu Ser Asp Lys Asp Ile Val Ala Leu Ser
145                 150                 155                 160

Gly Ala His Thr Leu Gly Arg Cys His Lys Asp Arg Ser Gly Phe Glu
                165                 170                 175

Gly Ala Trp Thr Ser Asn Pro Leu Ile Phe Asp Asn Ser Tyr Phe Lys
            180                 185                 190

Glu Leu Leu Ser Gly Glu Lys Glu Gly Leu Leu Gln Leu Val Ser Asp
        195                 200                 205

Lys Ala Leu Leu Asp Asp Pro Val Phe Arg Pro Leu Val Glu Lys Tyr
    210                 215                 220

Ala Ala Asp Glu Asp Ala Phe Phe Ala Asp Tyr Ala Glu Ala His Met
225                 230                 235                 240

Lys Leu Ser Glu Leu Gly Phe Ala Asp Ala
                245                 250

<210> SEQ ID NO 30
<211> LENGTH: 251
<212> TYPE: PRT
<213> ORGANISM: Arabidopsis thaliana

<400> SEQUENCE: 30

Met Val Lys Lys Ser Tyr Pro Glu Val Lys Glu Glu Tyr Lys Lys Ala
1               5                   10                  15

Val Gln Arg Cys Lys Arg Lys Leu Arg Gly Leu Ile Ala Glu Lys His
            20                  25                  30

Cys Ala Pro Ile Val Leu Arg Leu Ala Trp His Ser Ala Gly Thr Phe
        35                  40                  45

Asp Val Lys Thr Lys Thr Gly Gly Pro Phe Gly Thr Ile Arg His Pro
```

```
                    50                  55                  60
Gln Glu Leu Ala His Asp Ala Asn Asn Gly Leu Asp Ile Ala Val Arg
 65                  70                  75                  80

Leu Leu Asp Pro Ile Lys Glu Leu Phe Pro Ile Leu Ser Tyr Ala Asp
                     85                  90                  95

Phe Tyr Gln Leu Ala Gly Val Val Ala Val Glu Ile Thr Gly Gly Pro
                    100                 105                 110

Glu Ile Pro Phe His Pro Gly Arg Leu Asp Lys Val Glu Pro Pro Pro
                115                 120                 125

Glu Gly Arg Leu Pro Gln Ala Thr Lys Gly Val Asp His Leu Arg Asp
130                 135                 140

Val Phe Gly Arg Met Gly Leu Asn Asp Lys Asp Ile Val Ala Leu Ser
145                 150                 155                 160

Gly Gly His Thr Leu Gly Arg Cys His Lys Glu Arg Ser Gly Phe Glu
                165                 170                 175

Gly Ala Trp Thr Pro Asn Pro Leu Ile Phe Asp Asn Ser Tyr Phe Lys
                180                 185                 190

Glu Ile Leu Ser Gly Glu Lys Glu Gly Leu Leu Gln Leu Pro Thr Asp
                195                 200                 205

Lys Ala Leu Leu Asp Asp Pro Leu Phe Leu Pro Phe Val Glu Lys Tyr
210                 215                 220

Ala Ala Asp Glu Asp Ala Phe Phe Glu Asp Tyr Thr Glu Ala His Leu
225                 230                 235                 240

Lys Leu Ser Glu Leu Gly Phe Ala Asp Lys Glu
                245                 250

<210> SEQ ID NO 31
<211> LENGTH: 250
<212> TYPE: PRT
<213> ORGANISM: Pisum sativum

<400> SEQUENCE: 31

Met Gly Lys Ser Tyr Pro Thr Val Ser Pro Asp Tyr Gln Lys Ala Ile
  1               5                  10                  15

Glu Lys Ala Lys Arg Lys Leu Arg Gly Phe Ile Ala Glu Lys Lys Cys
                 20                  25                  30

Ala Pro Leu Ile Leu Arg Leu Ala Trp His Ser Ala Gly Thr Phe Asp
                 35                  40                  45

Ser Lys Thr Lys Thr Gly Gly Pro Phe Gly Thr Ile Lys His Gln Ala
 50                  55                  60

Glu Leu Ala His Gly Ala Asn Asn Gly Leu Asp Ile Ala Val Arg Leu
 65                  70                  75                  80

Leu Glu Pro Ile Lys Glu Gln Phe Pro Ile Val Ser Tyr Ala Asp Phe
                 85                  90                  95

Tyr Gln Leu Ala Gly Val Val Ala Val Glu Ile Thr Gly Gly Pro Glu
                100                 105                 110

Val Pro Phe His Pro Gly Arg Glu Asp Lys Pro Glu Pro Pro Pro Glu
                115                 120                 125

Gly Arg Leu Pro Asp Ala Thr Lys Gly Ser Asp His Leu Arg Asp Val
130                 135                 140

Phe Gly Lys Ala Met Gly Leu Ser Asp Gln Asp Ile Val Ala Leu Ser
145                 150                 155                 160

Gly Gly His Thr Ile Gly Ala Ala His Lys Glu Arg Ser Gly Phe Glu
                165                 170                 175
```

```
Gly Pro Trp Thr Ser Asn Pro Leu Ile Phe Asp Asn Ser Tyr Phe Thr
            180                 185                 190

Glu Leu Leu Thr Gly Glu Lys Asp Gly Leu Leu Gln Leu Pro Ser Asp
        195                 200                 205

Lys Ala Leu Leu Thr Asp Ser Val Phe Arg Pro Leu Val Glu Lys Tyr
210                 215                 220

Ala Ala Asp Glu Asp Val Phe Phe Ala Asp Tyr Ala Glu Ala His Leu
225                 230                 235                 240

Lys Leu Ser Glu Leu Gly Phe Ala Glu Ala
            245                 250

<210> SEQ ID NO 32
<211> LENGTH: 250
<212> TYPE: PRT
<213> ORGANISM: Artificial
<220> FEATURE:
<223> OTHER INFORMATION: soybean ascorbate peroxidase

<400> SEQUENCE: 32

Met Gly Lys Ser Tyr Pro Thr Val Ser Ala Asp Tyr Gln Asp Ala Val
1               5                   10                  15

Glu Lys Ala Lys Lys Lys Leu Arg Gly Phe Ile Ala Glu Lys Arg Cys
            20                  25                  30

Ala Pro Leu Met Leu Arg Leu Ala Phe His Ser Ala Gly Thr Phe Asp
        35                  40                  45

Lys Gly Thr Lys Thr Gly Gly Pro Phe Gly Thr Ile Lys His Pro Ala
    50                  55                  60

Glu Leu Ala His Ser Ala Asn Asn Gly Leu Asp Ile Ala Val Arg Leu
65                  70                  75                  80

Leu Glu Pro Leu Lys Ala Glu Phe Pro Ile Leu Ser Tyr Ala Asp Phe
                85                  90                  95

Tyr Gln Leu Ala Gly Val Val Ala Val Glu Val Thr Gly Gly Pro Lys
            100                 105                 110

Val Pro Phe His Pro Gly Arg Glu Asp Lys Pro Glu Pro Pro Pro Glu
        115                 120                 125

Gly Arg Leu Pro Asp Pro Thr Lys Gly Ser Asp His Leu Arg Asp Val
    130                 135                 140

Phe Gly Lys Ala Met Gly Leu Thr Asp Gln Asp Ile Val Ala Leu Ser
145                 150                 155                 160

Gly Gly His Thr Ile Gly Ala Ala His Lys Glu Arg Ser Gly Phe Glu
                165                 170                 175

Gly Pro Trp Thr Ser Asn Pro Leu Ile Phe Asp Asn Ser Tyr Phe Thr
            180                 185                 190

Glu Leu Leu Ser Gly Glu Lys Glu Gly Leu Leu Gln Leu Pro Ser Asp
        195                 200                 205

Lys Ala Leu Leu Ser Asp Pro Val Phe Arg Pro Leu Val Asp Lys Tyr
    210                 215                 220

Ala Ala Asp Glu Asp Ala Phe Phe Ala Asp Tyr Ala Glu Ala His Gln
225                 230                 235                 240

Lys Leu Ser Glu Leu Gly Phe Ala Asp Ala
                245                 250

<210> SEQ ID NO 33
<211> LENGTH: 299
<212> TYPE: PRT
<213> ORGANISM: Armoracia rusticana
```

<400> SEQUENCE: 33

Met Gln Leu Thr Pro Thr Phe Tyr Asp Asn Ser Cys Pro Asn Val Ser
1               5                   10                  15

Asn Ile Val Arg Asp Thr Ile Val Asn Glu Leu Arg Ser Asp Pro Arg
            20                  25                  30

Ile Ala Ala Ser Ile Leu Arg Leu His Phe His Asp Cys Phe Val Asn
        35                  40                  45

Gly Cys Asp Ala Ser Ile Leu Leu Asp Asn Thr Thr Asn Ala Asn Ser
    50                  55                  60

Ala Arg Gly Phe Pro Val Ile Asp Arg Met Lys Ala Ala Val Glu Ser
65                  70                  75                  80

Ala Cys Pro Arg Thr Val Ser Cys Ala Asp Leu Leu Thr Ile Ala Ala
                85                  90                  95

Gln Gln Ser Val Thr Leu Ala Gly Gly Pro Ser Trp Arg Val Pro Leu
            100                 105                 110

Gly Arg Arg Asp Ser Leu Gln Ala Phe Leu Asp Leu Ala Asn Ala Asn
        115                 120                 125

Leu Pro Ala Pro Phe Phe Thr Leu Pro Gln Leu Lys Asp Ser Phe Arg
    130                 135                 140

Asn Val Gly Leu Asn Arg Ser Ser Asp Leu Val Ala Leu Ser Gly Gly
145                 150                 155                 160

His Thr Phe Gly Lys Asn Gln Cys Arg Phe Ile Met Asp Arg Leu Tyr
                165                 170                 175

Asn Phe Ser Asn Thr Gly Leu Pro Asp Pro Thr Leu Asn Thr Thr Tyr
            180                 185                 190

Leu Gln Thr Leu Arg Gly Leu Cys Pro Leu Asn Gly Asn Leu Ser Ala
        195                 200                 205

Leu Val Asp Phe Asp Leu Arg Thr Pro Thr Ile Phe Asp Asn Lys Tyr
    210                 215                 220

Tyr Val Asn Leu Glu Glu Gln Lys Gly Leu Ile Gln Ser Asp Gln Glu
225                 230                 235                 240

Leu Phe Ser Ser Pro Asn Ala Thr Asp Thr Ile Pro Leu Val Arg Ser
                245                 250                 255

Phe Ala Asn Ser Thr Gln Thr Phe Phe Asn Ala Phe Val Glu Ala Met
            260                 265                 270

Asp Arg Met Gly Asn Ile Thr Pro Leu Thr Gly Thr Gln Gly Gln Ile
        275                 280                 285

Arg Leu Asn Cys Arg Val Val Asn Ser Asn Ser
    290                 295

<210> SEQ ID NO 34
<211> LENGTH: 489
<212> TYPE: PRT
<213> ORGANISM: Artificial
<220> FEATURE:
<223> OTHER INFORMATION: Alkaline phosphatase

<400> SEQUENCE: 34

Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Leu Gln Gly Thr Ala
            20                  25                  30

Val Asp Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg

```
             50                  55                  60
Leu Thr Gly Asp Gln Thr Ala Ala Leu Arg Asp Ser Leu Ser Asp Lys
 65                  70                  75                  80

Pro Ala Lys Asn Ile Ile Leu Leu Ile Gly Asp Gly Met Gly Asp Ser
                     85                  90                  95

Glu Ile Thr Ala Ala Arg Asn Tyr Ala Glu Gly Ala Gly Gly Phe Phe
                    100                 105                 110

Lys Gly Ile Asp Ala Leu Pro Leu Thr Gly Gln Tyr Thr His Tyr Ala
                115                 120                 125

Leu Asn Lys Lys Thr Gly Lys Pro Asp Tyr Val Thr Asp Ser Ala Ala
    130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
                180                 185                 190

Asp Ala Thr Pro Ala Ala Leu Val Ala His Val Thr Ser Arg Lys Cys
                195                 200                 205

Tyr Gly Pro Ser Ala Thr Ser Glu Lys Cys Pro Gly Asn Ala Leu Glu
    210                 215                 220

Lys Gly Gly Lys Gly Ser Ile Thr Glu Gln Leu Leu Asn Ala Arg Ala
225                 230                 235                 240

Asp Val Thr Leu Gly Gly Gly Ala Lys Thr Phe Ala Glu Thr Ala Thr
                    245                 250                 255

Ala Gly Glu Trp Gln Gly Lys Thr Leu Arg Glu Gln Ala Gln Ala Arg
                260                 265                 270

Gly Tyr Gln Leu Val Ser Asp Ala Ala Ser Leu Asn Ser Val Thr Glu
    275                 280                 285

Ala Asn Gln Gln Lys Pro Leu Leu Gly Leu Phe Ala Asp Gly Asn Met
    290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                    325                 330                 335

Pro Thr Leu Ala Gln Met Thr Asp Lys Ala Ile Glu Leu Leu Ser Lys
                340                 345                 350

Asn Glu Lys Gly Phe Phe Leu Gln Val Glu Gly Ala Ser Ile Asp Lys
    355                 360                 365

Gln Asp His Ala Ala Asn Pro Cys Gly Gln Ile Gly Glu Thr Val Asp
    370                 375                 380

Leu Asp Glu Ala Val Gln Arg Ala Leu Glu Phe Ala Lys Lys Glu Gly
385                 390                 395                 400

Asn Thr Leu Val Ile Val Thr Ala Asp His Ala His Ala Ser Gln Ile
                    405                 410                 415

Val Ala Pro Asp Thr Lys Ala Pro Gly Leu Thr Gln Ala Leu Asn Thr
                420                 425                 430

Lys Asp Gly Ala Val Met Val Met Ser Tyr Gly Asn Ser Glu Glu Asp
                435                 440                 445

Ser Gln Glu His Thr Gly Ser Gln Leu Arg Ile Ala Ala Tyr Gly Pro
    450                 455                 460

His Ala Ala Asn Val Val Gly Leu Thr Asp Gln Thr Asp Leu Phe Tyr
465                 470                 475                 480
```

Thr Met Lys Ala Ala Leu Gly Leu Lys
                485

<210> SEQ ID NO 35
<211> LENGTH: 471
<212> TYPE: PRT
<213> ORGANISM: Escherichia coli

<400> SEQUENCE: 35

Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Leu Glu Asn Arg
            20                  25                  30

Ala Ala Gln Gly Asp Ile Thr Ala Pro Gly Gly Ala Arg Arg Leu Thr
        35                  40                  45

Gly Asp Gln Thr Ala Ala Leu Arg Asp Ser Leu Ser Asp Lys Pro Ala
    50                  55                  60

Lys Asn Ile Ile Leu Leu Ile Gly Asp Gly Met Gly Asp Ser Glu Ile
65                  70                  75                  80

Thr Ala Ala Arg Asn Tyr Ala Glu Gly Ala Gly Gly Phe Phe Lys Gly
                85                  90                  95

Ile Asp Ala Leu Pro Leu Thr Gly Gln Tyr Thr His Tyr Ala Leu Asn
            100                 105                 110

Lys Lys Thr Gly Lys Pro Asp Tyr Val Thr Asp Ser Ala Ala Ser Ala
        115                 120                 125

Thr Ala Trp Ser Thr Gly Val Lys Thr Tyr Asn Gly Ala Leu Gly Val
    130                 135                 140

Asp Ile His Glu Lys Asp His Pro Thr Ile Leu Glu Met Ala Lys Ala
145                 150                 155                 160

Ala Gly Leu Ala Thr Gly Asn Val Ser Thr Ala Glu Leu Gln Asp Ala
                165                 170                 175

Thr Pro Ala Ala Leu Val Ala His Val Thr Ser Arg Lys Cys Tyr Gly
            180                 185                 190

Pro Ser Ala Thr Ser Glu Lys Cys Pro Gly Asn Ala Leu Glu Lys Gly
        195                 200                 205

Gly Lys Gly Ser Ile Thr Glu Gln Leu Leu Asn Ala Arg Ala Asp Val
    210                 215                 220

Thr Leu Gly Gly Gly Ala Lys Thr Phe Ala Glu Thr Ala Thr Ala Gly
225                 230                 235                 240

Glu Trp Gln Gly Lys Thr Leu Arg Glu Gln Ala Gln Ala Arg Gly Tyr
                245                 250                 255

Gln Leu Val Ser Asp Ala Ala Ser Leu Asn Ser Val Thr Glu Ala Asn
            260                 265                 270

Gln Gln Lys Pro Leu Leu Gly Leu Phe Ala Asp Gly Asn Met Pro Val
        275                 280                 285

Arg Trp Leu Gly Pro Lys Ala Thr Tyr His Gly Asn Ile Asp Lys Pro
    290                 295                 300

Ala Val Thr Cys Thr Pro Asn Pro Gln Arg Asn Asp Ser Val Pro Thr
305                 310                 315                 320

Leu Ala Gln Met Thr Asp Lys Ala Ile Glu Leu Leu Ser Lys Asn Glu
                325                 330                 335

Lys Gly Phe Phe Leu Gln Val Glu Gly Ala Ser Ile Asp Lys Gln Asp
            340                 345                 350

His Ala Ala Asn Pro Cys Gly Gln Ile Gly Glu Thr Val Asp Leu Asp

```
                355                 360                 365
Glu Ala Val Gln Arg Ala Leu Glu Phe Ala Lys Lys Glu Gly Asn Thr
370                 375                 380

Leu Val Ile Val Thr Ala Asp His Ala His Ala Ser Gln Val Val Ala
385                 390                 395                 400

Pro Asp Thr Lys Ala Pro Gly Leu Thr Gln Ala Leu Asn Thr Lys Asp
                405                 410                 415

Gly Ala Val Met Val Met Ser Tyr Gly Asn Ser Glu Glu Asp Ser Gln
                420                 425                 430

Glu His Thr Gly Ser Gln Leu Arg Ile Ala Ala Tyr Gly Pro His Ala
                435                 440                 445

Ala Asn Val Val Gly Leu Thr Asp Gln Thr Asp Leu Phe Tyr Thr Met
450                 455                 460

Lys Ala Ala Leu Gly Leu Lys
465                 470

<210> SEQ ID NO 36
<211> LENGTH: 602
<212> TYPE: PRT
<213> ORGANISM: Escherichia coli

<400> SEQUENCE: 36

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
                20                  25                  30

Arg Trp Trp Glu Ser Ala Leu Gln Glu Ser Arg Ala Ile Ala Val Pro
            35                  40                  45

Gly Ser Phe Asn Asp Gln Phe Ala Asp Ala Asp Ile Arg Asn Tyr Ala
        50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255
```

```
Lys Ser Gln Thr Glu Cys Asp Ile Tyr Pro Leu Arg Val Gly Ile Arg
            260                 265                 270

Ser Val Ala Val Lys Gly Gln Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Val His Gly Asn Ile Ser Pro Leu Ala Glu Ala Thr Arg
            420                 425                 430

Lys Leu Asp Pro Thr Arg Pro Ile Thr Cys Val Asn Val Met Phe Cys
        435                 440                 445

Asp Ala His Thr Asp Thr Ile Ser Asp Leu Phe Asp Val Leu Cys Leu
    450                 455                 460

Asn Arg Tyr Tyr Gly Trp Tyr Val Gln Ser Gly Asp Leu Glu Thr Ala
465                 470                 475                 480

Glu Lys Val Leu Glu Lys Glu Leu Leu Ala Trp Gln Glu Lys Leu His
                485                 490                 495

Gln Pro Ile Ile Ile Thr Glu Tyr Gly Val Asp Thr Leu Ala Gly Leu
            500                 505                 510

His Ser Met Tyr Thr Asp Met Trp Ser Glu Glu Tyr Gln Cys Ala Trp
        515                 520                 525

Leu Asp Met Tyr His Arg Val Phe Asp Arg Val Ser Ala Val Val Gly
    530                 535                 540

Glu Gln Val Trp Asn Phe Ala Asp Phe Ala Thr Ser Gln Gly Ile Leu
545                 550                 555                 560

Arg Val Gly Gly Asn Lys Lys Gly Ile Phe Thr Arg Asp Arg Lys Pro
                565                 570                 575

Lys Ser Ala Ala Phe Leu Leu Gln Lys Arg Trp Thr Gly Met Asn Phe
            580                 585                 590

Gly Glu Lys Pro Gln Gln Gly Gly Lys Gln
        595                 600

<210> SEQ ID NO 37
<211> LENGTH: 555
<212> TYPE: PRT
<213> ORGANISM: Francisella tularensis

<400> SEQUENCE: 37

Met Ser Thr Asn Ser Asn Ile Arg Gln Lys Leu Gly Gln Leu Ile Met
1               5                   10                  15

Met Asp Phe Arg Tyr Trp Gly Glu Asp Ser Asn Asn Gln Arg Ile Pro
            20                  25                  30
```

-continued

```
Phe Thr Lys Thr Asn Asp Ile Val Asn Lys Ile Phe Lys Asp Tyr Asn
         35                  40                  45
Leu Gly Gly Phe Ile Leu Phe Arg Glu Asn Ile Gln Asn Asn Glu Gln
 50                  55                  60
Val Ile Ser Leu Leu Arg Asp Leu Gln Ala Asn Thr Asn Thr Pro Ile
 65                  70                  75                  80
Phe Phe Ala Thr Asp Gln Glu Gly Gly Arg Val Asn Arg Leu Gln Gln
                 85                  90                  95
Gly Thr Ser Gly Cys Gly Asn Met Ala Leu Ala Ala Thr Asp Asn Pro
            100                 105                 110
His Asn Ala Tyr Thr Met Ala Lys Ile Ile Gly Asp Glu Leu Tyr Ser
            115                 120                 125
Leu Gly Ile Asn Ile Asn Phe Ala Pro Ala Val Asp Val Asn Ser Asn
130                 135                 140
Lys Asn Asn Pro Ile Ile Gly Val Arg Ser Tyr Ser Asp Asn Pro Asp
145                 150                 155                 160
Ile Val Ile Asp Tyr Ala Lys Asn Ala Ile Asn Gly Tyr His Asp Ala
                165                 170                 175
Lys Ile Ile Asp Cys Ile Lys His Phe Pro Gly His Gly Asp Thr Ala
            180                 185                 190
Thr Asp Ser His Leu Gly Asn Val Asn Leu Asp Lys Thr Leu Lys Glu
            195                 200                 205
Leu Gln Thr Thr Glu Leu Leu Pro Phe Ser Lys Leu Ala Arg Asp Cys
210                 215                 220
Ser Met Ile Met Thr Ala His Ile Ser Val Pro Ala Leu Asp Asp Thr
225                 230                 235                 240
Gln Tyr Gln Ser Val Ser Thr Ser Glu Asn Ile Tyr Val Pro Ala Thr
                245                 250                 255
Leu Ser Tyr Lys Ile Ile Thr Lys Leu Leu Lys Gln Gln Met Lys Phe
            260                 265                 270
Asp Gly Leu Val Val Ser Asp Ala Met Asp Met His Ala Ile Ala Lys
            275                 280                 285
His Phe Gly Thr Ile Glu Ala Ser Lys Leu Ala Ile Leu Ala Gly Ile
290                 295                 300
Asp Ile Leu Leu Met Pro Val Arg Val Trp Ser Glu Asn Asp Leu Tyr
305                 310                 315                 320
Lys Leu Glu Glu Leu Phe Cys Glu Leu Glu Lys Gly Tyr Asn Gln Asn
                325                 330                 335
Ser Asn Phe Ala Asn Ala Val Asp Val Tyr Thr Asn Ile Thr Asp
            340                 345                 350
Phe Lys Ala Lys His Lys Leu Asp Glu Ser Leu Ile Phe Lys Leu Ser
            355                 360                 365
Gln Asp Glu Gln Leu Lys Tyr Ala Asn Gln Ile Val Asn Ser Asn Lys
370                 375                 380
His Gln Gln Ile Ala Leu Asp Ile Ala Lys Gln Ser Thr Thr Val Val
385                 390                 395                 400
Lys Asn Ser Gly Ile Ile Pro Cys Asp Leu Asn Lys Leu Lys Asn Ile
                405                 410                 415
Leu Ile Val Asp Ser Asp Asn Gln Arg Leu Ala Asp Phe His Ser Glu
            420                 425                 430
Leu Gln Lys Ile Val Leu Asp Asn Asn Ser Asn Val Ile Ile Asn Cys
            435                 440                 445
```

```
Glu Asn Ile Asn Asn His Asn Ile Lys Thr Ile Ile Glu Asn Ala Asp
    450                 455                 460

Leu Ile Leu Leu Ile Ser Ala Asn Leu Arg Glu Tyr Asn Gln Thr Tyr
465                 470                 475                 480

Ser Tyr Ile Thr Ser Ile Lys Pro Gln Thr Ile Asn Ile Ala Ala
                485                 490                 495

Leu Thr Pro Tyr Asp Ile Asn Tyr Ile Asp Asn Ile Ile Asn Tyr Val
                500                 505                 510

Cys Ile Tyr Gly Ala Thr Ser Met Asp Gln Thr Asn Tyr Thr Lys Thr
                515                 520                 525

Ser Leu Lys Ile Asn Ile Gln Thr Thr Leu Glu Asn Ile Phe Gly Asn
530                 535                 540

Lys Glu Ile Lys Gly Val Leu Pro Val Ser Leu
545                 550                 555

<210> SEQ ID NO 38
<211> LENGTH: 321
<212> TYPE: PRT
<213> ORGANISM: Escherichia coli

<400> SEQUENCE: 38

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
                100                 105                 110

Gln Ala Gly Arg Gly Arg Arg Gly Arg Lys Trp Phe Ser Pro Phe Gly
            115                 120                 125

Ala Asn Leu Tyr Leu Ser Met Phe Trp Arg Leu Glu Gln Gly Pro Ala
            130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ile Asn
            195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270
```

```
Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Glu Gln Asp Gly
290                 295                 300

Ile Ile Lys Pro Trp Met Gly Gly Glu Ile Ser Leu Arg Ser Ala Glu
305                 310                 315                 320

Lys

<210> SEQ ID NO 39
<211> LENGTH: 258
<212> TYPE: PRT
<213> ORGANISM: Artificial
<220> FEATURE:
<223> OTHER INFORMATION: Biotin ligase

<400> SEQUENCE: 39

Met Ile Pro Leu Leu Asn Ala Lys Gln Ile Leu Gly Gln Leu Asp Gly
1               5                   10                  15

Gly Ser Val Ala Val Leu Pro Val Val Asp Ser Thr Asn Gln Tyr Leu
            20                  25                  30

Leu Asp Arg Ile Gly Glu Leu Lys Ser Gly Asp Ala Cys Ile Ala Glu
            35                  40                  45

Tyr Gln Gln Ala Gly Arg Gly Ser Arg Gly Arg Lys Trp Phe Ser Pro
50                  55                  60

Phe Gly Ala Asn Leu Tyr Leu Ser Met Phe Trp Arg Leu Lys Arg Gly
65                  70                  75                  80

Pro Ala Ala Ile Gly Leu Gly Pro Val Ile Gly Ile Val Met Ala Glu
                85                  90                  95

Ala Leu Arg Lys Leu Gly Ala Asp Lys Val Arg Val Lys Trp Pro Asn
            100                 105                 110

Asp Leu Tyr Leu Gln Asp Arg Lys Leu Ala Gly Ile Leu Val Glu Leu
            115                 120                 125

Ala Gly Ile Thr Gly Asp Ala Ala Gln Ile Val Ile Gly Ala Gly Ile
            130                 135                 140

Asn Val Ala Met Arg Arg Val Glu Glu Ser Val Val Asn Gln Gly Trp
145                 150                 155                 160

Ile Thr Leu Gln Glu Ala Gly Ile Asn Leu Asp Arg Asn Thr Leu Ala
                165                 170                 175

Ala Met Leu Ile Arg Glu Leu Arg Ala Ala Leu Glu Leu Phe Glu Gln
            180                 185                 190

Glu Gly Leu Ala Pro Tyr Leu Ser Arg Trp Glu Lys Leu Asp Asn Phe
            195                 200                 205

Ile Asn Arg Pro Val Lys Leu Ile Ile Gly Asp Lys Glu Ile Phe Gly
            210                 215                 220

Ile Ser Arg Gly Ile Asp Lys Gln Gly Ala Leu Leu Leu Glu Gln Asp
225                 230                 235                 240

Gly Val Ile Lys Pro Trp Met Gly Gly Glu Ile Ser Leu Arg Ser Ala
                245                 250                 255

Glu Lys

<210> SEQ ID NO 40
<211> LENGTH: 320
<212> TYPE: PRT
<213> ORGANISM: Artificial
<220> FEATURE:
<223> OTHER INFORMATION: Biotin ligase
```

-continued

<400> SEQUENCE: 40

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Pro Leu Leu Asn Ala Lys Gln Ile Leu Gly Gln Leu Asp Gly Gly Ser
65                  70                  75                  80

Val Ala Val Leu Pro Val Val Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Ser Arg Gly Arg Lys Trp Phe Ser Pro Phe Gly
        115                 120                 125

Ala Asn Leu Tyr Leu Ser Met Phe Trp Arg Leu Lys Arg Gly Pro Ala
    130                 135                 140

Ala Ile Gly Leu Gly Pro Val Ile Gly Ile Val Met Ala Glu Ala Leu
145                 150                 155                 160

Arg Lys Leu Gly Ala Asp Lys Val Arg Val Lys Trp Pro Asn Asp Leu
                165                 170                 175

Tyr Leu Gln Asp Arg Lys Leu Ala Gly Ile Leu Val Glu Leu Ala Gly
            180                 185                 190

Ile Thr Gly Asp Ala Ala Gln Ile Val Ile Gly Ala Gly Ile Asn Val
        195                 200                 205

Ala Met Arg Arg Val Glu Glu Ser Val Val Asn Gln Gly Trp Ile Thr
    210                 215                 220

Leu Gln Glu Ala Gly Ile Asn Leu Asp Arg Asn Thr Leu Ala Ala Thr
225                 230                 235                 240

Leu Ile Arg Glu Leu Arg Ala Ala Leu Glu Leu Phe Glu Gln Glu Gly
                245                 250                 255

Leu Ala Pro Tyr Leu Pro Arg Trp Glu Lys Leu Asp Asn Phe Ile Asn
            260                 265                 270

Arg Pro Val Lys Leu Ile Ile Gly Asp Lys Glu Ile Phe Gly Ile Ser
        275                 280                 285

Arg Gly Ile Asp Lys Gln Gly Ala Leu Leu Leu Glu Gln Asp Gly Val
    290                 295                 300

Ile Lys Pro Trp Met Gly Gly Glu Ile Ser Leu Arg Ser Ala Glu Lys
305                 310                 315                 320

<210> SEQ ID NO 41
<211> LENGTH: 334
<212> TYPE: PRT
<213> ORGANISM: Artificial
<220> FEATURE:
<223> OTHER INFORMATION: Biotin ligase

<400> SEQUENCE: 41

Met Asp Tyr Lys Asp Asp Asp Lys Ser Pro Arg Ser Met Lys Asp
1               5                   10                  15

Asn Thr Val Pro Leu Lys Leu Ile Ala Leu Leu Ala Asn Gly Glu Phe
            20                  25                  30

His Ser Gly Glu Gln Leu Gly Glu Thr Leu Gly Met Ser Arg Ala Ala
                35                  40                  45

Ile Asn Lys His Ile Gln Thr Leu Arg Asp Trp Gly Val Asp Val Phe
 50                  55                  60

Thr Val Pro Gly Lys Gly Tyr Ser Leu Pro Glu Pro Ile Gln Leu Leu
 65                  70                  75                  80

Asn Ala Lys Gln Ile Leu Gly Gln Leu Asp Gly Gly Ser Val Ala Val
                85                  90                  95

Leu Pro Val Ile Asp Ser Thr Asn Gln Tyr Leu Leu Asp Arg Ile Gly
               100                 105                 110

Glu Leu Lys Ser Gly Asp Ala Cys Ile Ala Glu Tyr Gln Gln Ala Gly
               115                 120                 125

Arg Gly Arg Arg Gly Arg Lys Trp Phe Ser Pro Phe Gly Ala Asn Leu
130                 135                 140

Tyr Leu Ser Met Phe Trp Arg Leu Glu Gln Gly Pro Ala Ala Ala Ile
145                 150                 155                 160

Gly Leu Ser Leu Val Ile Gly Ile Val Met Ala Glu Val Leu Arg Lys
               165                 170                 175

Leu Gly Ala Asp Lys Val Arg Val Lys Trp Pro Asn Asp Leu Tyr Leu
               180                 185                 190

Gln Asp Arg Lys Leu Ala Gly Ile Leu Val Glu Leu Thr Gly Lys Thr
               195                 200                 205

Gly Asp Ala Ala Gln Ile Val Ile Gly Ala Gly Ile Asn Met Ala Met
               210                 215                 220

Arg Arg Val Glu Glu Ser Val Val Asn Gln Gly Trp Ile Thr Leu Gln
225                 230                 235                 240

Glu Ala Gly Ile Asn Leu Asp Arg Asn Thr Leu Ala Ala Met Leu Ile
               245                 250                 255

Arg Glu Leu Arg Ala Ala Leu Glu Leu Phe Glu Gln Glu Gly Leu Ala
               260                 265                 270

Pro Tyr Leu Ser Arg Trp Glu Lys Leu Asp Asn Phe Ile Asn Arg Pro
               275                 280                 285

Val Lys Leu Ile Ile Gly Asp Lys Glu Ile Phe Gly Ile Ser Arg Gly
               290                 295                 300

Ile Asp Lys Gln Gly Ala Leu Leu Leu Glu Gln Asp Gly Ile Ile Lys
305                 310                 315                 320

Pro Trp Met Gly Gly Glu Ile Ser Leu Arg Ser Ala Glu Lys
               325                 330

<210> SEQ ID NO 42
<211> LENGTH: 746
<212> TYPE: PRT
<213> ORGANISM: Homo sapiens

<400> SEQUENCE: 42

Met Gly Gln Thr Gly Lys Lys Ser Glu Lys Gly Pro Val Cys Trp Arg
 1               5                  10                  15

Lys Arg Val Lys Ser Glu Tyr Met Arg Leu Arg Gln Leu Lys Arg Phe
                20                  25                  30

Arg Arg Ala Asp Glu Val Lys Ser Met Phe Ser Ser Asn Arg Gln Lys
                35                  40                  45

Ile Leu Glu Arg Thr Glu Ile Leu Asn Gln Glu Trp Lys Gln Arg Arg
 50                  55                  60

Ile Gln Pro Val His Ile Leu Thr Ser Val Ser Ser Leu Arg Gly Thr
 65                  70                  75                  80

-continued

```
Arg Glu Cys Ser Val Thr Ser Asp Leu Asp Phe Pro Thr Gln Val Ile
            85                  90                  95

Pro Leu Lys Thr Leu Asn Ala Val Ala Ser Val Pro Ile Met Tyr Ser
        100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp Asp
            180                 185                 190

Pro Glu Glu Arg Glu Glu Lys Gln Lys Asp Leu Glu Asp His Arg Asp
                195                 200                 205

Asp Lys Glu Ser Arg Pro Pro Arg Lys Phe Pro Ser Asp Lys Ile Phe
        210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
        290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
            340                 345                 350

Arg Arg Arg Gly Arg Leu Pro Asn Asn Ser Ser Arg Pro Ser Thr Pro
        355                 360                 365

Thr Ile Asn Val Leu Glu Ser Lys Asp Thr Asp Ser Asp Arg Glu Ala
        370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
            420                 425                 430

Ser Gly Ala Glu Ala Ser Met Phe Arg Val Leu Ile Gly Thr Tyr Tyr
        435                 440                 445

Asp Asn Phe Cys Ala Ile Ala Arg Leu Ile Gly Thr Lys Thr Cys Arg
        450                 455                 460

Gln Val Tyr Glu Phe Arg Val Lys Glu Ser Ser Ile Ile Ala Pro Ala
465                 470                 475                 480

Pro Ala Glu Asp Val Asp Thr Pro Pro Arg Lys Lys Lys Arg Lys His
                485                 490                 495
```

Arg Leu Trp Ala Ala His Cys Arg Lys Ile Gln Leu Lys Lys Asp Gly
            500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
            530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
            565                 570                 575

Val Arg Glu Cys Asp Pro Asp Leu Cys Leu Thr Cys Gly Ala Ala Asp
            580                 585                 590

His Trp Asp Ser Lys Asn Val Ser Cys Lys Asn Cys Ser Ile Gln Arg
            595                 600                 605

Gly Ser Lys Lys His Leu Leu Leu Ala Pro Ser Asp Val Ala Gly Trp
            610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
            645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
            675                 680                 685

His Ser Val Asn Pro Asn Cys Tyr Ala Lys Val Met Met Val Asn Gly
            690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
            725                 730                 735

Val Gly Ile Glu Arg Glu Met Glu Ile Pro
            740                 745

<210> SEQ ID NO 43
<211> LENGTH: 439
<212> TYPE: PRT
<213> ORGANISM: Homo sapiens

<400> SEQUENCE: 43

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
            50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
            85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
            115                 120                 125

-continued

```
Ile Ile Gln Asp Cys Met Trp Ser Gly Phe Ser Ala Ala Lys Leu
        130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ser Glu Cys Ile Asp Pro Ser
        180                 185                 190

Val Val Phe Pro Tyr Pro Leu Asn Asp Ser Ser Pro Lys Ser Cys
            195                 200                 205

Ala Ser Gln Asp Ser Ser Ala Phe Ser Pro Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
        370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435

<210> SEQ ID NO 44
<211> LENGTH: 380
<212> TYPE: PRT
<213> ORGANISM: Homo sapiens

<400> SEQUENCE: 44

Met Met Phe Ser Gly Phe Asn Ala Asp Tyr Glu Ala Ser Ser Ser Arg
1               5                   10                  15

Cys Ser Ser Ala Ser Pro Ala Gly Asp Ser Leu Ser Tyr Tyr His Ser
                20                  25                  30

Pro Ala Asp Ser Phe Ser Ser Met Gly Ser Pro Val Asn Ala Gln Asp
            35                  40                  45

Phe Cys Thr Asp Leu Ala Val Ser Ser Ala Asn Phe Ile Pro Thr Val
```

```
            50                  55                  60
Thr Ala Ile Ser Thr Ser Pro Asp Leu Gln Trp Leu Val Gln Pro Ala
 65                  70                  75                  80

Leu Val Ser Ser Val Ala Pro Ser Gln Thr Arg Ala Pro His Pro Phe
                 85                  90                  95

Gly Val Pro Ala Pro Ser Ala Gly Ala Tyr Ser Arg Ala Gly Val Val
            100                 105                 110

Lys Thr Met Thr Gly Gly Arg Ala Gln Ser Ile Gly Arg Arg Gly Lys
        115                 120                 125

Val Glu Gln Leu Ser Pro Glu Glu Glu Lys Arg Arg Ile Arg Arg
130                 135                 140

Glu Arg Asn Lys Met Ala Ala Lys Cys Arg Asn Arg Arg Arg Glu
145                 150                 155                 160

Leu Thr Asp Thr Leu Gln Ala Glu Thr Asp Gln Leu Glu Asp Glu Lys
                165                 170                 175

Ser Ala Leu Gln Thr Glu Ile Ala Asn Leu Leu Lys Glu Lys Glu Lys
            180                 185                 190

Leu Glu Phe Ile Leu Ala Ala His Arg Pro Ala Cys Lys Ile Pro Asp
        195                 200                 205

Asp Leu Gly Phe Pro Glu Glu Met Ser Val Ala Ser Leu Asp Leu Thr
    210                 215                 220

Gly Gly Leu Pro Glu Val Ala Thr Pro Glu Ser Glu Glu Ala Phe Thr
225                 230                 235                 240

Leu Pro Leu Leu Asn Asp Pro Glu Pro Lys Pro Ser Val Glu Pro Val
                245                 250                 255

Lys Ser Ile Ser Ser Met Glu Leu Lys Thr Glu Pro Phe Asp Asp Phe
            260                 265                 270

Leu Phe Pro Ala Ser Ser Arg Pro Ser Gly Ser Glu Thr Ala Arg Ser
        275                 280                 285

Val Pro Asp Met Asp Leu Ser Gly Ser Phe Tyr Ala Ala Asp Trp Glu
    290                 295                 300

Pro Leu His Ser Gly Ser Leu Gly Met Gly Pro Met Ala Thr Glu Leu
305                 310                 315                 320

Glu Pro Leu Cys Thr Pro Val Val Thr Cys Thr Pro Ser Cys Thr Ala
                325                 330                 335

Tyr Thr Ser Ser Phe Val Phe Thr Tyr Pro Glu Ala Asp Ser Phe Pro
            340                 345                 350

Ser Cys Ala Ala Ala His Arg Lys Gly Ser Ser Ser Asn Glu Pro Ser
        355                 360                 365

Ser Asp Ser Leu Ser Ser Pro Thr Leu Leu Ala Leu
    370                 375                 380

<210> SEQ ID NO 45
<211> LENGTH: 331
<212> TYPE: PRT
<213> ORGANISM: Homo sapiens

<400> SEQUENCE: 45

Met Thr Ala Lys Met Glu Thr Thr Phe Tyr Asp Asp Ala Leu Asn Ala
 1               5                  10                  15

Ser Phe Leu Pro Ser Glu Ser Gly Pro Tyr Gly Tyr Ser Asn Pro Lys
                20                  25                  30

Ile Leu Lys Gln Ser Met Thr Leu Asn Leu Ala Asp Pro Val Gly Ser
            35                  40                  45
```

-continued

```
Leu Lys Pro His Leu Arg Ala Lys Asn Ser Asp Leu Leu Thr Ser Pro
 50                  55                  60

Asp Val Gly Leu Leu Lys Leu Ala Ser Pro Glu Leu Glu Arg Leu Ile
 65                  70                  75                  80

Ile Gln Ser Ser Asn Gly His Ile Thr Thr Thr Pro Thr Pro Thr Gln
                 85                  90                  95

Phe Leu Cys Pro Lys Asn Val Thr Asp Glu Gln Gly Phe Ala Glu
            100                 105                 110

Gly Phe Val Arg Ala Leu Ala Glu Leu His Ser Gln Asn Thr Leu Pro
            115                 120                 125

Ser Val Thr Ser Ala Ala Gln Pro Val Asn Gly Ala Gly Met Val Ala
130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
            195                 200                 205

His His Leu Pro Gln Gln Met Pro Val Gln His Pro Arg Leu Gln Ala
210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
            275                 280                 285

Ala Gln Asn Ser Glu Leu Ala Ser Thr Ala Asn Met Leu Arg Glu Gln
            290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330

<210> SEQ ID NO 46
<211> LENGTH: 327
<212> TYPE: PRT
<213> ORGANISM: Homo sapiens

<400> SEQUENCE: 46

Met Thr Met Glu Ser Gly Ala Glu Asn Gln Gln Ser Gly Asp Ala Ala
 1               5                  10                  15

Val Thr Glu Ala Glu Asn Gln Gln Met Thr Val Gln Ala Gln Pro Gln
                 20                  25                  30

Ile Ala Thr Leu Ala Gln Val Ser Met Pro Ala Ala His Ala Thr Ser
             35                  40                  45

Ser Ala Pro Thr Val Thr Leu Val Gln Leu Pro Asn Gly Gln Thr Val
 50                  55                  60

Gln Val His Gly Val Ile Gln Ala Ala Gln Pro Ser Val Ile Gln Ser
 65                  70                  75                  80

Pro Gln Val Gln Thr Val Gln Ile Ser Thr Ile Ala Glu Ser Glu Asp
                 85                  90                  95
```

```
Ser Gln Glu Ser Val Asp Ser Val Thr Asp Ser Gln Lys Arg Arg Glu
            100                 105                 110

Ile Leu Ser Arg Arg Pro Ser Tyr Arg Lys Ile Leu Asn Asp Leu Ser
            115                 120                 125

Ser Asp Ala Pro Gly Val Pro Arg Ile Glu Glu Lys Ser Glu Glu
130                 135                 140

Glu Thr Ser Ala Pro Ala Ile Thr Thr Val Thr Val Pro Thr Pro Ile
145                 150                 155                 160

Tyr Gln Thr Ser Ser Gly Gln Tyr Ile Ala Ile Thr Gln Gly Gly Ala
                165                 170                 175

Ile Gln Leu Ala Asn Asn Gly Thr Asp Gly Val Gln Gly Leu Gln Thr
            180                 185                 190

Leu Thr Met Thr Asn Ala Ala Ala Thr Gln Pro Gly Thr Thr Ile Leu
            195                 200                 205

Gln Tyr Ala Gln Thr Thr Asp Gly Gln Gln Ile Leu Val Pro Ser Asn
    210                 215                 220

Gln Val Val Val Gln Ala Ala Ser Gly Asp Val Gln Thr Tyr Gln Ile
225                 230                 235                 240

Arg Thr Ala Pro Thr Ser Thr Ile Ala Pro Gly Val Val Met Ala Ser
                245                 250                 255

Ser Pro Ala Leu Pro Thr Gln Pro Ala Glu Glu Ala Ala Arg Lys Arg
            260                 265                 270

Glu Val Arg Leu Met Lys Asn Arg Glu Ala Ala Arg Glu Cys Arg Arg
            275                 280                 285

Lys Lys Lys Glu Tyr Val Lys Cys Leu Glu Asn Arg Val Ala Val Leu
        290                 295                 300

Glu Asn Gln Asn Lys Thr Leu Ile Glu Glu Leu Lys Ala Leu Lys Asp
305                 310                 315                 320

Leu Tyr Cys His Lys Ser Asp
                325

<210> SEQ ID NO 47
<211> LENGTH: 474
<212> TYPE: PRT
<213> ORGANISM: Homo sapiens

<400> SEQUENCE: 47

Met Glu Val Ala Pro Glu Gln Pro Gly Trp Met Ala His Pro Ala Val
1               5                   10                  15

Leu Asn Ala Gln His Pro Asp Ser His His Pro Gly Leu Ala His Asn
            20                  25                  30

Tyr Met Glu Pro Ala His Val Leu Pro Pro Asp Glu Val Asp Val Phe
        35                  40                  45

Phe Asn His Leu Asp Ser Gln Gly Asn Pro Tyr Tyr Ala Asn Pro Ala
    50                  55                  60

Gln Arg Gly Val Ser Tyr Ser Pro Ala His Ala Arg Leu Thr Gly Gly
65                  70                  75                  80

Gln Met Cys Arg Pro His Leu Leu His Ser Pro Gly Leu Pro Trp Leu
                85                  90                  95

Asp Gly Gly Lys Ala Ala Leu Ser Ala Ala His His Lys Thr Trp Thr
            100                 105                 110

Val Ser Pro Phe Ser Lys Thr Pro Leu His Pro Ser Ala Ala Gly Gly
        115                 120                 125

Pro Gly Gly His Ser Leu Cys Thr Gln Gly Leu Gly Val Gly Gly Gly
```

```
              130                 135                 140
Ser Ser Gly Ser Ser Val Ala Ser Leu Thr Pro Thr Ala Ala His Ser
145                 150                 155                 160

Gly Ser His Leu Phe Gly Phe Pro Arg His Pro Lys Glu Leu Ser
                165                 170                 175

Pro Asp Pro Ser Thr Thr Gly Ala Ala Ser Pro Ala Ser Ser Ser Ala
            180                 185                 190

Gly Gly Ser Ser Ala Arg Gly Glu Asp Lys Asp Gly Val Lys Tyr Gln
                195                 200                 205

Ala Ser Leu Thr Glu Ser Met Lys Met Glu Ser Gly Arg Pro Leu Arg
            210                 215                 220

Pro Gly Leu Ala Thr Met Gly Thr Gln Pro Ala Thr His His Pro Ile
225                 230                 235                 240

Pro Thr Tyr Pro Ser Tyr Val Pro Ala Ala His Asp Tyr Ser Ser
                245                 250                 255

Gly Leu Phe His Pro Gly Ser Phe Leu Gly Pro Ala Ser Ser Phe
                260                 265                 270

Thr Pro Lys Gln Arg Ser Lys Thr Arg Ser Cys Ser Glu Gly Arg Glu
                275                 280                 285

Cys Val Asn Cys Gly Ala Thr Ala Thr Pro Leu Trp Arg Arg Asp Gly
            290                 295                 300

Thr Gly His Tyr Leu Cys Asn Ala Cys Gly Phe Tyr His Lys Met Lys
305                 310                 315                 320

Gly Gln Asn Arg Pro Leu Ile Lys Pro Lys Arg Arg Leu Ser Ala Ala
                325                 330                 335

Arg Arg Ala Gly Thr Cys Cys Ala Asn Cys Gln Thr Thr Thr Thr
            340                 345                 350

Leu Trp Arg Arg Asn Ala Asn Gly Asp Pro Val Cys Asn Ala Cys Gly
                355                 360                 365

Leu Tyr Tyr Lys Leu His Asn Val Asn Arg Pro Leu Thr Met Lys Lys
            370                 375                 380

Glu Gly Ile Gln Thr Arg Asn Arg Lys Met Ser Asn Lys Ser Lys Lys
385                 390                 395                 400

Ser Lys Lys Gly Ala Glu Cys Phe Glu Glu Leu Ser Lys Cys Met Gln
                405                 410                 415

Glu Lys Ser Ser Pro Phe Ser Ala Ala Leu Ala Gly His Met Ala
            420                 425                 430

Pro Met Gly His Leu Pro Pro Phe Ser His Ser Gly His Ile Leu Pro
                435                 440                 445

Thr Pro Thr Pro Ile His Pro Ser Ser Ser Leu Ser Phe Gly His Pro
            450                 455                 460

His Pro Ser Ser Met Val Thr Ala Met Gly
465                 470

<210> SEQ ID NO 48
<211> LENGTH: 881
<212> TYPE: PRT
<213> ORGANISM: Saccharomyces cerevisiae

<400> SEQUENCE: 48

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30
```

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Glu Glu Ser Ser Asn Lys Gly Gln Arg Gln Leu
    130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
                180                 185                 190

Asn Asn Gly Phe Phe Gly Asp Gly Ser Leu Leu Cys Ile Leu Arg Ser
                195                 200                 205

Ile Gly Phe Lys Pro Glu Asn Tyr Thr Asn Ser Asn Val Asn Arg Leu
                210                 215                 220

Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
                245                 250                 255

Ile Val His Ser Pro Thr Leu Met Met Leu Tyr Asn Asn Gln Ile Glu
                260                 265                 270

Ile Ala Ser Lys Asp Gln Trp Gln Ile Leu Phe Asn Cys Ile Leu Ala
                275                 280                 285

Ile Gly Ala Trp Cys Ile Glu Gly Glu Ser Thr Asp Ile Asp Val Phe
                290                 295                 300

Tyr Tyr Gln Asn Ala Lys Ser His Leu Thr Ser Lys Val Phe Glu Ser
305                 310                 315                 320

Gly Ser Ile Ile Leu Val Thr Ala Leu His Leu Leu Ser Arg Tyr Thr
                    325                 330                 335

Gln Trp Arg Gln Lys Thr Asn Thr Ser Tyr Asn Phe His Ser Phe Ser
                340                 345                 350

Ile Arg Met Ala Ile Ser Leu Gly Leu Asn Arg Asp Leu Pro Ser Ser
                355                 360                 365

Phe Ser Asp Ser Ser Ile Leu Glu Gln Arg Arg Ile Trp Trp Ser
    370                 375                 380

Val Tyr Ser Trp Glu Ile Gln Leu Ser Leu Leu Tyr Gly Arg Ser Ile
385                 390                 395                 400

Gln Leu Ser Gln Asn Thr Ile Ser Phe Pro Ser Ser Val Asp Val
                    405                 410                 415

Gln Arg Thr Thr Thr Gly Pro Thr Ile Tyr His Gly Ile Ile Glu Thr
                420                 425                 430

Ala Arg Leu Leu Gln Val Phe Thr Lys Ile Tyr Glu Leu Asp Lys Thr
                435                 440                 445

Val Thr Ala Glu Lys Ser Pro Ile Cys Ala Lys Lys Cys Leu Met Ile

```
            450                 455                 460
Cys Asn Glu Ile Glu Glu Val Ser Arg Gln Ala Pro Lys Phe Leu Gln
465                 470                 475                 480

Met Asp Ile Ser Thr Thr Ala Leu Thr Asn Leu Leu Lys Glu His Pro
                485                 490                 495

Trp Leu Ser Phe Thr Arg Phe Glu Leu Lys Trp Lys Gln Leu Ser Leu
                500                 505                 510

Ile Ile Tyr Val Leu Arg Asp Phe Phe Thr Asn Phe Thr Gln Lys Lys
                515                 520                 525

Ser Gln Leu Glu Gln Asp Gln Asn Asp His Gln Ser Tyr Glu Val Lys
                530                 535                 540

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
                565                 570                 575

Asn Cys Ser Tyr Tyr Leu Phe Asn Ala Val Leu Val Pro Ile Lys Thr
                580                 585                 590

Leu Leu Ser Asn Ser Lys Ser Asn Ala Glu Asn Asn Glu Thr Ala Gln
                595                 600                 605

Leu Leu Gln Gln Ile Asn Thr Val Leu Met Leu Leu Lys Lys Leu Ala
                610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
                645                 650                 655

Ile Ser Tyr Asn Asn Ser Asn Gly Ser Ala Ile Lys Asn Ile Val Gly
                660                 665                 670

Ser Ala Thr Ile Ala Gln Tyr Pro Thr Leu Pro Glu Gly Asn Val Asn
                675                 680                 685

Asn Ile Ser Val Lys Tyr Val Ser Pro Gly Ser Val Gly Pro Ser Pro
                690                 695                 700

Val Pro Leu Lys Ser Gly Ala Ser Phe Ser Asp Leu Val Lys Leu Leu
705                 710                 715                 720

Ser Asn Arg Pro Pro Ser Arg Asn Ser Pro Val Thr Ile Pro Arg Ser
                725                 730                 735

Thr Pro Ser His Arg Ser Val Thr Pro Phe Leu Gly Gln Gln Gln Gln
                740                 745                 750

Leu Gln Ser Leu Val Pro Leu Thr Pro Ser Ala Leu Phe Gly Gly Ala
                755                 760                 765

Asn Phe Asn Gln Ser Gly Asn Ile Ala Asp Ser Ser Leu Ser Phe Thr
770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Ser Asn Val His Asp Asn
                805                 810                 815

Phe Met Asn Asn Glu Ile Thr Ala Ser Lys Ile Asp Asp Gly Asn Asn
                820                 825                 830

Ser Lys Pro Leu Ser Pro Gly Trp Thr Asp Gln Thr Ala Tyr Asn Ala
                835                 840                 845

Phe Gly Ile Thr Thr Gly Met Phe Asn Thr Thr Met Asp Asp Val
                850                 855                 860

Tyr Asn Tyr Leu Phe Asp Asp Glu Asp Thr Pro Pro Asn Pro Lys Lys
865                 870                 875                 880
```

Glu

```
<210> SEQ ID NO 49
<211> LENGTH: 278
<212> TYPE: PRT
<213> ORGANISM: Saccharomyces cerevisiae

<400> SEQUENCE: 49
```

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ile Glu Phe Ser Arg Gly Arg Thr Arg Asn Asn Tyr Gly
145                 150                 155                 160

Ser Thr Ile Glu Gly Leu Leu Asp Leu Pro Asp Asp Asp Ala Pro
                165                 170                 175

Ala Glu Ala Gly Leu Val Ala Pro Arg Met Ser Phe Leu Ser Ala Gly
            180                 185                 190

Gln Arg Pro Arg Arg Leu Ser Thr Thr Ala Pro Ile Thr Asp Val Ser
        195                 200                 205

Leu Val Asp Glu Leu Arg Leu Asp Gly Glu Glu Val Asp Met Thr Pro
    210                 215                 220

Ala Asp Ala Leu Asp Asp Phe Asp Leu Glu Met Leu Gly Asp Val Glu
225                 230                 235                 240

Ser Pro Ser Pro Gly Met Thr His Asp Pro Val Ser Tyr Gly Ala Leu
                245                 250                 255

Asp Val Asp Asp Phe Glu Phe Glu Gln Met Phe Thr Asp Ala Leu Gly
            260                 265                 270

Ile Asp Asp Phe Gly Gly
        275

```
<210> SEQ ID NO 50
<211> LENGTH: 47
<212> TYPE: PRT
<213> ORGANISM: Homo sapiens

<400> SEQUENCE: 50
```

Met Ala Arg Arg Pro Arg His Ser Ile Tyr Ser Ser Asp Glu Asp Asp
1               5                   10                  15

Glu Asp Phe Glu Met Cys Asp His Asp Tyr Asp Gly Leu Leu Pro Lys
            20                  25                  30

```
Ser Gly Lys Arg His Leu Gly Lys Thr Arg Trp Thr Arg Glu Glu
        35                  40                  45
```

<210> SEQ ID NO 51
<211> LENGTH: 318
<212> TYPE: PRT
<213> ORGANISM: Mus musculus

<400> SEQUENCE: 51

```
Met Glu Leu Leu Ser Pro Pro Leu Arg Asp Ile Asp Leu Thr Gly Pro
1               5                   10                  15

Asp Gly Ser Leu Cys Ser Phe Glu Thr Ala Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Val His Val Gly Ala Leu Leu Lys Pro Glu Glu His Ala His
    50                  55                  60

Phe Ser Thr Ala Val His Pro Gly Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Ser Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Pro Arg Arg Gln Asn Gly
    210                 215                 220

Tyr Asp Thr Ala Tyr Tyr Ser Glu Ala Val Arg Glu Ser Arg Pro Gly
225                 230                 235                 240

Lys Ser Ala Ala Val Ser Ser Leu Asp Cys Leu Ser Ser Ile Val Glu
                245                 250                 255

Arg Ile Ser Thr Asp Ser Pro Ala Ala Pro Ala Leu Leu Leu Ala Asp
            260                 265                 270

Ala Pro Pro Glu Ser Pro Pro Gly Pro Pro Glu Gly Ala Ser Leu Ser
        275                 280                 285

Asp Thr Glu Gln Gly Thr Gln Thr Pro Ser Pro Asp Ala Ala Pro Gln
    290                 295                 300

Cys Pro Ala Gly Ser Asn Pro Asn Ala Ile Tyr Gln Val Leu
305                 310                 315
```

<210> SEQ ID NO 52
<211> LENGTH: 537
<212> TYPE: PRT
<213> ORGANISM: Homo sapiens

<400> SEQUENCE: 52

-continued

```
Met Asp Glu Leu Phe Pro Leu Ile Phe Pro Ala Glu Gln Pro Lys Gln
1               5                   10                  15

Arg Gly Met Arg Phe Arg Tyr Lys Cys Glu Gly Arg Ser Ala Gly Ser
            20                  25                  30

Ile Pro Gly Glu Arg Ser Thr Asp Thr Thr Lys Thr His Pro Thr Ile
            35                  40                  45

Lys Ile Asn Gly Tyr Thr Gly Pro Gly Thr Val Arg Ile Ser Leu Val
50                  55                  60

Thr Lys Asp Pro Pro His Arg Pro His Pro Glu Leu Val Gly Lys
65                  70                  75                  80

Asp Cys Arg Asp Gly Phe Tyr Glu Ala Glu Leu Cys Pro Asp Arg Cys
                85                  90                  95

Ile His Ser Phe Gln Asn Leu Gly Ile Gln Cys Val Lys Lys Arg Asp
            100                 105                 110

Leu Glu Gln Ala Ile Ser Gln Arg Ile Gln Thr Asn Asn Asn Pro Phe
            115                 120                 125

Gln Val Pro Ile Glu Glu Gln Arg Gly Asp Tyr Asp Leu Asn Ala Val
            130                 135                 140

Arg Leu Cys Phe Gln Val Thr Val Arg Asp Pro Ser Gly Arg Pro Leu
145                 150                 155                 160

Arg Leu Pro Pro Val Leu Ser His Pro Ile Phe Asp Asn Arg Ala Pro
                165                 170                 175

Asn Thr Ala Glu Leu Lys Ile Cys Arg Val Asn Arg Asn Ser Gly Ser
            180                 185                 190

Cys Leu Gly Gly Asp Glu Ile Phe Leu Leu Cys Asp Lys Val Gln Lys
            195                 200                 205

Glu Asp Ile Glu Val Tyr Phe Thr Gly Pro Gly Trp Glu Ala Arg Gly
210                 215                 220

Ser Phe Ser Gln Ala Asp Val His Arg Gln Val Ala Ile Val Phe Arg
225                 230                 235                 240

Thr Pro Pro Tyr Ala Asp Pro Ser Leu Gln Ala Pro Val Arg Val Ser
                245                 250                 255

Met Gln Leu Arg Arg Pro Ser Asp Arg Glu Leu Ser Glu Pro Met Glu
            260                 265                 270

Phe Gln Tyr Leu Pro Asp Thr Asp Asp Arg His Arg Ile Glu Glu Lys
            275                 280                 285

Arg Lys Arg Thr Tyr Glu Thr Phe Lys Ser Ile Met Lys Lys Ser Pro
            290                 295                 300

Phe Ser Gly Pro Thr Asp Pro Arg Pro Pro Arg Arg Ile Ala Val
305                 310                 315                 320

Pro Ser Arg Ser Ser Ala Ser Val Pro Lys Pro Ala Pro Gln Pro Tyr
                325                 330                 335

Pro Phe Thr Ser Ser Leu Ser Thr Ile Asn Tyr Asp Glu Phe Pro Thr
            340                 345                 350

Met Val Phe Pro Ser Gly Gln Ile Ser Gln Ala Ser Ala Leu Ala Pro
            355                 360                 365

Ala Pro Pro Gln Val Leu Pro Gln Ala Pro Ala Pro Ala Pro Ala Pro
370                 375                 380

Ala Met Val Ser Ala Leu Ala Gln Ala Pro Ala Pro Val Pro Val Leu
385                 390                 395                 400

Ala Pro Gly Pro Pro Gln Ala Val Ala Pro Ala Pro Lys Pro Thr
                405                 410                 415

Gln Ala Gly Glu Gly Thr Leu Ser Glu Ala Leu Leu Gln Leu Gln Phe
```

```
                    420            425            430
Asp Asp Glu Asp Leu Gly Ala Leu Leu Gly Asn Ser Thr Asp Pro Ala
            435                440                445

Val Phe Thr Asp Leu Ala Ser Val Asp Asn Ser Glu Phe Gln Gln Leu
        450                455                460

Leu Asn Gln Gly Ile Pro Val Ala Pro His Thr Thr Glu Pro Met Leu
465                470                475                480

Met Glu Tyr Pro Glu Ala Ile Thr Arg Leu Val Thr Ala Gln Arg Pro
                485                490                495

Pro Asp Pro Ala Pro Ala Pro Leu Gly Ala Pro Gly Leu Pro Asn Gly
            500                505                510

Leu Leu Ser Gly Asp Glu Asp Phe Ser Ser Ile Ala Asp Met Asp Phe
            515                520                525

Ser Ala Leu Leu Ser Gln Ile Ser Ser
            530                535

<210> SEQ ID NO 53
<211> LENGTH: 225
<212> TYPE: PRT
<213> ORGANISM: Artificial
<220> FEATURE:
<223> OTHER INFORMATION: TetR

<400> SEQUENCE: 53

Met Phe Ile Ser Asp Lys Val Ser Ser Met Thr Lys Leu Gln Pro Asn
1               5                   10                  15

Thr Val Ile Arg Ala Ala Leu Asp Leu Leu Asn Glu Val Gly Val Asp
            20                  25                  30

Gly Leu Thr Thr Arg Lys Leu Ala Glu Arg Leu Gly Val Gln Gln Pro
        35                  40                  45

Ala Leu Tyr Trp His Phe Arg Asn Lys Arg Ala Leu Leu Asp Ala Leu
    50                  55                  60

Ala Glu Ala Met Leu Ala Glu Asn His Thr His Ser Val Pro Arg Ala
65                  70                  75                  80

Asp Asp Asp Trp Arg Ser Phe Leu Ile Gly Asn Ala Arg Ser Phe Arg
                85                  90                  95

Gln Ala Leu Leu Ala Tyr Arg Asp Gly Ala Arg Ile His Ala Gly Thr
            100                 105                 110

Arg Pro Gly Ala Pro Gln Met Glu Thr Ala Asp Ala Gln Leu Arg Phe
        115                 120                 125

Leu Cys Glu Ala Gly Phe Ser Ala Gly Asp Ala Val Asn Ala Leu Met
    130                 135                 140

Thr Ile Ser Tyr Phe Thr Val Gly Ala Val Leu Glu Glu Gln Ala Gly
145                 150                 155                 160

Asp Ser Asp Ala Gly Glu Arg Gly Thr Val Glu Gln Ala Pro Leu
                165                 170                 175

Ser Pro Leu Leu Arg Ala Ala Ile Asp Ala Phe Asp Glu Ala Gly Pro
            180                 185                 190

Asp Ala Ala Phe Glu Gln Gly Leu Ala Val Ile Val Asp Gly Leu Ala
        195                 200                 205

Lys Arg Arg Leu Val Val Arg Asn Val Glu Gly Pro Arg Lys Gly Asp
    210                 215                 220

Asp
225
```

```
<210> SEQ ID NO 54
<211> LENGTH: 16
<212> TYPE: PRT
<213> ORGANISM: Artificial
<220> FEATURE:
<223> OTHER INFORMATION: Tat peptide consensus sequence
<220> FEATURE:
<221> NAME/KEY: MISC_FEATURE
<222> LOCATION: (1)..(1)
<223> OTHER INFORMATION: Xaa at position 1 can be S or A
<220> FEATURE:
<221> NAME/KEY: MISC_FEATURE
<222> LOCATION: (2)..(2)
<223> OTHER INFORMATION: Xaa at position 2 can be G or A
<220> FEATURE:
<221> NAME/KEY: MISC_FEATURE
<222> LOCATION: (3)..(3)
<223> OTHER INFORMATION: Xaa at position 3 can be P or A
<220> FEATURE:
<221> NAME/KEY: MISC_FEATURE
<222> LOCATION: (4)..(4)
<223> OTHER INFORMATION: Xaa at position 4 can be R or K
<220> FEATURE:
<221> NAME/KEY: MISC_FEATURE
<222> LOCATION: (5)..(5)
<223> OTHER INFORMATION: Xaa at position 5 can be P, A, I, Y, K, or R
<220> FEATURE:
<221> NAME/KEY: MISC_FEATURE
<222> LOCATION: (6)..(6)
<223> OTHER INFORMATION: Xaa at position 6 can be R, K, V, or Y
<220> FEATURE:
<221> NAME/KEY: MISC_FEATURE
<222> LOCATION: (7)..(7)
<223> OTHER INFORMATION: Xaa at position 7 can be G, A, or R
<220> FEATURE:
<221> NAME/KEY: MISC_FEATURE
<222> LOCATION: (8)..(8)
<223> OTHER INFORMATION: Xaa at position 8 can be T or A
<220> FEATURE:
<221> NAME/KEY: MISC_FEATURE
<222> LOCATION: (9)..(9)
<223> OTHER INFORMATION: Xaa at position 9 can be R or K
<220> FEATURE:
<221> NAME/KEY: MISC_FEATURE
<222> LOCATION: (10)..(10)
<223> OTHER INFORMATION: Xaa at position 10 can be G or A
<220> FEATURE:
<221> NAME/KEY: MISC_FEATURE
<222> LOCATION: (11)..(11)
<223> OTHER INFORMATION: Xaa at position 11 can be K or A
<220> FEATURE:
<221> NAME/KEY: MISC_FEATURE
<222> LOCATION: (12)..(12)
<223> OTHER INFORMATION: Xaa at position 12 can be G or A
<220> FEATURE:
<221> NAME/KEY: MISC_FEATURE
<222> LOCATION: (13)..(13)
<223> OTHER INFORMATION: Xaa at position 13 can be R or K
<220> FEATURE:
<221> NAME/KEY: MISC_FEATURE
<222> LOCATION: (14)..(14)
<223> OTHER INFORMATION: Xaa at position 14 can be I or A
<220> FEATURE:
<221> NAME/KEY: MISC_FEATURE
<222> LOCATION: (15)..(15)
<223> OTHER INFORMATION: Xaa at position 15 can be R, K, Y, or G
<220> FEATURE:
<221> NAME/KEY: MISC_FEATURE
<222> LOCATION: (16)..(16)
<223> OTHER INFORMATION: X at position 16 can be R, K, V, T, or Y

<400> SEQUENCE: 54

Xaa Xaa Xaa Xaa Xaa Xaa Xaa Xaa Xaa Xaa Xaa Xaa Xaa Xaa Xaa Xaa
 1               5                  10                  15

<210> SEQ ID NO 55
<211> LENGTH: 16
```

```
<212> TYPE: PRT
<213> ORGANISM: Artificial
<220> FEATURE:
<223> OTHER INFORMATION: Tat peptide

<400> SEQUENCE: 55

Ser Gly Pro Arg Pro Arg Gly Thr Arg Gly Lys Gly Arg Ile Arg Arg
1               5                   10                  15

<210> SEQ ID NO 56
<211> LENGTH: 28
<212> TYPE: RNA
<213> ORGANISM: Artificial
<220> FEATURE:
<223> OTHER INFORMATION: RNA binding site consensus sequence
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (14)..(17)
<223> OTHER INFORMATION: n is a, c, g, or u
<220> FEATURE:
<221> NAME/KEY: misc_feature
<222> LOCATION: (24)..(28)
<223> OTHER INFORMATION: n is a, c, g, or u

<400> SEQUENCE: 56
nnnnnshsyw sbmnnnndsb hbsnnnnn                                          28

<210> SEQ ID NO 57
<211> LENGTH: 28
<212> TYPE: RNA
<213> ORGANISM: Artificial
<220> FEATURE:
<223> OTHER INFORMATION: TAR RNA

<400> SEQUENCE: 57 ggcucguguga gcucauuagc uccgagcc                                         28

<210> SEQ ID NO 58
<211> LENGTH: 29
<212> TYPE: RNA
<213> ORGANISM: Artificial
<220> FEATURE:
<223> OTHER INFORMATION: RNA aptamer consensus sequence
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (15)..(18)
<223> OTHER INFORMATION: n is a, c, g, or u
<220> FEATURE:
<221> NAME/KEY: misc_feature
<222> LOCATION: (25)..(29)
<223> OTHER INFORMATION: n is a, c, g, or u

<400> SEQUENCE: 58
nnnnnshcys wsbmnnnnds bhbsnnnnn                                         29

<210> SEQ ID NO 59
<211> LENGTH: 29
<212> TYPE: RNA
<213> ORGANISM: Artificial
<220> FEATURE:
<223> OTHER INFORMATION: TAR Variant-1

<400> SEQUENCE: 59
```

```
ggcucgucug agcucauuag cuccgagcc                                              29
```

<210> SEQ ID NO 60
<211> LENGTH: 28
<212> TYPE: RNA
<213> ORGANISM: Artificial
<220> FEATURE:
<223> OTHER INFORMATION: RNA aptamer consensus sequence
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (14)..(17)
<223> OTHER INFORMATION: n is a, c, g, or u
<220> FEATURE:
<221> NAME/KEY: misc_feature
<222> LOCATION: (24)..(28)
<223> OTHER INFORMATION: n is a, c, g, or u

<400> SEQUENCE: 60

```
nnnnnshysw sbmnnnndsb hbsnnnnn                                               28
```

<210> SEQ ID NO 61
<211> LENGTH: 28
<212> TYPE: RNA
<213> ORGANISM: Artificial
<220> FEATURE:
<223> OTHER INFORMATION: TAR Variant-2

<400> SEQUENCE: 61

```
ggcucguuga gcucauuagc uccgagcc                                               28
```

<210> SEQ ID NO 62
<211> LENGTH: 18
<212> TYPE: PRT
<213> ORGANISM: Artificial
<220> FEATURE:
<223> OTHER INFORMATION: destabilization domain consensus sequence
<220> FEATURE:
<221> NAME/KEY: MISC_FEATURE
<222> LOCATION: (1)..(1)
<223> OTHER INFORMATION: Xaa at position 1 can be S or A
<220> FEATURE:
<221> NAME/KEY: MISC_FEATURE
<222> LOCATION: (2)..(2)
<223> OTHER INFORMATION: Xaa at position 2 can be G or A
<220> FEATURE:
<221> NAME/KEY: MISC_FEATURE
<222> LOCATION: (3)..(3)
<223> OTHER INFORMATION: Xaa at position 3 can be P or A
<220> FEATURE:
<221> NAME/KEY: MISC_FEATURE
<222> LOCATION: (4)..(4)
<223> OTHER INFORMATION: Xaa at position 4 can be R or K
<220> FEATURE:
<221> NAME/KEY: MISC_FEATURE
<222> LOCATION: (5)..(5)
<223> OTHER INFORMATION: Xaa at position 5 can be P, A, I, Y, K, or R
<220> FEATURE:
<221> NAME/KEY: MISC_FEATURE
<222> LOCATION: (6)..(6)
<223> OTHER INFORMATION: Xaa at position 6 can be R, K, V, or Y
<220> FEATURE:
<221> NAME/KEY: MISC_FEATURE
<222> LOCATION: (7)..(7)
<223> OTHER INFORMATION: Xaa at position 7 can be G, A, or R
<220> FEATURE:
<221> NAME/KEY: MISC_FEATURE
<222> LOCATION: (8)..(8)
<223> OTHER INFORMATION: Xaa at position 8 can be T or A
<220> FEATURE:

```
<221> NAME/KEY: MISC_FEATURE
<222> LOCATION: (9)..(9)
<223> OTHER INFORMATION: Xaa at position 9 can be R or K
<220> FEATURE:
<221> NAME/KEY: MISC_FEATURE
<222> LOCATION: (10)..(10)
<223> OTHER INFORMATION: Xaa at position 10 can be G or A
<220> FEATURE:
<221> NAME/KEY: MISC_FEATURE
<222> LOCATION: (11)..(11)
<223> OTHER INFORMATION: Xaa at position 11 can be K or A
<220> FEATURE:
<221> NAME/KEY: MISC_FEATURE
<222> LOCATION: (12)..(12)
<223> OTHER INFORMATION: Xaa at position 12 can be G or A
<220> FEATURE:
<221> NAME/KEY: MISC_FEATURE
<222> LOCATION: (13)..(13)
<223> OTHER INFORMATION: Xaa at position 13 can be R or K
<220> FEATURE:
<221> NAME/KEY: MISC_FEATURE
<222> LOCATION: (14)..(14)
<223> OTHER INFORMATION: Xaa at position 14 can be I or A
<220> FEATURE:
<221> NAME/KEY: MISC_FEATURE
<222> LOCATION: (15)..(15)
<223> OTHER INFORMATION: Xaa at position 15 can be R, K, Y, or G
<220> FEATURE:
<221> NAME/KEY: MISC_FEATURE
<222> LOCATION: (16)..(16)
<223> OTHER INFORMATION: Xaa at position 16 can be R, K, V, T, or Y
<220> FEATURE:
<221> NAME/KEY: MISC_FEATURE
<222> LOCATION: (17)..(17)
<223> OTHER INFORMATION: Xaa at position 17 can be any amino acid but
      preferably R, G, E, S, or C
<220> FEATURE:
<221> NAME/KEY: MISC_FEATURE
<222> LOCATION: (18)..(18)
<223> OTHER INFORMATION: Xaa at position 18 is optional and can be any
      amino acid, but preferably G, E, O, N, D, or E

<400> SEQUENCE: 62

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 63
<211> LENGTH: 19
<212> TYPE: PRT
<213> ORGANISM: Artificial
<220> FEATURE:
<223> OTHER INFORMATION: tDeg

<400> SEQUENCE: 63

Ser Gly Pro Arg Pro Arg Gly Thr Arg Gly Lys Gly Arg Arg Ile Arg
1               5                   10                  15

Arg Arg Gly

<210> SEQ ID NO 64
<211> LENGTH: 28
<212> TYPE: DNA
<213> ORGANISM: Artificial
<220> FEATURE:
<223> OTHER INFORMATION: lentiviral Tar RNA consensus sequence
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (14)..(17)
<223> OTHER INFORMATION: n is a, c, g, or t
```

```
<220> FEATURE:
<221> NAME/KEY: misc_feature
<222> LOCATION: (24)..(28)
<223> OTHER INFORMATION: n is a, c, g, or t

<400> SEQUENCE: 64
nnnnnshsyw sbmnnnndsb hbsnnnnn                                              28

<210> SEQ ID NO 65
<211> LENGTH: 28
<212> TYPE: DNA
<213> ORGANISM: Artificial
<220> FEATURE:
<223> OTHER INFORMATION: TAR RNA

<400> SEQUENCE: 65
ggctcgtgta gctcattagc tccgagcc                                              28

<210> SEQ ID NO 66
<211> LENGTH: 29
<212> TYPE: DNA
<213> ORGANISM: Artificial
<220> FEATURE:
<223> OTHER INFORMATION: lentiviral TAR RNA consensus sequence
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (15)..(18)
<223> OTHER INFORMATION: n is a, c, g, or t
<220> FEATURE:
<221> NAME/KEY: misc_feature
<222> LOCATION: (25)..(29)
<223> OTHER INFORMATION: n is a, c, g, or t

<400> SEQUENCE: 66
nnnnnshcys wsbmnnnnds bhbsnnnnn                                             29

<210> SEQ ID NO 67
<211> LENGTH: 29
<212> TYPE: DNA
<213> ORGANISM: Artificial
<220> FEATURE:
<223> OTHER INFORMATION: TAR Variant-1

<400> SEQUENCE: 67
ggctcgtctg agctcattag ctccgagcc                                             29

<210> SEQ ID NO 68
<211> LENGTH: 28
<212> TYPE: DNA
<213> ORGANISM: Artificial
<220> FEATURE:
<223> OTHER INFORMATION: lentiviral TAR RNA consensus sequence
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (14)..(17)
<223> OTHER INFORMATION: n is a, c, g, or t
<220> FEATURE:
<221> NAME/KEY: misc_feature
<222> LOCATION: (24)..(28)
<223> OTHER INFORMATION: n is a, c, g, or t

<400> SEQUENCE: 68
```
nnnnnshysw sbmnnnndsb hbsnnnnn                                              28

<210> SEQ ID NO 69
<211> LENGTH: 28
<212> TYPE: DNA
<213> ORGANISM: Artificial
<220> FEATURE:
<223> OTHER INFORMATION: TAR Variant-2 (Pepper)

<400> SEQUENCE: 69
ggctcgttga gctcattagc tccgagcc                                              28

<210> SEQ ID NO 70
<211> LENGTH: 586
<212> TYPE: RNA
<213> ORGANISM: Artificial
<220> FEATURE:
<223> OTHER INFORMATION: (Pepper)10 tag

<400> SEQUENCE: 70
ggcucgucug agcucauuag cuccgagccg uccagcgcaa acuauuacga aaaacauccg            60
acgggcucgu ugagcucauu agcuccgagc ccgcugcgga aaaccucaca aaaacacgac           120
aaacgggcuc guugagcuca uuagcuccga gcccgccgac aacccacaaa cuuacaacca           180
ggcaaacggc ucgucugagc ucauuagcuc cgagccguau caagaccgaa cggcgcaaga           240
uauugacacg ggcucguuga gcucauuagc uccgagcccg accugcuag auauguuagg            300 uucuuaggca uggcucguu gagcucauua gcuccgagcc aaagaucgac ugcaauuccg            360
auuagacgua cacggcucgu cugagcucau uagcuccgag ccgauccaac cuacuuccuc           420
cauaacuaac cuccggcucg uugagcucau uagcuccgag ccgaucauaa cgcaauaccg           480
uacacugucc aauccggcuc guugagcuca uuagcuccga gccggacaac caaucgacau           540
acaucacacc acaacucggc ucgucugagc ucauuagcuc cgagcc                         586

<210> SEQ ID NO 71
<211> LENGTH: 1466
<212> TYPE: RNA
<213> ORGANISM: Artificial
<220> FEATURE:
<223> OTHER INFORMATION: (F30-1xPepper)10 tag

<400> SEQUENCE: 71
uugccaugug uauguggau gcguugccac guuucccaca uacucugaug auccgcuagc             60
aaaggcucgu cugagcucau uagcuccgag cccgagguac cggaucauuc auggcaaguc           120
cagcgcaauc uauuacgaaa aucauccgac gucgcgaugu cuaugcggga ugcguugcca           180
cguuucccgc auagucugau cauccgcuag caaaggcucg uugagcucau uagcuccgag           240
cccgagguac cggaugauuc aucgcgacgc ugcggaaaau cucacaaaau cacgucaaac           300 gucgccugu uguguagga ugcguugcca cguuccuac acacucugac gauccgcuag              360
caaaggcucg uugagcucau uagcuccgag cccgagguac cggaucguuc acggcgacgc           420
cgauaaucca cauacuuaca aucaggcaau cuugccaugu guauggga ugcguugcca             480 cguuucccac auacucugau gauccgcuag caaaggcucg uugagcucau uagcuccgag           540
cccgagguac cggaucauuc auggcaagua ucaagaucga acggcgcaag auauugucac           600
gucgcgaugu cuaugcggga ugcguugcca cguuucccgc auagucugau caaccgcuag           660
caaaggcucg ucuagcuca uuagcuccga gcccgaggua ccggaugauu caucgcgacg           720
uccucgcuag auauguuagg uucuuaggca uuucgccgug uguguuagg augcguugcc           780

```
acguuuccua cacacucuga cgauccgcua gcaaaggcuc guugagcuca uuagcuccga      840
gcccgaggua ccggaucguu cacgcgaaa agaucgucug caauuccgau uagacguaca      900
cuugccaugu guaugggga ugcguugcca cguuucccac auacucugau gauccgcuag      960
caaaggcucg uugagcucau uagcuccgag cccgagguac cggaucauuc auggcaagau     1020
ccaagcuacu uccuccauac cuauccuccu cgcgaugucu augcgggaug cguugccacg     1080
uuucccgcau agucugauca uccgcuagca aaggcucguu gagcucauua gcuccgagcc    1140
cgagguaccg gaugauucau cgcgagauca uaacgcaaua ccguacacug uccaauccuc    1200
gccgugugug uguaggaugc guugccacgu uccuacaca cucugacgau ccgcuagcaa     1260
aggcucgucu gagcucauua gcuccgagcc cgagguaccg gaucguucac ggcgaggaua    1320
aucaauccac auacaucaca ccacaauucu ugccaugugu augugggaug cguugccacg    1380
uuucccacau acucugauga uccgcuagca aaggcucguc ugagcucauu agcuccgagc    1440
ccgagguacc ggaucauuca uggcaa                                        1466

<210> SEQ ID NO 72
<211> LENGTH: 1228
<212> TYPE: RNA
<213> ORGANISM: Artificial
<220> FEATURE:
<223> OTHER INFORMATION: (Pepper)20 tag

<400> SEQUENCE: 72
ggcucgucug agcucauuag cuccgagccg uccagcgcaa acuauuacga aaaacauccg      60
acgggcucgu ugagcucauu agcuccgagc ccgcugcgga aaaccucaca aaaacacgac     120
aaacgggcuc guugagcuca uuagcuccga gcccgccgac aacccacaaa cuuacaacca    180
ggcaaacggc ucgucugagc ucauuagcuc cgagccguau caagaccgaa cggcgcaaga    240
uauugacacg ggcucguuga gcucauuagc uccgagcccg accucgcuag auauguuagg    300
uucuuaggca uuggcucguu gagcucauua gcuccgagcc aaagaucgac ugcaauuccg    360
auuagacgua cacggcucgu cugagcucau uagcuccgag ccgauccaac cuacuuccuc    420
cauaacuaac cuccggcucg uugagcucau uagcuccgag ccgaucauaa cgcaauaccg    480 uacacuguccc aauccggcuc guugagcuca uuagcuccga gccggacaac caaucgacau    540
acaucacacc acaacucggc ucgucugagc ucauuagcuc cgagccgaau uggucguucu    600
ucuuggcggc cgcucgacua aggugacaac uggacaaacc cucggcucgu ugagcucauu    660
agcuccgagc cgacucucac caacaagaca aaaacuacuc uucuaggcuc guugagcuca    720
uuagcuccga gccuaaacac ucaagcauac auugugccua uuucuuggcu cgucugagcu    780
cauuagcucc gagccaugcu cucacgaauu ucaaaacacg acaaggggc ucguugagcu     840 cauuagcucc gagcccguuc cacguccaau acgauuacuu accuucgggg cucguugagc    900
ucauuagcuc cgagcccgca gcuacaucac uuccacucag acauucaagg gcucgucug    960 agcucauuag cuccgagccc uccacaaguc uaaccacag aaacuaccaa augggcucgu    1020
ugagcucauu agcuccgagc ccacuccuac cucaaaccuc uucccacaaa acuggggcuc   1080
guugagcuca uuagcuccga gccccccauuc caacauacca aaucaaaaac aauuacuggc   1140
ucgucugagc ucauuagcuc cgagccagcc cacaucucuc acuacuauca aaaccaaac    1200 ggcucguuga gcucauuagc uccgagcc                                      1228

<210> SEQ ID NO 73
```

<211> LENGTH: 1812
<212> TYPE: RNA
<213> ORGANISM: Artificial
<220> FEATURE:
<223> OTHER INFORMATION: (F30-2xPepper)10 tag

<400> SEQUENCE: 73

| | | | | | |
|---|---|---|---|---|---|
| uugccaugug | uaugugggaa | gcguagaaag | gcucguugag | cucauuagcu | ccgagcccga | 60 |
| cuacguuucc | cacauacucu | gaugauccgc | uagcaaaggc | ucgucugagc | ucauuagcuc | 120 |
| cgagcccgag | guaccggauc | auucauggca | aguccagcgc | aaucuauuac | gaaaaucauc | 180 |
| cgacgucgcg | augucuaugc | gggaagcgua | gaaaggcucg | ucugagcuca | uuagccccga | 240 |
| gcccgacuac | guuucccgca | uagucugauc | auccgcuagc | aaaggcucgu | ugagcucauu | 300 |
| agcuccgagc | ccgagguacc | ggaugauuca | ucgcgacgcu | gcggaaaauc | ucacaaaauc | 360 |
| acgucaaacg | ucgccgugug | uguaggaa | gcguagaaag | gcucgucuga | gcucauuagc | 420 |
| uccgagcccg | acuacguuuc | cuacacacuc | ugacgauccg | cuagcaaagg | cucguugagc | 480 |
| ucauuagcuc | cgagcccgag | guaccggauc | guucacggcg | acgccgauaa | uccacauacu | 540 |
| acaaucagg | caaucuugcc | auguguaugu | gggaagcgua | gaaaggcucg | uugagcucau | 600 |
| uagcuccgag | cccgacuacg | uuucccacau | acucugauga | uccgcuagca | aaggcucguu | 660 |
| gagcucauua | gcuccgagcc | cgagguaccg | gaucauucau | ggcaaguauc | aagaucgaac | 720 |
| ggcgcaagau | auugucacgu | cgcgaugucu | augcgggaag | cguagaaagg | cucguugagc | 780 |
| ucauuagcuc | cgagcccgac | uacguuuccc | gcauagucug | aucauccgcu | agcaaaggcu | 840 |
| cgucugagcu | cauuagcucc | gagcccgagg | uaccggauga | uucaucgcga | cguccucgcu | 900 |
| agauauguua | gguucuuagg | cauuucgccg | ugugugugua | ggaagcguag | aaaggcucgu | 960 |
| ugagcucauu | agcuccgagc | ccgacuacgu | uuccuacaca | cucugacgau | ccgcuagcaa | 1020 |
| aggcucgucu | gagcucauua | gcuccgagcc | cgagguaccg | gaucguucac | ggcgaaaaga | 1080 |
| ucgucugcaa | uuccgauuag | acguacacuu | gccaugugua | ugugggaagc | guagaaaggc | 1140 |
| ucgucugagc | ucauuagcuc | cgagcccgac | uacguuuccc | acauacucug | augauccgcu | 1200 |
| agcaaaggcu | cguugagcuc | auuagcuccg | agcccgaggu | accggaucau | ucauggcaag | 1260 |
| auccaagcua | cuuccuccau | accuauccuc | ucgcgaugu | cuaugcggga | agcguagaaa | 1320 |
| ggcucgucug | agcucauuag | cuccgagccc | gacuacguuu | cccgcauagu | cugaucaucc | 1380 |
| gcuagcaaag | gcucguugag | cucauuagcu | ccgagcccga | gguaccggau | gauucaucgc | 1440 |
| gagaucauaa | cgcaauaccg | uacacugucc | aauccucgcc | gugugugugu | aggaagcgua | 1500 |
| gaaaggcucg | ucugagcuca | uuagccccga | gcccgacuac | guuccuaca | cacucugacg | 1560 |
| auccgcuagc | aaaggcucgu | ugagcucauu | agcuccgagc | ccgagguacc | ggaucguuca | 1620 |
| cggcgaggau | aaucaaucca | cauacaucac | accacaauuc | uugccaugug | uaugugggaa | 1680 |
| gcguagaaag | gcucgucuga | gcucauuagc | uccgagcccg | acuacguuuc | ccacauacuc | 1740 |
| ugaugauccg | cuagcaaagg | cucgucugag | cucauuagcu | ccgagcccga | gguaccggau | 1800 |
| cauucauggc | aa | | | | | 1812 |

<210> SEQ ID NO 74
<211> LENGTH: 8010
<212> TYPE: DNA
<213> ORGANISM: Artificial
<220> FEATURE:
<223> OTHER INFORMATION: pCMV-mCherry-(F30-2xPepper)10

<400> SEQUENCE: 74

-continued

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgac gcaaatgggc      780 ggtaggcgtg tacggtggga ggtctatata agcagagctc tctggctaac tagagaaccc     840
actgcttact ggcttatcga aattaatacg actcactata gggagaccca gctggctag     900 cgtttaaact taagcttgcc accatggtga gcaagggcga ggaggataac atggccatca     960
tcaaggagtt catgcgcttc aaggtgcaca tggagggctc cgtgaacggc cacgagttcg    1020
agatcgaggg cgagggcgag ggccgcccct acgagggcac ccagaccgcc aagctgaagg    1080
tgaccaaggg tggccccctg cccttcgcct gggacatcct gtcccctcag ttcatgtacg    1140
gctccaaggc ctacgtgaag caccccgccg acatccccga ctacttgaag ctgtccttcc    1200
ccgagggctt caagtgggag cgcgtgatga acttcgagga cggcggcgtg gtgaccgtga    1260
cccaggactc ctccctgcag gacggcgagt tcatctacaa ggtgaagctg cgcggcacca    1320
acttcccctc cgacggcccc gtaatgcaga agaagaccat gggctgggag gcctcctccg    1380
agcggatgta ccccgaggac ggcgccctga agggcgagat caagcagagg ctgaagctga    1440
aggacggcgg ccactacgac gctgaggtca agaccaccta caaggccaag aagcccgtgc    1500
agctgcccgg cgcctacaac gtcaacatca gttggacat cacctcccac aacgaggact    1560
acaccatcgt ggaacagtac gaacgcgccg agggccgcca ctccaccggc ggcatggacg    1620
agctgtacaa gtaactcgag atccgttacg gccggaatca atcgctaatc actcaacttg    1680
ccatgtgtat gtgggaagcg tagaaaggct cgttgagctc attagctccg agcccgacta    1740
cgtttcccac atactctgat gatccgctag caaaggctcg tctgagctca ttagctccga    1800
gcccgaggta ccggatcatt catggcaagt ccagcgcaat ctattacgaa atcatccga    1860 cgtcgcgatg tctatgcggg aagcgtagaa aggctcgtct gagctcatta gctccgagcc    1920
cgactacgtt tcccgcatag tctgatcatc cgctagcaaa ggctcgttga gctcattagc    1980
tccgagcccg aggtaccgga tgattcatcg cgacgctgcg gaaaatctca caaatcacg    2040 tcaaacgtcg ccgtgtgtgt gtaggaagcg tagaaaggct cgtctgagct cattagctcc    2100
gagcccgact acgtttccta cacactctga cgatccgcta gcaaaggctc gttgagctca    2160
ttagctccga gcccgaggta ccggatcgtt cacggcgacg ccgataatcc acatacttac    2220
aatcaggcaa tcttgccatg tgtatgtggg aagcgtagaa aggctcgttg agctcattag    2280
ctccgagccc gactacgttt cccacatact ctgatgatcc gctagcaaag gctcgttgag    2340
```

```
ctcattagct ccgagcccga ggtaccggat cattcatggc aagtatcaag atcgaacggc    2400
gcaagatatt gtcacgtcgc gatgtctatg cgggaagcgt agaaaggctc gttgagctca    2460
ttagctccga gcccgactac gtttcccgca tagtctgatc atccgctagc aaaggctcgt    2520
ctgagctcat tagctccgag cccgaggtac cggatgattc atcgcgacgt cctcgctaga    2580
tatgttaggt tcttaggcat ttcgccgtgt gtgtgtagga agcgtagaaa ggctcgttga    2640
gctcattagc tccgagcccg actacgtttc ctacacactc tgacgatccg ctagcaaagg    2700
ctcgtctgag ctcattagct ccgagcccga ggtaccggat cgttcacggc gaaaagatcg    2760
tctgcaattc cgattagacg tacacttgcc atgtgtatgt gggaagcgta gaaaggctcg    2820
tctgagctca ttagctccga gcccgactac gtttcccaca tactctgatg atccgctagc    2880
aaaggctcgt tgagctcatt agctccgagc ccgaggtacc ggatcattca tggcaagatc    2940
caagctactt cctccatacc tatcctcctc gcgatgtcta tgcgggaagc gtagaaaggc    3000
tcgtctgagc tcattagctc cgagcccgac tacgtttccc gcatagtctg atcatccgct    3060
agcaaaggct cgttgagctc attagctccg agcccgaggt accggatgat tcatcgcgag    3120
atcataacgc aataccgtac actgtccaat cctcgccgtg tgtgtgtagg aagcgtagaa    3180
aggctcgtct gagctcatta gctccgagcc cgactacgtt tcctacacac tctgacgatc    3240
cgctagcaaa ggctcgttga gctcattagc tccgagcccg aggtaccgga tcgttcacgg    3300
cgaggataat caatccacat acatcacacc acaattcttg ccatgtgtat gtgggaagcg    3360
tagaaaggct cgtctgagct cattagctcc gagcccgact acgtttccca catactctga    3420
tgatccgcta gcaaaggctc gtctgagctc attagctccg agcccgaggt accggatcat    3480
tcatggcaag aattggtcgt tcttcttggc ggccgctcga ctaaatcacc ggtaatcttc    3540
ttgtccatct agaccttata aagatctttg tacaagggcc cgtttaaacc cgctgatcag    3600
cctcgactgt gccttctagt tgccagccat ctgttgtttg cccctccccc gtgccttcct    3660
tgaccctgga aggtgccac tcccactgtc ctttcctaat aaaatgagga aattgcatcg    3720
cattgtctga gtaggtgtca ttctattctg ggggtgggg gtggggcag acagcaagg    3780 gggaggattg ggaagacaat agcaggcatg ctggggatgc ggtgggctct atggcttctg    3840
aggcggaaag aaccagctgg ggctctaggg ggtatcccca cgcgccctgt agcggcgcat    3900
taagcgcggc gggtgtggtg gttacgcgca gcgtgaccgc tacacttgcc agcgccctag    3960
cgcccgctcc tttcgctttc ttcccttcct ttctcgccac gttcgccggc tttccccgtc    4020
aagctctaaa tcgggggctc cctttagggt tccgatttag tgctttacgg cacctcgacc    4080
ccaaaaaact tgattagggt gatggttcac gtagtgggcc atcgccctga tagacggttt    4140
ttcgcccttt gacgttggag tccacgttct ttaatagtgg actcttgttc caaactggaa    4200
caacactcaa ccctatctcg gtctattctt ttgatttata agggattttg ccgatttcgg    4260
cctattggtt aaaaaatgag ctgatttaac aaaaatttaa cgcgaattaa ttctgtggaa    4320
tgtgtgtcag ttagggtgtg aaagtcccca ggctccccca gcaggcagaa gtatgcaaag    4380
catgcatctc aattagtcag caaccaggtg tggaaagtcc ccaggctccc cagcaggcag    4440
aagtatgcaa agcatgcatc tcaattagtc agcaaccata gtcccgcccc taactccgcc    4500
catcccgccc ctaactccgc ccagttccgc ccattctccg ccccatggct gactaatttt    4560
ttttatttat gcagaggccg aggccgcctc tgcctctgag ctattccaga agtagtgagg    4620 aggcttttt ggaggcctag gcttttgcaa aaagctcccg ggagcttgta tatccatttt    4680
cggatctgat caagagacag gatgaggatc gtttcgcatg attgaacaag atggattgca    4740
```

```
cgcaggttct ccggccgctt gggtggagag gctattcggc tatgactggg cacaacagac    4800
aatcggctgc tctgatgccg ccgtgttccg gctgtcagcg caggggcgcc cggttctttt    4860
tgtcaagacc gacctgtccg gtgccctgaa tgaactgcag gacgaggcag cgcggctatc    4920
gtggctggcc acgacgggcg ttccttgcgc agctgtgctc gacgttgtca ctgaagcggg    4980
aagggactgg ctgctattgg gcgaagtgcc ggggcaggat ctcctgtcat ctcaccttgc    5040
tcctgccgag aaagtatcca tcatggctga tgcaatgcgg cggctgcata cgcttgatcc    5100
ggctacctgc ccattcgacc accaagcgaa acatcgcatc gagcgagcac gtactcggat    5160
ggaagccggt cttgtcgatc aggatgatct ggacgaagag catcagggc tcgcgccagc    5220 cgaactgttc gccaggctca aggcgcgcat gcccgacggc gaggatctcg tcgtgaccca    5280
tggcgatgcc tgcttgccga atatcatggt ggaaaatggc cgcttttctg gattcatcga    5340
ctgtggccgg ctgggtgtgg cggaccgcta tcaggacata gcgttggcta cccgtgatat    5400
tgctgaagag cttggcggcg aatgggctga ccgcttcctc gtgctttacg gtatcgccgc    5460
tcccgattcg cagcgcatcg ccttctatcg ccttcttgac gagttcttct gagcgggact    5520
ctggggttca aaatgaccga ccaagcgacg cccaacctgc catcacgaga tttcgattcc    5580
accgccgcct tctatgaaag gttgggcttc ggaatcgttt tccgggacgc cggctggatg    5640
atcctccagc gcggggatct catgctggag ttcttcgccc accccaactt gtttattgca    5700
gcttataatg gttacaaata aagcaatagc atcacaaatt tcacaaataa agcatttttt    5760
tcactgcatt ctagttgtgg tttgtccaaa ctcatcaatg tatcttatca gtctgtata    5820 ccgtcgacct ctagctagag cttggcgtaa tcatggtcat agctgtttcc tgtgtgaaat    5880
tgttatccgc tcacaattcc acacaacata cgagccggaa gcataaagtg taaagcctgg    5940
ggtgcctaat gagtgagcta actcacatta attgcgttgc gctcactgcc cgcttttccag   6000 tcgggaaacc tgtcgtgcca gctgcattaa tgaatcggcc aacgcgcggg gagaggcggt    6060
ttgcgtattg ggcgctcttc cgcttcctcg ctcactgact cgctgcgctc ggtcgttcgg    6120
ctgcggcgag cggtatcagc tcactcaaag gcggtaatac ggttatccac agaatcaggg    6180
gataacgcag gaaagaacat gtgagcaaaa ggccagcaaa aggccaggaa ccgtaaaaag    6240
gccgcgttgc tggcgttttt ccataggctc cgcccccctg acgagcatca caaaaatcga    6300
cgctcaagtc agaggtggcg aaacccgaca ggactataaa gataccaggc gtttccccct    6360
ggaagctccc tcgtgcgctc tcctgttccg accctgccgc ttaccggata cctgtccgcc    6420
tttctccctt cgggaagcgt ggcgctttct catagctcac gctgtaggta tctcagttcg    6480
gtgtaggtcg ttcgctccaa gctgggctgt gtgcacgaac cccccgttca gcccgaccgc    6540
tgcgccttat ccggtaacta tcgtcttgag tccaacccgg taagacacga cttatcgcca    6600
ctggcagcag ccactggtaa caggattagc agagcgaggt atgtaggcgg tgctacagag    6660
ttcttgaagt ggtggcctaa ctacggctac actagaagaa cagtatttgg tatctgcgct    6720
ctgctgaagc cagttacctt cggaaaaaga gttggtagct cttgatccgg caaacaaacc    6780
accgctggta gcggtttttt tgtttgcaag cagcagatta cgcgcagaaa aaaaggatct    6840
caagaagatc ctttgatctt ttctacgggg tctgacgctc agtggaacga aaactcacgt    6900
taagggattt tggtcatgag attatcaaaa aggatcttca cctagatcct ttaaattaa    6960 aaatgaagtt ttaaatcaat ctaaagtata tatgagtaaa cttggtctga cagttaccaa    7020
tgcttaatca gtgaggcacc tatctcagcg atctgtctat ttcgttcatc catagttgcc    7080
```

| | |
|---|---|
| tgactccccg tcgtgtagat aactacgata cgggagggct taccatctgg ccccagtgct | 7140 |
| gcaatgatac cgcgagaccc acgctcaccg gctccagatt tatcagcaat aaaccagcca | 7200 |
| gccggaaggg ccgagcgcag aagtggtcct gcaactttat ccgcctccat ccagtctatt | 7260 |
| aattgttgcc gggaagctag agtaagtagt tcgccagtta atagtttgcg caacgttgtt | 7320 |
| gccattgcta caggcatcgt ggtgtcacgc tcgtcgtttg gtatggcttc attcagctcc | 7380 |
| ggttcccaac gatcaaggcg agttacatga tcccccatgt tgtgcaaaaa agcggttagc | 7440 |
| tccttcggtc ctccgatcgt tgtcagaagt aagttggccg cagtgttatc actcatggtt | 7500 |
| atggcagcac tgcataattc tcttactgtc atgccatccg taagatgctt ttctgtgact | 7560 |
| ggtgagtact caaccaagtc attctgagaa tagtgtatgc ggcgaccgag ttgctcttgc | 7620 |
| ccggcgtcaa tacgggataa taccgcgcca catagcagaa ctttaaaagt gctcatcatt | 7680 |
| ggaaaacgtt cttcggggcg aaaactctca aggatcttac cgctgttgag atccagttcg | 7740 |
| atgtaaccca ctcgtgcacc caactgatct tcagcatctt ttactttcac cagcgtttct | 7800 |
| gggtgagcaa aaacaggaag gcaaaatgcc gcaaaaaagg gaataagggc gacacggaaa | 7860 |
| tgttgaatac tcatactctt cctttttcaa tattattgaa gcatttatca gggttattgt | 7920 |
| ctcatgagcg gatacatatt tgaatgtatt tagaaaaata aacaataggg gttccgcgc | 7980 |
| acatttcccc gaaaagtgcc acctgacgtc | 8010 |

<210> SEQ ID NO 75
<211> LENGTH: 7762
<212> TYPE: DNA
<213> ORGANISM: Artificial
<220> FEATURE:
<223> OTHER INFORMATION: pminiCMV-(mNeonGreen)4-tDeg

<400> SEQUENCE: 75

| | |
|---|---|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttggtagg | 240 |
| cgtgtacggt gggaggccta tataagcaga gctaagcttg ccaccatggt gagcaagggc | 300 |
| gaggaggata acatggcctc tctcccagcg acacatgagt tacacatctt tggctccatc | 360 |
| aacggtgtgg actttgacat ggtgggtcag ggcaccggca atccaaatga tggttatgag | 420 |
| gagttaaacc tgaagtccac caagggtgac ctccagttct cccctggat tctggtccct | 480 |
| catatcgggt atggcttcca tcagtacctg ccctaccctg acgggatgtc gcctttccag | 540 |
| gccgccatgg tagatggctc cggataccaa gtccatcgca caatgcagtt tgaagatggt | 600 |
| gcctcctta ctgttaacta ccgctacacc tacgagggaa gccacatcaa aggagaggcc | 660 |
| caggtgaagg ggactggttt ccctgctgac ggtcctgtga tgaccaactc gctgaccgct | 720 |
| gcggactggt gcaggtcgaa gaagacttac cccaacgaca aaaccatcat cagtaccttt | 780 |
| aagtggagtt acaccactgg aaatggcaag cgctaccgga gcactgcgcg gaccacctac | 840 |
| acctttgcca agccaatggc ggctaactat ctgaagaacc agccgatgta cgtgttccgt | 900 |
| aagacggagc tcaagcactc caagaccgag ctcaacttca aggagtggca aaaggccttt | 960 |
| accgatgtga tggcatgga cgagctgtac aagggtggac atatgggcac agggtccaca | 1020 |
| ggcggtaccg gcgagtttc caaggagaa gaagacaata tggcatcact ccccgcaacc | 1080 |
| cacgagttgc atattttcgg ttcaattaat ggagtagatt tcgatatggt tggccaggga | 1140 |

```
acaggaaacc caaacgacgg atatgaagag cttaatctca aaagtaccaa aggcgatctg   1200 caatttctc cgtggatact cgtgccacac attggatacg gatttcacca atatctcccg   1260
tatccggatg aatgtcccc ctttcaagca gcaatggtgg acgggagtgg ttatcaggta   1320
cacagaacca tgcagttcga ggacggggct tctctgaccg taaattatag gtatacttat   1380
gaaggctcac atattaaggg cgaagcacag gttaaggaa ccgggtttcc tgcggatggc   1440
cccgtcatga ctaattctct gacagccgca gattggtgtc gctccaaaaa gacatacccg   1500
aatgataaga ctataatctc aacattcaaa tggtcctata cgacaggcaa cgggaaacga   1560
tatagatcca cggctcgaac aacttacaca ttcgctaaac ctatggccgc caattacctc   1620
aaaaatcagc ccatgtatgt gtttaggaaa accgaattga agcattctaa acggaactt    1680 aattttaagg aatggcagaa ggctttcaca gacgtaatgg ggatggatga actctataaa   1740
tcaggtctcg agtcctcagg gggaacgggt gggtccggag gagttagtaa aggtgaagag   1800
gacaatatgg caagtttgcc tgcgactcac gagcttcata tctttgggtc tataaatggc   1860
gttgacttcg atatggttgg ccaaggtact ggcaacccca atgacggtta cgaggagttg   1920
aatctcaagt ccacaaaagg tgatcttcag ttcagccctt ggattctcgt acctcatatt   1980
ggatatggct ttcaccagta ccttccatac ccagacggta tgtcacccctt tcaagctgcg   2040 atggtggatg gttccggcta tcaggtccac cgaacgatgc aattcgagga cggggccagc   2100
ctcaccgtta attataggta cacctatgag ggaagtcaca taagggaga agcccaagtg   2160 aaaggaacag gattcccagc tgatggtcca gtaatgacga actccttgac agcggctgac   2220
tggtgtagaa gcaaaaagac gtatcctaat gacaagacca tcattagcac tttcaaatgg   2280
agttatacca caggaaacgg caaacggtac agaagcactg ctagaactac ctacactttc   2340
gcaaagccga tggctgcaaa ctatttgaag aatcagccca tgtacgtgtt tcgaaaaacg   2400
gaacttaagc acagtaagac tgaacttaat ttcaaggagt ggcagaaggc gttcacggat   2460
gtcatgggta tggatgaact gtataaggga gggtctggca ctggggcac tgccagcagc   2520 ggatccggtg gcggtgtgag caagggcgag gaggataaca tggcctctct cccagcgaca   2580
catgagttac acatctttgg ctccatcaac ggtgtggact ttgacatggt gggtcagggc   2640
accggcaatc caaatgatgg ttatgaggag ttaaacctga gtccaccaa gggtgacctc   2700 cagttctccc cctggattct ggtccctcat atcgggtatg gcttccatca gtacctgccc   2760
taccctgacg ggatgtcgcc tttccaggcc gccatggtag atggctccgg ataccaagtc   2820
catcgcacaa tgcagtttga agatggtgcc tcccttactg ttaactaccg ctacacctac   2880
gagggaagcc acatcaaagg agaggcccag gtgaagggga ctggtttccc tgctgacggt   2940
cctgtgatga ccaactcgct gaccgctgcg gactggtgca ggtcgaagaa gcttacccc    3000 aacgacaaaa ccatcatcag tacctttaag tggagttaca ccactggaaa tggcaagcgc   3060
taccggagca ctgcgcggac cacctacacc tttgccaagc caatggcggc taactatctg   3120
aagaaccagc cgatgtacgt gttccgtaag acggagctca agcactccaa gaccgagctc   3180
aacttcaagg agtggcaaaa ggcctttacc gatgtgatgg gcatggacga gctgtacaag   3240
ggcggaagat ccggtggtgg ttctggtcct cgtcccgtg gtactcgtgg taaaggtcgc   3300
cgtattcgtc gccgcggtta atctagaggg cccgtttaaa cccgctgatc agcctcgact   3360
gtgccttcta gttgccagcc atctgttgtt tgccctccc ccgtgccttc cttgaccctg    3420
gaaaggtgcc actcccactg tcctttccta ataaaatgag gaaattgcat cgcattgtct   3480
```

```
gagtaggtgt cattctattc tgggggtgg gggtggggc aggacagcaa gggggaggat   3540
tgggaagaca atagcaggca tgctggggat gcggtgggct ctatggcttc tgaggcggaa   3600
agaaccagct ggggctctag ggggtatccc cacgcgccct gtagcggcgc attaagcgcg   3660
gcgggtgtgg tggttacgcg cagcgtgacc gctacacttg ccagcgccct agcgcccgct   3720
cctttcgctt tcttcccttc ctttctcgcc acgttcgccg gctttccccg tcaagctcta   3780 aatcggggc tcccttttagg gttccgattt agtgctttac ggcacctcga ccccaaaaaa   3840
cttgattagg gtgatggttc acgtagtggg ccatcgccct gatagacggt ttttcgccct   3900
ttgacgttgg agtccacgtt ctttaatagt ggactcttgt tccaaactgg aacaacactc   3960
aaccctatct cggtctattc ttttgattta aagggattt tgccgatttc ggcctattgg   4020 ttaaaaatg agctgattta acaaaaattt aacgcgaatt aattctgtgg aatgtgtgtc   4080
agttagggtg tggaaagtcc ccaggctccc cagcaggcag aagtatgcaa agcatgcatc   4140
tcaattagtc agcaaccagg tgtggaaagt ccccaggctc cccagcaggc agaagtatgc   4200
aaagcatgca tctcaattag tcagcaacca tagtcccgcc cctaactccg cccatcccgc   4260
ccctaactcc gcccagttcc gcccattctc cgccccatgg ctgactaatt ttttttattt   4320
atgcagaggc cgaggccgcc tctgcctctg agctattcca gaagtagtga ggaggctttt   4380
ttggaggcct aggcttttgc aaaaagctcc cggagcttg tatatccatt ttcggatctg   4440
atcaagagac aggatgagga tcgtttcgca tgattgaaca agatggattg cacgcaggtt   4500
ctccggccgc ttgggtggag aggctattcg gctatgactg ggcacaacag acaatcggct   4560
gctctgatgc cgccgtgttc cggctgtcag cgcaggggcg cccggttctt tttgtcaaga   4620
ccgacctgtc cggtgccctg aatgaactgc aggacgaggc agcgcggcta tcgtggctgg   4680
ccacgacggg cgttccttgc gcagctgtgc tcgacgttgt cactgaagcg ggaagggact   4740
ggctgctatt gggcgaagtg ccggggcagg atctcctgtc atctcacctt gctcctgccg   4800
agaaagtatc catcatggct gatgcaatgc ggcggctgca tacgcttgat ccggctacct   4860
gcccattcga ccaccaagcg aaacatcgca tcgagcgagc acgtactcgg atggaagccg   4920
gtcttgtcga tcaggatgat ctggacgaag agcatcaggg gctcgcgcca gccgaactgt   4980
tcgccaggct caaggcgcgc atgcccgacg gcgaggatct cgtcgtgacc catggcgatg   5040
cctgcttgcc gaatatcatg gtggaaaatg gccgcttttc tggattcatc gactgtggcc   5100
ggctgggtgt ggcggaccgc tatcaggaca tagcgttggc tacccgtgat attgctgaag   5160
agcttggcgg cgaatgggct gaccgcttcc tcgtgcttta cggtatcgcc gctcccgatt   5220
cgcagcgcat cgccttctat cgccttcttg acgagttctt ctgagcggga ctctgggtt   5280 cgaaatgacc gaccaagcga cgcccaacct gccatcacga gatttcgatt ccaccgccgc   5340
cttctatgaa aggttgggct tcggaatcgt tttccgggac gccggctgga tgatcctcca   5400 gcgcgggat ctcatgctgg agttcttcgc ccaccccaac ttgtttattg cagcttataa   5460
tggttacaaa taaagcaata gcatcacaaa tttcacaaat aaagcatttt tttcactgca   5520
ttctagttgt ggtttgtcca aactcatcaa tgtatcttat catgtctgta taccgtcgac   5580
ctctagctag agcttggcgt aatcatggtc atagctgttt cctgtgtgaa attgttatcc   5640
gctcacaatt ccacacaaca tacgagccgg aagcataaag tgtaaagcct ggggtgccta   5700
atgagtgagc taactcacat taattgcgtt gcgctcactg cccgctttcc agtcgggaaa   5760
cctgtcgtgc cagctgcatt aatgaatcgg ccaacgcgcg gggagaggcg gtttgcgtat   5820
tgggcgctct tccgcttcct cgctcactga ctcgctgcgc tcggtcgttc ggctgcggcg   5880
```

```
agcggtatca gctcactcaa aggcggtaat acggttatcc acagaatcag gggataacgc      5940
aggaaagaac atgtgagcaa aaggccagca aaaggccagg aaccgtaaaa aggccgcgtt      6000
gctggcgttt ttccataggc tccgcccccc tgacgagcat cacaaaaatc gacgctcaag      6060
tcagaggtgg cgaaacccga caggactata aagataccag gcgttccccc tggaagctc       6120
cctcgtgcgc tctcctgttc cgaccctgcc gcttaccgga tacctgtccg cctttctccc      6180
ttcgggaagc gtggcgcttt ctcatagctc acgctgtagg tatctcagtt cggtgtaggt      6240
cgttcgctcc aagctgggct gtgtgcacga accccccgtt cagcccgacc gctgcgcctt      6300
atccggtaac tatcgtcttg agtccaaccc ggtaagacac gacttatcgc cactggcagc      6360
agccactggt aacaggatta gcagagcgag gtatgtaggc ggtgctacag agttcttgaa      6420
gtggtggcct aactacggct acactagaag aacagtattt ggtatctgcg ctctgctgaa      6480
gccagttacc ttcggaaaaa gagttggtag ctcttgatcc ggcaaacaaa ccaccgctgg      6540
tagcggtttt tttgtttgca agcagcagat tacgcgcaga aaaaaaggat ctcaagaaga      6600
tcctttgatc ttttctacgg ggtctgacgc tcagtggaac gaaaactcac gttaagggat      6660
tttggtcatg agattatcaa aaaggatctt cacctagatc cttttaaatt aaaaatgaag      6720
ttttaaatca atctaaagta tatatgagta aacttggtct gacagttacc aatgcttaat      6780
cagtgaggca cctatctcag cgatctgtct atttcgttca tccatagttg cctgactccc      6840
cgtcgtgtag ataactacga tacgggaggg cttaccatct ggccccagtg ctgcaatgat      6900
accgcgagac ccacgctcac cggctccaga tttatcagca ataaaccagc cagccggaag      6960
ggccgagcgc agaagtggtc ctgcaacttt atccgcctcc atccagtcta ttaattgttg      7020
ccgggaagct agagtaagta gttcgccagt taatagtttg cgcaacgttg ttgccattgc      7080
tacaggcatc gtggtgtcac gctcgtcgtt tggtatggct tcattcagct ccggttccca      7140
acgatcaagg cgagttacat gatcccccat gttgtgcaaa aaagcggtta gctccttcgg      7200
tcctccgatc gttgtcagaa gtaagttggc cgcagtgtta tcactcatgg ttatggcagc      7260
actgcataat tctcttactg tcatgccatc cgtaagatgc ttttctgtga ctggtgagta      7320
ctcaaccaag tcattctgag aatagtgtat gcggcgaccg agttgctctt gcccggcgtc      7380
aatacgggat aataccgcgc cacatagcag aactttaaaa gtgctcatca ttggaaaacg      7440
ttcttcgggg cgaaaactct caaggatctt accgctgttg agatccagtt cgatgtaacc      7500
cactcgtgca cccaactgat cttcagcatc ttttactttc accagcgttt ctgggtgagc      7560
aaaaacagga aggcaaaatg ccgcaaaaaa gggaataagg gcgacacgga aatgttgaat      7620
actcatactc ttcctttttc aatattattg aagcatttat cagggttatt gtctcatgag      7680
cggatacata tttgaatgta tttagaaaaa taaacaaata ggggttccgc gcacatttcc      7740
ccgaaaagtg ccacctgacg tc                                              7762

<210> SEQ ID NO 76
<211> LENGTH: 8130
<212> TYPE: DNA
<213> ORGANISM: Artificial
<220> FEATURE:
<223> OTHER INFORMATION: pCMV-CytERM-mCherry-(F30-2xPepper)10

<400> SEQUENCE: 76
gacggatcgg gagatctccc gatccctat ggtgcactct cagtacaatc tgctctgatg        60
ccgcatagtt aagccagtat ctgctccctg cttgtgtgtt ggaggtcgct gagtagtgcg       120
```

```
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgac gcaaatgggc     780
ggtaggcgtg tacggtggga ggtctatata agcagagctc tctggctaac tagagaaccc    840
actgcttact ggcttatcga aattaatacg actcactata gggagaccca agctggctag    900
cgtttaaact tgccaccatg gaccctgtgg tggtgctggg gctctgtctc tcctgtttgc    960
ttctcctttc actctggaaa cagagctatg ggggagggaa actgggcgga agcggaggga   1020
cgggggggttc aggaacttca gggggtgtga gcaagggcga ggaggataac atggccatca   1080
tcaaggagtt catgcgcttc aaggtgcaca tggagggctc cgtgaacggc cacgagttcg   1140
agatcgaggg cgagggcgag ggccgcccct acgagggcac ccagaccgcc aagctgaagg   1200
tgaccaaggg tggccccctg cccttcgcct gggacatcct gtcccctcag ttcatgtacg   1260
gctccaaggc ctacgtgaag caccccgccg acatccccga ctacttgaag ctgtccttcc   1320
ccgagggctt caagtgggag cgcgtgatga acttcgagga cggcggcgtg gtgaccgtga   1380
cccaggactc ctccctgcag gacggcgagt tcatctacaa ggtgaagctg cgcggcacca   1440
acttcccctc cgacggcccc gtaatgcaga gaagaccat gggctgggag gcctcctccg   1500
agcggatgta ccccgaggac ggcgccctga agggcgagat caagcagagg ctgaagctga   1560
aggacggcgg ccactacgac gctgaggtca agaccaccta caaggccaag aagcccgtgc   1620
agctgcccgg cgcctacaac gtcaacatca gttggacat cacctcccac aacgaggact   1680
acaccatcgt ggaacagtac gaacgcgccg agggccgcca ctccaccggc ggcatggacg   1740
agctgtacaa gtaactcgag atccgttacg gccggaatca atcgctaatc actcaacttg   1800
ccatgtgtat gtgggaagcg tagaaaggct cgttgagctc attagctccg agcccgacta   1860
cgtttcccac atactctgat gatccgctag caaaggctcg tctgagctca ttagctccga   1920
gcccgaggta ccggatcatt catggcaagt ccagcgcaat ctattacgaa atcatccga    1980
cgtcgcgatg tctatgcggg aagcgtagaa aggctcgtct gagctcatta gctccgagcc   2040
cgactacgtt tcccgcatag tctgatcatc cgctagcaaa ggctcgttga gctcattagc   2100
tccgagcccg aggtaccgga tgattcatcg cgacgctgcg aaaatctca caaaatcacg    2160
tcaaacgtcg ccgtgtgtgt gtaggaagcg tagaaaggct cgtctgagct cattagctcc   2220
gagcccgact acgtttccta cacactctga cgatccgcta gcaaaggctc gttgagctca   2280
ttagctccga gcccgaggta ccggatcgtt cacggcgacg ccgataatcc acatacttac   2340
aatcaggcaa tcttgccatg tgtatgtggg aagcgtagaa aggctcgttg agctcattag   2400
ctccgagccc gactacgttt cccacatact ctgatgatcc gctagcaaag gctcgttgag   2460
ctcattagct ccgagcccga ggtaccggat cattcatggc aagtatcaag atcgaacggc   2520
```

```
gcaagatatt gtcacgtcgc gatgtctatg cgggaagcgt agaaaggctc gttgagctca   2580
ttagctccga gcccgactac gtttcccgca tagtctgatc atccgctagc aaaggctcgt   2640
ctgagctcat tagctccgag cccgaggtac cggatgattc atcgcgacgt cctcgctaga   2700
tatgttaggt tcttaggcat ttcgccgtgt gtgtgtagga agcgtagaaa ggctcgttga   2760
gctcattagc tccgagcccg actacgtttc ctacacactc tgacgatccg ctagcaaagg   2820
ctcgtctgag ctcattagct ccgagcccga ggtaccggat cgttcacggc gaaagatcg    2880 tctgcaattc cgattagacg tacacttgcc atgtgtatgt gggaagcgta gaaaggctcg   2940
tctgagctca ttagctccga gcccgactac gtttcccaca tactctgatg atccgctagc   3000
aaaggctcgt tgagctcatt agctccgagc ccgaggtacc ggatcattca tggcaagatc   3060
caagctactt cctccatacc tatcctcctc gcgatgtcta tgcgggaagc gtagaaaggc   3120
tcgtctgagc tcattagctc cgagcccgac tacgtttccc gcatagtctg atcatccgct   3180
agcaaaggct cgttgagctc attagctccg agcccgaggt accggatgat tcatcgcgag   3240
atcataacgc aataccgtac actgtccaat cctcgccgtg tgtgtgtagg aagcgtagaa   3300
aggctcgtct gagctcatta gctccgagcc cgactacgtt tcctacacac tctgacgatc   3360
cgctagcaaa ggctcgttga gctcattagc tccgagcccg aggtaccgga tcgttcacgg   3420
cgaggataat caatccacat acatcacacc acaattcttg ccatgtgtat gtgggaagcg   3480
tagaaaggct cgtctgagct cattagctcc gagcccgact acgtttccca catactctga   3540
tgatccgcta gcaaaggctc gtctgagctc attagctccg agcccgaggt accggatcat   3600
tcatggcaag aattggtcgt tcttcttggc ggccgctcga ctaaatcacc ggtaatcttc   3660
ttgtccatct agaccttata aagatctttg tacaagggcc cgtttaaacc cgctgatcag   3720
cctcgactgt gccttctagt tgccagccat ctgttgtttg cccctccccc gtgccttcct   3780
tgaccctgga aggtgccac tcccactgtc ctttcctaat aaaatgagga aattgcatcg    3840
cattgtctga gtaggtgtca ttctattctg ggggtgggg gtggggggcag acagcaagg    3900 gggaggattg ggaagacaat agcaggcatg ctggggatgc ggtgggctct atggcttctg   3960
aggcggaaag aaccagctgg ggctctaggg ggtatcccca cgcgccctgt agcggcgcat   4020
taagcgcggc gggtgtggtg gttacgcgca gcgtgaccgc tacacttgcc agcgccctag   4080
cgcccgctcc tttcgctttc ttcccttcct ttctcgccac gttcgccggc tttccccgtc   4140
aagctctaaa tcggggggctc cctttagggt tccgatttag tgctttacgg cacctcgacc   4200
ccaaaaaact tgattagggt gatggttcac gtagtgggcc atcgccctga tagacggttt   4260
ttcgcccttt gacgttggag tccacgttct ttaatagtgg actcttgttc caaactggaa   4320
caacactcaa ccctatctcg gtctattctt ttgatttata agggattttg ccgatttcgg   4380
cctattggtt aaaaaatgag ctgatttaac aaaaatttaa cgcgaattaa ttctgtggaa   4440
tgtgtgtcag ttagggtgtg gaaagtcccc aggctcccca gcaggcagaa gtatgcaaag   4500
catgcatctc aattagtcag caaccaggtg tggaaagtcc ccaggctccc cagcaggcag   4560
aagtatgcaa agcatgcatc tcaattagtc agcaaccata gtcccgcccc taactccgcc   4620
catcccgccc ctaactccgc ccagttccgc ccattctccg ccccatggct gactaatttt   4680
ttttatttat gcagaggccg aggccgcctc tgcctctgag ctattccaga agtagtgagg   4740
aggctttttt ggaggcctag gcttttgcaa aaagctcccg ggagcttgta tatccatttt   4800
cggatctgat caagagacag gatgaggatc gtttcgcatg attgaacaag atggattgca   4860
```

-continued

```
cgcaggttct ccggccgctt gggtggagag gctattcggc tatgactggg cacaacagac    4920
aatcggctgc tctgatgccg ccgtgttccg gctgtcagcg caggggcgcc cggttctttt    4980
tgtcaagacc gacctgtccg gtgccctgaa tgaactgcag gacgaggcag cgcggctatc    5040
gtggctggcc acgacgggcg ttccttgcgc agctgtgctc gacgttgtca ctgaagcggg    5100
aagggactgg ctgctattgg gcgaagtgcc ggggcaggat ctcctgtcat ctcaccttgc    5160
tcctgccgag aaagtatcca tcatggctga tgcaatgcgg cggctgcata cgcttgatcc    5220
ggctacctgc ccattcgacc accaagcgaa acatcgcatc gagcgagcac gtactcggat    5280
ggaagccggt cttgtcgatc aggatgatct ggacgaagag catcaggggc tcgcgccagc    5340
cgaactgttc gccaggctca aggcgcgcat gcccgacggc gaggatctcg tcgtgaccca    5400
tggcgatgcc tgcttgccga atatcatggt ggaaaatggc cgcttttctg gattcatcga    5460
ctgtggccgg ctgggtgtgg cggaccgcta tcaggacata gcgttggcta cccgtgatat    5520
tgctgaagag cttggcggcg aatgggctga ccgcttcctc gtgctttacg gtatcgccgc    5580
tcccgattcg cagcgcatcg ccttctatcg ccttcttgac gagttcttct gagcgggact    5640
ctggggttcg aaatgaccga ccaagcgacg cccaacctgc catcacgaga tttcgattcc    5700
accgccgcct tctatgaaag gttgggcttc ggaatcgttt tccgggacgc cggctggatg    5760
atcctccagc gcgggatct catgctggag ttcttcgccc accccaactt gtttattgca    5820
gcttataatg gttacaaata aagcaatagc atcacaaatt tcacaaataa agcatttttt    5880
tcactgcatt ctagttgtgg tttgtccaaa ctcatcaatg tatcttatca tgtctgtata    5940
ccgtcgacct ctagctagag cttggcgtaa tcatggtcat agctgtttcc tgtgtgaaat    6000
tgttatccgc tcacaattcc acacaacata cgagccggaa gcataaagtg taaagcctgg    6060
ggtgcctaat gagtgagcta actcacatta attgcgttgc gctcactgcc cgctttccag    6120
tcgggaaacc tgtcgtgcca gctgcattaa tgaatcggcc aacgcgcggg gagaggcggt    6180
ttgcgtattg ggcgctcttc cgcttcctcg ctcactgact cgctgcgctc ggtcgttcgg    6240
ctgcggcgag cggtatcagc tcactcaaag gcggtaatac ggttatccac agaatcaggg    6300
gataacgcag gaaagaacat gtgagcaaaa ggccagcaaa aggccaggaa ccgtaaaaag    6360
gccgcgttgc tggcgttttt ccataggctc cgcccccctg acgagcatca caaaaatcga    6420
cgctcaagtc agaggtggcg aaacccgaca ggactataaa gataccaggc gtttccccct    6480
ggaagctccc tcgtgcgctc tcctgttccg accctgccgc ttaccggata cctgtccgcc    6540
tttctccctt cgggaagcgt ggcgctttct catagctcac gctgtaggta tctcagttcg    6600
gtgtaggtcg ttcgctccaa gctgggctgt gtgcacgaac ccccgttca gcccgaccgc    6660 tgcgccttat ccggtaacta tcgtcttgag tccaacccgg taagacacga cttatcgcca    6720
ctggcagcag ccactggtaa caggattagc agagcgaggt atgtaggcgg tgctacagag    6780
ttcttgaagt ggtggcctaa ctacggctac actagaagaa cagtatttgg tatctgcgct    6840
ctgctgaagc cagttacctt cggaaaaaga gttggtagct cttgatccgg caaacaaacc    6900
accgctggta gcggtttttt tgtttgcaag cagcagatta cgcgcagaaa aaaggatct    6960 caagaagatc ctttgatctt ttctacgggg tctgacgctc agtggaacga aaactcacgt    7020
taagggattt tggtcatgag attatcaaaa aggatcttca cctagatcct tttaaattaa    7080
aaatgaagtt ttaaatcaat ctaaagtata tatgagtaaa cttggtctga cagttaccaa    7140
tgcttaatca gtgaggcacc tatctcagcg atctgtctat ttcgttcatc catagttgcc    7200
tgactccccg tcgtgtagat aactacgata cgggagggct taccatctgg ccccagtgct    7260
```
gcaatgatac cgcgagaccc acgctcaccg gctccagatt tatcagcaat aaaccagcca    7320
gccggaaggg ccgagcgcag aagtggtcct gcaactttat ccgcctccat ccagtctatt    7380
aattgttgcc gggaagctag agtaagtagt tcgccagtta atagtttgcg caacgttgtt    7440
gccattgcta caggcatcgt ggtgtcacgc tcgtcgtttg gtatggcttc attcagctcc    7500
ggttcccaac gatcaaggcg agttacatga tcccccatgt tgtgcaaaaa agcggttagc    7560
tccttcggtc ctccgatcgt tgtcagaagt aagttggccg cagtgttatc actcatggtt    7620
atggcagcac tgcataattc tcttactgtc atgccatccg taagatgctt ttctgtgact    7680
ggtgagtact caaccaagtc attctgagaa tagtgtatgc ggcgaccgag ttgctcttgc    7740
ccggcgtcaa tacgggataa taccgcgcca catagcagaa ctttaaaagt gctcatcatt    7800
ggaaaacgtt cttcggggcg aaaactctca aggatcttac cgctgttgag atccagttcg    7860
atgtaaccca ctcgtgcacc caactgatct tcagcatctt ttactttcac cagcgtttct    7920
gggtgagcaa aaacaggaag gcaaaatgcc gcaaaaaagg gaataagggc gacacggaaa    7980
tgttgaatac tcatactctt cctttttcaa tattattgaa gcatttatca gggttattgt    8040
ctcatgagcg gatacatatt tgaatgtatt tagaaaaata acaaataggg gttccgcgc    8100 acatttcccc gaaaagtgcc acctgacgtc                                    8130

<210> SEQ ID NO 77
<211> LENGTH: 8122
<212> TYPE: DNA
<213> ORGANISM: Artificial
<220> FEATURE:
<223> OTHER INFORMATION: pUbC-(mNeonGreen)4-tDeg

<400> SEQUENCE: 77
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttggcctc     240
cgcgccgggt tttggcgcct cccgcgggcg ccccctcct cacggcgagc gctgccacgt     300
cagacgaagg gcgcagcgag cgtcctgatc cttccgcccg gacgctcagg acagcggccc     360
gctgctcata agactcggcc ttagaacccc agtatcagca aaggacatt ttaggacggg     420 acttgggtga ctctagggca ctggttttct ttccagagag cggaacaggc gaggaaaagt     480
agtcccttct cggcgattct gcggagggat ctccgtgggg cggtgaacgc cgatgattat     540
ataaggacgc gccgggtgtg gcacagctag ttccgtcgca gccgggattt gggtcgcggt     600 tcttgttgt ggatcgctgt gatcgtcact tggaagcttg ccaccatggt gagcaagggc      660
gaggaggata acatggcctc tctcccagcg acacatgagt tacacatctt ggctccatc      720 aacggtgtgg actttgacat ggtgggtcag ggcaccggca atccaaatga tggttatgag      780
gagttaaacc tgaagtccac caagggtgac ctccagttct cccctggat tctggtccct     840 catatcgggt atggcttcca tcagtacctg ccctaccctg acgggatgtc gcctttccag     900
gccgccatgg tagatggctc cggataccaa gtccatcgca caatgcagtt tgaagatggt     960
gcctccctta ctgttaacta ccgctacacc tacgagggaa gccacatcaa aggagaggcc    1020
caggtgaagg ggactggttt ccctgctgac ggtcctgtga tgaccaactc gctgaccgct    1080
gcggactggt gcaggtcgaa gaagacttac cccaacgaca aaaccatcat cagtaccttt    1140

-continued

```
aagtggagtt acaccactgg aaatggcaag cgctaccgga gcactgcgcg gaccacctac   1200
acctttgcca agccaatggc ggctaactat ctgaagaacc agccgatgta cgtgttccgt   1260
aagacggagc tcaagcactc caagaccgag ctcaacttca aggagtggca aaaggccttt   1320
accgatgtga tgggcatgga cgagctgtac aagggtggac atatgggcac agggtccaca   1380
ggcggtaccg gcggagtttc caaggagaa gaagacaata tggcatcact ccccgcaacc   1440
cacgagttgc atattttcgg ttcaattaat ggagtagatt tcgatatggt tggccaggga   1500
acaggaaacc caaacgacgg atatgaagag cttaatctca aaagtaccaa aggcgatctg   1560
caattttctc cgtggatact cgtgccacac attggatacg gatttcacca atatctcccg   1620
tatccggatg gaatgtcccc cttcaagca gcaatggtgg acgggagtgg ttatcaggta   1680
cacagaacca tgcagttcga ggacggggct tctctgaccg taaattatag gtatacttat   1740
gaaggctcac atattaaggg cgaagcacag gttaaaggaa ccgggtttcc tgcggatggc   1800
cccgtcatga ctaattctct gacagccgca gattggtgtc gctccaaaaa gacatacccg   1860
aatgataaga ctataatctc aacattcaaa tggtcctata cgacaggcaa cgggaaacga   1920
tatagatcca cggctcgaac aacttacaca ttcgctaaac ctatggccgc caattacctc   1980
aaaaatcagc ccatgtatgt gtttaggaaa accgaattga agcattctaa aacgaacttt   2040
aattttaagg aatggcagaa ggcttttcaca gacgtaatgg ggatggatga actctataaa   2100
tcaggtctcg agtcctcagg gggaacgggt gggtccggag gagttagtaa aggtgaagag   2160
gacaatatgg caagtttgcc tgcgactcac gagcttcata tctttgggtc tataaatggc   2220
gttgacttcg atatggttgg ccaaggtact ggcaacccca atgacggtta cgaggagttg   2280
aatctcaagt ccacaaaagg tgatcttcag ttcagccctt ggattctcgt acctcatatt   2340
ggatatggct tcaccagta ccttccatac ccagacggta tgtcacccctt tcaagctgcg   2400 atggtggatg gttccggcta tcaggtccac cgaacgatgc aattcgagga cggggccagc   2460
ctcaccgtta attataggta cacctatgag ggaagtcaca taaagggaga agcccaagtg   2520
aaaggaacag gattcccagc tgatggtcca gtaatgacga actccttgac agcggctgac   2580
tggtgtagaa gcaaaaagac gtatcctaat gacaagacca tcattagcac tttcaaatgg   2640
agttatacca caggaaacgg caaacggtac agaagcactg ctagaactac ctacactttc   2700
gcaaagccga tggctgcaaa ctatttgaag aatcagccca tgtacgtgtt tcgaaaaacg   2760
gaacttaagc acagtaagac tgaacttaat ttcaaggagt ggcagaaggc gttcacggat   2820
gtcatgggta tggatgaact gtataaggga gggtctggca ctgggggcac tgccagcagc   2880
ggatccggtg gcggtgtgag caagggcgag gaggataaca tggcctctct cccagcgaca   2940
catgagttac acatctttgg ctccatcaac ggtgtggact ttgacatggt gggtcagggc   3000
accggcaatc caaatgatgg ttatgaggag ttaaacctga agtccaccaa gggtgacctc   3060
cagttctccc cctggattct ggtccctcat atcgggtatg gcttccatca gtacctgccc   3120
taccctgacg ggatgtcgcc tttccaggcc gccatggtag atggtccgg ataccaagtc   3180 catcgcacaa tgcagtttga agatggtgcc tcccttactg ttaactaccg ctacacctac   3240
gagggaagcc acatcaaagg agaggcccag gtgaagggga ctggtttccc tgctgacggt   3300
cctgtgatga ccaactcgct gaccgctgcg gactggtgca ggtcgaagaa gacttacccc   3360
aacgacaaaa ccatcatcag tacctttaag tggagttaca ccactggaaa tggcaagcgc   3420
taccggagca ctgcgcggac cacctacacc tttgccaagc caatggcggc taactatctg   3480
aagaaccagc cgatgtacgt gttccgtaag acggagctca agcactccaa gaccgagctc   3540
```

```
aacttcaagg agtggcaaaa ggcctttacc gatgtgatgg gcatggacga gctgtacaag    3600
ggcggaagat ccggtggtgg ttctggtcct cgtccccgtg gtactcgtgg taaaggtcgc    3660
cgtattcgtc gccgcggtta atctagaggg cccgtttaaa cccgctgatc agcctcgact    3720
gtgccttcta gttgccagcc atctgttgtt tgcccctccc ccgtgccttc cttgaccctg    3780
gaaggtgcc actcccactg tccttccta ataaaatgag gaaattgcat cgcattgtct    3840
gagtaggtgt cattctattc tggggggtgg ggtgggggc aggacagcaa ggggaggat    3900
tgggaagaca atagcaggca tgctggggat gcggtgggct ctatggcttc tgaggcggaa    3960
agaaccagct ggggctctag ggggtatccc cacgcgccct gtagcggcgc attaagcgcg    4020
gcgggtgtgg tggttacgcg cagcgtgacc gctacacttg ccagcgccct agcgcccgct    4080
cctttcgctt tcttcccttc ctttctcgcc acgttcgccg gctttcccg tcaagctcta    4140
aatcggggc tcccttagg gttccgattt agtgctttac ggcacctcga ccccaaaaaa    4200
cttgattagg gtgatggttc acgtagtggg ccatcgccct gatagacggt ttttcgccct    4260
ttgacgttgg agtccacgtt ctttaatagt ggactcttgt tccaaactgg aacaacactc    4320
aaccctatct cggtctattc ttttgattta agggatttt gccgatttc ggcctattgg    4380
ttaaaaaatg agctgattta acaaaaattt aacgcgaatt aattctgtgg aatgtgtgtc    4440
agttagggtg tggaaagtcc ccaggctccc cagcaggcag aagtatgcaa agcatgcatc    4500
tcaattagtc agcaaccagg tgtggaaagt ccccaggctc cccagcaggc agaagtatgc    4560
aaagcatgca tctcaattag tcagcaacca tagtcccgcc cctaactccg cccatcccgc    4620
ccctaactcc gcccagttcc gcccattctc cgccccatgg ctgactaatt tttttattt    4680
atgcagaggc cgaggccgcc tctgcctctg agctattcca gaagtagtga ggaggctttt    4740
ttggaggcct aggcttttgc aaaaagctcc cgggagcttg tatatccatt ttcggatctg    4800
atcaagagac aggatgagga tcgtttcgca tgattgaaca agatggattg cacgcaggtt    4860
ctccggccgc ttgggtggag aggctattcg gctatgactg ggcacaacag acaatcggct    4920
gctctgatgc cgccgtgttc cggctgtcag cgcaggggcg cccggttctt tttgtcaaga    4980
ccgacctgtc cggtgccctg aatgaactgc aggacgagga gcgcggcta tcgtggctgg    5040
ccacgacggg cgttccttgc gcagctgtgc tcgacgttgt cactgaagcg ggaagggact    5100
ggctgctatt gggcgaagtg ccggggcagg atctcctgtc atctcacctt gctcctgccg    5160
agaaagtatc catcatggct gatgcaatgc ggcggctgca tacgcttgat ccggctacct    5220
gcccattcga ccaccaagcg aaacatcgca tcgagcgagc acgtactcgg atggaagccg    5280
gtcttgtcga tcaggatgat ctggacgaag agcatcaggg gctcgcgcca gccgaactgt    5340
tcgccaggct caaggcgcgc atgcccgacg gcgaggatct cgtcgtgacc catggcgatg    5400
cctgcttgcc gaatatcatg gtggaaaatg gccgcttttc tggattcatc gactgtggcc    5460
ggctgggtgt ggcggaccgc tatcaggaca tagcgttggc tacccgtgat attgctgaag    5520
agcttggcgg cgaatgggct gaccgcttcc tcgtgcttta cggtatcgcc gctcccgatt    5580
cgcagcgcat cgccttctat cgccttcttg acgagttctt ctgagcggga ctctggggtt    5640
cgaaatgacc gaccaagcga cgcccaacct gccatcacga gatttcgatt ccaccgccgc    5700
cttctatgaa aggttgggct tcggaatcgt tttccgggac gccggctgga tgatcctcca    5760
gcgcggggat ctcatgctgg agttcttcgc ccaccccaac ttgtttattg cagcttataa    5820
tggttacaaa taaagcaata gcatcacaaa tttcacaaat aaagcatttt tttcactgca    5880
```

```
ttctagttgt ggtttgtcca aactcatcaa tgtatcttat catgtctgta taccgtcgac    5940
ctctagctag agcttggcgt aatcatggtc atagctgttt cctgtgtgaa attgttatcc    6000
gctcacaatt ccacacaaca tacgagccgg aagcataaag tgtaaagcct ggggtgccta    6060
atgagtgagc taactcacat taattgcgtt gcgctcactg cccgctttcc agtcgggaaa    6120
cctgtcgtgc cagctgcatt aatgaatcgg ccaacgcgcg gggagaggcg gtttgcgtat    6180
tgggcgctct tccgcttcct cgctcactga ctcgctgcgc tcggtcgttc ggctgcggcg    6240
agcggtatca gctcactcaa aggcggtaat acggttatcc acagaatcag gggataacgc    6300
aggaaagaac atgtgagcaa aaggccagca aaaggccagg aaccgtaaaa aggccgcgtt    6360
gctggcgttt ttccataggc tccgcccccc tgacgagcat cacaaaaatc gacgctcaag    6420
tcagaggtgg cgaaacccga caggactata aagataccag gcgtttcccc ctggaagctc    6480
cctcgtgcgc tctcctgttc cgaccctgcc gcttaccgga tacctgtccg cctttctccc    6540
ttcgggaagc gtggcgcttt ctcatagctc acgctgtagg tatctcagtt cggtgtaggt    6600
cgttcgctcc aagctgggct gtgtgcacga accccccgtt cagcccgacc gctgcgcctt    6660
atccggtaac tatcgtcttg agtccaaccc ggtaagacac gacttatcgc cactggcagc    6720
agccactggt aacaggatta gcagagcgag gtatgtaggc ggtgctacag agttcttgaa    6780
gtggtggcct aactacggct acactagaag aacagtattt ggtatctgcg ctctgctgaa    6840
gccagttacc ttcggaaaaa gagttggtag ctcttgatcc ggcaaacaaa ccaccgctgg    6900
tagcggtttt tttgtttgca agcagcagat tacgcgcaga aaaaaggat ctcaagaaga    6960
tcctttgatc ttttctacgg ggtctgacgc tcagtggaac gaaaactcac gttaagggat    7020
tttggtcatg agattatcaa aaaggatctt cacctagatc cttttaaatt aaaaatgaag    7080
ttttaaatca atctaaagta tatatgagta aacttggtct gacagttacc aatgcttaat    7140
cagtgaggca cctatctcag cgatctgtct atttcgttca tccatagttg cctgactccc    7200
cgtcgtgtag ataactacga tacgggaggg cttaccatct ggccccagtg ctgcaatgat    7260
accgcgagac ccacgctcac cggctccaga tttatcagca ataaaccagc cagccggaag    7320
ggccgagcgc agaagtggtc ctgcaacttt atccgcctcc atccagtcta ttaattgttg    7380
ccgggaagct agagtaagta gttcgccagt taatagtttg cgcaacgttg ttgccattgc    7440
tacaggcatc gtggtgtcac gctcgtcgtt tggtatggct tcattcagct ccggttccca    7500
acgatcaagg cgagttacat gatccccat gttgtgcaaa aaagcggtta gctccttcgg    7560
tcctccgatc gttgtcagaa gtaagttggc cgcagtgtta tcactcatgg ttatggcagc    7620
actgcataat tctcttactg tcatgccatc cgtaagatgc ttttctgtga ctggtgagta    7680
ctcaaccaag tcattctgag aatagtgtat gcggcgaccg agttgctctt gcccggcgtc    7740
aatacgggat aataccgcgc cacatagcag aactttaaaa gtgctcatca ttggaaaacg    7800
ttcttcgggg cgaaaactct caaggatctt accgctgttg agatccagtt cgatgtaacc    7860
cactcgtgca cccaactgat cttcagcatc ttttactttc accagcgttt ctgggtgagc    7920
aaaaacagga aggcaaaatg ccgcaaaaaa gggaataagg gcgacacgga aatgttgaat    7980
actcatactc ttcctttttc aatattattg aagcatttat cagggttatt gtctcatgag    8040
cggatacata tttgaatgta tttagaaaaa taaacaaata ggggttccgc gcacatttcc    8100
ccgaaaagtg ccacctgacg tc                                             8122
```

<210> SEQ ID NO 78
<211> LENGTH: 6425

```
<212> TYPE: DNA
<213> ORGANISM: Artificial
<220> FEATURE:
<223> OTHER INFORMATION: pAV-U6+27-Tornado-F30-Pepper(TAR Variant-2)

<400> SEQUENCE: 78
```

| | | | | | |
|---|---|---|---|---|---|
| gccggatcca | aggtcgggca | ggaagagggc | ctatttccca | tgattccttc | atatttgcat | 60 |
| atacgataca | aggctgttag | agagataatt | agaattaatt | tgactgtaaa | cacaaagata | 120 |
| ttagtacaaa | atacgtgacg | tagaaagtaa | taatttcttg | ggtagtttgc | agttttaaaa | 180 |
| ttatgtttta | aaatggacta | tcatatgctt | accgtaactt | gaaagtattt | cgatttcttg | 240 |
| gctttatata | tcttgtggaa | aggacgaaac | accgtgctcg | cttcggcagc | acatatacta | 300 |
| gtcgacgggc | cgcactcgcc | ggtcccaagc | ccggataaaa | tgggaggggg | cgggaaaccg | 360 |
| cctaaccatg | ccgagtgcgg | ccgcttgcca | tgtgtatgtg | ggacgcgttg | ccacgtttcc | 420 |
| cacatactct | gatgatccgc | tagcaaaggc | tcgttgagct | cattagctcc | gagcccgagg | 480 |
| taccggatca | ttcatggcaa | gcggccgcgg | tcggcgtgga | ctgtagaaca | ctgccaatgc | 540 |
| cggtcccaag | cccggataaa | agtggagggt | acagtccacg | ctctagagcg | gacttcggtc | 600 |
| cgcttttttac | taggacctgc | aggcatgcaa | gcttgacgtc | ggttaccgat | atccatatgg | 660 |
| cgaccgcatc | gatctcgagc | cgaggactag | taacttgttt | attgcagctt | ataatggtta | 720 |
| caaataaagc | aatagcatca | caaatttcac | aaataaagca | ttttttttcac | tgcattctag | 780 |
| ttgtggtttg | tccaaactca | tcaatgtatc | ttatcatgtc | ttacgtagat | aagtagcatg | 840 |
| gcgggttaat | cattaactac | aaggaacccc | tagtgatgga | gttggccact | ccctctctgc | 900 |
| gcgctcgctc | gctcactgag | gccgggcgac | caaaggtcgc | ccgacgcccg | ggctttgccc | 960 |
| gggcggcctc | agtgagcgag | cgagcgcgca | gagagggagt | ggccaaagat | ctctggcgta | 1020 |
| atagcgaaga | ggcccgcacc | gatcgccctt | cccaacagtt | gcgcagcctg | aatggctaat | 1080 |
| gggaaattgt | aaacgttaat | attttgttaa | tattttgtta | aaattcgcgt | taaattttttg | 1140 |
| ttaaatcagc | tcatttttta | accaataggc | cgaaatcggc | aaaatccctt | ataaatcaaa | 1200 |
| agaatagacc | gagatagggt | tgagtgttgt | tccagtttgg | aacaagagtc | cactattaaa | 1260 |
| gaacgtggac | tccaacgtca | aagggcgaaa | aaccgtctat | cagggcgatg | gcccactacg | 1320 |
| tgaaccatca | ccctaatcaa | gttttttggg | gtcgaggtgc | cgtaaagcac | taaatcggaa | 1380 |
| ccctaaaggg | atgccccgat | ttagagcttg | acggggaaag | ccggcgaacg | tggcgagaaa | 1440 |
| ggaagggaag | aaagcgaaag | gagcgggcgc | tagggcgctg | gcaagtgtag | cggtcacgct | 1500 |
| gcgcgtaacc | accacacccg | ccgcgcttaa | tgcgccgcta | cagggcgcgt | caggtggcac | 1560 |
| ttttcgggga | aatgtgcgcg | gaacccctat | ttgtttattt | ttctaaatac | attcaaatat | 1620 |
| gtatccgctc | atgagacaat | aaccctgata | aatgcttcaa | taatattgaa | aaaggaagag | 1680 |
| tatgagtatt | caacatttcc | gtgtcgccct | tattcccttt | tttgcggcat | tttgccttcc | 1740 |
| tgttttttgct | cacccagaaa | cgctggtgaa | agtaaaagat | gctgaagatc | agttgggtgc | 1800 |
| acgagtgggt | tacatcgaac | tggatctcaa | cagcggtaag | atccttgaga | gttttcgccc | 1860 |
| cgaagaacgt | tttccaatga | tgagcacttt | taaagttctg | ctatgtggcg | cggtattatc | 1920 |
| ccgtattgac | gccgggcaag | agcaactcgg | tcgccgcata | cactattctc | agaatgactt | 1980 |
| ggttgagtac | tcaccagtca | cagaaaagca | tcttacggat | ggcatgacag | taagagaatt | 2040 |
| atgcagtgct | gccataacca | tgagtgataa | cactgcggcc | aacttacttc | tgacaacgat | 2100 |
| cggaggaccg | aaggagctaa | ccgcttttttt | gcacaacatg | ggggatcatg | taactcgcct | 2160 |

-continued

```
tgatcgttgg gaaccggagc tgaatgaagc cataccaaac gacgagcgtg acaccacgat    2220
gcctgtagca atggcaacaa cgttgcgcaa actattaact ggcgaactac ttactctagc    2280
ttcccggcaa caattaatag actggatgga ggcggataaa gttgcaggac cacttctgcg    2340
ctcggccctt ccggctggct ggtttattgc tgataaatct ggagccggtg agcgtgggtc    2400
tcgcggtatc attgcagcac tggggccaga tggtaagccc tcccgtatcg tagttatcta    2460
cacgacgggg agtcaggcaa ctatggatga acgaaataga cagatcgctg agataggtgc    2520
ctcactgatt aagcattggt aactgtcaga ccaagtttac tcatatatac tttagattga    2580
tttaaaactt catttttaat ttaaaaggat ctaggtgaag atcctttttg ataatctcat    2640
gaccaaaatc ccttaacgtg agttttcgtt ccactgagcg tcagaccccg tagaaaagat    2700
caaaggatct tcttgagatc ctttttttct gcgcgtaatc tgctgcttgc aaacaaaaaa    2760
accaccgcta ccagcggtgg tttgtttgcc ggatcaagag ctaccaactc tttttccgaa    2820
ggtaactggc ttcagcagag cgcagatacc aaatactgtc cttctagtgt agccgtagtt    2880
aggccaccac ttcaagaact ctgtagcacc gcctacatac ctcgctctgc taatcctgtt    2940
accagtggct gctgccagtg gcgataagtc gtgtcttacc gggttggact caagacgata    3000
gttaccggat aaggcgcagc ggtcgggctg aacggggggt tcgtgcaaca cagccagctt    3060
ggagcgaacg acctacaccg aactgagata cctacagcgt gagcattgag aaagcgccac    3120
gcttcccgaa gggagaaagg cggacaggta tccggtaagc ggcagggtcg gaacaggaga    3180
gcgcacgagg gagcttccag ggggaaacgc ctggtatctt tatagtcctg tcgggtttcg    3240
ccacctctga cttgagcgtc gatttttgtg atgctcgtca gggggcgga gcctatggaa    3300 aaacgccagc aacgcggcct ttttacggtt cctggccttt tgctggcctt ttgctcacat    3360
gttctttcct gcgttatccc ctgattctgt ggataaccgt attaccgcct ttgagtgagc    3420
tgataccgct cgccgcagcc gaacgaccga gcgcagcgag tcagtgagcg aggaagcgga    3480
agagcgccca atacgcaaac cgcctctccc cgcgcgttgg ccgattcatt aatgcagaga    3540
tctttggcca ctccctctct gcgcgctcgc tcgctcactg aggccgggcg accaaaggtc    3600
gcccgacgcc cgggctttgc ccgggcggcc tcagtgagcg agcgagcgcg cagagaggga    3660
gtggccaact ccatcactag gggttcctgg aggggtggag tcgtgacgtg aattacgtca    3720
tagggttagg gaggtcctgg atcgatccag acatgataag atacattgat gagtttggac    3780
aaaccacaac tagaatgcag tgaaaaaaat gctttatttg tgaaatttgt gatgctattg    3840
ctttatttgt aaccattata agctgcaata acaagttaa caacaacaat tgcattcatt    3900
ttatgtttca ggttcagggg gaggtgtggg aggttttta aagcaagtaa aacctctaca    3960
aatgtggtat ggctgattat gatctctagt caaggcacta tacatcaaat attccttatt    4020
aaccccttta caaattaaaa agctaaaggt acacaatttt tgagcatagt tattaatagc    4080
agacactcta tgcctgtgtg gagtaagaaa aaacagtatg ttatgattat aactgttatg    4140
cctacttata aaggttacag aatatttttc cataattttc ttgtatagca gtgcagcttt    4200
ttcctttgtg gtgtaaatag caaagcaagc aagagttcta ttactaaaca cagcatgact    4260
caaaaaactt agcaattctg aaggaaagtc cttgggtct tctacctttc tcttcttttt    4320
tggaggagta gaatgttgag agtcagcagt agcctcatca tcactagatg gcatttcttc    4380
tgagcaaaac aggttttcct cattaaaggc attccaccac tgctcccatt catcagttcc    4440
ataggttgga atctaaaata cacaaacaat tagaatcagt agtttaacac attatacact    4500
taaaaatttt atatttacct tagagcttta aatctctgta ggtagtttgt ccaattatgt    4560
```

```
cacaccacag aagtaaggtt ccttcacaaa gatccgggac caaagcggcc atcgtgcctc    4620
cccactcctg cagttcgggg gcatggatgc gcggatagcc gctgctggtt tcctggatgc    4680
cgacggattt gcactgccgg tagaactccg cgaggtcgtc cagcctcagg cagcagctga    4740
accaactcgc gaggggatcg agcccggggt gggcgaagaa ctccagcatg agatccccgc    4800
gctggaggat catccagccg gcgtcccgga aaacgattcc gaagcccaac ctttcataga    4860
aggcggcggt ggaatcgaaa tctcgtgatg gcaggttggg cgtcgcttgg tcggtcattt    4920
cgaacccag agtcccgctc agaagaactc gtcaagaagg cgatagaagg cgatgcgctg    4980
cgaatcggga gcggcgatac cgtaaagcac gaggaagcgg tcagcccatt cgccgccaag    5040
ctcttcagca atatcacggg tagccaacgc tatgtcctga tagcggtccg ccacacccag    5100
ccggccacag tcgatgaatc cagaaaagcg gccattttcc accatgatat tcggcaagca    5160
ggcatcgcca tgggtcacga cgagatcctc gccgtcgggc atgcgcgcct tgagcctggc    5220
gaacagttcg gctggcgcga gcccctgatg ctcttgtcca gatcatcctg atcgacaaga    5280
ccggcttcca tccgagtacg tgctcgctcg atgcgatgtt cgcttggtgg tcgaatgggc    5340
aggtagccgg atcaagcgta tgcagccgcc gcattgcatc agccatgatg gatactttct    5400
cggcaggagc aaggtgagat gacaggagat cctgccccgg cacttcgccc aatagcagcc    5460
agtcccttcc cgcttcagtg acaacgtcga gcacagctgc gcaaggaacg cccgtcgtgg    5520
ccagccacga tagccgcgct gcctcgtcct gcagttcatt cagggcaccg gacaggtcgg    5580
tcttgacaaa aagaaccggg cgcccctgcg ctgacagccg gaacacgcg gcatcagagc    5640
agccgattgt ctgttgtgcc cagtcatagc cgaatagcct ctccacccaa gcggccggag    5700
aacctgcgtg caatccatct tgttcaatca tgcgaaacga tcctcatcct gtctcttgat    5760
cagatcttga tccctgcgc catcagatcc ttggcggcaa gaaagccatc cagtttactt    5820
tgcagggctt cccaacctta ccagagggcg cccagctgg caattccggt tcgcttgctg    5880
tccataaaac cgcccagtct agctatcggc atgtaagccc actgcaagct acctgctttc    5940
tctttgcgct tgcgtttttcc cttgtccaga tagcccagta gctgacattc atccggggtc    6000
agcaccgttt ctgcggactg gctttctacg tgttccgctt cctttagcag cccttgcgcc    6060
ctgagtgctt gcggcagcgt gaagcttttt gcaaaagcct aggcctccaa aaaagcctcc    6120
tcactacttc tggaatagct cagaggccga ggcggcctcg gcctctgcat aaataaaaaa    6180
aattagtcag ccatggggcg gagaatgggc ggaactgggc ggagttaggg gcgggatggg    6240
cggagttagg ggcgggacta tggttgctga ctaattgaga tgcatgcttt gcatacttct    6300
gcctgctggg gagcctgggg actttccaca cctggttgct gactaattga gatgcatgct    6360
ttgcatactt ctgcctgctg gggagcctgg ggactttcca caccctaact gacacacatt    6420
ccaca                                                                6425

<210> SEQ ID NO 79
<211> LENGTH: 6426
<212> TYPE: DNA
<213> ORGANISM: Artificial
<220> FEATURE:
<223> OTHER INFORMATION: pAV-U6+27-Tornado-F30-TAR Variant-1

<400> SEQUENCE: 79
gccggatcca aggtcgggca ggaagagggc ctatttccca tgattccttc atatttgcat      60
atacgataca aggctgttag agagataatt agaattaatt tgactgtaaa cacaaagata     120
```

-continued

```
ttagtacaaa atacgtgacg tagaaagtaa taatttcttg ggtagtttgc agttttaaaa      180
ttatgtttta aaatggacta tcatatgctt accgtaactt gaaagtattt cgatttcttg      240
gctttatata tcttgtggaa aggacgaaac accgtgctcg cttcggcagc acatatacta      300
gtcgacgggc cgcactcgcc ggtcccaagc ccggataaaa tgggaggggg cgggaaaccg      360
cctaaccatg ccgagtgcgg ccgcttgcca tgtgtatgtg ggacgcgttg ccacgtttcc      420
cacatactct gatgatccgc tagcaaaggc tcgtctgagc tcattagctc cgagcccgag      480
gtaccggatc attcatggca agcggccgcg gtcggcgtgg actgtagaac actgccaatg      540
ccggtcccaa gcccggataa aagtggaggg tacagtccac gctctagagc ggacttcggt      600
ccgctttta ctaggacctg caggcatgca agcttgacgt cggttaccga tatccatatg       660
gcgaccgcat cgatctcgag ccgaggacta gtaacttgtt tattgcagct tataatggtt      720
acaaataaag caatagcatc acaaatttca caaataaagc attttttca ctgcattcta       780
gttgtggttt gtccaaactc atcaatgtat cttatcatgt cttacgtaga taagtagcat      840
ggcgggttaa tcattaacta caaggaaccc ctagtgatga agttggccac tccctctctg      900
cgcgctcgct cgctcactga ggccgggcga ccaaaggtcg cccgacgccc gggctttgcc      960
cgggcggcct cagtgagcga gcgagcgcgc agagaggag tggccaaaga tctctggcgt      1020
aatagcgaag aggcccgcac cgatcgccct tcccaacagt tgcgcagcct gaatggctaa     1080
tgggaaattg taaacgttaa tattttgtta atatttgtt aaaattcgcg ttaaattttt      1140
gttaaatcag ctcatttttt aaccaatagg ccgaaatcgg caaaatccct tataaatcaa     1200
aagaatagac cgagataggg ttgagtgttg ttccagtttg gaacaagagt ccactattaa     1260
agaacgtgga ctccaacgtc aaagggcgaa aaaccgtcta tcagggcgat ggcccactac     1320
gtgaaccatc accctaatca agttttttgg ggtcgaggtg ccgtaaagca ctaaatcgga     1380
accctaaagg gatgccccga tttagagctt gacggggaaa gccggcgaac gtggcgagaa     1440
aggaagggaa gaaagcgaaa ggagcgggcg ctagggcgct ggcaagtgta gcggtcacgc     1500
tgcgcgtaac caccacaccc gccgcgctta atgcgccgct acagggcgcg tcaggtggca     1560
cttttcgggg aaatgtgcgc ggaaccccta tttgtttatt tttctaaata cattcaaata     1620
tgtatccgct catgagacaa taaccctgat aaatgcttca ataatattga aaaggaaga     1680
gtatgagtat tcaacatttc cgtgtcgccc ttattccctt ttttgcggca ttttgccttc     1740
ctgttttgc tcacccagaa acgctggtga agtaaaaga tgctgaagat cagttgggtg       1800
cacgagtggg ttacatcgaa ctggatctca acagcggtaa gatccttgag agttttcgcc     1860
ccgaagaacg ttttccaatg atgagcactt ttaaagttct gctatgtggc gcggtattat     1920
cccgtattga cgccgggcaa gagcaactcg gtcgccgcat acactattct cagaatgact     1980
tggttgagta ctcaccagtc acagaaaagc atcttacgga tggcatgaca gtaagagaat     2040
tatgcagtgc tgccataacc atgagtgata acactgcggc caacttactt ctgacaacga     2100
tcggaggacc gaaggagcta accgcttttt tgcacaacat gggggatcat gtaactcgcc     2160
ttgatcgttg gaaccggag ctgaatgaag ccataccaaa cgacgagcgt gacaccacga      2220
tgcctgtagc aatggcaaca acgttgcgca actattaac tggcgaacta cttactctag      2280
cttcccggca acaattaata gactggatgg aggcggataa agttgcagga ccacttctgc     2340
gctcggccct tccggctggc tggtttattg ctgataaatc tggagccggt gagcgtgggt     2400
ctcgcggtat cattgcagca ctggggccag atggtaagcc ctcccgtatc gtagttatct     2460
acacgacggg gagtcaggca actatggatg aacgaaatag acagatcgct gagataggtg     2520
```

```
cctcactgat taagcattgg taactgtcag accaagttta ctcatatata ctttagattg   2580
atttaaaact tcattttttaa tttaaaagga tctaggtgaa gatccttttt gataatctca   2640
tgaccaaaat cccttaacgt gagttttcgt tccactgagc gtcagacccc gtagaaaaga   2700
tcaaaggatc ttcttgagat ccttttttc tgcgcgtaat ctgctgcttg caaacaaaaa    2760
aaccaccgct accagcggtg gtttgtttgc cggatcaaga gctaccaact cttttttccga  2820
aggtaactgg cttcagcaga gcgcagatac caaatactgt ccttctagtg tagccgtagt   2880
taggccacca cttcaagaac tctgtagcac cgcctacata cctcgctctg ctaatcctgt   2940
taccagtggc tgctgccagt ggcgataagt cgtgtcttac cgggttggac tcaagacgat   3000
agttaccgga taaggcgcag cggtcgggct gaacggggg ttcgtgcaac acagccagct    3060
tggagcgaac gacctacacc gaactgagat acctacagcg tgagcattga aaagcgcca    3120
cgcttcccga agggagaaag gcggacaggt atccggtaag cggcagggtc ggaacaggag   3180
agcgcacgag ggagcttcca gggggaaacg cctggtatct ttatagtcct gtcgggtttc   3240
gccacctctg acttgagcgt cgatttttgt gatgctcgtc aggggggcgg agcctatgga   3300
aaaacgccag caacgcggcc ttttacggt tcctggcctt ttgctggcct tttgctcaca    3360
tgttctttcc tgcgttatcc cctgattctg tggataaccg tattaccgcc tttgagtgag   3420
ctgataccgc tcgccgcagc cgaacgaccg agcgcagcga gtcagtgagc gaggaagcgg   3480
aagagcgccc aatacgcaaa ccgcctctcc ccgcgcgttg gccgattcat taatgcagag   3540
atctttggcc actccctctc tgcgcgctcg ctcgctcact gaggccgggc gaccaaaggt   3600
cgcccgacgc ccgggctttg cccgggcggc ctcagtgagc gagcgagcgc gcagagaggg   3660
agtggccaac tccatcacta ggggttcctg gaggggtgga gtcgtgacgt gaattacgtc   3720
atagggttag ggaggtcctg gatcgatcca gacatgataa gatacattga tgagtttgga   3780
caaaccacaa ctagaatgca gtgaaaaaa tgctttattt gtgaaatttg tgatgctatt    3840
gctttatttg taaccattat aagctgcaat aaacaagtta caacaacaa ttgcattcat    3900
tttatgtttc aggttcaggg ggaggtgtgg gaggtttttt aaagcaagta aaacctctac   3960
aaatgtggta tggctgatta tgatctctag tcaaggcact atacatcaaa tattccttat   4020
taaccccttt acaaattaaa aagctaaagg tacacaattt ttgagcatag ttattaatag   4080
cagacactct atgcctgtgt ggagtaagaa aaaacagtat gttatgatta taactgttat   4140
gcctacttat aaaggttaca gaatattttt ccataatttt cttgtatagc agtgcagctt   4200
tttcctttgt ggtgtaaata gcaaagcaag caagagttct attactaaac acagcatgac   4260
tcaaaaaact tagcaattct gaaggaaagt ccttggggtc ttctacccttt ctcttctttt   4320
ttggaggagt agaatgttga gagtcagcag tagcctcatc atcactagat ggcatttctt   4380
ctgagcaaaa caggttttcc tcattaaagg cattccacca ctgctcccat tcatcagttc   4440
cataggttgg aatctaaaat acacaaacaa ttagaatcag tagtttaaca cattatacac   4500
ttaaaatttt tatatttacc ttagagcttt aaatctctgt aggtagtttg tccaattatg   4560
tcacaccaca gaagtaaggt tccttcacaa agatccggga ccaaagcggc catcgtgcct   4620
ccccactcct gcagttcggg ggcatggatg cgcggatagc cgctgctggt ttcctggatg   4680
ccgacggatt tgcactgccg gtagaactcc gcgaggtcgt ccagcctcag gcagcagctg   4740
aaccaactcg cgaggggatc gagcccgggg tgggcgaaga actccagcat gagatccccg   4800
cgctggagga tcatccagcc ggcgtcccgg aaaacgattc cgaagcccaa cctttcatag   4860
```

-continued

```
aaggcggcgg tggaatcgaa atctcgtgat ggcaggttgg gcgtcgcttg gtcggtcatt    4920
tcgaacccca gagtcccgct cagaagaact cgtcaagaag gcgatagaag gcgatgcgct    4980
gcgaatcggg agcggcgata ccgtaaagca cgaggaagcg gtcagcccat cgccgccaa    5040 gctcttcagc aatatcacgg gtagccaacg ctatgtcctg atagcggtcc gccacaccca    5100
gccggccaca gtcgatgaat ccagaaaagc ggccattttc caccatgata ttcggcaagc    5160
aggcatcgcc atgggtcacg acgagatcct cgccgtcggg catgcgcgcc ttgagcctgg    5220
cgaacagttc ggctggcgcg agcccctgat gctcttgtcc agatcatcct gatcgacaag    5280
accggcttcc atccgagtac gtgctcgctc gatgcgatgt tcgcttggtg gtcgaatggg    5340
caggtagccg atcaagcgt atgcagccgc cgcattgcat cagccatgat ggatactttc    5400
tcggcaggag caaggtgaga tgacaggaga tcctgccccg gcacttcgcc aatagcagc    5460 cagtccttc ccgcttcagt gacaacgtcg agcacagctg cgcaaggaac gcccgtcgtg    5520
gccagccacg atagccgcgc tgcctcgtcc tgcagttcat tcagggcacc ggacaggtcg    5580
gtcttgacaa aaagaaccgg gcgcccctgc gctgacagcc ggaacacggc ggcatcagag    5640
cagccgattg tctgttgtgc ccagtcatag ccgaatagcc tctccaccca agcggccgga    5700
gaacctgcgt gcaatccatc ttgttcaatc atgcgaaacg atcctcatcc tgtctcttga    5760
tcagatcttg atcccctgcg ccatcagatc cttggcggca agaaagccat ccagtttact    5820
ttgcagggct tcccaacctt accagagggc gccccagctg gcaattccgg ttcgcttgct    5880
gtccataaaa ccgcccagtc tagctatcgg catgtaagcc cactgcaagc tacctgcttt    5940
ctctttgcgc ttgcgttttc ccttgtccag atagcccagt agctgacatt catccggggt    6000
cagcaccgtt tctgcggact ggctttctac gtgttccgct tcctttagca gcccttgcgc    6060
cctgagtgct tgcggcagcg tgaagctttt tgcaaaagcc taggcctcca aaaaagcctc    6120
ctcactactt ctggaatagc tcagaggccg aggcggcctc ggcctctgca taaataaaaa    6180
aaattagtca gccatggggc ggagaatggg cggaactggg cggagttagg gcgggatgg    6240 gcggagttag gggcgggact atggttgctg actaattgag atgcatgctt tgcatacttc    6300
tgcctgctgg ggagcctggg gactttccac acctggttgc tgactaattg agatgcatgc    6360
tttgcatact tctgcctgct ggggagcctg gggactttcc acaccctaac tgacacacat    6420
tccaca                                                                6426
```

<210> SEQ ID NO 80
<211> LENGTH: 1011
<212> TYPE: PRT
<213> ORGANISM: Artificial
<220> FEATURE:
<223> OTHER INFORMATION: (mNeonGreen)4-tDeg

<400> SEQUENCE: 80

```
Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
                20                  25                  30

Val Gly Gln Gly Thr Gly Asn Pro Asn Asp Gly Tyr Glu Glu Leu Asn
            35                  40                  45

Leu Lys Ser Thr Lys Gly Asp Leu Gln Phe Ser Pro Trp Ile Leu Val
        50                  55                  60

Pro His Ile Gly Tyr Gly Phe His Gln Tyr Leu Pro Tyr Pro Asp Gly
65                  70                  75                  80
```

```
Met Ser Pro Phe Gln Ala Ala Met Val Asp Gly Ser Gly Tyr Gln Val
                85                  90                  95
His Arg Thr Met Gln Phe Glu Asp Gly Ala Ser Leu Thr Val Asn Tyr
            100                 105                 110
Arg Tyr Thr Tyr Glu Gly Ser His Ile Lys Gly Glu Ala Gln Val Lys
        115                 120                 125
Gly Thr Gly Phe Pro Ala Asp Gly Pro Val Met Thr Asn Ser Leu Thr
    130                 135                 140
Ala Ala Asp Trp Cys Arg Ser Lys Lys Thr Tyr Pro Asn Asp Lys Thr
145                 150                 155                 160
Ile Ile Ser Thr Phe Lys Trp Ser Tyr Thr Thr Gly Asn Gly Lys Arg
                165                 170                 175
Tyr Arg Ser Thr Ala Arg Thr Thr Tyr Thr Phe Ala Lys Pro Met Ala
            180                 185                 190
Ala Asn Tyr Leu Lys Asn Gln Pro Met Tyr Val Phe Arg Lys Thr Glu
        195                 200                 205
Leu Lys His Ser Lys Thr Glu Leu Asn Phe Lys Glu Trp Gln Lys Ala
    210                 215                 220
Phe Thr Asp Val Met Gly Met Asp Glu Leu Tyr Lys Gly Gly His Met
225                 230                 235                 240
Gly Thr Gly Ser Thr Gly Gly Thr Gly Val Ser Lys Gly Glu Glu
                245                 250                 255
Asp Asn Met Ala Ser Leu Pro Ala Thr His Glu Leu His Ile Phe Gly
            260                 265                 270
Ser Ile Asn Gly Val Asp Phe Asp Met Val Gly Gln Gly Thr Gly Asn
        275                 280                 285
Pro Asn Asp Gly Tyr Glu Glu Leu Asn Leu Lys Ser Thr Lys Gly Asp
    290                 295                 300
Leu Gln Phe Ser Pro Trp Ile Leu Val Pro His Ile Gly Tyr Gly Phe
305                 310                 315                 320
His Gln Tyr Leu Pro Tyr Pro Asp Gly Met Ser Pro Phe Gln Ala Ala
                325                 330                 335
Met Val Asp Gly Ser Gly Tyr Gln Val His Arg Thr Met Gln Phe Glu
            340                 345                 350
Asp Gly Ala Ser Leu Thr Val Asn Tyr Arg Tyr Thr Tyr Glu Gly Ser
        355                 360                 365
His Ile Lys Gly Glu Ala Gln Val Lys Gly Thr Gly Phe Pro Ala Asp
    370                 375                 380
Gly Pro Val Met Thr Asn Ser Leu Thr Ala Ala Asp Trp Cys Arg Ser
385                 390                 395                 400
Lys Lys Thr Tyr Pro Asn Asp Lys Thr Ile Ile Ser Thr Phe Lys Trp
                405                 410                 415
Ser Tyr Thr Thr Gly Asn Gly Lys Arg Tyr Arg Ser Thr Ala Arg Thr
            420                 425                 430
Thr Tyr Thr Phe Ala Lys Pro Met Ala Ala Asn Tyr Leu Lys Asn Gln
        435                 440                 445
Pro Met Tyr Val Phe Arg Lys Thr Glu Leu Lys His Ser Lys Thr Glu
    450                 455                 460
Leu Asn Phe Lys Glu Trp Gln Lys Ala Phe Thr Asp Val Met Gly Met
465                 470                 475                 480
Asp Glu Leu Tyr Lys Ser Gly Leu Glu Ser Gly Thr Gly Gly
                485                 490                 495
Ser Gly Gly Val Ser Lys Gly Glu Glu Asp Asn Met Ala Ser Leu Pro
```

```
                500             505             510
Ala Thr His Glu Leu His Ile Phe Gly Ser Ile Asn Gly Val Asp Phe
            515             520             525
Asp Met Val Gly Gln Gly Thr Gly Asn Pro Asn Asp Gly Tyr Glu Glu
        530             535             540
Leu Asn Leu Lys Ser Thr Lys Gly Asp Leu Gln Phe Ser Pro Trp Ile
545             550             555             560
Leu Val Pro His Ile Gly Tyr Gly Phe His Gln Tyr Leu Pro Tyr Pro
                565             570             575
Asp Gly Met Ser Pro Phe Gln Ala Ala Met Val Asp Gly Ser Gly Tyr
            580             585             590
Gln Val His Arg Thr Met Gln Phe Glu Asp Gly Ala Ser Leu Thr Val
        595             600             605
Asn Tyr Arg Tyr Thr Tyr Glu Gly Ser His Ile Lys Gly Glu Ala Gln
610             615             620
Val Lys Gly Thr Gly Phe Pro Ala Asp Gly Pro Val Met Thr Asn Ser
625             630             635             640
Leu Thr Ala Ala Asp Trp Cys Arg Ser Lys Lys Thr Tyr Pro Asn Asp
            645             650             655
Lys Thr Ile Ile Ser Thr Phe Lys Trp Ser Tyr Thr Thr Gly Asn Gly
        660             665             670
Lys Arg Tyr Arg Ser Thr Ala Arg Thr Thr Tyr Thr Phe Ala Lys Pro
    675             680             685
Met Ala Ala Asn Tyr Leu Lys Asn Gln Pro Met Tyr Val Phe Arg Lys
    690             695             700
Thr Glu Leu Lys His Ser Lys Thr Glu Leu Asn Phe Lys Glu Trp Gln
705             710             715             720
Lys Ala Phe Thr Asp Val Met Gly Met Asp Glu Leu Tyr Lys Gly Gly
            725             730             735
Ser Gly Thr Gly Gly Thr Ala Ser Ser Gly Ser Gly Gly Val Ser
        740             745             750
Lys Gly Glu Glu Asp Asn Met Ala Ser Leu Pro Ala Thr His Glu Leu
    755             760             765
His Ile Phe Gly Ser Ile Asn Gly Val Asp Phe Asp Met Val Gly Gln
    770             775             780
Gly Thr Gly Asn Pro Asn Asp Gly Tyr Glu Glu Leu Asn Leu Lys Ser
785             790             795             800
Thr Lys Gly Asp Leu Gln Phe Ser Pro Trp Ile Leu Val Pro His Ile
            805             810             815
Gly Tyr Gly Phe His Gln Tyr Leu Pro Tyr Pro Asp Gly Met Ser Pro
        820             825             830
Phe Gln Ala Ala Met Val Asp Gly Ser Gly Tyr Gln Val His Arg Thr
    835             840             845
Met Gln Phe Glu Asp Gly Ala Ser Leu Thr Val Asn Tyr Arg Tyr Thr
    850             855             860
Tyr Glu Gly Ser His Ile Lys Gly Glu Ala Gln Val Lys Gly Thr Gly
865             870             875             880
Phe Pro Ala Asp Gly Pro Val Met Thr Asn Ser Leu Thr Ala Ala Asp
            885             890             895
Trp Cys Arg Ser Lys Lys Thr Tyr Pro Asn Asp Lys Thr Ile Ile Ser
        900             905             910
Thr Phe Lys Trp Ser Tyr Thr Thr Gly Asn Gly Lys Arg Tyr Arg Ser
    915             920             925
```

```
Thr Ala Arg Thr Thr Tyr Thr Phe Ala Lys Pro Met Ala Ala Asn Tyr
            930                 935                 940

Leu Lys Asn Gln Pro Met Tyr Val Phe Arg Lys Thr Glu Leu Lys His
945                 950                 955                 960

Ser Lys Thr Glu Leu Asn Phe Lys Glu Trp Gln Lys Ala Phe Thr Asp
                965                 970                 975

Val Met Gly Met Asp Glu Leu Tyr Lys Gly Gly Arg Ser Gly Gly Gly
                980                 985                 990

Ser Gly Pro Arg Pro Arg Gly Thr Arg Gly Lys Gly Arg Arg Ile Arg
        995                1000                1005

Arg Arg Gly
    1010

<210> SEQ ID NO 81
<211> LENGTH: 266
<212> TYPE: PRT
<213> ORGANISM: Artificial
<220> FEATURE:
<223> OTHER INFORMATION: mNeonGreen-tDeg

<400> SEQUENCE: 81

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
210                 215                 220

Phe Thr Asp Val Met Gly Met Asp Glu Leu Tyr Lys Gly Gly His Met
225                 230                 235                 240

Gly Gly Gly Ser Gly Gly Gly Ser Gly Pro Arg Pro Arg Gly Thr Arg
                245                 250                 255

Gly Lys Gly Arg Arg Ile Arg Arg Arg Gly
            260                 265
```

<210> SEQ ID NO 82
<211> LENGTH: 261
<212> TYPE: PRT
<213> ORGANISM: Artificial
<220> FEATURE:
<223> OTHER INFORMATION: mCherry-tDeg

<400> SEQUENCE: 82

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Gly Gly Ser Gly
225                 230                 235                 240

Gly Gly Ser Gly Pro Arg Pro Arg Gly Thr Arg Gly Lys Gly Arg Arg
                245                 250                 255

Ile Arg Arg Arg Gly
            260
```

<210> SEQ ID NO 83
<211> LENGTH: 201
<212> TYPE: PRT
<213> ORGANISM: Artificial
<220> FEATURE:
<223> OTHER INFORMATION: NanoLuc-tDeg

<400> SEQUENCE: 83

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
```

```
                35                  40                  45
Ser Gly Glu Asn Gly Leu Lys Ile Asp Ile His Val Ile Ile Pro Tyr
 50                  55                  60

Glu Gly Leu Ser Gly Asp Gln Met Gly Gln Ile Glu Lys Ile Phe Lys
 65                  70                  75                  80

Val Val Tyr Pro Val Asp His His Phe Lys Val Ile Leu His Tyr
                 85                  90                  95

Gly Thr Leu Val Ile Asp Gly Val Thr Pro Asn Met Ile Asp Tyr Phe
                100                 105                 110

Gly Arg Pro Tyr Glu Gly Ile Ala Val Phe Asp Gly Lys Lys Ile Thr
                115                 120                 125

Val Thr Gly Thr Leu Trp Asn Gly Asn Lys Ile Ile Asp Glu Arg Leu
                130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Gly Gly Ser His Met
                165                 170                 175

Gly Gly Ser Gly Gly Gly Ser Gly Pro Arg Pro Arg Gly Thr Arg Gly
                180                 185                 190

Lys Gly Arg Arg Ile Arg Arg Gly
                195                 200

<210> SEQ ID NO 84
<211> LENGTH: 264
<212> TYPE: PRT
<213> ORGANISM: Artificial
<220> FEATURE:
<223> OTHER INFORMATION: EYFP-tDeg

<400> SEQUENCE: 84

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
                 35                  40                  45

Cys Thr Thr Gly Lys Leu Pro Val Pro Trp Pro Thr Leu Val Thr Thr
 50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Tyr Gln Ser Ala Leu
```

```
                195                 200                 205
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Gly Ser Gly Gly Ser Gly Pro Arg Pro Arg Gly Thr Arg Gly Lys
                245                 250                 255

Gly Arg Arg Ile Arg Arg Gly
            260

<210> SEQ ID NO 85
<211> LENGTH: 482
<212> TYPE: PRT
<213> ORGANISM: Artificial
<220> FEATURE:
<223> OTHER INFORMATION: EGFP-TetR-tDeg

<400> SEQUENCE: 85

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Thr Gly Ala Cys Gly Thr Ser Gly Gly Arg Leu Asp Lys Ser Lys Val
                245                 250                 255

Ile Asn Ser Ala Leu Glu Leu Leu Asn Glu Val Gly Ile Glu Gly Leu
            260                 265                 270

Thr Thr Arg Lys Leu Ala Gln Lys Leu Gly Val Glu Gln Pro Thr Leu
        275                 280                 285

Tyr Trp His Val Lys Asn Lys Arg Ala Leu Leu Asp Ala Leu Ala Ile
```

```
                290                 295                 300
Glu Met Leu Asp Arg His His Thr His Phe Cys Pro Leu Glu Gly Glu
305                 310                 315                 320

Ser Trp Gln Asp Phe Leu Arg Asn Asn Ala Lys Ser Phe Arg Cys Ala
                325                 330                 335

Leu Leu Ser His Arg Asp Gly Ala Lys Val His Leu Gly Thr Arg Pro
                340                 345                 350

Thr Glu Lys Gln Tyr Glu Thr Leu Glu Asn Gln Leu Ala Phe Leu Cys
                355                 360                 365

Gln Gln Gly Phe Ser Leu Glu Asn Ala Leu Tyr Ala Leu Ser Ala Val
                370                 375                 380

Gly His Phe Thr Leu Gly Cys Val Leu Glu Asp Gln Glu His Gln Val
385                 390                 395                 400

Ala Lys Glu Glu Arg Glu Thr Pro Thr Thr Asp Ser Met Pro Pro Leu
                405                 410                 415

Leu Arg Gln Ala Ile Glu Leu Phe Asp His Gln Gly Ala Glu Pro Ala
                420                 425                 430

Phe Leu Phe Gly Leu Glu Leu Ile Ile Cys Gly Leu Glu Lys Gln Leu
                435                 440                 445

Lys Cys Glu Ser Gly Ser Gly Ser Gly Thr Gly Gly Thr Gly Gly Ser
                450                 455                 460

Gly Pro Arg Pro Arg Gly Thr Arg Gly Lys Gly Arg Arg Ile Arg Arg
465                 470                 475                 480

Arg Gly

<210> SEQ ID NO 86
<211> LENGTH: 479
<212> TYPE: PRT
<213> ORGANISM: Artificial
<220> FEATURE:
<223> OTHER INFORMATION: mCherry-TetR-tDeg

<400> SEQUENCE: 86

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
                35                  40                  45

Ala Lys Leu Lys Val Thr Lys Gly Gly Pro Leu Pro Phe Ala Trp Asp
                50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Gln Lys Lys
                130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175
```

```
His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys Gly Thr Gly Ala
225                 230                 235                 240

Cys Gly Thr Ser Gly Gly Arg Leu Asp Lys Ser Lys Val Ile Asn Ser
                245                 250                 255

Ala Leu Glu Leu Leu Asn Glu Val Gly Ile Glu Gly Leu Thr Thr Arg
            260                 265                 270

Lys Leu Ala Gln Lys Leu Gly Val Glu Gln Pro Thr Leu Tyr Trp His
        275                 280                 285

Val Lys Asn Lys Arg Ala Leu Leu Asp Ala Leu Ala Ile Glu Met Leu
290                 295                 300

Asp Arg His His Thr His Phe Cys Pro Leu Glu Gly Glu Ser Trp Gln
305                 310                 315                 320

Asp Phe Leu Arg Asn Asn Ala Lys Ser Phe Arg Cys Ala Leu Leu Ser
                325                 330                 335

His Arg Asp Gly Ala Lys Val His Leu Gly Thr Arg Pro Thr Glu Lys
            340                 345                 350

Gln Tyr Glu Thr Leu Glu Asn Gln Leu Ala Phe Leu Cys Gln Gln Gly
        355                 360                 365

Phe Ser Leu Glu Asn Ala Leu Tyr Ala Leu Ser Ala Val Gly His Phe
370                 375                 380

Thr Leu Gly Cys Val Leu Glu Asp Gln Glu His Gln Val Ala Lys Glu
385                 390                 395                 400

Glu Arg Glu Thr Pro Thr Thr Asp Ser Met Pro Pro Leu Leu Arg Gln
                405                 410                 415

Ala Ile Glu Leu Phe Asp His Gln Gly Ala Glu Pro Ala Phe Leu Phe
            420                 425                 430

Gly Leu Glu Leu Ile Ile Cys Gly Leu Glu Lys Gln Leu Lys Cys Glu
        435                 440                 445

Ser Gly Ser Gly Ser Gly Thr Gly Thr Gly Ser Gly Pro Arg
450                 455                 460

Pro Arg Gly Thr Arg Gly Lys Gly Arg Arg Ile Arg Arg Gly
465                 470                 475

<210> SEQ ID NO 87
<211> LENGTH: 1023
<212> TYPE: PRT
<213> ORGANISM: Artificial
<220> FEATURE:
<223> OTHER INFORMATION: EGFP-EZH2-tDeg

<400> SEQUENCE: 87

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Thr Gly Ala Cys Gly Thr Ser Gly Gly Met Gly Gln Thr Gly Lys Lys
                245                 250                 255

Ser Glu Lys Gly Pro Val Cys Trp Arg Lys Arg Val Lys Ser Glu Tyr
            260                 265                 270

Met Arg Leu Arg Gln Leu Lys Arg Phe Arg Arg Ala Asp Glu Val Lys
            275                 280                 285

Ser Met Phe Ser Ser Asn Arg Gln Lys Ile Leu Glu Arg Thr Glu Ile
290                 295                 300

Leu Asn Gln Glu Trp Lys Gln Arg Arg Ile Gln Pro Val His Ile Leu
305                 310                 315                 320

Thr Ser Val Ser Ser Leu Arg Gly Thr Arg Glu Cys Ser Val Thr Ser
                325                 330                 335

Asp Leu Asp Phe Pro Thr Gln Val Ile Pro Leu Lys Thr Leu Asn Ala
            340                 345                 350

Val Ala Ser Val Pro Ile Met Tyr Ser Trp Ser Pro Leu Gln Gln Asn
            355                 360                 365

Phe Met Val Glu Asp Glu Thr Val Leu His Asn Ile Pro Tyr Met Gly
            370                 375                 380

Asp Glu Val Leu Asp Gln Asp Gly Thr Phe Ile Glu Glu Leu Ile Lys
385                 390                 395                 400

Asn Tyr Asp Gly Lys Val His Gly Asp Arg Glu Cys Gly Phe Ile Asn
                405                 410                 415

Asp Glu Ile Phe Val Glu Leu Val Asn Ala Leu Gly Gln Tyr Asn Asp
            420                 425                 430

Asp Asp Asp Asp Asp Asp Gly Asp Pro Glu Glu Arg Glu Glu Lys
            435                 440                 445

Gln Lys Asp Leu Glu Asp His Arg Asp Asp Lys Glu Ser Arg Pro Pro
            450                 455                 460

Arg Lys Phe Pro Ser Asp Lys Ile Phe Glu Ala Ile Ser Ser Met Phe
465                 470                 475                 480
```

-continued

```
Pro Asp Lys Gly Thr Ala Glu Glu Leu Lys Glu Lys Tyr Lys Glu Leu
                485                 490                 495
Thr Glu Gln Gln Leu Pro Gly Ala Leu Pro Pro Glu Cys Thr Pro Asn
            500                 505                 510
Ile Asp Gly Pro Asn Ala Lys Ser Val Gln Arg Glu Gln Ser Leu His
            515                 520                 525
Ser Phe His Thr Leu Phe Cys Arg Arg Cys Phe Lys Tyr Asp Cys Phe
            530                 535                 540
Leu His Pro Phe His Ala Thr Pro Asn Thr Tyr Lys Arg Lys Asn Thr
545                 550                 555                 560
Glu Thr Ala Leu Asp Asn Lys Pro Cys Gly Pro Gln Cys Tyr Gln His
                565                 570                 575
Leu Glu Gly Ala Lys Glu Phe Ala Ala Ala Leu Thr Ala Glu Arg Ile
                580                 585                 590
Lys Thr Pro Pro Lys Arg Pro Gly Gly Arg Arg Gly Arg Leu Pro
                595                 600                 605
Asn Asn Ser Ser Arg Pro Ser Thr Pro Thr Ile Asn Val Leu Glu Ser
            610                 615                 620
Lys Asp Thr Asp Ser Asp Arg Glu Ala Gly Thr Glu Thr Gly Gly Glu
625                 630                 635                 640
Asn Asn Asp Lys Glu Glu Glu Lys Lys Asp Glu Thr Ser Ser Ser
                645                 650                 655
Ser Glu Ala Asn Ser Arg Cys Gln Thr Pro Ile Lys Met Lys Pro Asn
                660                 665                 670
Ile Glu Pro Pro Glu Asn Val Glu Trp Ser Gly Ala Glu Ala Ser Met
                675                 680                 685
Phe Arg Val Leu Ile Gly Thr Tyr Tyr Asp Asn Phe Cys Ala Ile Ala
            690                 695                 700
Arg Leu Ile Gly Thr Lys Thr Cys Arg Gln Val Tyr Glu Phe Arg Val
705                 710                 715                 720
Lys Glu Ser Ser Ile Ile Ala Pro Ala Pro Ala Glu Asp Val Asp Thr
                725                 730                 735
Pro Pro Arg Lys Lys Lys Arg Lys His Arg Leu Trp Ala Ala His Cys
                740                 745                 750
Arg Lys Ile Gln Leu Lys Lys Asp Gly Ser Ser Asn His Val Tyr Asn
            755                 760                 765
Tyr Gln Pro Cys Asp His Pro Arg Gln Pro Cys Asp Ser Ser Cys Pro
            770                 775                 780
Cys Val Ile Ala Gln Asn Phe Cys Glu Lys Phe Cys Gln Cys Ser Ser
785                 790                 795                 800
Glu Cys Gln Asn Arg Phe Pro Gly Cys Arg Cys Lys Ala Gln Cys Asn
                805                 810                 815
Thr Lys Gln Cys Pro Cys Tyr Leu Ala Val Arg Glu Cys Asp Pro Asp
            820                 825                 830
Leu Cys Leu Thr Cys Gly Ala Ala Asp His Trp Asp Ser Lys Asn Val
            835                 840                 845
Ser Cys Lys Asn Cys Ser Ile Gln Arg Gly Ser Lys Lys His Leu Leu
            850                 855                 860
Leu Ala Pro Ser Asp Val Ala Gly Trp Gly Ile Phe Ile Lys Asp Pro
865                 870                 875                 880
Val Gln Lys Asn Glu Phe Ile Ser Glu Tyr Cys Gly Glu Ile Ile Ser
                885                 890                 895
Gln Asp Glu Ala Asp Arg Arg Gly Lys Val Tyr Asp Lys Tyr Met Cys
```

900             905             910
Ser Phe Leu Phe Asn Leu Asn Asn Asp Phe Val Val Asp Ala Thr Arg
            915                 920             925

Lys Gly Asn Lys Ile Arg Phe Ala Asn His Ser Val Asn Pro Asn Cys
        930                 935             940

Tyr Ala Lys Val Met Met Val Asn Gly Asp His Arg Ile Gly Ile Phe
945                 950                 955                 960

Ala Lys Arg Ala Ile Gln Thr Gly Glu Glu Leu Phe Phe Asp Tyr Arg
                965                 970                 975

Tyr Ser Gln Ala Asp Ala Leu Lys Tyr Val Gly Ile Glu Arg Glu Met
            980                 985                 990

Glu Ile Pro Gly Ser Gly Thr Gly Gly Thr Gly Gly Ser Gly Pro Arg
            995                 1000                1005

Pro Arg Gly Thr Arg Gly Lys Gly Arg Arg Ile Arg Arg Arg Gly
        1010                1015                1020

<210> SEQ ID NO 88
<211> LENGTH: 1020
<212> TYPE: PRT
<213> ORGANISM: Artificial
<220> FEATURE:
<223> OTHER INFORMATION: mCherry-EZH2-tDeg

<400> SEQUENCE: 88

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Gly Thr Gly Ala
225                 230                 235                 240

Cys Gly Thr Ser Gly Gly Met Gly Gln Thr Gly Lys Lys Ser Glu Lys

-continued

```
            245                 250                 255
Gly Pro Val Cys Trp Lys Arg Val Lys Ser Glu Tyr Met Arg Leu
            260                 265                 270
Arg Gln Leu Lys Arg Phe Arg Ala Asp Glu Val Lys Ser Met Phe
            275                 280                 285
Ser Ser Asn Arg Gln Lys Ile Leu Glu Arg Thr Glu Ile Leu Asn Gln
            290                 295                 300
Glu Trp Lys Gln Arg Arg Ile Gln Pro Val His Ile Leu Thr Ser Val
305                 310                 315                 320
Ser Ser Leu Arg Gly Thr Arg Glu Cys Ser Val Thr Ser Asp Leu Asp
                325                 330                 335
Phe Pro Thr Gln Val Ile Pro Leu Lys Thr Leu Asn Ala Val Ala Ser
            340                 345                 350
Val Pro Ile Met Tyr Ser Trp Ser Pro Leu Gln Gln Asn Phe Met Val
            355                 360                 365
Glu Asp Glu Thr Val Leu His Asn Ile Pro Tyr Met Gly Asp Glu Val
370                 375                 380
Leu Asp Gln Asp Gly Thr Phe Ile Glu Glu Leu Ile Lys Asn Tyr Asp
385                 390                 395                 400
Gly Lys Val His Gly Asp Arg Glu Cys Gly Phe Ile Asn Asp Glu Ile
                405                 410                 415
Phe Val Glu Leu Val Asn Ala Leu Gly Gln Tyr Asn Asp Asp Asp Asp
                420                 425                 430
Asp Asp Asp Gly Asp Asp Pro Glu Glu Arg Glu Glu Lys Gln Lys Asp
                435                 440                 445
Leu Glu Asp His Arg Asp Asp Lys Glu Ser Arg Pro Pro Arg Lys Phe
450                 455                 460
Pro Ser Asp Lys Ile Phe Glu Ala Ile Ser Ser Met Phe Pro Asp Lys
465                 470                 475                 480
Gly Thr Ala Glu Glu Leu Lys Glu Lys Tyr Lys Glu Leu Thr Glu Gln
                485                 490                 495
Gln Leu Pro Gly Ala Leu Pro Pro Glu Cys Thr Pro Asn Ile Asp Gly
            500                 505                 510
Pro Asn Ala Lys Ser Val Gln Arg Glu Gln Ser Leu His Ser Phe His
            515                 520                 525
Thr Leu Phe Cys Arg Arg Cys Phe Lys Tyr Asp Cys Phe Leu His Pro
            530                 535                 540
Phe His Ala Thr Pro Asn Thr Tyr Lys Arg Lys Asn Thr Glu Thr Ala
545                 550                 555                 560
Leu Asp Asn Lys Pro Cys Gly Pro Gln Cys Tyr Gln His Leu Glu Gly
                565                 570                 575
Ala Lys Glu Phe Ala Ala Ala Leu Thr Ala Glu Arg Ile Lys Thr Pro
            580                 585                 590
Pro Lys Arg Pro Gly Gly Arg Arg Gly Arg Leu Pro Asn Asn Ser
            595                 600                 605
Ser Arg Pro Ser Thr Pro Thr Ile Asn Val Leu Glu Ser Lys Asp Thr
            610                 615                 620
Asp Ser Asp Arg Glu Ala Gly Thr Glu Thr Gly Gly Glu Asn Asn Asp
625                 630                 635                 640
Lys Glu Glu Glu Glu Lys Lys Asp Glu Thr Ser Ser Ser Ser Glu Ala
                645                 650                 655
Asn Ser Arg Cys Gln Thr Pro Ile Lys Met Lys Pro Asn Ile Glu Pro
            660                 665                 670
```

```
Pro Glu Asn Val Glu Trp Ser Gly Ala Glu Ser Met Phe Arg Val
        675                 680                 685

Leu Ile Gly Thr Tyr Tyr Asp Asn Phe Cys Ala Ile Ala Arg Leu Ile
    690                 695                 700

Gly Thr Lys Thr Cys Arg Gln Val Tyr Glu Phe Arg Val Lys Glu Ser
705                 710                 715                 720

Ser Ile Ile Ala Pro Ala Pro Ala Glu Asp Val Asp Thr Pro Pro Arg
            725                 730                 735

Lys Lys Lys Arg Lys His Arg Leu Trp Ala Ala His Cys Arg Lys Ile
            740                 745                 750

Gln Leu Lys Lys Asp Gly Ser Ser Asn His Val Tyr Asn Tyr Gln Pro
            755                 760                 765

Cys Asp His Pro Arg Gln Pro Cys Asp Ser Ser Cys Pro Cys Val Ile
        770                 775                 780

Ala Gln Asn Phe Cys Glu Lys Phe Cys Gln Cys Ser Ser Glu Cys Gln
785                 790                 795                 800

Asn Arg Phe Pro Gly Cys Arg Cys Lys Ala Gln Cys Asn Thr Lys Gln
                805                 810                 815

Cys Pro Cys Tyr Leu Ala Val Arg Glu Cys Asp Pro Asp Leu Cys Leu
            820                 825                 830

Thr Cys Gly Ala Ala Asp His Trp Asp Ser Lys Asn Val Ser Cys Lys
            835                 840                 845

Asn Cys Ser Ile Gln Arg Gly Ser Lys Lys His Leu Leu Leu Ala Pro
        850                 855                 860

Ser Asp Val Ala Gly Trp Gly Ile Phe Ile Lys Asp Pro Val Gln Lys
865                 870                 875                 880

Asn Glu Phe Ile Ser Glu Tyr Cys Gly Glu Ile Ile Ser Gln Asp Glu
                885                 890                 895

Ala Asp Arg Arg Gly Lys Val Tyr Asp Lys Tyr Met Cys Ser Phe Leu
            900                 905                 910

Phe Asn Leu Asn Asn Asp Phe Val Val Asp Ala Thr Arg Lys Gly Asn
            915                 920                 925

Lys Ile Arg Phe Ala Asn His Ser Val Asn Pro Asn Cys Tyr Ala Lys
        930                 935                 940

Val Met Met Val Asn Gly Asp His Arg Ile Gly Ile Phe Ala Lys Arg
945                 950                 955                 960

Ala Ile Gln Thr Gly Glu Glu Leu Phe Phe Asp Tyr Arg Tyr Ser Gln
                965                 970                 975

Ala Asp Ala Leu Lys Tyr Val Gly Ile Glu Arg Glu Met Glu Ile Pro
            980                 985                 990

Gly Ser Gly Thr Gly Gly Thr Gly  Gly Ser Gly Pro Arg  Pro Arg Gly
            995                 1000                1005

Thr Arg  Gly Lys Gly Arg Arg  Ile Arg Arg Gly
    1010                1015                1020

<210> SEQ ID NO 89
<211> LENGTH: 746
<212> TYPE: PRT
<213> ORGANISM: Artificial
<220> FEATURE:
<223> OTHER INFORMATION: EGFP-NFkB-tDeg

<400> SEQUENCE: 89

Met Val Ser Lys Gly Glu Glu Leu Phe Thr Gly Val Val Pro Ile Leu
1               5                   10                  15
```

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Gly Ser Gly Gly Ser Gly Gly Ser Gly Gly Thr Gly Ala
                245                 250                 255

Glu Asp Asp Pro Tyr Leu Gly Arg Pro Glu Gln Met Phe His Leu Asp
            260                 265                 270

Pro Ser Leu Thr His Thr Ile Phe Asn Pro Glu Val Phe Gln Pro Gln
        275                 280                 285

Met Ala Leu Pro Thr Ala Asp Gly Pro Tyr Leu Gln Ile Leu Glu Gln
    290                 295                 300

Pro Lys Gln Arg Gly Phe Arg Phe Arg Tyr Val Cys Glu Gly Pro Ser
305                 310                 315                 320

His Gly Gly Leu Pro Gly Ala Ser Ser Glu Lys Asn Lys Lys Ser Tyr
                325                 330                 335

Pro Gln Val Lys Ile Cys Asn Tyr Val Gly Pro Ala Lys Val Ile Val
            340                 345                 350

Gln Leu Val Thr Asn Gly Lys Asn Ile His Leu His Ala His Ser Leu
        355                 360                 365

Val Gly Lys His Cys Glu Asp Gly Ile Cys Thr Val Thr Ala Gly Pro
    370                 375                 380

Lys Asp Met Val Val Gly Phe Ala Asn Leu Gly Ile Leu His Val Thr
385                 390                 395                 400

Lys Lys Lys Val Phe Glu Thr Leu Glu Ala Arg Met Thr Glu Ala Cys
                405                 410                 415

Ile Arg Gly Tyr Asn Pro Gly Leu Leu Val His Pro Asp Leu Ala Tyr
            420                 425                 430

```
Leu Gln Ala Glu Gly Gly Gly Asp Arg Gln Leu Gly Asp Arg Glu Lys
            435                 440                 445

Glu Leu Ile Arg Gln Ala Ala Leu Gln Gln Thr Lys Glu Met Asp Leu
        450                 455                 460

Ser Val Val Arg Leu Met Phe Thr Ala Phe Leu Pro Asp Ser Thr Gly
465                 470                 475                 480

Ser Phe Thr Arg Arg Leu Glu Pro Val Val Ser Asp Ala Ile Tyr Asp
            485                 490                 495

Ser Lys Ala Pro Asn Ala Ser Asn Leu Lys Ile Val Arg Met Asp Arg
        500                 505                 510

Thr Ala Gly Cys Val Thr Gly Gly Glu Glu Ile Tyr Leu Leu Cys Asp
        515                 520                 525

Lys Val Gln Lys Asp Asp Ile Gln Ile Arg Phe Tyr Glu Glu Glu Glu
        530                 535                 540

Asn Gly Gly Val Trp Glu Gly Phe Gly Asp Phe Ser Pro Thr Asp Val
545                 550                 555                 560

His Arg Gln Phe Ala Ile Val Phe Lys Thr Pro Lys Tyr Lys Asp Ile
            565                 570                 575

Asn Ile Thr Lys Pro Ala Ser Val Phe Val Gln Leu Arg Arg Lys Ser
        580                 585                 590

Asp Leu Glu Thr Ser Glu Pro Lys Pro Phe Leu Tyr Tyr Pro Glu Ile
        595                 600                 605

Lys Asp Lys Glu Glu Val Gln Arg Lys Arg Gln Lys Leu Met Pro Asn
        610                 615                 620

Phe Ser Asp Ser Phe Gly Gly Ser Gly Ala Gly Ala Gly Gly Gly
625                 630                 635                 640

Gly Met Phe Gly Ser Gly Gly Gly Gly Gly Thr Gly Ser Thr Gly
            645                 650                 655

Pro Gly Tyr Ser Phe Pro His Tyr Gly Phe Pro Thr Tyr Gly Gly Ile
            660                 665                 670

Thr Phe His Pro Gly Thr Thr Lys Ser Asn Ala Gly Met Lys His Gly
            675                 680                 685

Thr Met Asp Thr Glu Ser Lys Lys Asp Pro Glu Gly Cys Asp Lys Ser
        690                 695                 700

Asp Asp Lys Asn Thr Val Asn Leu Phe Gly Lys Asp Pro Arg Gly Ser
705                 710                 715                 720

Leu Ser Gly Gly Thr Gly Gly Ser Gly Pro Arg Pro Arg Gly Thr Arg
            725                 730                 735

Gly Lys Gly Arg Arg Ile Arg Arg Gly
            740                 745

<210> SEQ ID NO 90
<211> LENGTH: 743
<212> TYPE: PRT
<213> ORGANISM: Artificial
<220> FEATURE:
<223> OTHER INFORMATION: mCherry- NFkB-tDeg

<400> SEQUENCE: 90

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45
```

```
Ala Lys Leu Lys Val Thr Lys Gly Gly Pro Leu Pro Phe Ala Trp Asp
 50              55                  60

Ile Leu Ser Pro Gln Phe Met Tyr Gly Ser Lys Ala Tyr Val Lys His
 65              70                  75                      80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Val Val Thr Val
             100                 105                 110

Thr Gln Asp Ser Ser Leu Gln Asp Gly Glu Phe Ile Tyr Lys Val Lys
                 115                 120                 125

Leu Arg Gly Thr Asn Phe Pro Ser Asp Gly Pro Val Met Gln Lys Lys
 130                 135                 140

Thr Met Gly Trp Glu Ala Ser Ser Glu Arg Met Tyr Pro Glu Asp Gly
 145                 150                 155                 160

Ala Leu Lys Gly Glu Ile Lys Gln Arg Leu Lys Leu Lys Asp Gly Gly
                 165                 170                 175

His Tyr Asp Ala Glu Val Lys Thr Thr Tyr Lys Ala Lys Lys Pro Val
             180                 185                 190

Gln Leu Pro Gly Ala Tyr Asn Val Asn Ile Lys Leu Asp Ile Thr Ser
             195                 200                 205

His Asn Glu Asp Tyr Thr Ile Val Glu Gln Tyr Glu Arg Ala Glu Gly
 210                 215                 220

Arg His Ser Thr Gly Gly Met Asp Glu Leu Tyr Lys Gly Gly Ser Gly
 225                 230                 235                 240

Gly Ser Gly Gly Ser Gly Gly Ser Gly Gly Thr Gly Ala Glu Asp Asp
                 245                 250                 255

Pro Tyr Leu Gly Arg Pro Glu Gln Met Phe His Leu Asp Pro Ser Leu
             260                 265                 270

Thr His Thr Ile Phe Asn Pro Glu Val Phe Gln Pro Gln Met Ala Leu
     275                 280                 285

Pro Thr Ala Asp Gly Pro Tyr Leu Gln Ile Leu Glu Gln Pro Lys Gln
 290                 295                 300

Arg Gly Phe Arg Phe Arg Tyr Val Cys Glu Gly Pro Ser His Gly Gly
 305                 310                 315                 320

Leu Pro Gly Ala Ser Ser Glu Lys Asn Lys Lys Ser Tyr Pro Gln Val
                 325                 330                 335

Lys Ile Cys Asn Tyr Val Gly Pro Ala Lys Val Ile Val Gln Leu Val
             340                 345                 350

Thr Asn Gly Lys Asn Ile His Leu His Ala His Ser Leu Val Gly Lys
             355                 360                 365

His Cys Glu Asp Gly Ile Cys Thr Val Thr Ala Gly Pro Lys Asp Met
 370                 375                 380

Val Val Gly Phe Ala Asn Leu Gly Ile Leu His Val Thr Lys Lys Lys
 385                 390                 395                 400

Val Phe Glu Thr Leu Glu Ala Arg Met Thr Glu Ala Cys Ile Arg Gly
                 405                 410                 415

Tyr Asn Pro Gly Leu Leu Val His Pro Asp Leu Ala Tyr Leu Gln Ala
                 420                 425                 430

Glu Gly Gly Gly Asp Arg Gln Leu Gly Asp Arg Glu Lys Glu Leu Ile
                 435                 440                 445

Arg Gln Ala Ala Leu Gln Gln Thr Lys Glu Met Asp Leu Ser Val Val
 450                 455                 460

Arg Leu Met Phe Thr Ala Phe Leu Pro Asp Ser Thr Gly Ser Phe Thr
```

```
                465                 470                 475                 480
Arg Arg Leu Glu Pro Val Val Ser Asp Ala Ile Tyr Asp Ser Lys Ala
                    485                 490                 495
Pro Asn Ala Ser Asn Leu Lys Ile Val Arg Met Asp Arg Thr Ala Gly
                500                 505                 510
Cys Val Thr Gly Gly Glu Ile Tyr Leu Leu Cys Asp Lys Val Gln
                515                 520                 525
Lys Asp Asp Ile Gln Ile Arg Phe Tyr Glu Glu Glu Asn Gly Gly
                530                 535                 540
Val Trp Glu Gly Phe Gly Asp Phe Ser Pro Thr Asp Val His Arg Gln
545                 550                 555                 560
Phe Ala Ile Val Phe Lys Thr Pro Lys Tyr Lys Asp Ile Asn Ile Thr
                    565                 570                 575
Lys Pro Ala Ser Val Phe Val Gln Leu Arg Arg Lys Ser Asp Leu Glu
                580                 585                 590
Thr Ser Glu Pro Lys Pro Phe Leu Tyr Tyr Pro Glu Ile Lys Asp Lys
                595                 600                 605
Glu Glu Val Gln Arg Lys Arg Gln Lys Leu Met Pro Asn Phe Ser Asp
610                 615                 620
Ser Phe Gly Gly Gly Ser Gly Ala Gly Ala Gly Gly Gly Met Phe
625                 630                 635                 640
Gly Ser Gly Gly Gly Gly Gly Thr Gly Ser Thr Gly Pro Gly Tyr
                    645                 650                 655
Ser Phe Pro His Tyr Gly Phe Pro Thr Tyr Gly Gly Ile Thr Phe His
                660                 665                 670
Pro Gly Thr Thr Lys Ser Asn Ala Gly Met Lys His Gly Thr Met Asp
                675                 680                 685
Thr Glu Ser Lys Lys Asp Pro Glu Gly Cys Asp Lys Ser Asp Asp Lys
                690                 695                 700
Asn Thr Val Asn Leu Phe Gly Lys Asp Pro Arg Gly Ser Leu Ser Gly
705                 710                 715                 720
Gly Thr Gly Gly Ser Gly Pro Arg Pro Arg Gly Thr Arg Gly Lys Gly
                    725                 730                 735
Arg Arg Ile Arg Arg Gly
                740

<210> SEQ ID NO 91
<211> LENGTH: 597
<212> TYPE: PRT
<213> ORGANISM: Artificial
<220> FEATURE:
<223> OTHER INFORMATION: EGFP-TurboID-tDeg

<400> SEQUENCE: 91

Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
        50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
```

```
                    85                  90                  95
Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Lys Leu
                195                 200                 205

Ser Lys Asp Pro Asn Glu Lys Arg Asp His Met Val Leu Leu Glu Phe
                210                 215                 220

Val Thr Ala Ala Gly Ile Thr Leu Gly Met Asp Glu Leu Tyr Lys Gly
225                 230                 235                 240

Thr Gly Ala Cys Gly Thr Ser Gly Gly Met Lys Asp Asn Thr Val Pro
                245                 250                 255

Leu Lys Leu Ile Ala Leu Leu Ala Asn Gly Glu Phe His Ser Gly Glu
                260                 265                 270

Gln Leu Gly Glu Thr Leu Gly Met Ser Arg Ala Ala Ile Asn Lys His
                275                 280                 285

Ile Gln Thr Leu Arg Asp Trp Gly Val Asp Val Phe Thr Val Pro Gly
                290                 295                 300

Lys Gly Tyr Ser Leu Pro Glu Pro Ile Pro Leu Leu Asn Ala Lys Gln
305                 310                 315                 320

Ile Leu Gly Gln Leu Asp Gly Gly Ser Val Ala Val Leu Pro Val Val
                325                 330                 335

Asp Ser Thr Asn Gln Tyr Leu Leu Asp Arg Ile Gly Glu Leu Lys Ser
                340                 345                 350

Gly Asp Ala Cys Ile Ala Glu Tyr Gln Gln Ala Gly Arg Gly Ser Arg
                355                 360                 365

Gly Arg Lys Trp Phe Ser Pro Phe Gly Ala Asn Leu Tyr Leu Ser Met
                370                 375                 380

Phe Trp Arg Leu Lys Arg Gly Pro Ala Ala Ile Gly Leu Gly Pro Val
385                 390                 395                 400

Ile Gly Ile Val Met Ala Glu Ala Leu Arg Lys Leu Gly Ala Asp Lys
                405                 410                 415

Val Arg Val Lys Trp Pro Asn Asp Leu Tyr Leu Gln Asp Arg Lys Leu
                420                 425                 430

Ala Gly Ile Leu Val Glu Leu Ala Gly Ile Thr Gly Asp Ala Ala Gln
                435                 440                 445

Ile Val Ile Gly Ala Gly Ile Asn Val Ala Met Arg Arg Val Glu Glu
                450                 455                 460

Ser Val Val Asn Gln Gly Trp Ile Thr Leu Gln Glu Ala Gly Ile Asn
465                 470                 475                 480

Leu Asp Arg Asn Thr Leu Ala Ala Thr Leu Ile Arg Glu Leu Arg Ala
                485                 490                 495

Ala Leu Glu Leu Phe Glu Gln Glu Gly Leu Ala Pro Tyr Leu Pro Arg
                500                 505                 510
```

```
Trp Glu Lys Leu Asp Asn Phe Ile Asn Arg Pro Val Lys Leu Ile Ile
            515                 520                 525
Gly Asp Lys Glu Ile Phe Gly Ile Ser Arg Gly Ile Asp Lys Gln Gly
        530                 535                 540
Ala Leu Leu Leu Glu Gln Asp Gly Val Ile Lys Pro Trp Met Gly Gly
545                 550                 555                 560
Glu Ile Ser Leu Arg Ser Ala Glu Lys Gly Ser Gly Thr Gly Gly Thr
                565                 570                 575
Gly Gly Ser Gly Pro Arg Pro Arg Gly Thr Arg Gly Lys Gly Arg Arg
            580                 585                 590
Ile Arg Arg Arg Gly
        595

<210> SEQ ID NO 92
<211> LENGTH: 524
<212> TYPE: PRT
<213> ORGANISM: Artificial
<220> FEATURE:
<223> OTHER INFORMATION: EGFP-APEX-tDeg

<400> SEQUENCE: 92

Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Lys Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys Gly
225                 230                 235                 240
Thr Gly Ala Cys Gly Thr Ser Gly Lys Ser Tyr Pro Thr Val Ser Ala
                245                 250                 255
Asp Tyr Gln Asp Ala Val Glu Lys Ala Lys Lys Lys Leu Arg Gly Phe
            260                 265                 270
```

```
Ile Ala Glu Lys Arg Cys Ala Pro Leu Met Leu Arg Leu Ala Phe His
        275                 280                 285

Ser Ala Gly Thr Phe Asp Lys Gly Thr Lys Thr Gly Gly Pro Phe Gly
    290                 295                 300

Thr Ile Lys His Pro Ala Glu Leu Ala His Ser Ala Asn Asn Gly Leu
305                 310                 315                 320

Asp Ile Ala Val Arg Leu Leu Glu Pro Leu Lys Ala Glu Phe Pro Ile
                325                 330                 335

Leu Ser Tyr Ala Asp Phe Tyr Gln Leu Ala Gly Val Val Ala Val Glu
            340                 345                 350

Val Thr Gly Gly Pro Lys Val Pro Phe His Pro Gly Arg Glu Asp Lys
        355                 360                 365

Pro Glu Pro Pro Glu Gly Arg Leu Pro Asp Pro Thr Lys Gly Ser
370                 375                 380

Asp His Leu Arg Asp Val Phe Gly Lys Ala Met Gly Leu Thr Asp Gln
385                 390                 395                 400

Asp Ile Val Ala Leu Ser Gly His Thr Ile Gly Ala Ala His Lys
                405                 410                 415

Glu Arg Ser Gly Phe Glu Gly Pro Trp Thr Ser Asn Pro Leu Ile Phe
                420                 425                 430

Asp Asn Ser Tyr Phe Thr Glu Leu Leu Ser Gly Glu Lys Glu Gly Leu
            435                 440                 445

Leu Gln Leu Pro Ser Asp Lys Ala Leu Leu Ser Asp Pro Val Phe Arg
    450                 455                 460

Pro Leu Val Asp Lys Tyr Ala Ala Asp Glu Asp Ala Phe Phe Ala Asp
465                 470                 475                 480

Tyr Ala Glu Ala His Gln Lys Leu Ser Glu Leu Gly Phe Ala Asp Ala
                485                 490                 495

Gly Ser Gly Thr Gly Gly Thr Gly Gly Ser Gly Pro Arg Pro Arg Gly
            500                 505                 510

Thr Arg Gly Lys Gly Arg Arg Ile Arg Arg Gly
            515                 520

<210> SEQ ID NO 93
<211> LENGTH: 39
<212> TYPE: DNA
<213> ORGANISM: Artificial
<220> FEATURE:
<223> OTHER INFORMATION: miniCMV promoter

<400> SEQUENCE: 93
ggtaggcgtg tacggtggga ggcctatata agcagagct                                 39

<210> SEQ ID NO 94
<211> LENGTH: 19
<212> TYPE: DNA
<213> ORGANISM: Artificial
<220> FEATURE:
<223> OTHER INFORMATION: MS2 hairpin

<400> SEQUENCE: 94
acatgaggat cacccatgt                                                       19

<210> SEQ ID NO 95
<211> LENGTH: 20
<212> TYPE: DNA
<213> ORGANISM: Artificial
<220> FEATURE:
```

<223> OTHER INFORMATION: EYFP fw probe

<400> SEQUENCE: 95
acgtaaacgg ccacaagttc                                                    20

<210> SEQ ID NO 96
<211> LENGTH: 20
<212> TYPE: DNA
<213> ORGANISM: Artificial
<220> FEATURE:
<223> OTHER INFORMATION: EYFP rv probe

<400> SEQUENCE: 96
cttcatgtgg tcggggtagc                                                    20

<210> SEQ ID NO 97
<211> LENGTH: 20
<212> TYPE: DNA
<213> ORGANISM: Artificial
<220> FEATURE:
<223> OTHER INFORMATION: mCherry fw probe

<400> SEQUENCE: 97
cacgagttcg agatcgaggg                                                    20

<210> SEQ ID NO 98
<211> LENGTH: 20
<212> TYPE: DNA
<213> ORGANISM: Artificial
<220> FEATURE:
<223> OTHER INFORMATION: mCherry rv probe

<400> SEQUENCE: 98
caagtagtcg gggatgtcgg                                                    20

<210> SEQ ID NO 99
<211> LENGTH: 28
<212> TYPE: DNA
<213> ORGANISM: Artificial
<220> FEATURE:
<223> OTHER INFORMATION: Probe-1

<400> SEQUENCE: 99
gttgagtgat tagcgattga ttccggcc                                           28

<210> SEQ ID NO 100
<211> LENGTH: 30
<212> TYPE: DNA
<213> ORGANISM: Artificial
<220> FEATURE:
<223> OTHER INFORMATION: Probe-2

<400> SEQUENCE: 100
gtcggatgat tttcgtaata gattgcgctg                                         30

<210> SEQ ID NO 101
<211> LENGTH: 29
<212> TYPE: DNA
<213> ORGANISM: Artificial
<220> FEATURE:
<223> OTHER INFORMATION: Probe-3

<400> SEQUENCE: 101
ttgacgtgat tttgtgagat tttccgcag                                          29

```
<210> SEQ ID NO 102
<211> LENGTH: 29
<212> TYPE: DNA
<213> ORGANISM: Artificial
<220> FEATURE:
<223> OTHER INFORMATION: Probe-4

<400> SEQUENCE: 102
tgcctgattg taagtatgtg gattatcgg                                            29

<210> SEQ ID NO 103
<211> LENGTH: 27
<212> TYPE: DNA
<213> ORGANISM: Artificial
<220> FEATURE:
<223> OTHER INFORMATION: Probe-5

<400> SEQUENCE: 103
ggataggtat ggaggaagta gcttgga                                              27

<210> SEQ ID NO 104
<211> LENGTH: 26
<212> TYPE: DNA
<213> ORGANISM: Artificial
<220> FEATURE:
<223> OTHER INFORMATION: Probe-6

<400> SEQUENCE: 104
acaatatctt gcgccgttcg atcttg                                               26

<210> SEQ ID NO 105
<211> LENGTH: 22
<212> TYPE: DNA
<213> ORGANISM: Artificial
<220> FEATURE:
<223> OTHER INFORMATION: Probe-7

<400> SEQUENCE: 105
ggccgccaag aagaacgacc aa                                                   22

<210> SEQ ID NO 106
<211> LENGTH: 27
<212> TYPE: DNA
<213> ORGANISM: Artificial
<220> FEATURE:
<223> OTHER INFORMATION: Probe-8

<400> SEQUENCE: 106
cctaagaacc taacatatct agcgagg                                              27

<210> SEQ ID NO 107
<211> LENGTH: 22
<212> TYPE: DNA
<213> ORGANISM: Artificial
<220> FEATURE:
<223> OTHER INFORMATION: Probe-9

<400> SEQUENCE: 107
tgtgcacctt gaagcgcatg aa                                                   22

<210> SEQ ID NO 108
<211> LENGTH: 20
<212> TYPE: DNA
<213> ORGANISM: Artificial
<220> FEATURE:
<223> OTHER INFORMATION: Probe-10
```

<400> SEQUENCE: 108
cctgggtcac ggtcaccacg                                               20

<210> SEQ ID NO 109
<211> LENGTH: 19
<212> TYPE: DNA
<213> ORGANISM: Artificial
<220> FEATURE:
<223> OTHER INFORMATION: Probe-11

<400> SEQUENCE: 109
gcccatggtc ttcttctgc                                                19

<210> SEQ ID NO 110
<211> LENGTH: 20
<212> TYPE: DNA
<213> ORGANISM: Artificial
<220> FEATURE:
<223> OTHER INFORMATION: Probe-12

<400> SEQUENCE: 110
gggtgcttca cgtaggcctt                                               20

<210> SEQ ID NO 111
<211> LENGTH: 21
<212> TYPE: DNA
<213> ORGANISM: Artificial
<220> FEATURE:
<223> OTHER INFORMATION: Probe-13

<400> SEQUENCE: 111
gtcaccttca gcttggcggt c                                             21

<210> SEQ ID NO 112
<211> LENGTH: 23
<212> TYPE: DNA
<213> ORGANISM: Artificial
<220> FEATURE:
<223> OTHER INFORMATION: Probe-14

<400> SEQUENCE: 112
gcctctgctt gatctcgccc ttc                                           23

<210> SEQ ID NO 113
<211> LENGTH: 23
<212> TYPE: DNA
<213> ORGANISM: Artificial
<220> FEATURE:
<223> OTHER INFORMATION: Probe-15

<400> SEQUENCE: 113
gtcttgacct cagcgtcgta gtg                                           23

<210> SEQ ID NO 114
<211> LENGTH: 20
<212> TYPE: DNA
<213> ORGANISM: Artificial
<220> FEATURE:
<223> OTHER INFORMATION: Probe-16

<400> SEQUENCE: 114
cggcgcgttc gtactgttcc                                               20

<210> SEQ ID NO 115
<211> LENGTH: 28

```
<212> TYPE: DNA
<213> ORGANISM: Artificial
<220> FEATURE:
<223> OTHER INFORMATION: Probe-17

<400> SEQUENCE: 115
gccgataatc cacatactta caatcagg                                            28

<210> SEQ ID NO 116
<211> LENGTH: 43
<212> TYPE: PRT
<213> ORGANISM: Artificial
<220> FEATURE:
<223> OTHER INFORMATION: Linker sequence

<400> SEQUENCE: 116

Met Asp Pro Val Val Val Leu Gly Leu Cys Leu Ser Cys Leu Leu Leu
1               5                   10                  15

Leu Ser Leu Trp Lys Gln Ser Tyr Gly Gly Lys Leu Gly Gly Ser
            20                  25                  30

Gly Gly Thr Gly Gly Ser Gly Thr Ser Gly Gly
        35                  40

<210> SEQ ID NO 117
<211> LENGTH: 4
<212> TYPE: PRT
<213> ORGANISM: Artificial
<220> FEATURE:
<223> OTHER INFORMATION: Destabilization domain

<400> SEQUENCE: 117

Arg Arg Arg Gly
1

<210> SEQ ID NO 118
<211> LENGTH: 39
<212> TYPE: DNA
<213> ORGANISM: Artificial
<220> FEATURE:
<223> OTHER INFORMATION: miniCMV promoter

<400> SEQUENCE: 118
ggtaggcgtg tacggtggga ggcctatata agcagagct                                39

<210> SEQ ID NO 119
<211> LENGTH: 586
<212> TYPE: DNA
<213> ORGANISM: Artificial
<220> FEATURE:
<223> OTHER INFORMATION: (Pepper)10 tag sequence

<400> SEQUENCE: 119
ggctcgtctg agctcattag ctccgagccg tccagcgcaa actattacga aaaacatccg          60
acgggctcgt tgagctcatt agctccgagc ccgctgcgga aaacctcaca aaaacacgac         120
aaacgggctc gttgagctca ttagctccga gcccgccgac aacccacaaa cttacaacca         180
ggcaaacggc tcgtctgagc tcattagctc cgagccgtat caagaccgaa cggcgcaaga         240
tattgacacg ggctcgttga gctcattagc tccgagcccg acctcgctag atatgttagg         300
ttcttaggca ttggctcgtt gagctcatta gctccgagcc aaagatcgac tgcaattccg         360
attagacgta cacggctcgt ctgagctcat tagctccgag ccgatccaac ctacttcctc         420
cataactaac ctccggctcg ttgagctcat tagctccgag ccgatcataa cgcaataccg         480
```

| tacactgtcc aatccggctc gttgagctca ttagctccga gccggacaac caatcgacat | 540 |
| acatcacacc acaactcggc tcgtctgagc tcattagctc cgagcc | 586 |

<210> SEQ ID NO 120
<211> LENGTH: 1466
<212> TYPE: DNA
<213> ORGANISM: Artificial
<220> FEATURE:
<223> OTHER INFORMATION: (F30-1xPepper)10 tag sequence

<400> SEQUENCE: 120

| ttgccatgtg tatgtgggat gcgttgccac gtttcccaca tactctgatg atccgctagc | 60 |
| aaaggctcgt ctgagctcat tagctccgag cccgaggtac cggatcattc atggcaagtc | 120 |
| cagcgcaatc tattacgaaa atcatccgac gtcgcgatgt ctatgcggga tgcgttgcca | 180 |
| cgtttcccgc atagtctgat catccgctag caaaggctcg ttgagctcat tagctccgag | 240 |
| cccgaggtac cggatgattc atcgcgacgc tgcggaaaat ctcacaaaat cacgtcaaac | 300 |
| gtcgccgtgt gtgtgtagga tgcgttgcca cgtttcctac acactctgac gatccgctag | 360 |
| caaaggctcg ttgagctcat tagctccgag cccgaggtac cggatcgttc acggcgacgc | 420 |
| cgataatcca catacttaca atcaggcaat cttgccatgt gtatgtggga tgcgttgcca | 480 |
| cgtttcccac atactctgat gatccgctag caaaggctcg ttgagctcat tagctccgag | 540 |
| cccgaggtac cggatcattc atggcaagta tcaagatcga acggcgcaag atattgtcac | 600 |
| gtcgcgatgt ctatgcggga tgcgttgcca cgtttcccgc atagtctgat catccgctag | 660 |
| caaaggctcg tctgagctca ttagctccga gcccgaggta ccggatgatt catcgcgacg | 720 |
| tcctcgctag atatgttagg ttcttaggca tttcgccgtg tgtgtgtagg atgcgttgcc | 780 |
| acgtttccta cacactctga cgatccgcta gcaaaggctc gttgagctca ttagctccga | 840 |
| gcccgaggta ccggatcgtt cacggcgaaa agatcgtctg caattccgat tagacgtaca | 900 |
| cttgccatgt gtatgtggga tgcgttgcca cgtttcccac atactctgat gatccgctag | 960 |
| caaaggctcg ttgagctcat tagctccgag cccgaggtac cggatcattc atggcaagat | 1020 |
| ccaagctact tcctccatac ctatcctcct cgcgatgtct atgcgggatg cgttgccacg | 1080 |
| tttcccgcat agtctgatca tccgctagca aaggctcgtt gagctcatta gctccgagcc | 1140 |
| cgaggtaccg gatgattcat cgcgagatca taacgcaata ccgtacactg tccaatcctc | 1200 |
| gccgtgtgtg tgtaggatgc gttgccacgt ttcctacaca ctctgacgat ccgctagcaa | 1260 |
| aggctcgtct gagctcatta gctccgagcc cgaggtaccg gatcgttcac ggcgaggata | 1320 |
| atcaatccac atacatcaca ccacaattct tgccatgtgt atgtgggatg cgttgccacg | 1380 |
| tttcccacat actctgatga tccgctagca aaggctcgtc tgagctcatt agctccgagc | 1440 |
| ccgaggtacc ggatcattca tggcaa | 1466 |

<210> SEQ ID NO 121
<211> LENGTH: 1228
<212> TYPE: DNA
<213> ORGANISM: Artificial
<220> FEATURE:
<223> OTHER INFORMATION: (Pepper)20 tag sequence

<400> SEQUENCE: 121

| ggctcgtctg agctcattag ctccgagccg tccagcgcaa actattacga aaacatccg | 60 |
| acgggctcgt tgagctcatt agctccgagc ccgctgcgga aaacctcaca aaacacgac | 120 |
| aaacgggctc gttgagctca ttagctccga gcccgccgac aacccacaaa cttacaacca | 180 |

```
ggcaaacggc tcgtctgagc tcattagctc cgagccgtat caagaccgaa cggcgcaaga    240
tattgacacg ggctcgttga gctcattagc tccgagcccg acctcgctag atatgttagg    300
ttcttaggca ttggctcgtt gagctcatta gctccgagcc aaagatcgac tgcaattccg    360
attagacgta cacggctcgt ctgagctcat tagctccgag ccgatccaac ctacttcctc    420
cataactaac ctccggctcg ttgagctcat tagctccgag ccgatcataa cgcaataccg    480
tacactgtcc aatccggctc gttgagctca ttagctccga gccggacaac caatcgacat    540
acatcacacc acaactcggc tcgtctgagc tcattagctc cgagccgaat tggtcgttct    600
tcttggcggc cgctcgacta aggtgacaac tggacaaacc ctcggctcgt tgagctcatt    660
agctccgagc cgactctcac caacaagaca aaaactactc ttctaggctc gttgagctca    720
ttagctccga gcctaaacac tcaagcatac attgtgccta tttcttggct cgtctgagct    780
cattagctcc gagccatgct ctcacgaatt tcaaaacacg gacaagggc tcgttgagct     840 cattagctcc gagcccgttc cacgtccaat acgattactt acctttcggg ctcgttgagc    900
tcattagctc cgagcccgca gctacatcac ttccactcag gacattcaag ggctcgtctg    960
agctcattag ctccgagccc tccacaagtc tcaaccacag aaaactaccaa atgggctcgt    1020 tgagctcatt agctccgagc ccactcctac ctcaaacctc ttcccacaaa actggggctc    1080
gttgagctca ttagctccga gcccccattc aacatacca aatcaaaaac aattactggc     1140
tcgtctgagc tcattagctc cgagccagcc cacatctctc actactatca aaaccaaac     1200 ggctcgttga gctcattagc tccgagcc                                       1228

<210> SEQ ID NO 122
<211> LENGTH: 1812
<212> TYPE: DNA
<213> ORGANISM: Artificial
<220> FEATURE:
<223> OTHER INFORMATION: (F30-1xPepper)10 tag sequence

<400> SEQUENCE: 122
ttgccatgtg tatgtgggaa gcgtagaaag gctcgttgag ctcattagct ccgagcccga     60
ctacgtttcc cacatactct gatgatccgc tagcaaaggc tcgtctgagc tcattagctc    120
cgagcccgag gtaccggatc attcatggca agtccagcgc aatctattac gaaaatcatc    180
cgacgtcgcg atgtctatgc gggaagcgta gaaaggctcg tctgagctca ttagctccga    240
gcccgactac gtttcccgca tagtctgatc atccgctagc aaaggctcgt tgagctcatt    300
agctccgagc ccgaggtacc ggatgattca tcgcgacgct gcggaaaatc tcacaaaatc    360
acgtcaaacg tcgccgtgtg tgtgtaggaa gcgtagaaag gctcgtctga gctcattagc    420
tccgagcccg actacgtttc ctacacactc tgacgatccg ctagcaaagg ctcgttgagc    480
tcattagctc cgagcccgag gtaccggatc gttcacggcg acgccgataa tccacatact    540
tacaatcagg caatcttgcc atgtgtatgt gggaagcgta gaaaggctcg ttgagctcat    600
tagctccgag cccgactacg tttcccacat actctgatga tccgctagca aaggctcgtt    660
gagctcatta gctccgagcc cgaggtaccg gatcattcat ggcaagtatc aagatcgaac    720
ggcgcaagat attgtcacgt cgcgatgtct atgcgggaag cgtagaaagg ctcgttgagc    780
tcattagctc cgagcccgac tacgtttccc gcatagtctg atcatccgct agcaaaggct    840
cgtctgagct cattagctcc gagcccgagg taccggatga ttcatcgcga cgtcctcgct    900
agatatgtta ggttcttagg catttcgccg tgtgtgtgta ggaagcgtag aaaggctcgt    960
```

```
tgagctcatt agctccgagc ccgactacgt ttcctacaca ctctgacgat ccgctagcaa    1020
aggctcgtct gagctcatta gctccgagcc cgaggtaccg gatcgttcac ggcgaaaaga    1080
tcgtctgcaa ttccgattag acgtacactt gccatgtgta tgtgggaagc gtagaaaggc    1140
tcgtctgagc tcattagctc cgagcccgac tacgtttccc acatactctg atgatccgct    1200
agcaaaggct cgttgagctc attagctccg agcccgaggt accggatcat tcatggcaag    1260
atccaagcta cttcctccat acctatcctc tcgcgatgt ctatgcggga agcgtagaaa     1320
ggctcgtctg agctcattag ctccgagccc gactacgttt cccgcatagt ctgatcatcc    1380
gctagcaaag gctcgttgag ctcattagct ccgagcccga ggtaccggat gattcatcgc    1440
gagatcataa cgcaataccg tacactgtcc aatcctcgcc gtgtgtgtgt aggaagcgta    1500
gaaaggctcg tctgagctca ttagctccga gcccgactac gtttcctaca cactctgacg    1560
atccgctagc aaaggctcgt tgagctcatt agctccgagc cgaggtacc ggatcgttca     1620 cggcgaggat aatcaatcca catacatcac accacaattc ttgccatgtg tatgtgggaa    1680
gcgtagaaag gctcgtctga gctcattagc tccgagcccg actacgtttc ccacatactc    1740
tgatgatccg ctagcaaagg ctcgtctgag ctcattagct ccgagcccga ggtaccggat    1800
cattcatggc aa                                                        1812

<210> SEQ ID NO 123
<211> LENGTH: 22
<212> TYPE: PRT
<213> ORGANISM: Artificial
<220> FEATURE:
<223> OTHER INFORMATION: LambdaN RNA-binding domain

<400> SEQUENCE: 123

Met Asp Ala Arg Thr Arg Arg Arg Glu Arg Arg Ala Glu Lys Gln Ala
1               5                   10                  15

Gln Trp Lys Ala Ala Asn
            20

<210> SEQ ID NO 124
<211> LENGTH: 19
<212> TYPE: RNA
<213> ORGANISM: Artificial
<220> FEATURE:
<223> OTHER INFORMATION: BoxB RNA-binding domain

<400> SEQUENCE: 124
gggcccugaa gagggccc                                                   19

<210> SEQ ID NO 125
<211> LENGTH: 23
<212> TYPE: PRT
<213> ORGANISM: Artificial
<220> FEATURE:
<223> OTHER INFORMATION: HIV-1 Rev RNA-binding domain

<400> SEQUENCE: 125

Asp Thr Arg Gln Ala Arg Arg Asn Arg Arg Arg Arg Trp Arg Glu Arg
1               5                   10                  15

Gln Arg Ala Ala Ala Ala Arg
            20

<210> SEQ ID NO 126
<211> LENGTH: 32
<212> TYPE: RNA
<213> ORGANISM: Artificial
```

```
<220> FEATURE:
<223> OTHER INFORMATION: RRE RNA-binding domain

<400> SEQUENCE: 126
ggucugggcg cagcgcaagc ugcggacagg cc                                32

<210> SEQ ID NO 127
<211> LENGTH: 10
<212> TYPE: PRT
<213> ORGANISM: Artificial
<220> FEATURE:
<223> OTHER INFORMATION: HIV Tat-RRRG

<400> SEQUENCE: 127

Arg Lys Lys Arg Arg Gln Arg Arg Arg Gly
1               5                   10

<210> SEQ ID NO 128
<211> LENGTH: 37
<212> TYPE: RNA
<213> ORGANISM: Artificial
<220> FEATURE:
<223> OTHER INFORMATION: HIV TAR RNA

<400> SEQUENCE: 128
acgaagcuug aucccguuug ccggucgauc gcuucga                            37

<210> SEQ ID NO 129
<211> LENGTH: 9
<212> TYPE: PRT
<213> ORGANISM: Artificial
<220> FEATURE:
<223> OTHER INFORMATION: Tat peptide

<400> SEQUENCE: 129

Arg Lys Lys Arg Arg Gln Arg Arg Arg
1               5

<210> SEQ ID NO 130
<211> LENGTH: 4
<212> TYPE: PRT
<213> ORGANISM: Artificial
<220> FEATURE:
<223> OTHER INFORMATION: Degron peptide

<400> SEQUENCE: 130

Arg Arg Arg Gly
1
```